US011441156B2

(12) United States Patent
Mirkov et al.

(10) Patent No.: US 11,441,156 B2
(45) **Date of Patent: *Sep. 13, 2022**

(54) PATHOGEN RESISTANT COMPOSITIONS, ORGANISMS, SYSTEMS, AND METHODS

(71) Applicant: THE TEXAS A&M UNIVERSITY SYSTEM, College Station, TX (US)

(72) Inventors: T. Erik Mirkov, Harlingen, TX (US); Kranthi Kiran Mandadi, Weslaco, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/843,519

(22) Filed: Apr. 8, 2020

(65) Prior Publication Data

US 2020/0332312 A1 Oct. 22, 2020

Related U.S. Application Data

(63) Continuation of application No. 15/212,041, filed on Jul. 15, 2016, now Pat. No. 10,640,784.

(60) Provisional application No. 62/192,732, filed on Jul. 15, 2015.

(51) Int. Cl.
*C12N 15/82* (2006.01)
*C07K 14/415* (2006.01)

(52) U.S. Cl.
CPC ........ *C12N 15/8279* (2013.01); *C07K 14/415* (2013.01); *C12N 15/8281* (2013.01)

(58) Field of Classification Search
None
See application file for complete search history.

(56) References Cited

U.S. PATENT DOCUMENTS

| | | | | |
|---|---|---|---|---|
| 7,432,419 B2 * | 10/2008 | Gupta | .............. | C07K 14/43563 435/252.33 |
| 10,640,784 B2 * | 5/2020 | Mirkov | .............. | C12N 15/8281 |
| 2014/0109472 A1 | 4/2014 | Mirkov et al. | | |
| 2015/0067918 A1 | 3/2015 | Kress | | |

FOREIGN PATENT DOCUMENTS

| | | |
|---|---|---|
| WO | 2013112997 A1 | 8/2013 |
| WO | 2015031130 A1 | 3/2015 |

OTHER PUBLICATIONS

Alvarez et al (2016),5(2):109-118.*
Broekaert et al. Critical Reviews in Plant Sciences 16(3):297-323 (1997).*
Dutt et al. Biotechnology and Genomics (2008):259-264.*
Stover et al., "Screening Antimicrobial Peptides In Vitro for Use in Developing Transgenic Citrus Resistant to Huanglongbing and Citrus Canker," J. Amer. Soc. Hort. Sci. 138(2):142-148. 2013.
Office Action dated Jun. 29, 2020 in Argentinian Application No. P160102173.
Kim Bowman et al, "Overview of Efforts to Develop HLB-Resistant Transgenic Citrus", (Jan. 1, 2009), URL: http://www.imok.ufl.edu/hlb/database/pdf/00001999.pdf, (Oct. 15, 2015), XP055221237 [I] 1-5 * pp. 1-11.
Environmental Protection Agency, "Defensin proteins (SoD2 and SoD7) derived from spinach (*Spinacia oleracea* L.) in citrus plants; temporary exemption from the requirement of a tolerance", Federal Register, (May 6, 2015), vol. 80, No. 87, pp. 25943-25946, XP055350353 [X] 10 * See summary. * [A] 1-9, 11-41.

* cited by examiner

*Primary Examiner* — Medina A Ibrahim
(74) *Attorney, Agent, or Firm* — Hogan Lovells US LLP

(57) ABSTRACT

The present disclosure relates, according to some embodiments, to pathogen resistant plants, compositions, organisms, systems, and methods. For example, a composition may comprise a heterologous peptide (e.g., a defensin peptide) and/or a nucleic acid (e.g., a defensin nucleic acid). A pathogen resistant plant may comprise, in some embodiments, a heterologous defensin peptide and/or an expressible nucleic acid encoding a heterologous defensin peptide.

21 Claims, 30 Drawing Sheets

Specification includes a Sequence Listing.

CANKER INOCULATION TEST ON 'RIO RED' GRAPEFRUIT

NON-TRANSGENIC

CANKER INOCULATION TEST ON 'RIO RED' GRAPEFRUIT

TRANSGENIC FOR SPINACH DEFENSIN 2

GREENING INOCULATION TEST
ON 'RIO RED' GRAPEFRUIT

NON-TRANSGENIC BUDS GRAFTED
ON INFECTED ROOTSTOCK

SoD2 TRANSGENIC BUDS GRAFTED
ON INFECTED ROOTSTOCK

*Defensin1* & *Defensin2*

| | Def1 | Def2 | Def3 | Def4 | Def5 | Def6 | Def7 | SoD2 | SoD7 |
|---|---|---|---|---|---|---|---|---|---|
| Def1 | | Def1+ Def2 | Def1+ Def3 | Def1+ Def4 | Def1+ Def5 | Def1+ Def6 | Def1+ Def7 | Def1+ SoD2 | Def1+ SoD7 |
| Def2 | | | Def2+ Def3 | Def2+ Def4 | Def2+ Def5 | Def2+ Def6 | Def2+ Def7 | Def2+ SoD2 | Def2+ SoD7 |
| Def3 | | | | Def3+ Def4 | Def3+ Def5 | Def3+ Def6 | Def3+ Def7 | Def3+ SoD2 | Def3+ SoD7 |
| Def4 | | | | | Def4+ Def5 | Def4+ Def6 | Def4+ Def7 | Def4+ SoD2 | Def4+ SoD7 |
| Def5 | | | | | | Def5+ Def6 | Def5+ Def7 | Def5+ SoD2 | Def5+ SoD7 |
| Def6 | | | | | | | Def6+ Def7 | Def6+ SoD2 | Def6+ SoD7 |
| Def7 | | | | | | | | Def7+ SoD2 | Def7+ SoD7 |
| SoD2 | | | | | | | | | SoD2+ SoD7 |
| SoD7 | | | | | | | | | |

FIG. 28

PATHOGEN RESISTANT COMPOSITIONS, ORGANISMS, SYSTEMS, AND METHODS

CROSS-REFERENCE TO RELATED APPLICATIONS

This application is a continuation of U.S. application Ser. No. 15/212,041, filed on Jul. 15, 2016, which claims priority to U.S. Application No. 62/192,732 filed Jul. 15, 2015, the entire contents of which are hereby incorporated in this disclosure by reference.

FIELD OF THE DISCLOSURE

The present disclosure relates, in some embodiments, to pathogen resistant compositions, organisms, systems, and methods.

BACKGROUND OF THE DISCLOSURE

At present, there are no Citrus cultivars resistant to bacterial canker (*Xanthomonas axonopodis* pv. *citri*) (Xac), and/or citrus Huanglongbing (ex greening) caused by *Candidatus Liberibacter asiaticus* (Las). Indeed, no genetic resistance to these microbial pathogens has ever been found within the Citrus genus. Conventional cross-breeding efforts to produce resistant cultivars have been hindered by the complex reproductive biology and long life cycle of *Citrus* spp.

REFERENCE TO SEQUENCE LISTING SUBMITTED VIA EFS-WEB

This application includes an electronically submitted substitute sequence listing in .txt format. The .txt file contains a sequence listing entitled "026837-103013_SL.txt" created on Jun. 29, 2020 and is 165,397 bytes in size. The sequence listing contained in this .txt file is part of the specification and is hereby incorporated by reference herein in its entirety.

SUMMARY

Accordingly, a need has arisen for plants (e.g., citrus) with improved resistance to disease. A further need has arisen for improved methods, compositions, and systems for preparing genetically modified plants (e.g., citrus).

The present disclosure relates, according to some embodiments, to pathogen resistant citrus compositions, organisms, systems, and methods. For example, a composition may comprise a nucleic acid (e.g., a defensin nucleic acid). In some embodiments, a nucleic acid may comprise a nucleic acid sequence (a) having from about 75% to about 100% identity (e.g., about 98% identity) to a defensin sequence (e.g., SEQ ID NOS: 3, 4, 5, 6, 9, 10, 11, 12, 29, 46, 47, 48, 49, 50, 51, 52, 53, 54, 55, 56, 57, and/or 58) and/or (b) encoding an amino acid sequence having from about 95% to about 100% identity (e.g., 98% identity) to SEQ ID NOS: 1, 2, 7, 8, 28, 32, 33, 34, 35, 36, 37, and/or 38. A nucleic acid may comprise, in some embodiments, a nucleic acid sequence having about 98% identity to a sequence selected from the group consisting of SEQ ID NO: 3 and SEQ ID NO: 5 and encoding a peptide having an amino acid sequence having at least about 99% identity to SEQ ID NO: 1. A nucleic acid may comprise, in some embodiments, a nucleic acid sequence having about 98% identity to a sequence selected from the group consisting of SEQ ID NO: 4 and SEQ ID NO: 6 and encoding a peptide having an amino acid sequence having at least about 99% identity to SEQ ID NO: 2. According to some embodiments, a nucleic acid may comprise a nucleic acid sequence having about 98% identity to a sequence selected from the group consisting of SEQ ID NO: 9 and SEQ ID NO: 11 and encoding a peptide having an amino acid sequence having at least about 99% identity to SEQ ID NO: 7. A nucleic acid may comprise a nucleic acid sequence having about 98% identity to a sequence selected from the group consisting of SEQ ID NO: 10 and SEQ ID NO: 12 and encoding a peptide having an amino acid sequence having at least about 99% identity to SEQ ID NO: 8, in some embodiments. A nucleic acid may comprise, in some embodiments, a nucleic acid sequence having about 98% identity to a sequence selected from the group consisting of SEQ ID NO: 46 and SEQ ID NO: 52 and encoding a peptide having an amino acid sequence having at least about 99% identity to SEQ ID NO: 32. According to some embodiments, a nucleic acid may comprise a nucleic acid sequence having about 98% identity to a sequence selected from the group consisting of SEQ ID NO: 47 and SEQ ID NO: 53 and encoding a peptide having an amino acid sequence having at least about 99% identity to SEQ ID NO: 33. A nucleic acid may comprise, in some embodiments, a nucleic acid sequence having about 98% identity to a sequence selected from the group consisting of SEQ ID NO: 48 and SEQ ID NO: 54 and encoding a peptide having an amino acid sequence having at least about 99% identity to SEQ ID NO: 34. According to some embodiments, a nucleic acid may comprise a nucleic acid sequence having about 98% identity to a sequence selected from the group consisting of SEQ ID NO: 55 and encoding a peptide having an amino acid sequence having at least about 99% identity to SEQ ID NO: 35. A nucleic acid may comprise, in some embodiments, a nucleic acid sequence having about 98% identity to a sequence selected from the group consisting of SEQ ID NO: 49 and SEQ ID NO: 56 and encoding a peptide having an amino acid sequence having at least about 99% identity to SEQ ID NO: 36. According to some embodiments, a nucleic acid may comprise a nucleic acid sequence having about 98% identity to a sequence selected from the group consisting of SEQ ID NO: 50 and SEQ ID NO: 57 and encoding a peptide having an amino acid sequence having at least about 99% identity to SEQ ID NO: 37. A nucleic acid may comprise, in some embodiments, a nucleic acid sequence having about 98% identity to a sequence selected from the group consisting of SEQ ID NO: 51 and SEQ ID NO: 58 and encoding a peptide having an amino acid sequence having at least about 99% identity to SEQ ID NO: 38.

The present disclosure is related to nucleotide and amino acid sequences that are either (i) not found anywhere in nature or (ii) not found in nature in the organism into which they have been introduced. According to some embodiments, any nucleic acid sequence having less than 100% identity to a reference sequence shall differ from any naturally-occurring nucleic acid sequence of the same size by at least one nucleotide (e.g., by substitution, deletion, or insertion). Any amino acid sequence having less than 100% identity to a reference sequence shall differ from any naturally-occurring nucleic acid sequence of the same size by at least one amino acid (e.g., by substitution, deletion, or insertion).

The present disclosure relates, in some embodiments, to defensin expression vectors operable in citrus (e.g., citrus varieties, citrus rootstocks). For example, an expression vector may comprise, in a 5' to 3' direction, (a) an expression control sequence; (b) an expressible nucleic acid (e.g., a nucleic acid encoding an exogenous polypeptide) operably linked to the expression control sequence; and (c) a 3' termination sequence operably linked to the expressible nucleic acid. In some embodiments, an exogenous nucleic acid may comprise a nucleic acid sequence having at least about 75% identity (e.g., at least about 98% identity) to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 29, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58. An expression vector may be located in a bacterial cell or a plant cell according to some embodiments. An expression vector may comprise, in some embodiments, the nucleotide sequence AACAATGG at positions −4 to 4 relative to a coding sequence (e.g., encoded by an exogenous nucleic acid sequence). According to some embodiments, an expression vector may comprise a linker (e.g., 3' of the expression control sequence and/or 5' of the nucleic acid (e.g., a nucleic acid encoding an exogenous polypeptide) having a length of from about 1 to about 200 nucleotides.

The present disclosure relates, in some embodiments, to a bacterial cell comprising an expression vector. For example, a bacterial cell may comprise an expression vector comprising, in a 5' to 3' direction, (a) an expression control sequence; (b) an expressible nucleic acid (e.g., a nucleic acid encoding an exogenous polypeptide) operably linked to the expression control sequence; and (c) a 3' termination sequence operably linked to the expressible nucleic acid. A bacterial cell may comprise, for example, an expression vector comprising, in a 5' to 3' direction, (a) an expression control sequence; (b) an exogenous nucleic acid operably linked to the expression control sequence; and/or (c) a 3' termination sequence operably linked to the exogenous nucleic acid, wherein the exogenous nucleic acid comprises a nucleic acid sequence having at least about 98% identity to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58.

The present disclosure relates, in some embodiments, to a plant cell (e.g., a citrus plant cell) comprising an expression vector. For example, a plant cell (e.g., a citrus plant cell) may comprise an expression vector comprising, in a 5' to 3' direction, (a) an expression control sequence; (b) an expressible nucleic acid (e.g., a nucleic acid encoding an exogenous polypeptide) operably linked to the expression control sequence; and (c) a 3' termination sequence operably linked to the expressible nucleic acid. A plant cell (e.g., a citrus plant cell) may comprise, for example, an expression vector comprising, in a 5' to 3' direction, (a) an expression control sequence; (b) an exogenous nucleic acid operably linked to the expression control sequence; and/or (c) a 3' termination sequence operably linked to the exogenous nucleic acid, wherein the exogenous nucleic acid comprises a nucleic acid sequence having at least about 98% identity to a nucleic acid sequence selected from the group consisting of SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 29, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58. A plant cell (e.g., a citrus plant cell) may be located in a plant (e.g., a citrus plant) according to some embodiments. Examples of citrus plants include, without limitation, orange, grapefruit, lemon, and lime. A plant cell may comprise a defensin peptide. A defensin peptide may have, in some embodiments, an amino acid sequence having at least about 99% identity to SEQ ID NO: 1, SEQ ID NO: 2, SEQ ID NO: 7, SEQ ID NO: 8, SEQ ID NO: 28, SEQ ID NO: 32, SEQ ID NO: 33, SEQ ID NO: 34, SEQ ID NO: 35, SEQ ID NO: 36, SEQ ID NO: 37, or SEQ ID NO: 38 (e.g., encoded by and/or expressed from an expression vector nucleic acid) according to some embodiments.

In some embodiments, the present disclosure relates to a citrus plant (e.g., orange and/or grapefruit and/or lemon and/or lime) comprising an expression vector. A citrus plant may comprise an expression vector in a single cell, a plurality of cells (e.g., mosaic), or in all cells. A mosaic plant may arise from a graft in some embodiments. For example, a citrus plant may comprise a graft of a transgenic plant having an expression vector in all cells (e.g., scion) and a plant having a different expression vector or no expression vector in its cells (e.g., rootstock). A citrus plant may comprise, in some embodiments, in a single cell, a plurality of cells (e.g., mosaic), or in all cells a first expression vector (e.g., encoding a first defensin peptide) and in a single cell, a plurality of cells (e.g., mosaic), or in all cells a second expression vector (e.g., encoding a second defensin peptide). For example, a citrus plant cell may comprise (a) a first expression vector, the first expression vector comprising, in a 5' to 3' direction, (i) a first expression control sequence; (ii) a first exogenous nucleic acid operably linked to the first expression control sequence; and (iii) a first 3' termination sequence operably linked to the first exogenous nucleic acid, wherein the first exogenous nucleic acid comprises a nucleic acid sequence having at least about 98% identity to a nucleic acid sequence selected from the group consisting of SEQ ID NO: 3, SEQ ID NO: 5, SEQ ID NO: 9, SEQ ID NO: 11, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58; and (b) a second expression vector, the second expression vector comprising, in a 5' to 3' direction, (iv) a second expression control sequence; (v) a second exogenous nucleic acid operably linked to the second expression control sequence; and (vi) a second 3' termination sequence operably linked to the second exogenous nucleic acid, wherein the second exogenous nucleic acid comprises a nucleic acid sequence having at least about 98% identity to a nucleic acid sequence selected from the group consisting of SEQ ID NO: 4, SEQ ID NO: 6, SEQ ID NO: 10, and SEQ ID NO: 12, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58. According to some embodiments, a citrus plant may comprise in a single cell, a plurality of cells (e.g., mosaic), or in all cells an expression vector comprising a first nucleic acid sequence encoding a first defensin peptide (e.g., a peptide having at least 99% identity to SEQ ID NO: 32, 33, 34, 35, 36, 37, or 38) and a second nucleic acid sequence encoding a second defensin peptide (e.g., a peptide having at least 99% identity to SEQ ID NO: 32, 33, 34, 35, 36, 37, or 38). In some embodiments, a citrus plant may comprise a defensin peptide in a single cell, a plurality of cells (e.g., mosaic), or in all cells. A citrus plant may comprise in a single cell, a plurality of cells (e.g., mosaic), or in all cells a first defensin peptide (e.g., a peptide having at least 99% identity to SEQ ID NO: 32, 33, 34, 35, 36, 37, or 38) and in a single cell, a plurality of cells (e.g., mosaic), or in all cells a second defensin peptide (e.g., a peptide having at least 99% identity to SEQ ID NO: 32, 33, 34, 35, 36, 37, or 38).

The present disclosure relates, in some embodiments, to methods of expressing in a citrus plant an exogenous nucleic acid comprising a nucleic acid sequence encoding an expressed peptide (e.g., a defensin peptide). For example, a method may comprise contacting an expression cassette comprising an exogenous nucleic acid or an expression vector comprising an exogenous nucleic acid with the cytosol of a cell of a citrus plant under conditions that permit expression of the exogenous nucleic acid and formation of the expressed peptide. In some embodiments, an exogenous nucleic acid may comprise a nucleic acid sequence having at least 98% identity to a nucleic acid sequence selected from SEQ ID NO: 3, SEQ ID NO: 4, SEQ ID NO: 5, SEQ ID NO: 6, SEQ ID NO: 9, SEQ ID NO: 10, SEQ ID NO: 11, SEQ ID NO: 12, SEQ ID NO: 29, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID. NO: 54, SEQ ID NO: 55, SEQ ID NO: 56, SEQ ID NO: 57, and SEQ ID NO: 58. In some embodiments, an expression vector and/or an expression cassette may comprise, in a 5' to 3' direction, an expression control sequence, the exogenous nucleic acid operably linked to the expression control sequence, and a 3' termination sequence operably linked to the exogenous nucleic acid. An expressed peptide may comprise an amino acid sequence having at least 99% identity to an amino acid sequence selected from SEQ ID NO: 1, SEQ ID NO: 2, SEQ ID NO: 7, SEQ ID NO: 8, SEQ ID NO: 28, SEQ ID NO: 32, SEQ ID NO: 33, SEQ ID NO: 34, SEQ ID NO: 35, SEQ ID NO: 36, SEQ ID NO: 37, and/or SEQ ID NO: 38 according to some embodiments. Contacting an expression vector or cassette may further comprise, in some embodiments, co-cultivating the cell with an *Agrobacterium* cell comprising the expression vector or expression cassette to form a co-cultivated plant cell. According to some embodiments, a plant may be regenerated from a co-cultivated plant cell.

The present disclosure relates, in some embodiments, to methods for treating a citrus plant having and/or at risk of having a microbial infection (e.g., bacterial canker (*Xanthomonas axonopodis* pv. *citri*) (Xac), and/or citrus Huanglongbing (ex greening) caused by *Candidatus Liberibacter asiaticus* (Las)). For example, a method may comprise forming in the citrus plant at least one defensin peptide. Forming in the citrus plant at least one defensin peptide may comprise, in some embodiments, grafting the citrus plant with a cutting (e.g., a scion or a rootstock) from a second citrus plant, the second citrus plant comprising an expression vector and/or an expression cassette comprising, in a 5' to 3' direction, an expression control sequence, a defensin nucleic acid operably linked to the expression control sequence, and a 3' termination sequence operably linked to the defensin nucleic acid, wherein the defensin nucleic acid comprises a nucleic acid sequence encoding an amino acid sequence having at least 99% identity to an amino acid sequence selected from SEQ ID NO: 1, SEQ ID NO: 2, SEQ ID NO: 7, SEQ ID NO: 8, SEQ ID NO: 28, SEQ ID NO: 32, SEQ ID NO: 33, SEQ ID NO: 34, SEQ ID NO: 35, SEQ ID NO: 36, SEQ ID NO: 37, and/or SEQ ID NO: 38 under conditions that permit expression of the defensin nucleic acid.

The present disclosure relates, in some embodiments, to a citrus fruit (e.g., orange, grapefruit, lemon, lime) comprising at least one defensin peptide having the amino acid sequence of SEQ ID NO:87 or SEQ ID NO: 88.

BRIEF DESCRIPTION OF THE DRAWINGS

Some embodiments of the disclosure may be understood by referring, in part, to the present disclosure and the accompanying drawings, wherein.

Figure 11:
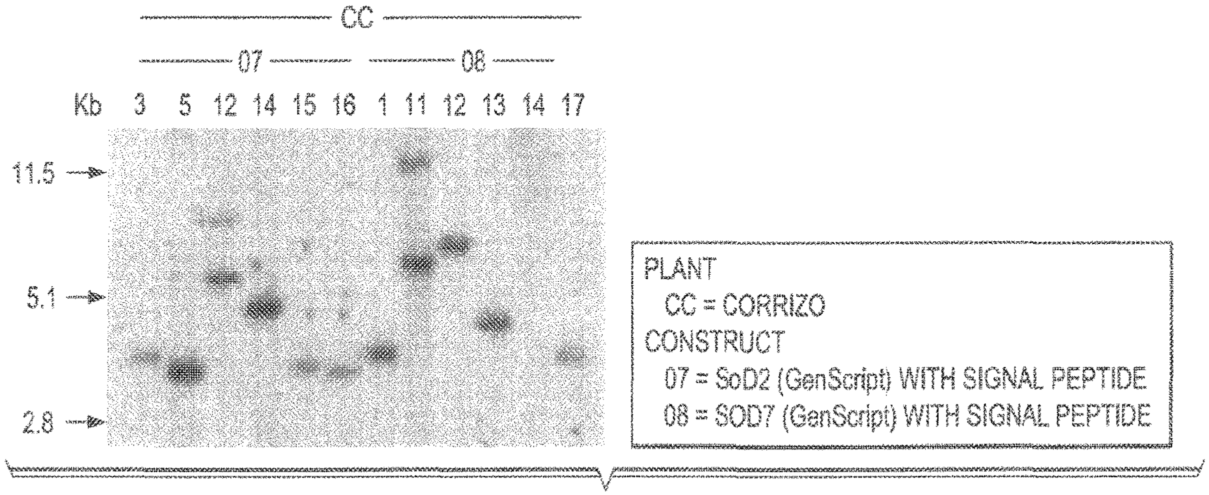
Figure 12:
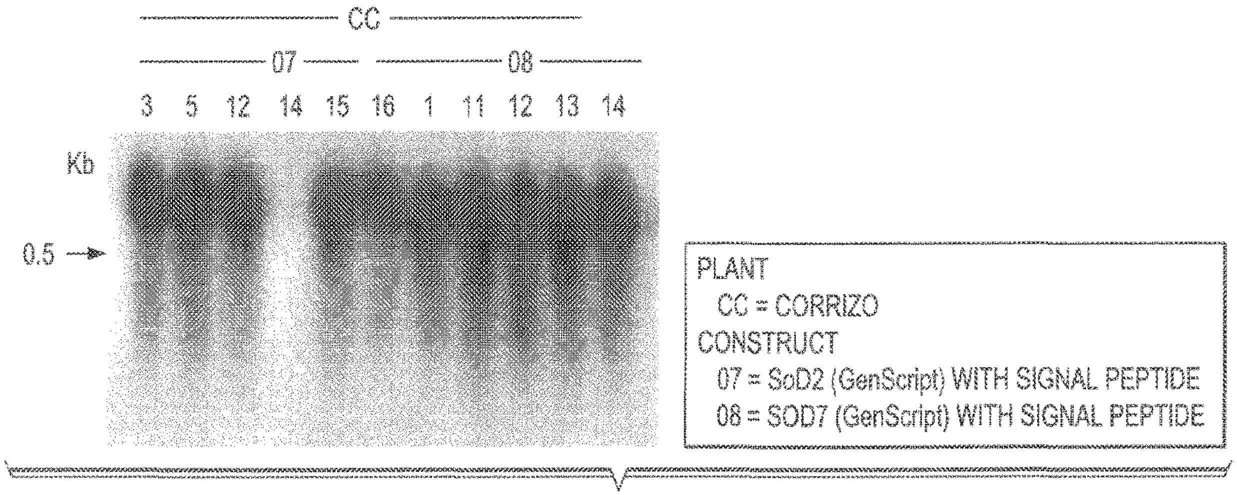
Figure 13A:
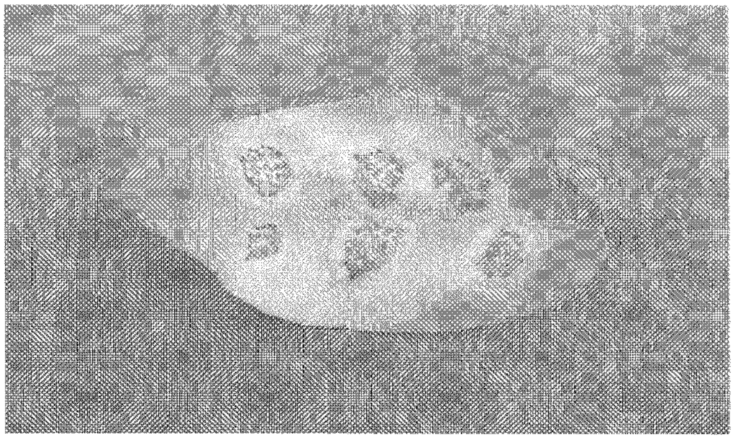
Figure 13B:
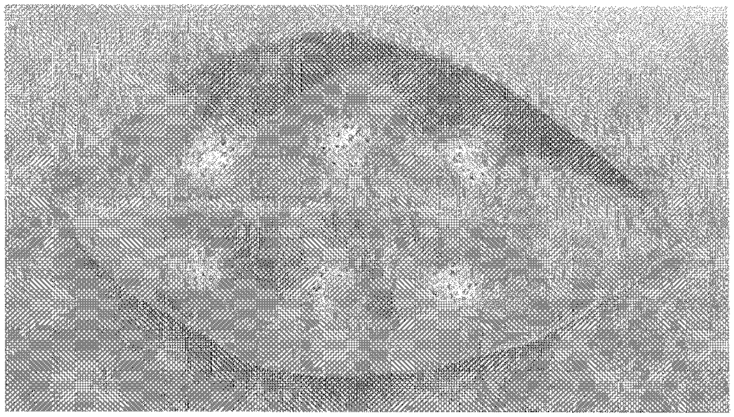
Figure 14:
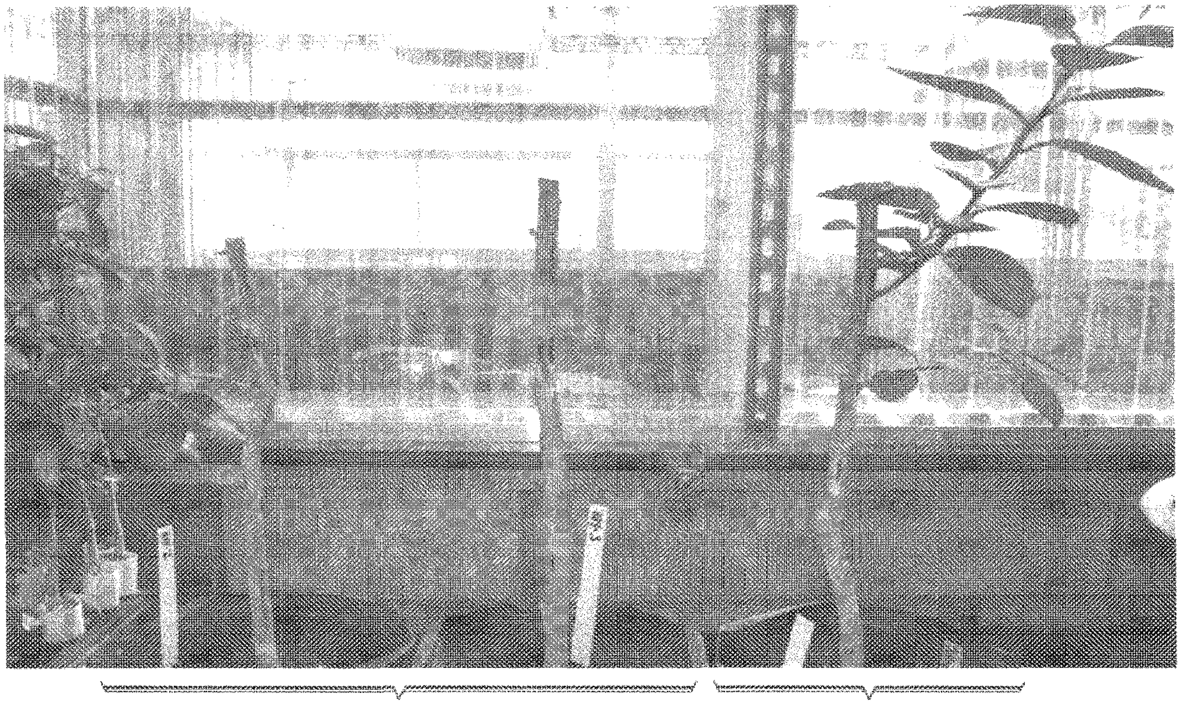
Figure 15A:
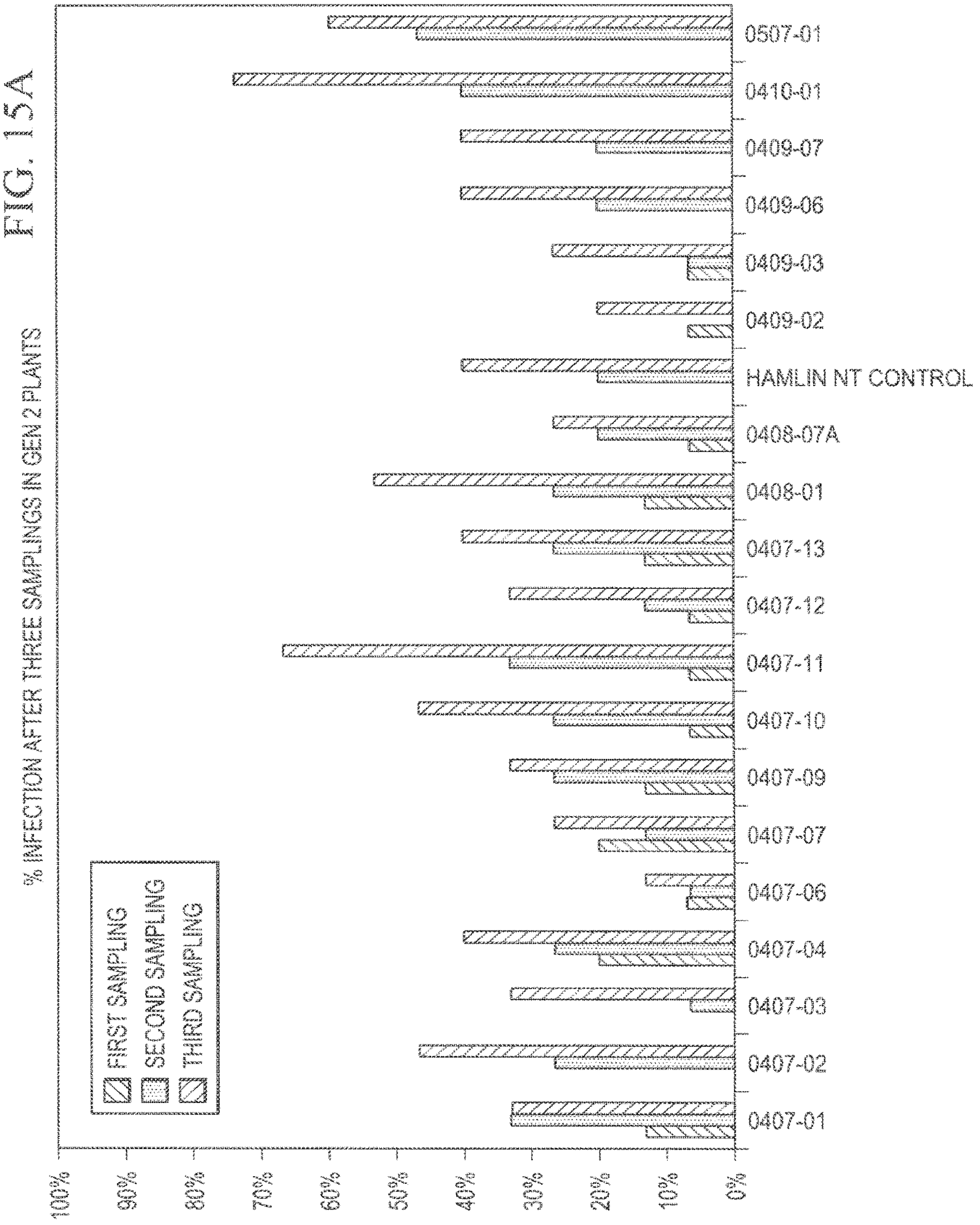
Figure 15B:
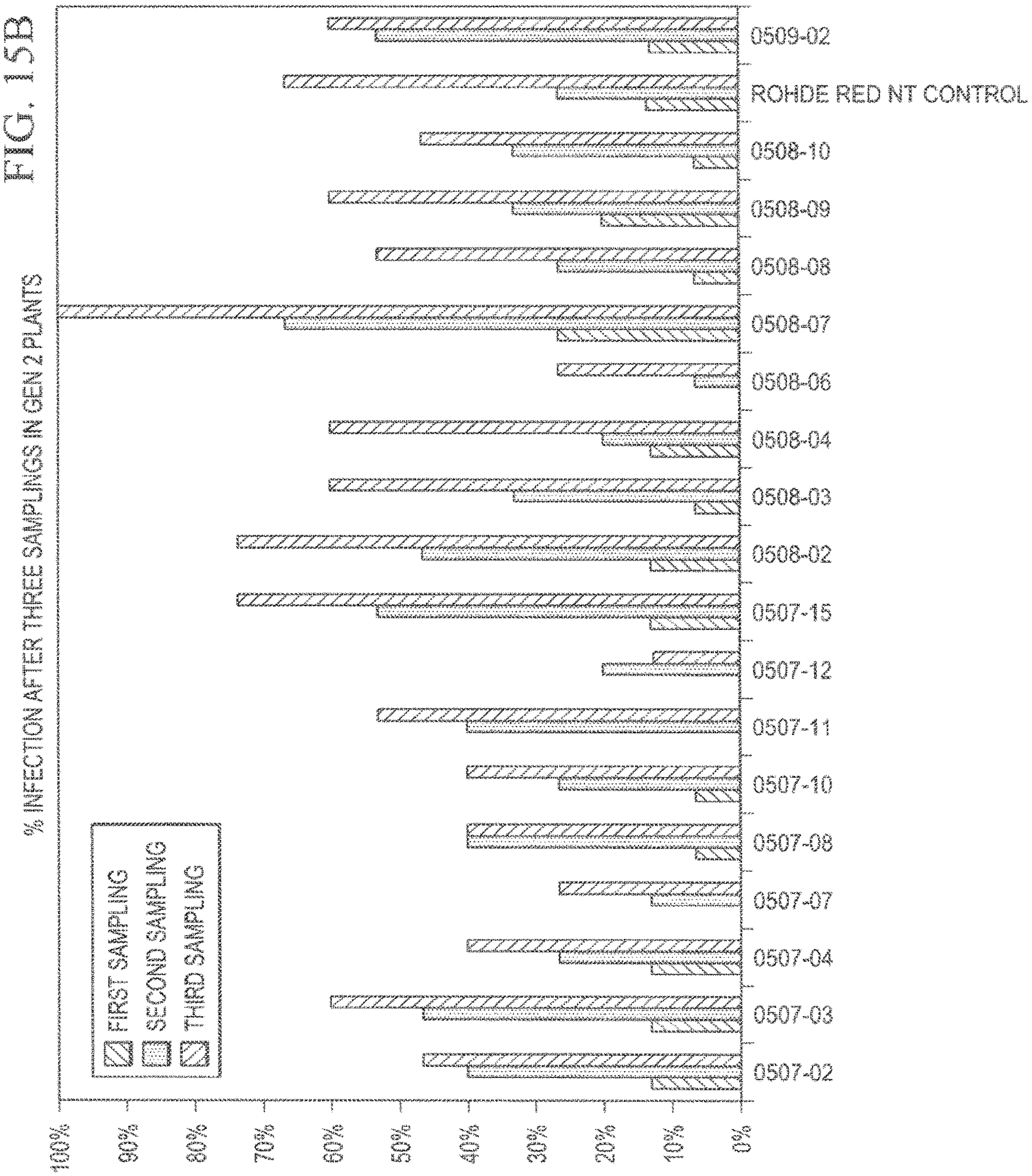
Figure 15C:
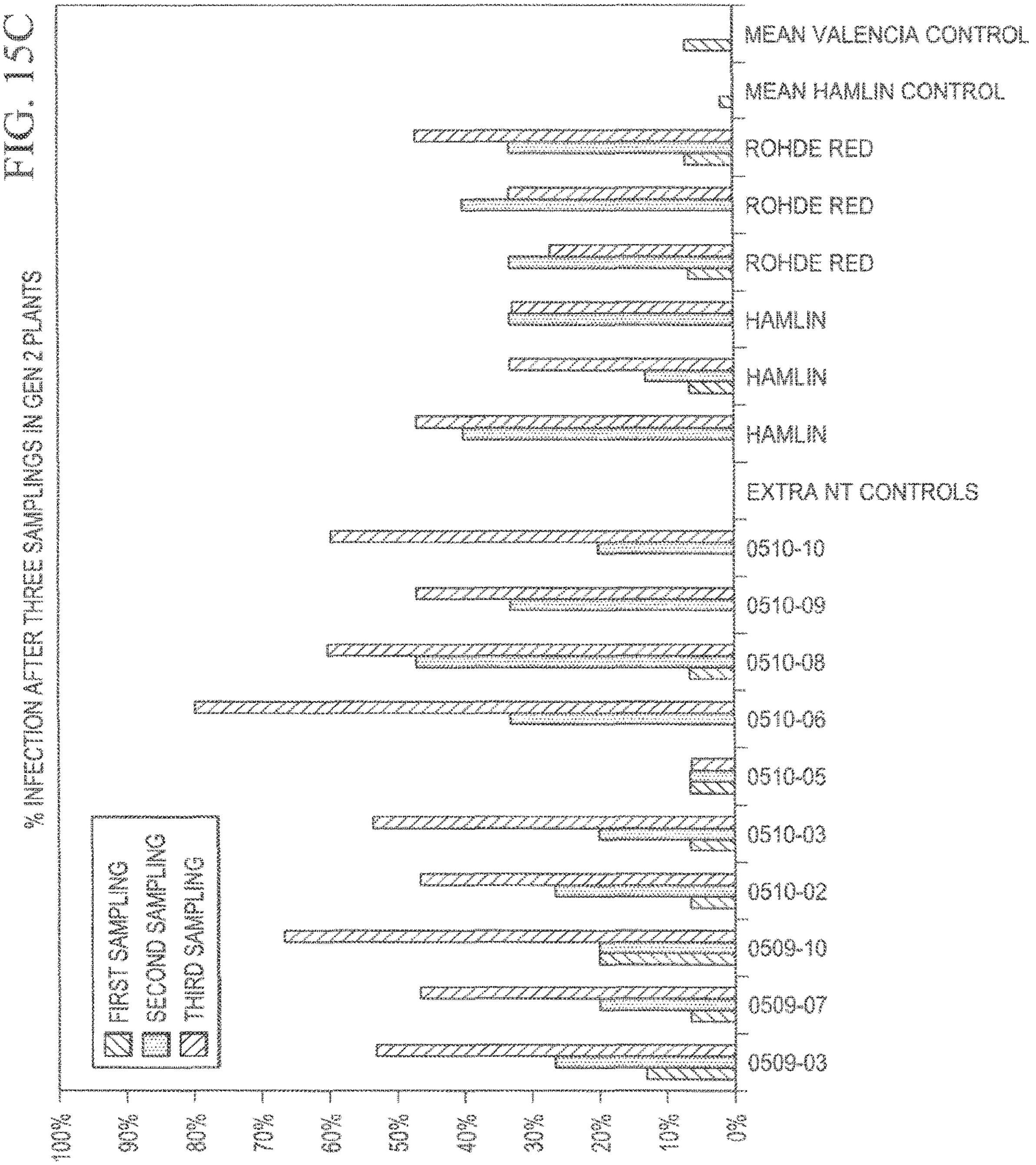
Figure 16A:
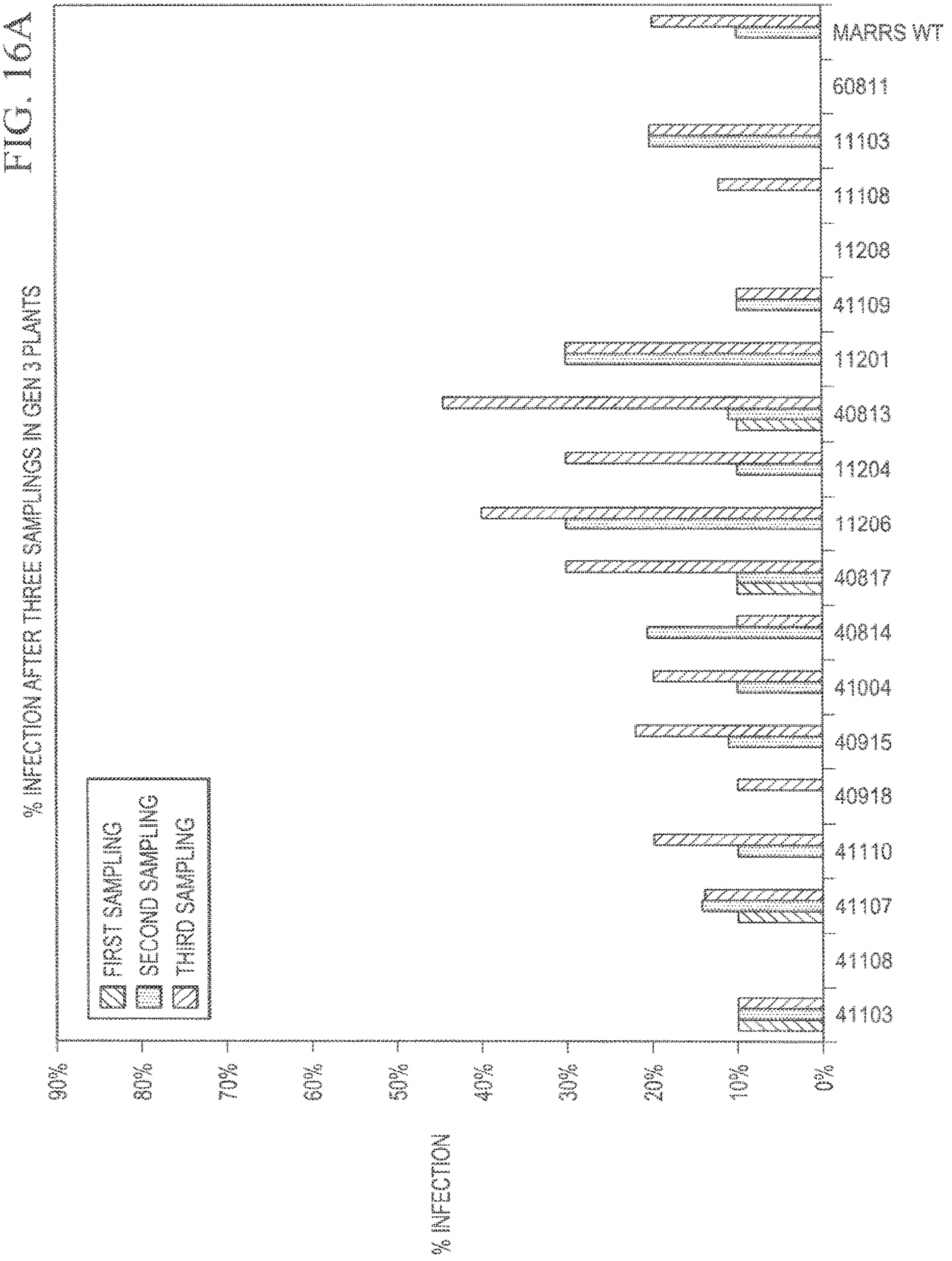
Figure 16B:
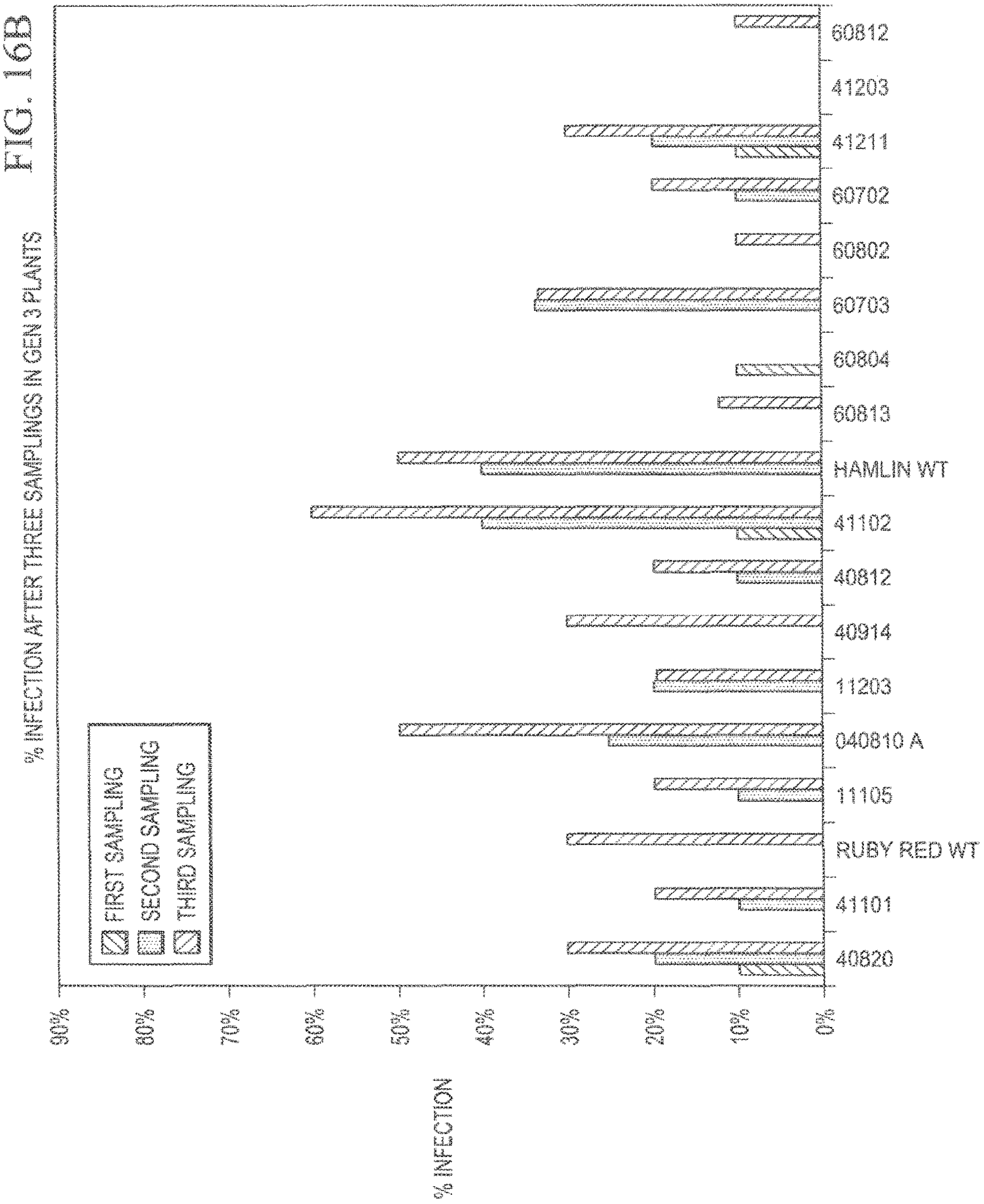
Figure 16C:
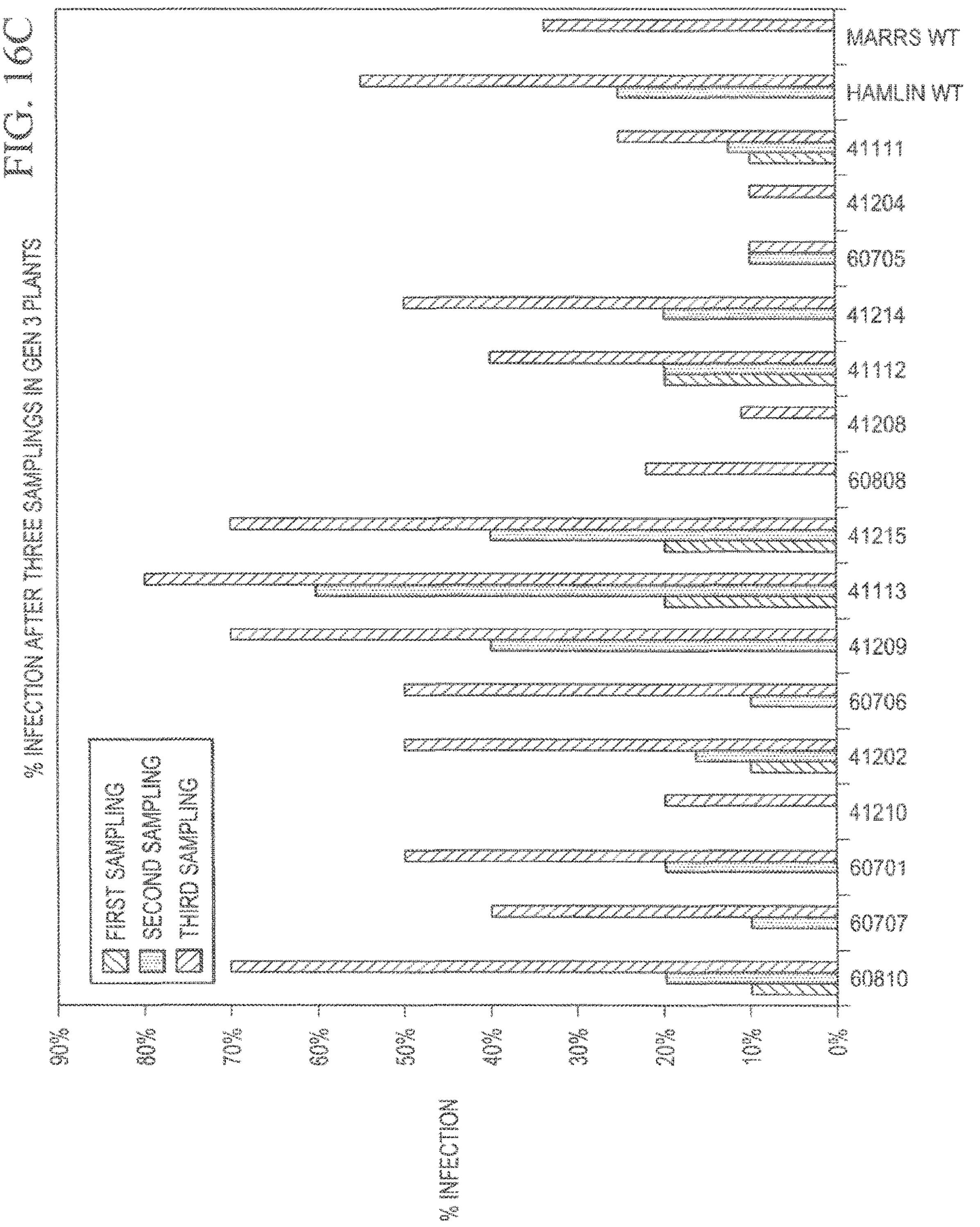
Figure 17:
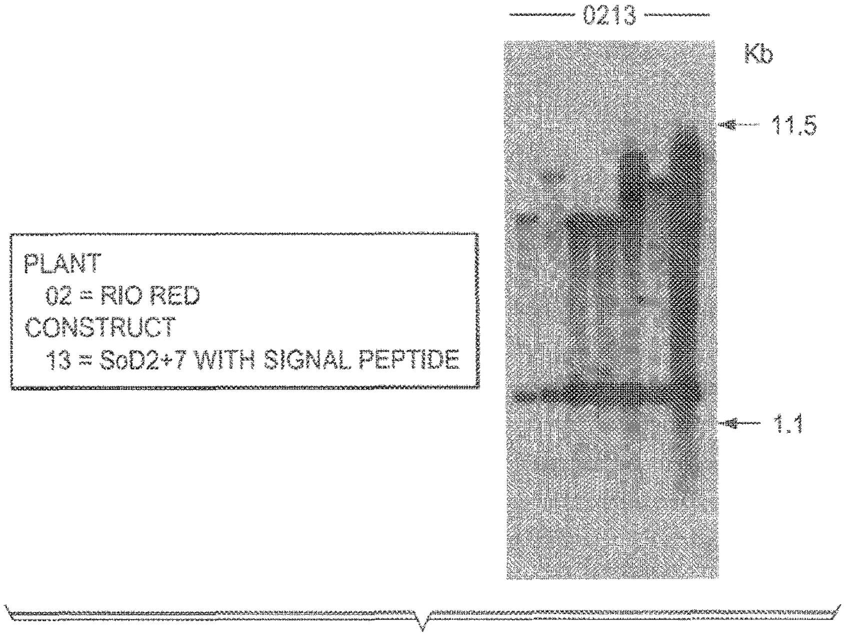
Figure 18:
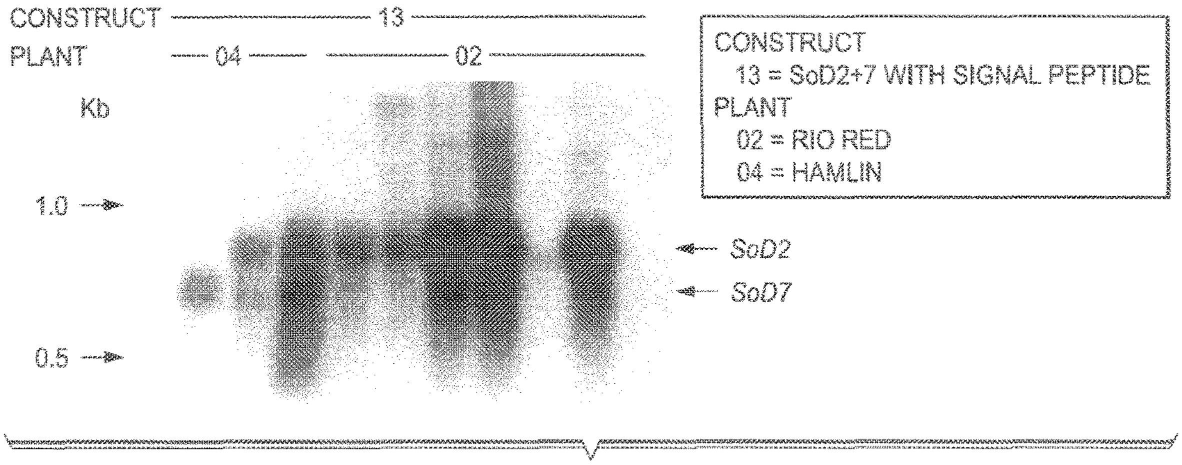
Figure 19:
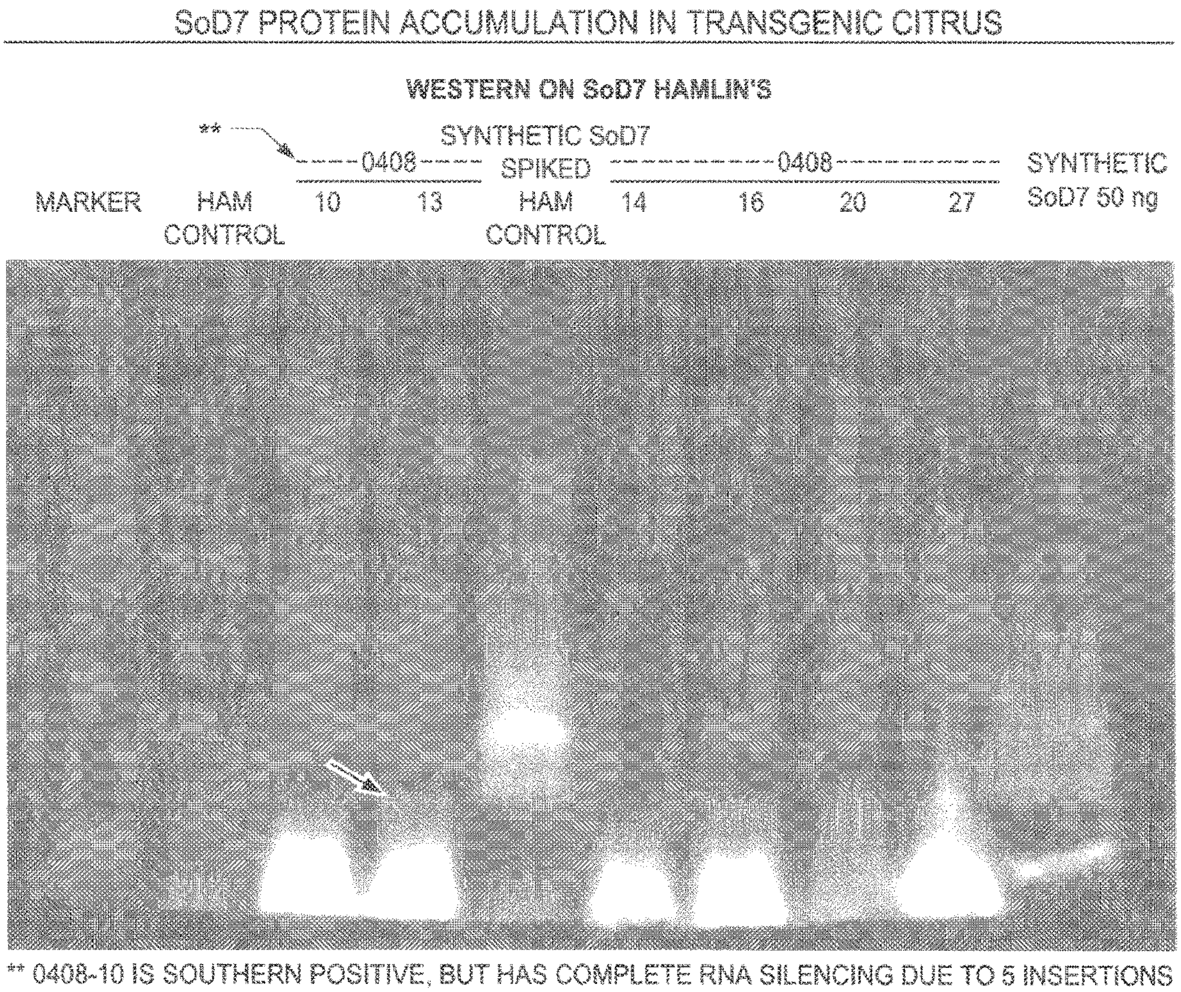

FIG. 11 is a representation of a Southern blot confirming insertion of defensins in Carrizo Citrange (CC) transformed with SoD2 (07) or SoD7 (08) nucleic acids, each comprising a GenScript-optimized sequence for expression in *Citrus*, according to a specific example embodiment of the disclosure;

FIG. 12 is a representation of a northern blot showing RNA transcripts among transgenic events in Carrizo Citrange (CC) transformed with SoD2 (07) or SoD7 (08) nucleic acids, each comprising a GenScript-optimized sequence for expression in *Citrus*, according to a specific example embodiment of the disclosure;

FIG. 13A is a photograph of an excised leaf from a non-transgenic grapefruit tree innoculated with a citrus canker pathogen according to specific example embodiments of the disclosure;

FIG. 13B is a photograph of an excised leaf from an SoD2 transgenic grapefruit tree innoculated with a citrus canker pathogen according to specific example embodiments of the disclosure;

FIG. 14 is a photograph of chimeric grapefruit trees resulting from the graft of uninfected, non-transgenic scions on citrus greening infected, non-transgenic rootstocks (left and center) or the graft of uninfected, SoD2 transgenic scions on citrus greening infected, non-transgenic rootstock (right), according to specific example embodiments of the disclosure;

FIG. 15A illustrates the percentage of Generation 2 citrus plants infected upon the first, second, and third sampling of challenged material, according to specific example embodiments of the disclosure;

FIG. 15B is a continuation of the bar graph of FIG. 15A illustrating the percentage of Generation 2 citrus plants infected upon the first, second, and third sampling of challenged material, according to specific example embodiments of the disclosure;

FIG. 15C is a continuation of the bar graph of FIG. 15A illustrating the percentage of Generation 2 citrus plants infected upon the first, second, and third sampling of challenged material, according to specific example embodiments of the disclosure;

FIG. 16A illustrates the percentage of Generations 2 and 3 citrus plants infected upon the first, second and third samplings of challenged material, according to specific example embodiments of the disclosure;

FIG. 16B is a continuation of the bar graph of FIG. 16A illustrating the percentage of Generations 2 and 3 citrus plants infected upon the first, second and third samplings of challenged material, according to specific example embodiments of the disclosure;

FIG. 16C is a continuation of the bar graph of FIG. 16A illustrating the percentage of Generations 2 and 3 citrus plants infected upon the first, second and third samplings of challenged material, according to specific example embodiments of the disclosure; and FIG. 17 is a representation of a Southern blot confirming insertion of defensins in Rio Red (02) transformed with both SoD2 and SoD7 (13) nucleic acids, each comprising a GenScript-optimized sequence for expression in *Citrus*, according to a specific example embodiment of the disclosure;

FIG. 18 is a representation of a northern blot showing RNA transcripts among transgenic events in Rio Red (02) or Hamlin (04), transformed with both SoD2 and SoD7 (13) nucleic acids, each comprising a GenScript-optimized sequence for expression in *Citrus*, according to a specific example embodiment of the disclosure; and FIG. 19 is a Western blot illustrating binding of an anti-SoD7 according to specific example embodiments of the disclosure to samples containing SoD7.

Figure 20:
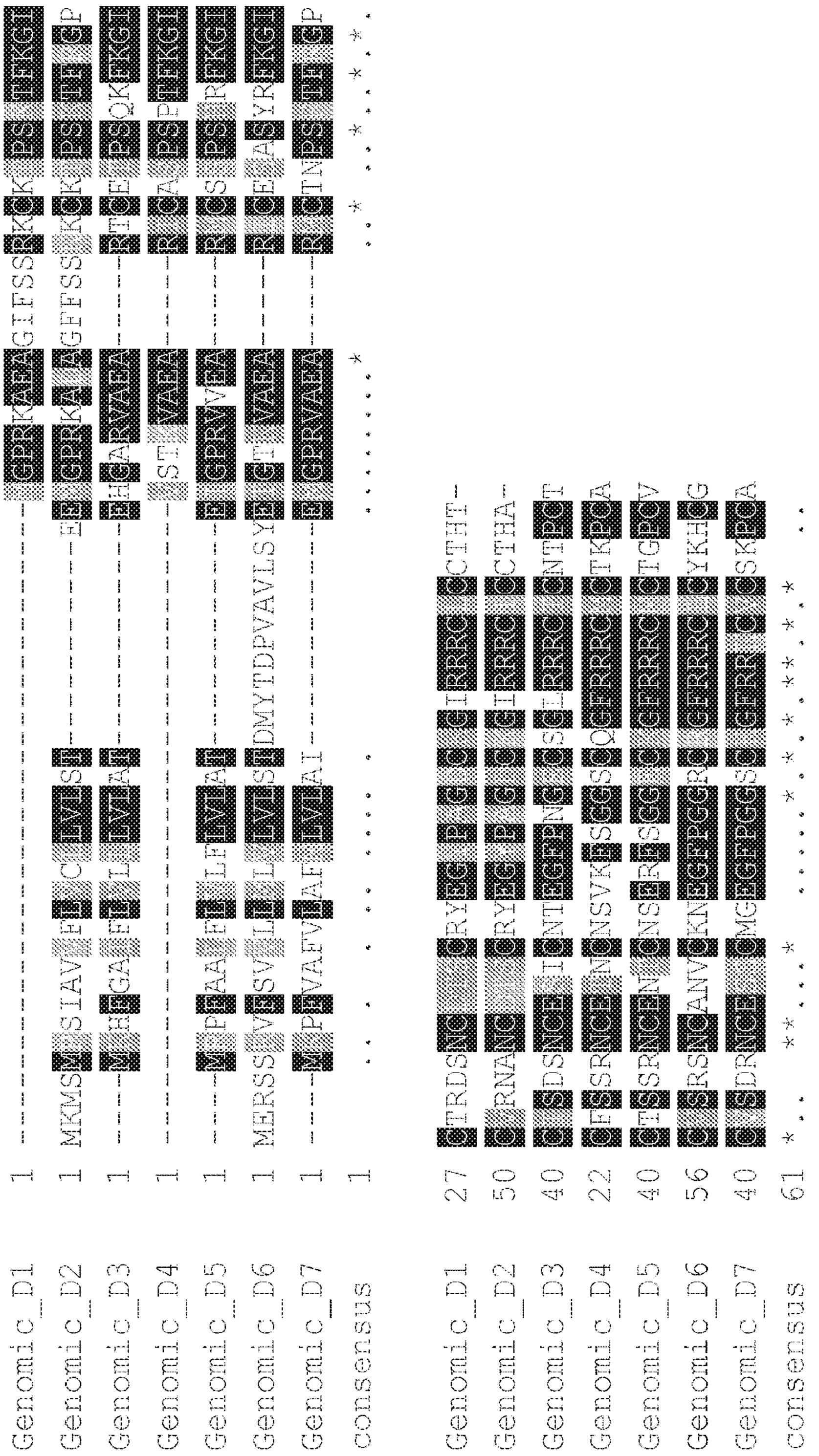

FIG. 20 illustrates a multiple sequence alignment of Genomic D1 (SEQ ID NO: 32), Genomic D2 (SEQ ID NO: 33), Genomic D3 (SEQ ID NO: 34), Genomic D4 (SEQ ID NO: 35), Genomic D5 (SEQ ID NO: 36, Genomic D6 (SEQ ID NO: 37), and Genomic D7 (SEQ ID NO: 38) according to a specific example embodiment of the disclosure.

Figure 21A:
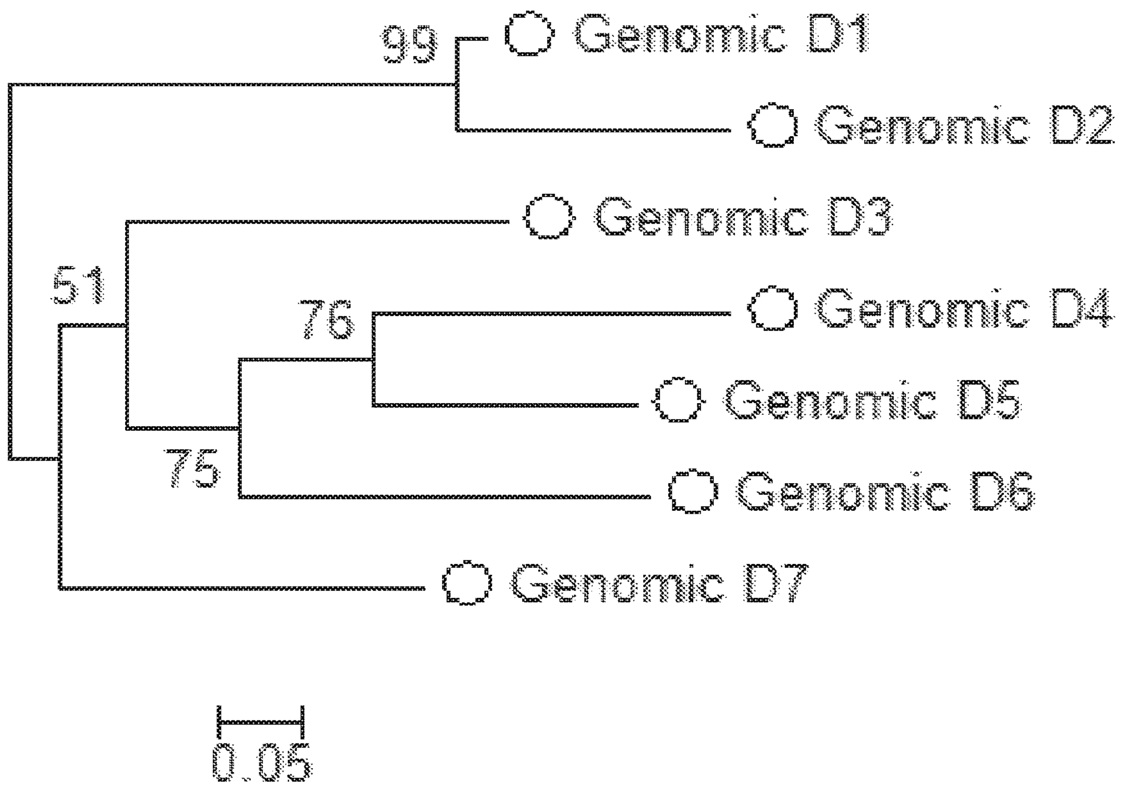

FIG. 21A is a representation of the results of phylogenetic analyses of SEQ ID NOS 32, 33, 34, 35, 36, 37, and 38 according to a specific example embodiment of the disclosure.

Figure 21B:
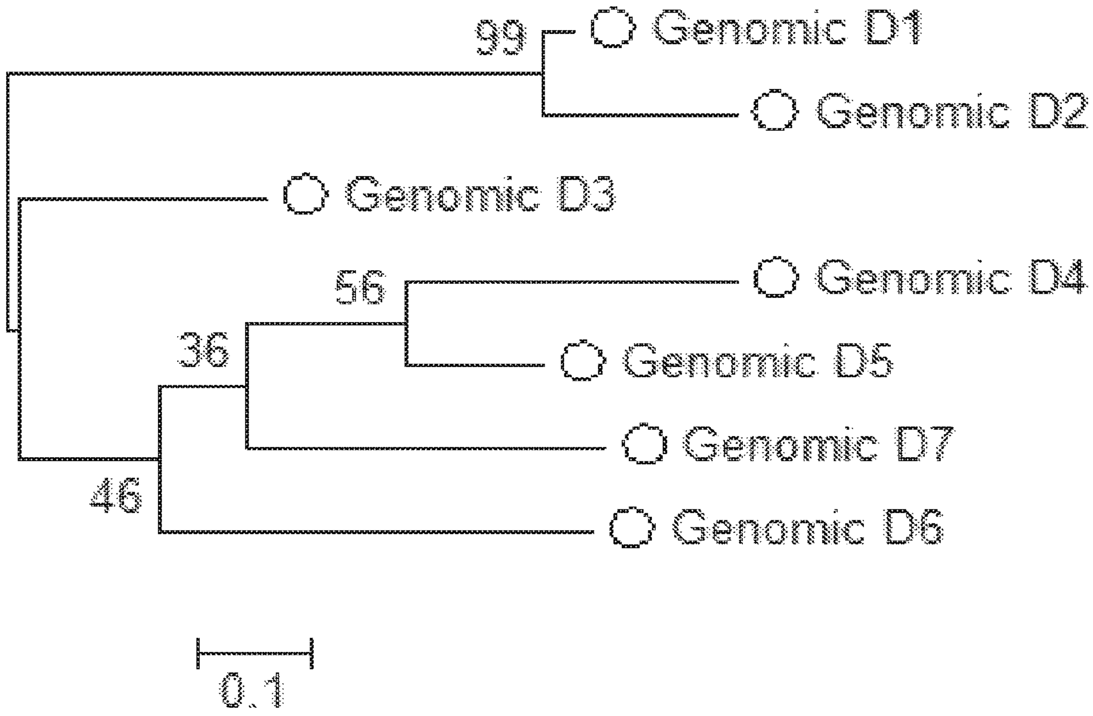

FIG. 21B is a representation of the results of phylogenetic analyses of SEQ ID NOS 32, 33, 34, 35, 36, 37, and 38 according to a specific example embodiment of the disclosure.

Figure 22:
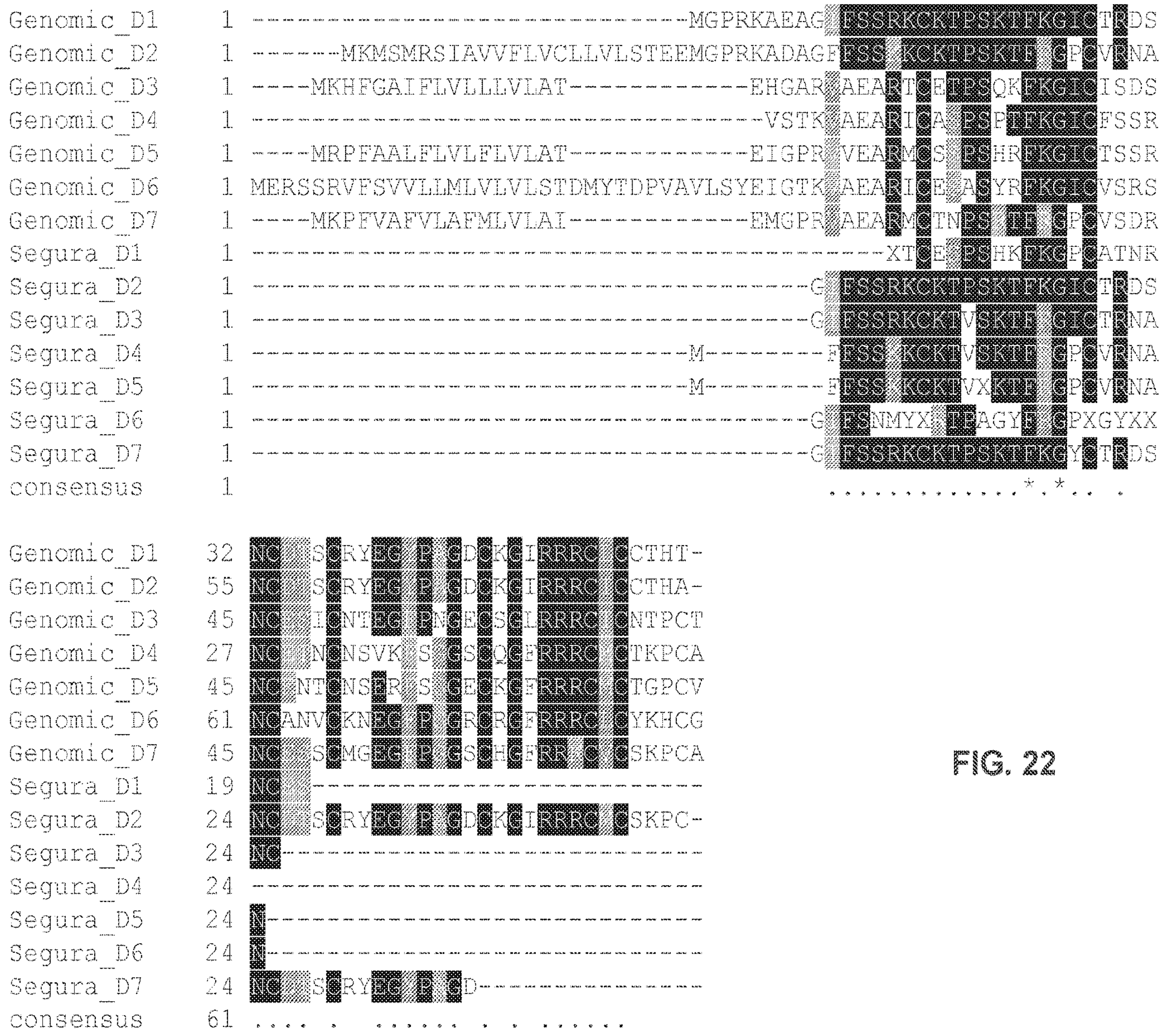

FIG. 22 illustrates the sequence alignments of Genomic D1 (SEQ ID NO: 32), Genomic D2 (SEQ ID NO: 33), Genomic D3 (SEQ ID NO: 34), Genomic D4 (SEQ ID NO: 35), Genomic D5 (SEQ ID NO: 36), Genomic D6 (SEQ ID NO: 37), and Genomic D7 (SEQ ID NO: 38), and Segura D1 (SEQ ID NO: 89), Segura D2 (SEQ ID NO: 90), Segura D3 (SEQ ID NO: 91), Segura D4 (SEQ ID NO: 92), Segura D5 (SEQ ID NO: 93), Segura D6 (SEQ ID NO: 94), and Segura D7 (SEQ ID NO: 95) according to a specific example embodiment of the disclosure.

Figure 23A:
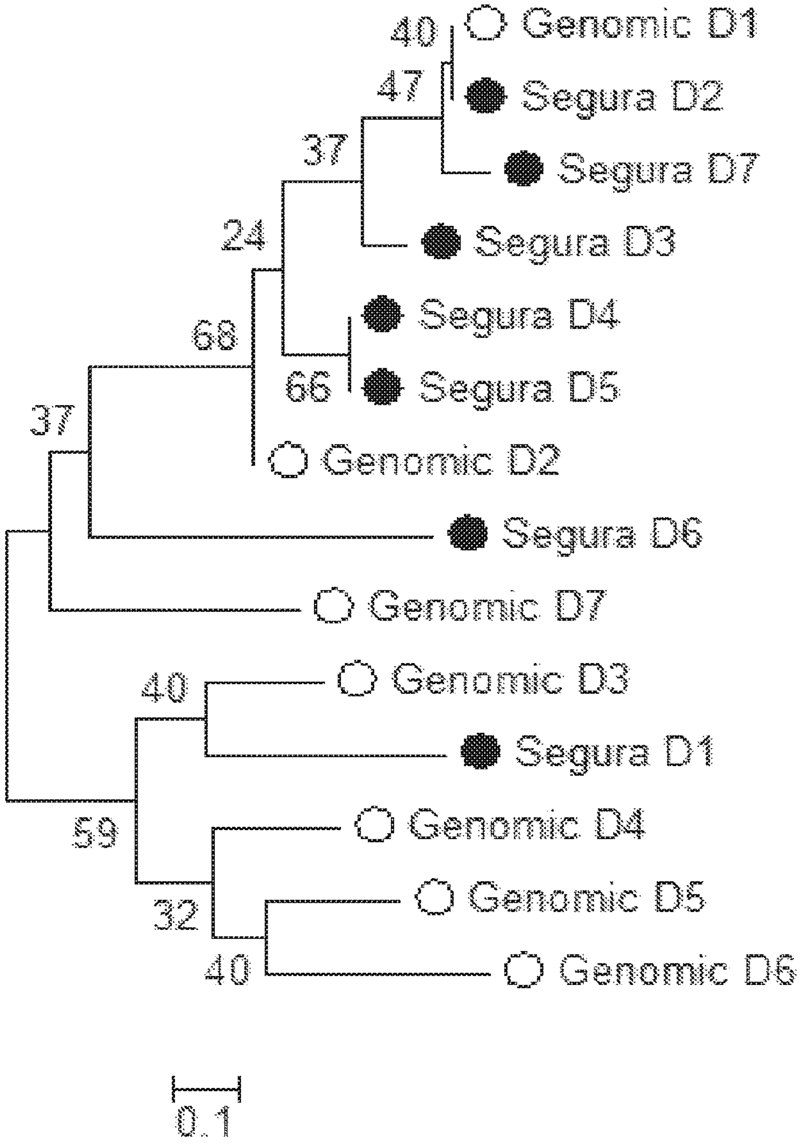

FIG. 23A is a representation of the results of phylogenetic analyses of SEQ ID NOS 32, 33, 34, 35, 36, 37, 38, and group IV defensin sequences according to a specific example embodiment of the disclosure.

Figure 23B:
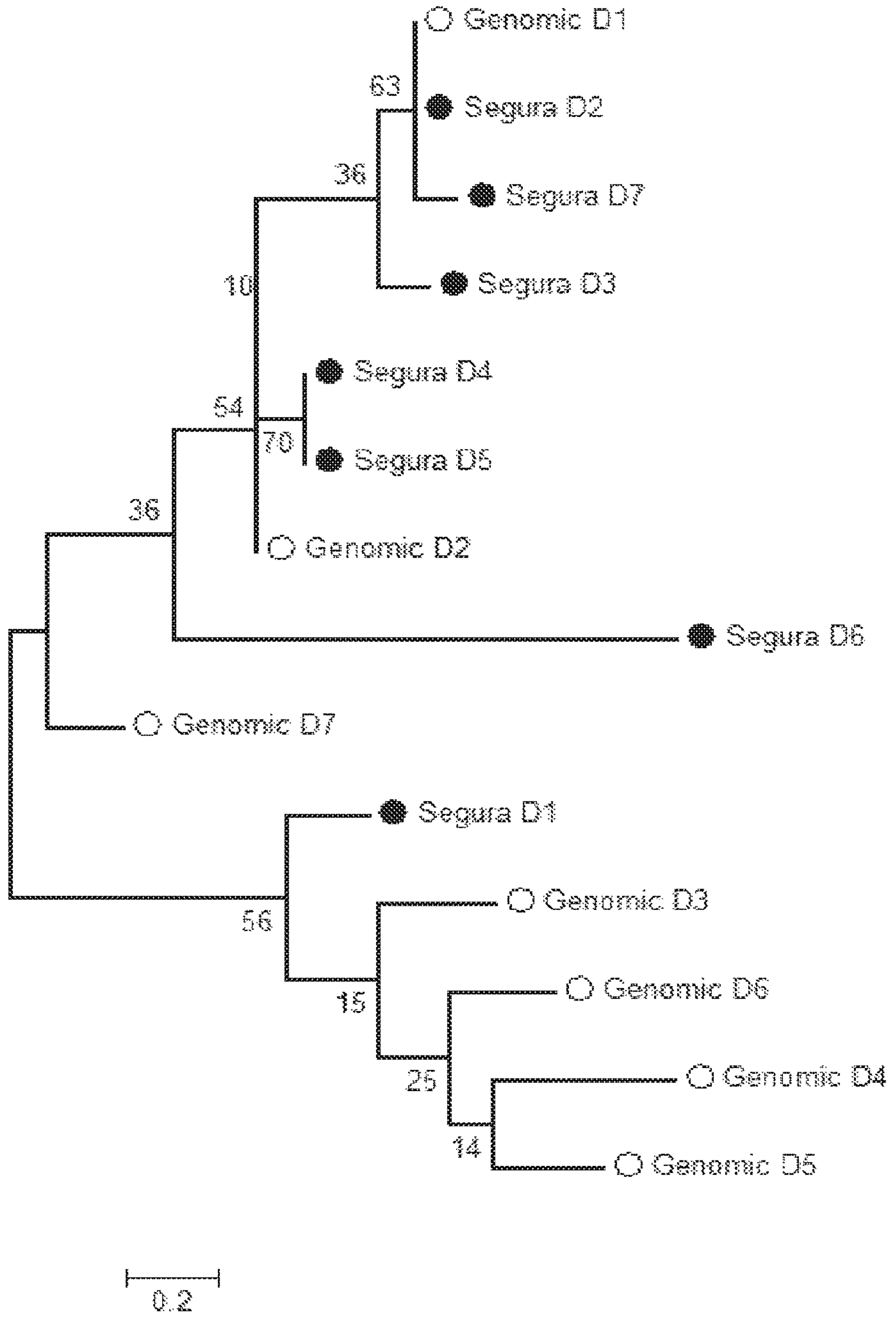

FIG. 23B is a representation of the results of phylogenetic analyses of SEQ ID NOS 32, 33, 34, 35, 36, 37, 38, and group IV defensin sequences according to a specific example embodiment of the disclosure.

Figure 24A:
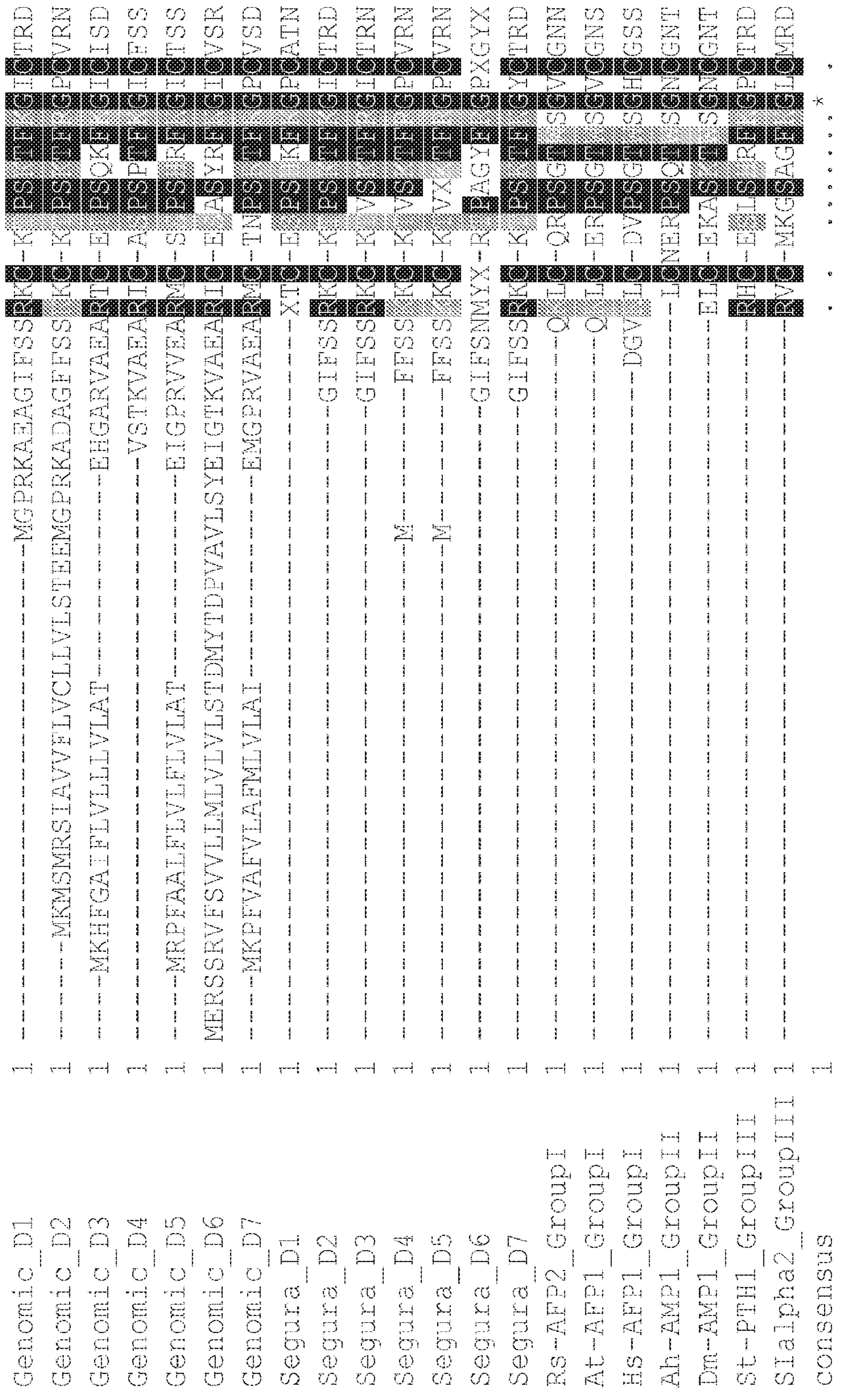
Figure 24B:
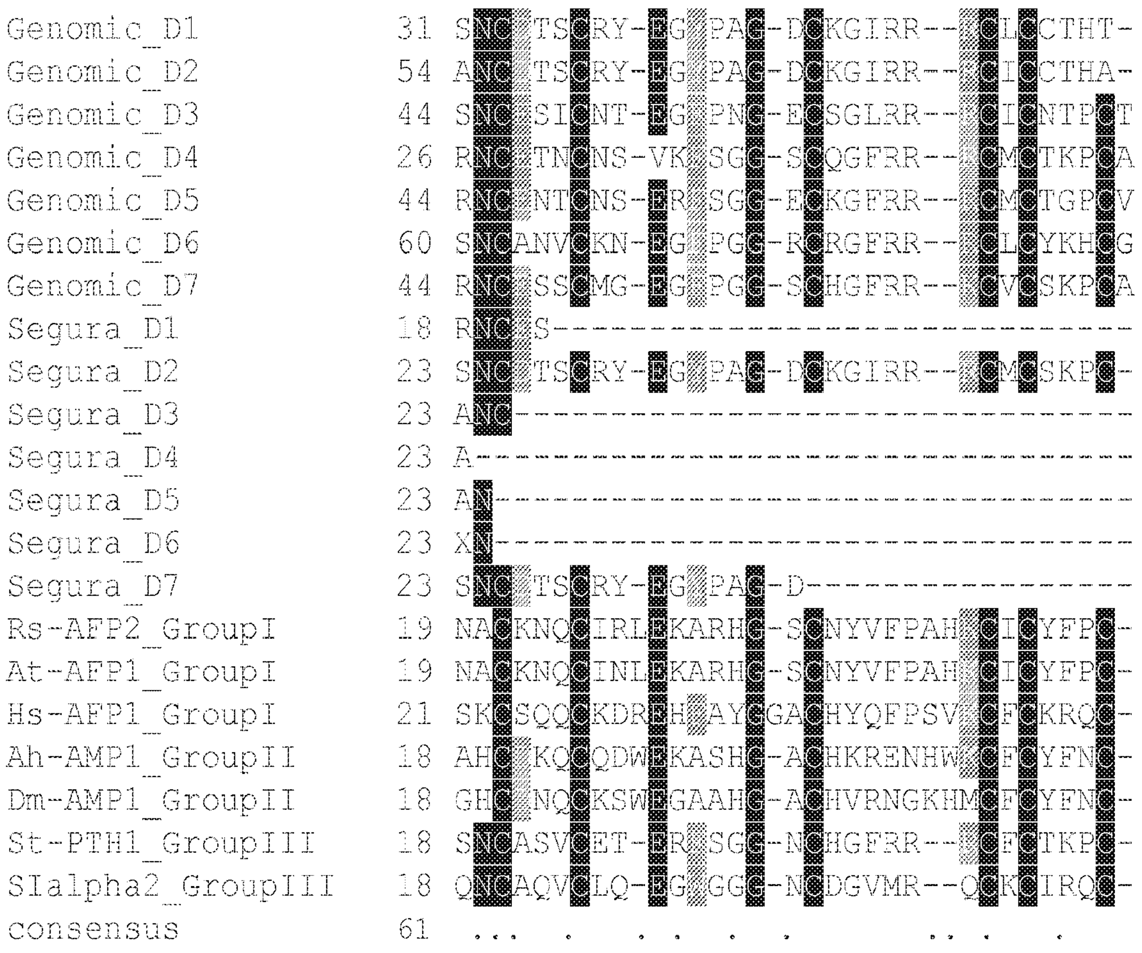

FIG. 24A and FIG. 24B illustrates the sequence alignments of Genomic D1 (SEQ ID NO: 32), Genomic D2 (SEQ ID NO: 33), Genomic D3 (SEQ ID NO: 34), Genomic D4 (SEQ ID NO: 35), Genomic D5 (SEQ ID NO: 36), Genomic D6 (SEQ ID NO: 37), and Genomic D7 (SEQ ID NO: 38), as well as, representative group I defensin sequences Rs-AFP2 (SEQ ID NO: 96), At-AFP1 (SEQ ID NO: 97), and Hs-AFP1 (SEQ ID NO: 98) as illustrated in Segura et al.; representative group II defensin sequences Ah-Ampl (SEQ ID NO:99) and Dm-Ampl (SEQ ID NO: 100) as illustrated in Segura et al.; and representative group III defensin sequences St-PTH1 (SEQ ID NO: 101) and Sia2 (SEQ ID NO: 102) as illustrated in Segura et. al.) according to a specific example embodiment of the disclosure. FIG. 24A illustrates the more N-terminal portion of the alignment. FIG. 24B illustrates the more C-terminal portion of the alignment.

Figure 25A:
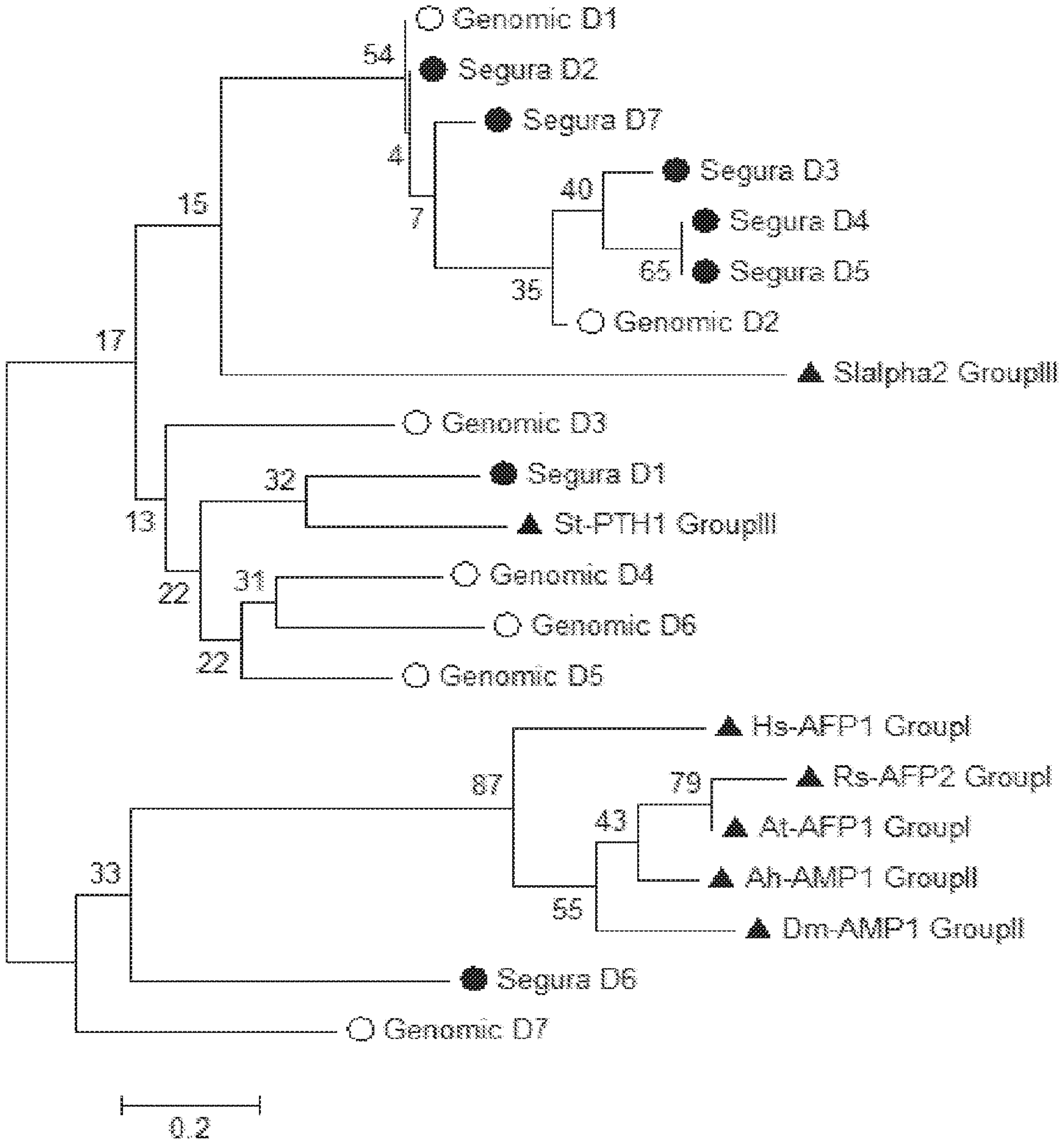

FIG. 25A is a representation of the results of phylogenetic analyses of SEQ ID NOS 32, 33, 34, 35, 36, 37, 38, and representative defensin sequences from groups I, II, III, and IV according to a specific example embodiment of the disclosure.

Figure 25B:
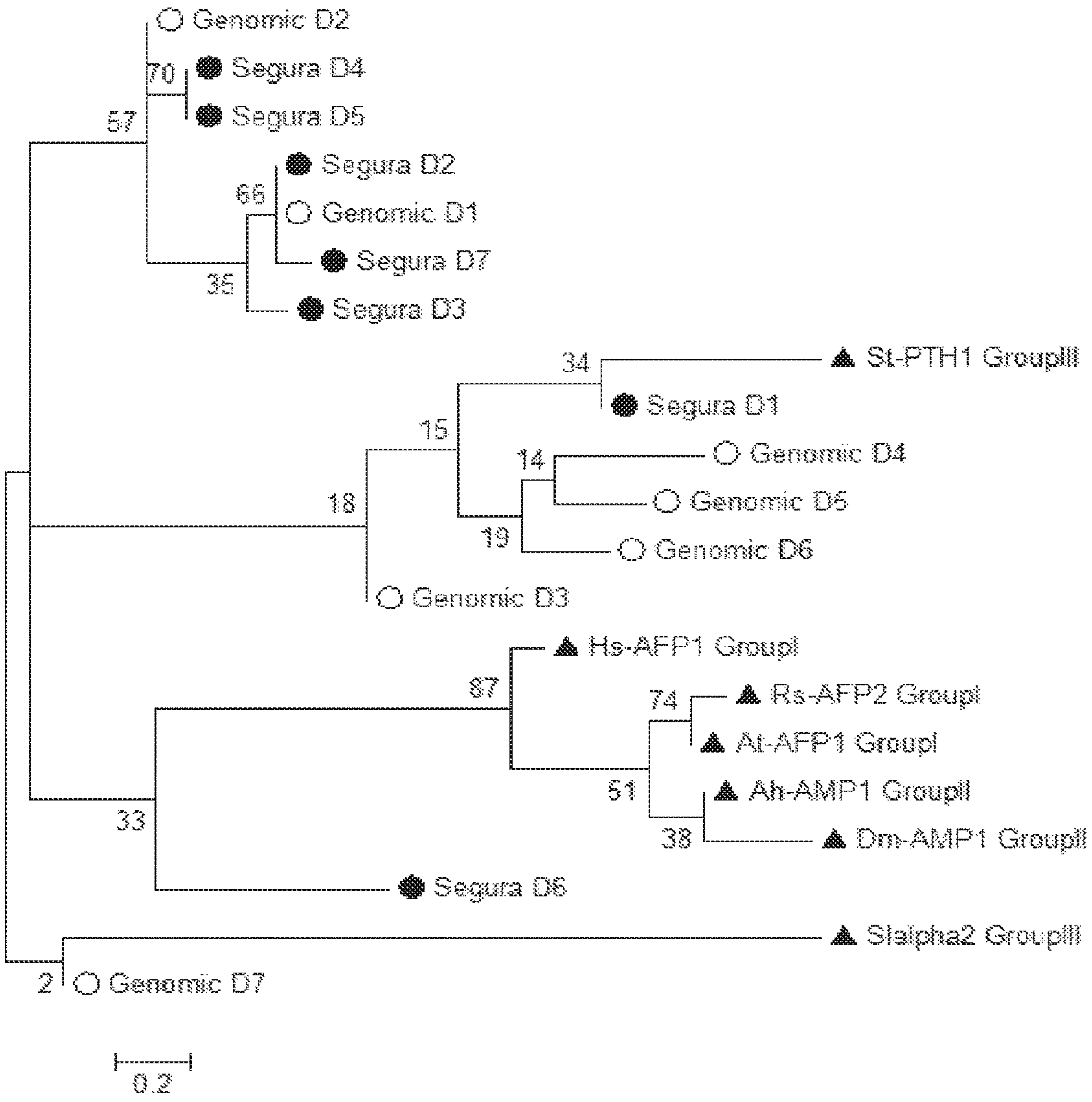

FIG. 25B is a representation of the results of phylogenetic analyses of SEQ ID NOS 32, 33, 34, 35, 36, 37, 38, and representative defensin sequences from groups I, II, III, and IV according to a specific example embodiment of the disclosure.

Figure 26A:
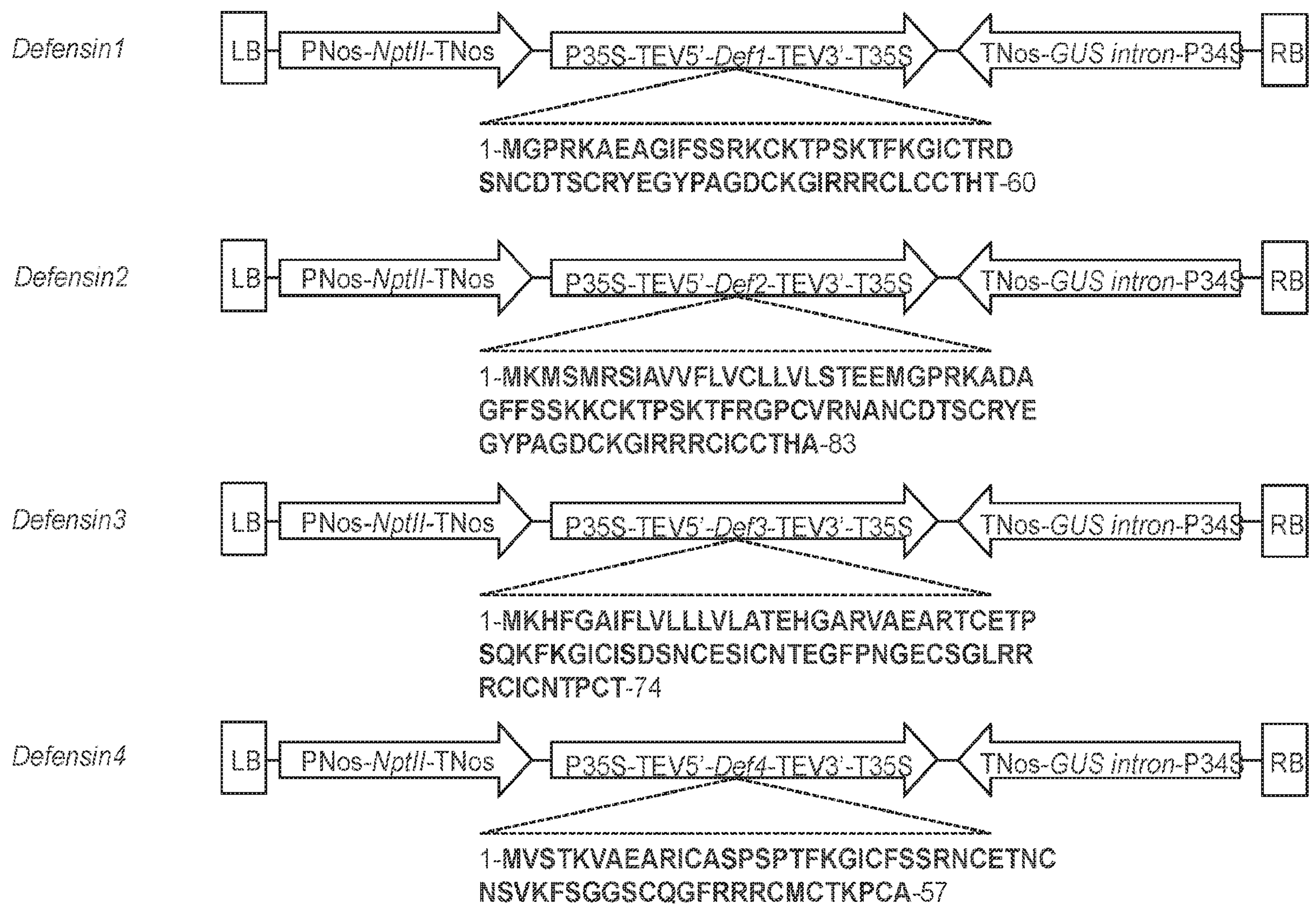

FIG. 26A illustrates expression cassettes encoding individual defensin genes codon-optimized for citrus including Def 1 (SEQ ID NO: 32), Def 2 (SEQ ID NO: 33), Def 3 (SEQ ID NO: 34), and Def 4 (SEQ ID NO: 35), according to a specific example embodiment of the disclosure.

Figure 26B:
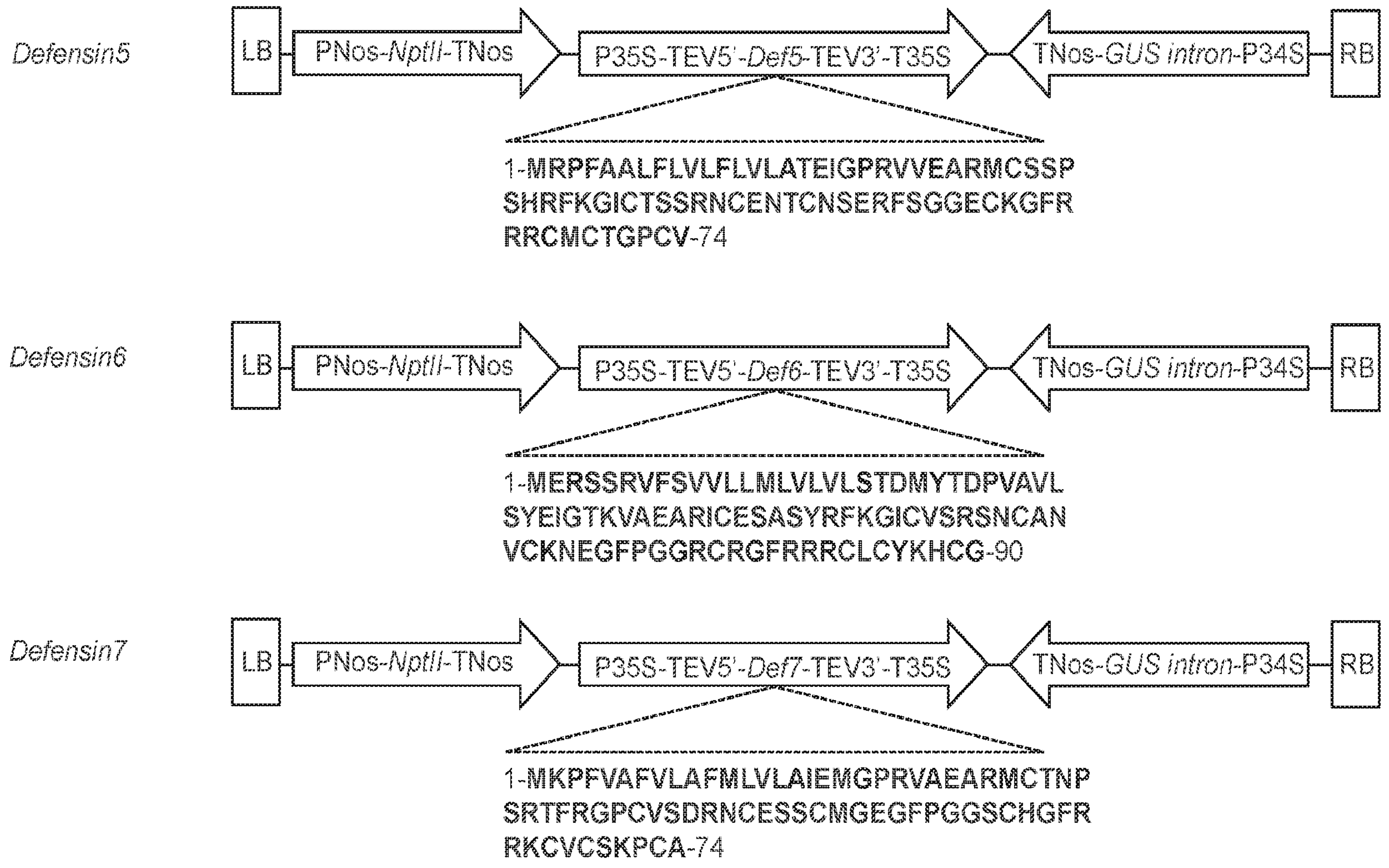

FIG. 26B illustrates expression cassettes encoding individual defensin genes codon-optimized for citrus including Def 5 (SEQ ID NO: 36), Def 6 (SEQ ID NO: 37), and Def 7 (SEQ ID NO: 38), according to a specific example embodiment of the disclosure.

Figure 27:
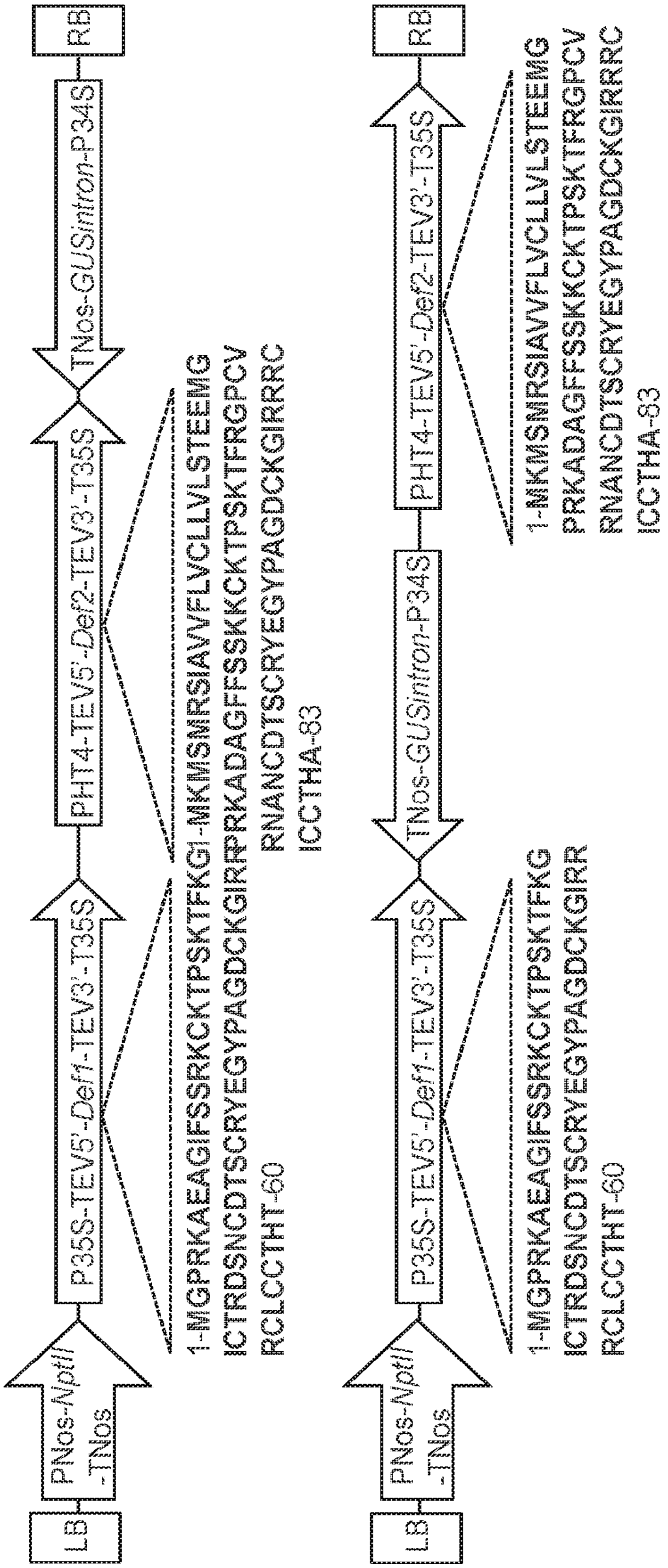

FIG. 27 illustrates expression cassettes for the co-expression of multiple defensin genes codon-optimized for citrus including Def1 (SEQ ID NO: 32), Def 2 (SEQ ID NO: 33), according to a specific example embodiment of the disclosure.

FIG. 28 illustrates the potential combinations for co-expression of spinach defensins, according to a specific example embodiment of the disclosure.

BRIEF DESCRIPTION OF THE SEQUENCE LISTING

Some embodiments of the disclosure may be understood by referring, in part, to the present disclosure and the accompanying sequence listing, wherein:

SEQ ID NO: 1 illustrates an amino acid sequence of a spinach (*Spinacia oleracea*) defensin (SoD2) according to a specific example embodiment of the disclosure;

SEQ ID NO: 2 illustrates an amino acid sequence of a spinach (*Spinacia oleracea*) defensin (SoD7) according to a specific example embodiment of the disclosure;

SEQ ID NO: 3 illustrates a GenScript-optimized nucleic acid sequence for expression of a spinach (*Spinacia oleracea*) defensin (SoD2) according to a specific example embodiment of the disclosure;

SEQ ID NO: 4 illustrates a GenScript-optimized nucleic acid sequence for expression of a spinach (*Spinacia oleracea*) defensin (SoD7) according to a specific example embodiment of the disclosure;

SEQ ID NO: 5 illustrates a CODA-optimized nucleic acid sequence for expression of a spinach (*Spinacia oleracea*) defensin (SoD2) according to a specific example embodiment of the disclosure;

SEQ ID NO: 6 illustrates a CODA-optimized nucleic acid sequence for expression of a spinach (*Spinacia oleracea*) defensin (SoD7) according to a specific example embodiment of the disclosure;

SEQ ID NO: 7 illustrates an amino acid sequence of a chimeric peptide comprising a PR-1b signal peptide and a spinach (*Spinacia oleracea*) defensin (SoD2) according to a specific example embodiment of the disclosure;

SEQ ID NO: 8 illustrates an amino acid sequence of a chimeric peptide comprising a PR-1b signal peptide and a spinach (*Spinacia oleracea*) defensin (SoD7) according to a specific example embodiment of the disclosure;

SEQ ID NO: 9 illustrates a chimeric nucleic acid sequence comprising a nucleic acid sequence encoding a PR-1b signal peptide and a GenScript-optimized nucleic acid sequence for expression of a spinach (*Spinacia oleracea*) defensin (SoD2) according to a specific example embodiment of the disclosure;

SEQ ID NO: 10 illustrates a chimeric nucleic acid sequence comprising a nucleic acid sequence encoding a PR-1b signal peptide and a GenScript-optimized nucleic acid sequence for expression of a spinach (*Spinacia oleracea*) defensin (SoD7) according to a specific example embodiment of the disclosure;

SEQ ID NO: 11 illustrates a chimeric nucleic acid sequence comprising a nucleic acid sequence encoding a PR-1b signal peptide and a CODA-optimized nucleic acid sequence for expression of a spinach (*Spinacia oleracea*) defensin (SoD2) according to a specific example embodiment of the disclosure;

SEQ ID NO: 12 illustrates a chimeric nucleic acid sequence comprising a nucleic acid sequence encoding a PR-1b signal peptide and a CODA-optimized nucleic acid sequence for expression of a spinach (*Spinacia oleracea*) defensin (SoD7) according to a specific example embodiment of the disclosure;

SEQ ID NO: 13 illustrates an expression cassette comprising a nucleic acid sequence encoding a PR-1b signal peptide and a GenScript-optimized nucleic acid sequence for expression of a spinach (*Spinacia oleracea*) defensin (SoD2) according to a specific example embodiment of the disclosure;

SEQ ID NO: 14 illustrates an expression cassette comprising a nucleic acid sequence encoding a PR-1b signal peptide and a GenScript-optimized nucleic acid sequence for expression of a spinach (*Spinacia oleracea*) defensin (SoD7) according to a specific example embodiment of the disclosure;

SEQ ID NO: 15 illustrates an expression cassette comprising a nucleic acid sequence encoding a PR-1b signal peptide and a CODA-optimized nucleic acid sequence for expression of a spinach (*Spinacia oleracea*) defensin (SoD2) according to a specific example embodiment of the disclosure;

SEQ ID NO: 16 illustrates an expression cassette comprising a nucleic acid sequence encoding a PR-1b signal peptide and a CODA-optimized nucleic acid sequence for expression of a spinach (*Spinacia oleracea*) defensin (SoD7) according to a specific example embodiment of the disclosure;

SEQ ID NO: 17 illustrates an expression control sequence (CaMV 35S promoter) according to a specific example embodiment of the disclosure;

SEQ ID NO: 18 illustrates an untranslated region (TEV 5'UTR) according to a specific example embodiment of the disclosure;

SEQ ID NO: 19 illustrates an expression control sequence (CaMV 35S terminator) according to a specific example embodiment of the disclosure;

SEQ ID NO: 20 illustrates a nucleic acid sequence of a primer designated Zn5 according to a specific example embodiment of the disclosure;

SEQ ID NO: 21 illustrates a nucleic acid sequence of a primer designated Zn6 according to a specific example embodiment of the disclosure;

SEQ ID NO: 22 illustrates a nucleic acid sequence of a primer designated Fcp according to a specific example embodiment of the disclosure;

SEQ ID NO: 23 illustrates a nucleic acid sequence of a primer designated Rcp according to a specific example embodiment of the disclosure;

SEQ ID NO: 24 illustrates a nucleic acid sequence of a primer designated GUSF according to a specific example embodiment of the disclosure;

SEQ ID NO: 25 illustrates a nucleic acid sequence of a primer designated GUSR according to a specific example embodiment of the disclosure;

SEQ ID NO: 26 illustrates an amino acid sequence of a chimeric peptide comprising a modified PR-1b signal peptide and a GenScript-optimized nucleic acid sequence having a single deletion for expression of a spinach (*Spinacia oleracea*) defensin (SoD2) according to a specific example embodiment of the disclosure;

SEQ ID NO: 27 illustrates a chimeric nucleic acid sequence comprising a nucleic acid sequence encoding a modified PR-1b signal peptide and a GenScript-optimized nucleic acid sequence having a single deletion for expression of a spinach (*Spinacia oleracea*) defensin (SoD2) according to a specific example embodiment of the disclosure;

SEQ ID NO: 28 illustrates a core amino acid sequence of a defensin according to a specific example embodiment of the disclosure;

SEQ ID NO: 29 illustrates a nucleic acid sequence for expression of a core defensin according to a specific example embodiment of the disclosure;

SEQ ID NO: 30 illustrates a DNA 2.0-optimized nucleic acid sequence for expression of a spinach (*Spinacia oleracea*) defensin (SoD2) according to a specific example embodiment of the disclosure; and SEQ ID NO: 31 illustrates a DNA 2.0-optimized nucleic acid sequence for expression of a spinach (*Spinacia oleracea*) defensin (SoD7) according to a specific example embodiment of the disclosure.

SEQ ID NO: 32 illustrates an amino acid sequence of a spinach (*Spinacia oleracea*) defensin (Def1) according to a specific example embodiment of the disclosure;

SEQ ID NO: 33 illustrates an amino acid sequence of a spinach (*Spinacia oleracea*) defensin (Def2) according to a specific example embodiment of the disclosure;

SEQ ID NO: 34 illustrates an amino acid sequence of a spinach (*Spinacia oleracea*) defensin (Def3) according to a specific example embodiment of the disclosure;

SEQ ID NO: 35 illustrates an amino acid sequence of a spinach (*Spinacia oleracea*) defensin (Def4) according to a specific example embodiment of the disclosure;

SEQ ID NO: 36 illustrates an amino acid sequence of a spinach (*Spinacia oleracea*) defensin (Def5) according to a specific example embodiment of the disclosure;

SEQ ID NO: 37 illustrates an amino acid sequence of a spinach (*Spinacia oleracea*) defensin (Def6) according to a specific example embodiment of the disclosure;

SEQ ID NO: 38 illustrates an amino acid sequence of a spinach (*Spinacia oleracea*) defensin (Def 7) according to a specific example embodiment of the disclosure;

SEQ ID NO: 39 illustrates a nucleic acid sequence of a spinach (*Spinacia oleracea*) defensin (Def1) according to a specific example embodiment of the disclosure;

SEQ ID NO: 40 illustrates a nucleic acid sequence of a spinach (*Spinacia oleracea*) defensin (Def2) according to a specific example embodiment of the disclosure;

SEQ ID NO: 41 illustrates a nucleic acid sequence of a spinach (*Spinacia oleracea*) defensin (Def3) according to a specific example embodiment of the disclosure;

SEQ ID NO: 42 illustrates a nucleic acid sequence of a spinach (*Spinacia oleracea*) defensin (Def4) according to a specific example embodiment of the disclosure;

SEQ ID NO: 43 illustrates a nucleic acid sequence of a spinach (*Spinacia oleracea*) defensin (Def5) according to a specific example embodiment of the disclosure;

SEQ ID NO: 44 illustrates a nucleic acid sequence of a spinach (*Spinacia oleracea*) defensin (Def6) according to a specific example embodiment of the disclosure;

SEQ ID NO: 45 illustrates a nucleic acid sequence of a spinach (*Spinacia oleracea*) defensin (Def7) according to a specific example embodiment of the disclosure;

SEQ ID NO: 46 illustrates a GenScript-optimized nucleic acid sequence for expression of a spinach (*Spinacia oleracea*) defensin (Def1) according to a specific example embodiment of the disclosure;

SEQ ID NO: 47 illustrates a GenScript-optimized nucleic acid sequence for expression of a spinach (*Spinacia oleracea*) defensin (Def2) according to a specific example embodiment of the disclosure;

SEQ ID NO: 48 illustrates a GenScript-optimized nucleic acid sequence for expression of a spinach (*Spinacia oleracea*) defensin (Def3) according to a specific example embodiment of the disclosure;

SEQ ID NO: 49 illustrates a GenScript-optimized nucleic acid sequence for expression of a spinach (*Spinacia oleracea*) defensin (Def5) according to a specific example embodiment of the disclosure;

SEQ ID NO: 50 illustrates a GenScript-optimized nucleic acid sequence for expression of a spinach (*Spinacia oleracea*) defensin (Def6) according to a specific example embodiment of the disclosure;

SEQ ID NO: 51 illustrates a GenScript-optimized nucleic acid sequence for expression of a spinach (*Spinacia oleracea*) defensin (Def7) according to a specific example embodiment of the disclosure;

SEQ ID NO: 52 illustrates a VGD-optimized nucleic acid sequence for expression of a spinach (*Spinacia oleracea*) defensin (Def1) according to a specific example embodiment of the disclosure;

SEQ ID NO: 53 illustrates a VGD-optimized nucleic acid sequence for expression of a spinach (*Spinacia oleracea*) defensin (Def2) according to a specific example embodiment of the disclosure;

SEQ ID NO: 54 illustrates a VGD-optimized nucleic acid sequence for expression of a spinach (*Spinacia oleracea*) defensin (Def3) according to a specific example embodiment of the disclosure;

SEQ ID NO: 55 illustrates a VGD-optimized nucleic acid sequence for expression of a spinach (*Spinacia oleracea*) defensin (Def4) according to a specific example embodiment of the disclosure;

SEQ ID NO: 56 illustrates a VGD-optimized nucleic acid sequence for expression of a spinach (*Spinacia oleracea*) defensin (Def5) according to a specific example embodiment of the disclosure;

SEQ ID NO: 57 illustrates a VGD-optimized nucleic acid sequence for expression of a spinach (*Spinacia oleracea*) defensin (Def6) according to a specific example embodiment of the disclosure;

SEQ ID NO: 58 illustrates a VGD-optimized nucleic acid sequence for expression of a spinach (*Spinacia oleracea*) defensin (Def7) according to a specific example embodiment of the disclosure;

SEQ ID NO: 59 illustrates a chimeric nucleic acid sequence comprising a nucleic acid sequence encoding a spinach (*Spinacia oleracea*) defensin (Def2) signal peptide and a GenScript-optimized nucleic acid sequence for expression of a spinach (*Spinacia oleracea*) defensin (Def2) according to a specific example embodiment of the disclosure;

SEQ ID NO: 60 illustrates a chimeric nucleic acid sequence comprising a nucleic acid sequence encoding a spinach (*Spinacia oleracea*) defensin (Def2) signal peptide and a VGD-optimized nucleic acid sequence for expression of a spinach (*Spinacia oleracea*) defensin (Def2) according to a specific example embodiment of the disclosure;

SEQ ID NO: 61 illustrates an expression cassette comprising a nucleic acid sequence encoding a GenScript-optimized nucleic acid sequence for expression of a spinach (*Spinacia oleracea*) defensin (Def1) according to a specific example embodiment of the disclosure;

SEQ ID NO: 62 illustrates an expression cassette comprising a nucleic acid sequence encoding a GenScript-optimized nucleic acid sequence for expression of a spinach (*Spinacia oleracea*) defensin (Def2) according to a specific example embodiment of the disclosure;

SEQ ID NO: 63 illustrates an expression cassette comprising a nucleic acid sequence encoding a GenScript-optimized nucleic acid sequence for expression of a spinach (*Spinacia oleracea*) defensin (Def3) according to a specific example embodiment of the disclosure;

SEQ ID NO: 64 illustrates an expression cassette comprising a nucleic acid sequence encoding a GenScript-optimized nucleic acid sequence for expression of a spinach (*Spinacia oleracea*) defensin (Defy) according to a specific example embodiment of the disclosure;

SEQ ID NO: 65 illustrates an expression cassette comprising a nucleic acid sequence encoding a GenScript-optimized nucleic acid sequence for expression of a spinach (*Spinacia oleracea*) defensin (Def6) according to a specific example embodiment of the disclosure;

SEQ ID NO: 66 illustrates an expression cassette comprising a nucleic acid sequence encoding a GenScript-optimized nucleic acid sequence for expression of a spinach (*Spinacia oleracea*) defensin (Def7) according to a specific example embodiment of the disclosure;

SEQ ID NO: 67 illustrates an expression cassette comprising a nucleic acid sequence encoding a VGD-optimized nucleic acid sequence for expression of a spinach (*Spinacia oleracea*) defensin (Def1) according to a specific example embodiment of the disclosure;

SEQ ID NO: 68 illustrates an expression cassette comprising a nucleic acid sequence encoding a VGD-optimized nucleic acid sequence for expression of a spinach (*Spinacia oleracea*) defensin (Def2) according to a specific example embodiment of the disclosure;

SEQ ID NO: 69 illustrates an expression cassette comprising a nucleic acid sequence encoding a VGD-optimized nucleic acid sequence for expression of a spinach (*Spinacia oleracea*) defensin (Def3) according to a specific example embodiment of the disclosure;

SEQ ID NO: 70 illustrates an expression cassette comprising a nucleic acid sequence encoding a VGD-optimized nucleic acid sequence for expression of a spinach (*Spinacia oleracea*) defensin (Def4) according to a specific example embodiment of the disclosure;

SEQ ID NO: 71 illustrates an expression cassette comprising a nucleic acid sequence encoding a VGD-optimized nucleic acid sequence for expression of a spinach (*Spinacia oleracea*) defensin (Defy) according to a specific example embodiment of the disclosure;

SEQ ID NO: 72 illustrates an expression cassette comprising a nucleic acid sequence encoding a VGD-optimized nucleic acid sequence for expression of a spinach (*Spinacia oleracea*) defensin (Def6) according to a specific example embodiment of the disclosure;

SEQ ID NO: 73 illustrates an expression cassette comprising a nucleic acid sequence encoding a VGD-optimized nucleic acid sequence for expression of a spinach (*Spinacia oleracea*) defensin (Def7) according to a specific example embodiment of the disclosure;

SEQ ID NO: 74 illustrates an expression control sequence (CaMV 35S promoter) according to a specific example embodiment of the disclosure;

SEQ ID NO: 75 illustrates an untranslated region (TEV 5'UTR) according to a specific example embodiment of the disclosure;

SEQ ID NO: 76 illustrates an untranslated region (TEV 3'UTR) according to a specific example embodiment of the disclosure;

SEQ ID NO: 77 illustrates an terminator sequence (CaMV 35S terminator) according to a specific example embodiment of the disclosure;

SEQ ID NO: 78 illustrates a promoter sequence (PHT4; 6 *Arabidopsis thaliana* promoter) according to a specific example embodiment of the disclosure;

SEQ ID NO: 79 illustrates a promoter sequence (PHT4; 2 *Arabidopsis thaliana* promoter) according to a specific example embodiment of the disclosure;

SEQ ID NO: 80 illustrates a promoter sequence (TPS-Cin *Arabidopsis thaliana* promoter) according to a specific example embodiment of the disclosure.

SEQ ID NO: 81 illustrates an assembled scaffold sequence of spinach (*Spinacia oleracea*) according to a specific example embodiment of the disclosure.

SEQ ID NO: 82 illustrates an assembled scaffold sequence of spinach (*Spinacia oleracea*) according to a specific example embodiment of the disclosure.

SEQ ID NO: 83 illustrates an assembled scaffold sequence of spinach (*Spinacia oleracea*) according to a specific example embodiment of the disclosure.

SEQ ID NO: 84 illustrates an assembled scaffold sequence of spinach (*Spinacia oleracea*) according to a specific example embodiment of the disclosure.

SEQ ID NO: 85 illustrates an assembled scaffold sequence of spinach (*Spinacia oleracea*) according to a specific example embodiment of the disclosure.

SEQ ID NO: 86 illustrates an assembled scaffold sequence of spinach (*Spinacia oleracea*) according to a specific example embodiment of the disclosure.

SEQ ID NO: 87 illustrates an amino acid sequence of a spinach (*Spinacia oleracea*) defensin peptide according to a specific example embodiment of the disclosure.

SEQ ID NO: 88 illustrates an amino acid sequence of a spinach (*Spinacia oleracea*) defensin peptide according to a specific example embodiment of the disclosure.

DETAILED DESCRIPTION

The present disclosure relates, in some embodiments, to compositions, organisms, systems, and methods for enhancing a plant's innate ability, if any, to respond to contact (e.g., infection) with a pathogen (e.g., bacteria, yeast, fungus, virus). In some embodiments, the present disclosure relates to compositions, organisms, systems, and methods for expressing a gene product (e.g., an antimicrobial peptide) in a plant (e.g., citrus). For example, the present disclosure relates to expression control sequences (e.g., promoters), expression cassettes, expression vectors, microorganisms, and/or plants comprising one or more antimicrobial peptides and/or one or more nucleic acids encoding one or more antimicrobial peptides.

I. Compositions

A. Antimicrobial Peptides

The present disclosure relates, according to some embodiments, to peptides and/or proteins having insecticidal activity, antimicrobial activity, and/or antiviral activity, which may include, without limitation, avidin, vegetative insecticidal proteins (e.g., Vip3A), insecticidal crystal proteins from *Bacillus thuringiensis* (e.g., Cry1, Cry1Ab, Cry2, Cry9), pea albumin (e.g., PA1b), hirsutellin A, lectins (e.g., snow drop lily lectin, garlic lectin, onion lectin), amylase inhibitors (e.g., alpha amylase inhibitor), arcelins (e.g., arcelins from beans), proteinase inhibitors, lysozymes (e.g., bovine lysozyme, human lysozyme, mollusk lysozyme), defensin (e.g., SoD2, SoD7, Def1, Def2, Def3, Def4, Def5, Def6, and/or Def7), chitinase, β-1,3-glucanase, variants thereof, and/or combinations thereof. An antimicrobial peptide may comprise, for example, one or more antimicrobial-peptides belonging to the family of plant defensins. These polypeptides were originally isolated from spinach leaves (*Spinacia oleracea*). In some embodiments, a defensin may be small (about 5 kDa), may be basic and/or may be cysteine-rich. In some embodiments, a defensin may comprise a peptide having an amino acid sequence sharing at least about 95% identity, at least about 96% identity, at least about 97% identity, at least about 98% identity, at least about 99% identity, and/or about 100% identity with SEQ ID NO: 1, SEQ ID NO: 2, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 87, and/or SEQ ID NO: 88. In some embodiments, an antimicrobial peptide may further comprise one or more amino acids that are independently and/or collectively either neutral (e.g., do not adversely impact antibacterial functionality) and/or augment antibacterial functionality (e.g., by directing the peptide to a desired location (e.g., cellular and/or extracellular). For example, a defensin may comprise a signal peptide derived from the tobacco pathogenesis-related (PR)-1b protein that allows the transport of the peptides into the apoplast of plant cells (e.g., via the secretory pathway) and/or accumulation in the intercellular spaces of leaves, stems, flowers, fruits, seeds, and/or roots. A defensin may comprise, according to some embodiments, a peptide having an amino acid sequence sharing at least about 95% identity, at least about 96% identity, at least about 97% identity, at least about 98% identity, at least about 99% identity, and/or about 100% identity with SEQ ID NO: 1, SEQ ID NO: 2, SEQ ID NO: 7, SEQ ID NO: 8; SEQ ID NO: 28, SEQ ID NO: 32, SEQ ID NO: 33, SEQ ID NO: 34, SEQ ID NO: 35, SEQ ID NO: 36, SEQ ID NO: 37, and/or SEQ ID NO: 38. Differences in peptide sequences among defensins may give rise to qualitative and/or quantitative differences in performance relative to one or more other defensins. For example, Def3, Def4, Def5, Def6, and/or Def7 (e.g., peptides having the sequence of SEQ ID NO: 34, 35, 36, 37, or 38) may perform differently than one or more other defensins within a plant cell or a plant tissue (e.g., increases or decreases in mobility, insecticidal activity, antimicrobial activity, susceptibility to processing and/or subcellular targeting, accumulation, peptide stability, degradation, and/or longevity as compared to other defensin peptides).

B. Nucleic Acids

The present disclosure relates, in some embodiments, to nucleic acids (e.g., cassettes, vectors) comprising one or more sequences encoding one or more antimicrobial peptides. For example, a nucleic acid may comprise a cassette comprising a synthetic or artificial defensin nucleic acid sequence (e.g. nucleic acid sequences SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, and/or SEQ ID NO: 73). A synthetic or artificial defensin nucleic acid may encode the same amino acid sequence as a native spinach defensin with codons modified (e.g., optimized) from the native nucleotide sequence for citrus codon usage. A nucleic acid comprising a defensin coding sequence may comprise a sequence encoding a signal peptide (e.g., SEQ ID NO: 59, SEQ ID NO: 60). In some embodiments, expression of a nucleic acid comprising a sequence encoding an antimicrobial peptide may be optimized by positioning an initiation codon in a favorable (e.g., optimal) 5' context. According to some embodiments, a nucleic acid may comprise an expression control sequence (e.g., operably linked to a coding sequence). For example, a nucleic acid may comprise a coding gene sequence under the control of a dual enhanced CaMV 35S promoter with a 5' UTR from TEV plant potyvirus (e.g., to provide a translation-enhancing activity to the defensin genes).

According to some embodiments, a nucleic acid may comprise a nucleotide sequence having at least about 75% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 80% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 85% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 90% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 95% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 97% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 98% identity to SEQ ID NOS: 3, 4, 5, 6, 9, 10, 11, 12, 29, 30, 31, 46, 47, 48, 49, 50, 51, 52, 53, 54, 55, 56, 57, and/or 58; at least about 99% identity to SEQ ID NOS: 3, 4, 5, 6, 9, 10, 11, 12, 29, 30, 31, 46, 47, 48, 49, 50, 51, 52, 53, 54, 55, 56, 57, and/or 58; and/or about 100% identity to SEQ ID NOS: 3, 4, 5, 6, 9, 10, 11, 12, 29, 30, 31, 46, 47, 48, 49, 50, 51, 52, 53, 54, 55, 56, 57, and/or 58. A nucleotide sequence may encode, in some embodiments, an amino acid sequence having at least about 98% identity to SEQ ID NOS: 1, 2, 7, 8, 28, 32, 33, 34, 35, 36, 37, and/or 38, at least about 99% identity to SEQ ID NOS: 1, 2, 7, 8, 28, 32, 33, 34, 35, 36, 37, and/or 38, and/or about 100% identity to SEQ ID NOS: 1, 2, 7, 8, 28, 32, 33, 34, 35, 36, 37, and/or 38. According to some embodiments, a nucleic acid may have a first measure of sequence identity to a reference nucleic acid sequence and may encode an amino acid sequence having a second measure of sequence identity to a reference amino acid sequence. For example, a nucleic acid may have about 85% identity to SEQ ID NOS: 3, 4, 5, 6, 9, 10, 11, 12, 29, 30, 31, 46, 47, 48, 49, 50, 51, 52, 53, 54, 55, 56, 57, and/or 58, and encode an amino acid sequence having about 100% identity with SEQ ID NOS: 1, 2, 7, 8, 28, 32, 33, 34, 35, 36, 37, and/or 38, according to some embodiments.

A nucleic acid sequence, according to some embodiments, may hybridize to a nucleic acid having the nucleotide sequence of SEQ ID NOS: 3, 4, 5, 6, 9, 10, 11, 12, 29, 30, 31, 46, 47, 48, 49, 50, 51, 52, 53, 54, 55, 56, 57, and/or 58 under stringent conditions. Stringent conditions may include, for example, (a) 4×SSC at 65° C. followed by 0.1×SSC at 65° for 60 minutes and/or (b) 50% formamide, 4×SSC at 65° C. A nucleic acid may comprise a deletion fragment (e.g., a deletion of from about 1 to about 12 bases) of a nucleic acid having a sequence of SEQ ID NOS: 3, 4, 5, 6, 9, 10, 11, 12, 29, 30, 31, 46, 47, 48, 49, 50, 51, 52, 53, 54, 55, 56, 57, and/or 58 that retains antimicrobial activity against at least one microorganism capable of infecting a citrus plant. One of ordinary skill in the art having the benefit of the present disclosure may prepare one or more deletion fragments of a nucleic acid having a sequence of SEQ ID NOS: 3, 4, 5, 6, 9, 10, 11, 12, 29, 30, 31, 46, 47, 48, 49, 50, 51, 52, 53, 54, 55, 56, 57, and/or 58 and screen the resulting fragments for antimicrobial activity against at least one microorganism capable of infecting a citrus plant.

A nucleic acid sequence having a sequence like SEQ ID NOS: 3, 4, 5, 6, 30, 31, 46, 47, 48, 49, 50, 51, 52, 53, 54, 55, 56, 57, and/or 58 may be identified by database searches using the sequence or elements thereof as the query sequence using the Gapped BLAST algorithm (Altschul et al., 1997 *Nucl. Acids Res.* 25:3389-3402) with the BLOSUM62 Matrix, a gap cost of 11 and persistence cost of 1 per residue and an E value of 10. Sequence identity may be assessed by any available method according to some embodiments. For example, two sequences may be compared with either ALIGN (Global alignment) or LALIGN (Local homology alignment) in the FASTA suite of applications (Pearson and Lipman, 1988 *Proc. Nat. Acad. Sci.* 85:2444-2448; Pearson, 1990 *Methods in Enzymology* 183: 63-98) with the BLOSUM50 matrix and gap penalties of −16, −4. Sequence similarity may be assessed according to ClustalW (Larkin et al., 2007, *Bioinformatics* 23(21): 2947-2948), BLAST, FASTA or similar algorithm.

C. Expression Cassettes and Vectors

The disclosure relates, in some embodiments, to expression vectors and/or expression cassettes for expressing a nucleic acid sequence (e.g., a coding sequence) in a cell and comprising an expression control sequence and the nucleic acid sequence operably linked to the expression control sequence. Thus, for example, an expression cassette may comprise a heterologous coding sequence, the expression of which may be desired in a plant.

1. Expression Vectors

The disclosure relates, in some embodiments, to an expression vector which may comprise, for example, a nucleic acid having an expression control sequence and a coding sequence operably linked to the expression control sequence. In some embodiments, an expression control sequence may comprise one or more promoters, one or more operators, one or more enhancers, one or more ribosome binding sites, and/or combinations thereof. An expression control sequence may comprise, for example, a nucleic acid having promoter activity. An expression control sequence, according to some embodiments, may be constitutively active or conditionally active in (a) an organ selected from root, leaf, stem, flower, seed, and/or fruit, and/or (b) active in a tissue selected from epidermis, periderm, parenchyma, collenchyma, sclerenchyma, xylem, phloem, and/or secretory structures. An expression control sequence, according to some embodiments, may be operable to drive expression of a nucleic acid sequence (e.g., a coding sequence) in a cell. Metrics for expression may include, for example, rate of appearance and/or accumulation of a gene product (e.g., RNA and/or protein) and/or total accumulation of a gene product as of one or more time points (e.g., elapsed time after a starting point and/or a stage of development). Comparative assays for gene products may be qualitative, semi-quantitative, and/or quantitative in some embodiments. Comparative assays may indirectly and/or directly assess the presence and/or amount of gene product. In some embodiments, an expression control sequence may be sensitive to one or more stimuli (e.g., one or more small molecules, one or more plant defense-inducing agents, mechanical damage, temperature, pressure). For example, activity of an expression control sequence may be enhanced or suppressed upon infection with a microorganism (e.g., a bacteria or a virus).

Figure 1:
FIG. 1 illustrates an *Agrobacterium* transformation construct comprising a nucleic acid encoding SoD2 (SEQ ID NO: 1) according to specific example embodiments of the disclosure.
Figure 2:
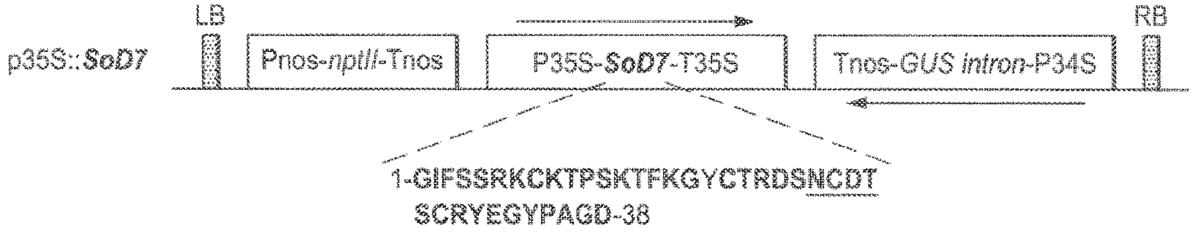
FIG. 2 illustrates an *Agrobacterium* transformation construct comprising a nucleic acid encoding SoD7 (SEQ ID NO: 2) according to specific example embodiments of the disclosure.

An expression vector may be contacted with a cell (e.g., a plant cell) under conditions that permit expression (e.g., transcription) of the coding sequence. Examples of expression vectors may include the *Agrobacterium* transformation constructs shown in FIG. 1 and FIG. 2. An expression control sequence may be contacted with a plant cell (e.g., an embryonic cell, a stem cell, a callous cell) under conditions that permit expression of the coding sequence in the cell and/or cells derived from the plant cell according to some embodiments. An expression vector may be contacted with a cell (e.g., a plant cell), in some embodiments, under conditions that permit inheritance of at least a portion of the expression vector in the cell's progeny. According to some embodiments, an expression vector may include one or more selectable markers. For example, an expression vector may include a marker for selection when the vector is in a bacterial host, a yeast host, and/or a plant host.

2. Expression Cassettes

According to some embodiments, the disclosure relates to an expression cassette which may comprise, for example, a nucleic acid having an expression control sequence and a coding sequence operably linked to the expression control sequence. An expression cassette may be comprised in an expression vector. A coding sequence, in some embodiments, may comprise any coding sequence expressible in at least one plant cell. For example, a coding sequence may comprise a plant sequence, a yeast sequence, a bacterial sequence, a viral sequence (e.g., plant virus), an artificial sequence, an antisense sequence thereof, a fragment thereof, a variant thereof, and/or combinations thereof. A coding sequence may comprise, in some embodiments, a sequence encoding one or more gene products with insecticidal, antibacterial, antifungal, antimicrobial, and/or antiviral activity. A coding sequence may comprise, in some embodiments, a start codon, an intron, and/or a translation termination sequence. According to some embodiments, a coding sequence may comprise one or more natural or artificial coding sequences (e.g., encoding a single protein or a chimera). According to some embodiments, an expression cassette may optionally comprise a termination sequence. A coding sequence, in some embodiments, may comprise a sequence at least partially codon optimized for expression in an organism of interest (e.g., a citrus plant).

An expression control sequence may be used, in some embodiments, to construct an expression cassette comprising, in the 5' to 3' direction, (a) the expression control sequence, (b) a heterologous gene or a coding sequence, or sequence complementary to a native plant gene under control of the expression control sequence, and/or (c) a 3' termination sequence (e.g., a termination sequence comprising a polyadenylation site). Examples of expression cassettes may include, in some embodiments, the cassettes shown in SEQ ID NOS: 13-16 and SEQ ID NOS: 61-73. An expression cassette may be incorporated into a variety of autonomously replicating vectors in order to construct an expression vector. An expression cassette may be constructed, for example, by ligating an expression control sequence to a sequence to be expressed (e.g., a coding sequence).

Some techniques for construction of expression cassettes are well known to those of ordinary skill in the art. For example, a variety of strategies are available for ligating fragments of DNA, the choice of which depends on the nature of the termini of the DNA fragments. An artisan of ordinary skill having the benefit of the present disclosure, a coding sequence (e.g., having antimicrobial activity) and/or portions thereof may be provided by other means, for example chemical or enzymatic synthesis. A nucleic acid may comprise, in a 5' to 3' direction, an expression control sequence, a linker (optional), and a coding sequence according to some embodiments. A nucleic acid may comprise, in some embodiments, one or more restriction sites and/or junction sites between an expression control sequence, a linker, and/or a coding sequence.

II. Microorganisms

The present disclosure relates, in some embodiments, to a microorganism comprising an antimicrobial peptide (e.g., a heterologous antimicrobial peptide) and/or a nucleic acid (e.g., a heterologous and/or expressible nucleic acid) comprising a nucleic acid sequence encoding an antimicrobial peptide. For example, a microorganism may comprise a bacteria, a yeast, and/or a virus. Examples of microorganisms may include, without limitation, *Agrobacterium tumefaciens, Escherichia coli*, a lepidopteran cell line, a Rice tungro bacilliform virus, a Commelina yellow mosaic virus, a Banana streak virus, a Taro bacilliform virus, and/or baculovirus. According to some embodiments, an antimicrobial peptide may be tolerated by and/or innocuous to its host microorganism. A microorganism may comprise an expression control sequence and an antimicrobial peptide coding sequence operably linked to the expression control sequence. A nucleic acid (e.g., a heterologous and/or expressible nucleic acid) comprising a nucleic acid sequence encoding an antimicrobial peptide may be present, in some embodiments, on a genomic nucleic acid and/or an extra-genomic nucleic acid.

III. Plants

The present disclosure relates, in some embodiments, to a plant cell (e.g., an embryonic cell, a stem cell, a callous cell), a tissue, and/or a plant comprising an antimicrobial peptide (e.g., a heterologous antimicrobial peptide) and/or a nucleic acid (e.g., a heterologous and/or expressible nucleic acid) comprising a nucleic acid sequence encoding an antimicrobial peptide. A plant and/or plant cell may be a dicot in some embodiments. Examples of a dicot may include, without limitation, coffee, tomato, pepper, tobacco, lima bean, *Arabidopsis*, rubber, orange, grapefruit, lemon, lime, tangerine, mandarin, pummelo, potato, squash, peas, and/or sugar beet. A plant cell may be included in a plant tissue, a plant organ, and/or a whole plant in some embodiments. A plant cell in a tissue, organ, and/or whole plant may be adjacent, according to some embodiments, to one or more isogenic cells and/or one or more heterogenic cells. In some embodiments, a plant may include primary transformants and/or progeny thereof. A plant comprising a nucleic acid (e.g., a heterologous and/or expressible nucleic acid) comprising a nucleic acid sequence encoding an antimicrobial peptide may further comprise an expression control sequence operably linked to the nucleic acid, in some embodiments. A nucleic acid sequence encoding an antimicrobial peptide may be expressed, according to some embodiments, in a plant in one or more up to all (e.g., substantially all) organs, tissues, and/or cell types including, without limitation, stalks, leaves, roots, seeds, flowers, fruit, meristem, parenchyma, storage parenchyma, collenchyma, sclerenchyma, epidermis, mesophyll, bundle sheath, guard cells, protoxylem, metaxylem, phloem, phloem companion, and/or combinations thereof. In some embodiments, a nucleic acid and/or its gene product (e.g., an antimicrobial peptide) may be located in and/or translocated to one or more organelles (e.g., vacuoles, chloroplasts, mitochondria, plastids).

IV. Methods

A. Transforming a Plant

The present disclosure relates, according to some embodiments, to methods for independent transformation of citrus (e.g., a native genome of a citrus plant). For example, a method may comprise independent transformation, using *Agrobacterium tumefaciens* (At), of the native genome of the orange (*Citrus sinensis*) cultivars "Rhode Red", "Hamlin", and/or "Marrs." A transformation method may comprise contacting a nucleic acid comprising a SoD2, SoD7, and/or another defensin sequence (e.g., the synthetic gene sequence SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and/or SEQ ID NO: 58) with a citrus plant according to some embodiments. A transformed plant (e.g., a transformed genome of a new orange cultivar) may independently contain, in some embodiments a sequence of a SoD2 gene, a SoD7 gene, and/or another defensin (e.g., the synthetic gene sequence SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and/or SEQ ID NO: 58) encoding microbial resistance not found within the native gene pool of the *Citrus* genus. According to some embodiments, a transformed orange cultivar plant may comprise a peptide encoded by a SoD2 gene, a SoD7 gene, and/or another defensin gene (e.g., the synthetic gene sequence SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and/or SEQ ID NO: 58). A transformed plant comprising a sequence of a SoD2 gene, a SoD7 gene, and/or another defensin gene (e.g., the synthetic gene sequence SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, and/or SEQ ID NO: 58) and/or comprising a peptide encoded by a SoD2 gene, a SoD7 gene, and/or another defensin gene (e.g. SEQ ID NO: 32, SEQ ID NO. 33, SEQ ID NO: 34, SEQ ID NO: 35, SEQ ID NO: 36, SEQ ID NO: 37, SEQ ID NO: 38, SEQ ID NO: 86, and/or SEQ ID NO: 87) may display resistance to a range (e.g., a broad range) of bacterial and/or fungal pathogens in some embodiments. For example, a transformed plant comprising a sequence of a SoD2 gene and/or a SoD7 gene and/or comprising a peptide encoded by a SoD2 gene and/or a SoD7 gene may display resistance to bacterial canker (*Xanthomonas axonopodis* pv. *citri*) (Xac), and/or citrus Huanglongbing (ex greening) caused by *Candidatus Liberibacter asiaticus* (Las). See EXAMPLE section below.

B. Grafting

The present disclosure relates to grafting at least a portion of a first plant (e.g., a citrus plant) with at least a portion of a second plant (e.g., a citrus plant), according to some embodiments. A first plant may be in any desired condition including, without limitation, a healthy condition, a diseased condition, an injured condition, a stressed condition (e.g., heat, cold, water, and the like), and/or combinations thereof. A first plant may have any desired genotype including, without limitation, wild type, transgenic, mutant, and/or the like with respect to a gene and/or trait of interest.

A second plant may be in any desired condition including, without limitation, a healthy condition, a diseased condition, an injured condition, a stressed condition (e.g., heat, cold, water, and the like), and/or combinations thereof. A second plant may have any desired genotype including, without limitation, wild type, transgenic, mutant, and/or the like with respect to a gene and/or trait of interest. A first and/or a second plant may comprises at least one antimicrobial peptide and/or at least one nucleic acid comprising a sequence encoding at least one antimicrobial peptide. Where both a first plant comprises at least one antimicrobial peptide and/or at least one nucleic acid comprising a sequence encoding at least one antimicrobial peptide and a second plant comprises at least one antimicrobial peptide and/or at least one nucleic acid comprising a sequence encoding at least one antimicrobial peptide, it may be desirable for the first and second plants to have the same and/or different antimicrobial peptides and/or nucleic acids encoding antimicrobial peptides. Grafting may comprise cutting a portion of a first plant to form a fresh cut site, cutting a portion of a second plant to create a second cut site, and/or contacting a first cut site with a second cut site. A cut site may comprise at least one vascular bundle. Grafting may comprise forming a graft junction and/or, optionally, sealing the graft junction (e.g., by coating the periphery of the graft junction with one or more barrier materials).

C. Treating Plant Disease

The present disclosure relates, in some embodiments, to compositions, organisms, systems, and methods for preventing, ameliorating, and/or treating a plant disease (e.g., a citrus disease) and/or at least one symptom of a plant disease. For example, a method may comprise grafting at least a portion of a plant (e.g., a citrus plant) having a plant disease and/or expressing at least one symptom of a plant disease with at least a portion of a plant (e.g., a citrus plant) comprising an antimicrobial peptide. Examples of a plant disease include, without limitation, bacterial canker (*Xanthomonas axonopodis* pv. *citri*) (Xac), and/or citrus Huanglongbing (ex greening) caused by *Candidatus Liberibacter asiaticus* (Las). According to some embodiments, preventing, ameliorating, and/or treating a plant disease (e.g., a citrus disease) and/or at least one symptom of a plant disease may comprise treating and/or curing one or more devastating bacterial diseases of citrus. For example, plants comprising stably integrated SoD2 and SoD7 transgenes in expressible form may display resistance to, without limitation, bacterial canker (*Xanthomonas axonopodis* pv. *citri*) (Xac), and/or citrus Huanglongbing (ex greening) caused by *Candidatus Liberibacter asiaticus* (Las). Such resistance has been observed as described in the Examples below.

According to some embodiments, the present disclosure relates to compositions, organisms, systems, and methods for augmenting a plant's native resistance to and/or conferring on a plant resistance to a plant disease (e.g., a citrus disease). For example, a method may comprise contacting a plant with an antimicrobial peptide and/or an expressible nucleic acid comprising a nucleic acid sequence encoding an antimicrobial peptide. An expressible nucleic acid comprising a nucleic acid sequence encoding an antimicrobial peptide may be and/or comprise an expression cassette in some embodiments. Contacting may comprise, according to some embodiments, grafting at least a portion of a target plant with a plant comprising an antimicrobial peptide and/or an expressible nucleic acid comprising a nucleic acid sequence encoding an antimicrobial peptide. In some embodiments, contacting may comprise contacting at least a portion of a target plant with a vector (e.g., via *Agrobacterium*-mediated transformation) comprising an antimicrobial peptide and/or an expressible nucleic acid comprising a nucleic acid sequence encoding an antimicrobial peptide. Examples of a plant disease include, without limitation, bacterial canker (*Xanthomonas axonopodis* pv. *citri*) (Xac), and/or citrus Huanglongbing (ex greening) caused by *Candidatus Liberibacter asiaticus* (Las).

D. Making a Citrus-Expressible Antimicrobial Peptide

In some embodiments, the present disclosure relates to compositions, organisms, systems, and methods for forming a citrus-expressible nucleic acid comprising a nucleic acid sequence encoding at least one spinach-derived antimicrobial peptide. For example, a method may comprise identifying an amino acid sequence of an antimicrobial peptide of interest, reverse translating the amino acid sequence to produce a first nucleic acid sequence; codon-optimizing the first nucleic acid sequence for expression in citrus to produce a second nucleic acid sequence, and/or synthesizing a nucleic acid having the second nucleic acid sequence. A method may comprise, in some embodiments, covalently bonding a nucleic acid having the second nucleic acid sequence with one or more nucleic acids having expression control sequences that are operable in citrus in an operable orientation and/or position relative to the nucleic acid having the second nucleic acid sequence.

As will be understood by those skilled in the art who have the benefit of the instant disclosure, other equivalent or alternative pathogen resistant citrus compositions, organisms, systems, and methods can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of expression control sequences, coding sequences, linkers, and/or terminator sequences may be varied. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a composition, device, and/or system of the disclosure. For example, a composition, device, and/or system may be prepared and or used as appropriate for microbial and/or plant (e.g., with regard to sanitary, infectivity, safety, toxicity, biometric, and other considerations). Where desired, some embodiments of the disclosure may be practiced to the exclusion of other embodiments. For example, some polypeptide embodiments may be practiced to the exclusion of a particular amino acid sequence (e.g., SEQ ID NO: 26) and/or some nucleic acid embodiments may be practiced to the exclusion of a particular nucleic acid sequence (e.g., SEQ ID NO: 27).

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each figure disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100.

These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

EXAMPLES

Some specific example embodiments of the disclosure may be illustrated by one or more of the examples provided herein.

Example 1: Plant Material

Plant materials (e.g., *Citrus sinensis*) were generally prepared for transformation as described by Yang et al., *Plant Cell Reports* (2000) 19:1203 et seq.

Example 2: Plasmid Construction and Bacterial Strains

Plasmid construction and bacterial strains were generally performed as described by Yang et al., *Plant Cell Reports* (2000) 19:1203 et seq.

Example 3: *Agrobacterium* Co-Culture and Plant Transformation

*Agrobacterium* co-culture and plant transformation were generally performed as described by Yang et al., *Plant Cell Reports* (2000) 19:1203 et seq.

Example 4: Selection and Regeneration of Transgenic Shoots

Selection and regeneration of transgenic shoots were generally performed as described by Yang et al., *Plant Cell Reports* (2000) 19:1203 et seq.

Example 5: Grafting of Transgenic Shoots

Grafting of transgenic shoots were generally performed as described by Yang et al., *Plant Cell Reports* (2000) 19:1203 et seq.

Example 6: Southern and Northern Analysis

Southern and northern analysis were generally performed as described by Yang et al., *Plant Cell Reports* (2000) 19:1203 et seq.

Example 7: Expression in *Citrus* Trees

Table 1 illustrates specific example embodiments of nucleic acid sequences codon-optimized for citrus. Signal peptides and structural gene coding sequences shown are flanked on either side by specific restriction enzyme sites. These sequences were used to construct expression cassettes, vectors, and transformed *Agrobacterium* for preparation of transgenic plants.

TABLE 1

Example embodiments of specific nucleotide sequences of antimicrobial genes. The nucleotide sequences were optimized for codon usage in *Citrus*.

| Anti-microbial Gene | Source of the Optimized Synthetic Gene (code) | Antimicrobial genes specific nucleotide sequences. The 5' nucleotides include the cloning site and a preferred context for the start codon. The 3' nucleotides include the cloning site. |
|---|---|---|
| SoD2 | GenScript (07) | SEQ ID NO: 9 |
| | CODA (09) | SEQ ID NO: 11 |
| SoD7 | GenScript (08) | SEQ ID NO: 10 |
| | CODA (10) | SEQ ID NO: 12 |
| SoD2 | DNA 2.0 (11) | SEQ ID NO: 30 |
| SoD7 | DNA 2.0 (12) | SEQ ID NO: 31 |
| SoD2 + SoD7 | GenScript (13) | SEQ ID NOS: 9 and 10 |
| SoD2 + SoD7 no SP | DNA 2.0 (16) | SEQ ID NO: 30 and 31 |

The following cultivars were selected for transformation:

Orange: Hamlin ("04"), Rhode Red ("05"), and Marrs ("06") (FIGS. 3-7);

Grapefruit: Ruby Red ("01") (FIGS. 8-11) and Rio Red ("02") (Example 14 below);

Carrizo Citrange ("CC") (FIGS. 12-13);

Flying Dragon rootstock ("13" and "16");

Frost Eureka and Frost Lisbon (13" and "16");

Swingle rootstock (13" and "16"); and

C22 rootstock.

Constructs used for each cultivar are shown in Table 2.

TABLE 2

Orange, grapefruit, lemon and citrus rootstock cultivars transformed (seedling epicotyls) with three different synthetic sequences of each SoD2 and SoD7 genes encoding antimicrobial peptides from spinach (*Spinacia oleracea*) (at least 521 events in total).

| Generation | Defensin Synthetic Genes | Synthetic Gene Optimized-Codon Sequence (Sequence Code) | *Citrus* Cultivars (Cultivar Code) | Transgenic Events Codes (Cultivar and Gene) | Number of Transgenic Events |
|---|---|---|---|---|---|
| 2 (141 events) | SoD2 + SP | GenScript (07) | Hamlin (04) | 0407 | 14 |
| | | | Rohde Red (05) | 0507 | 12 |
| | | | Marrs (06) | 0607 | 6 |
| | | | Carrizo Citrange (CC) | CC2 | 18 |
| | | CODA (09) | Hamlin (04) | 0409 | 16 |
| | | | Rohde Red (05) | 0509 | 6 |
| | SoD7 + SP | GenScript (08) | Hamlin (04) | 0408 | 12 |
| | | | Rohde Red (05) | 0508 | 8 |
| | | | Marrs (06) | 0608 | 7 |
| | | | Carrizo Citrange (CC) | CC7 | 29 |
| | | CODA (10) | Hamlin (04) | 0410 | 5 |
| | | | Rohde Red (05) | 0510 | 8 |
| 3 (36 events) | SoD2-no SP | DNA 2.0 (11) | Hamlin (04) | 0411 | 11 |
| | | | Ruby Red (01) | 0111 | 6 |
| | SoD7-no SP | DNA 2.0 (12) | Hamlin (04) | 0412 | 13 |
| | | | Ruby Red (01) | 0112 | 6 |

TABLE 2-continued

Orange, grapefruit, lemon and citrus rootstock cultivars transformed (seedling epicotyls) with three different synthetic sequences of each SoD2 and SoD7 genes encoding antimicrobial peptides from spinach (*Spinacia oleracea*) (at least 521 events in total).

| Generation | Defensin Synthetic Genes | Synthetic Gene Optimized-Codon Sequence (Sequence Code) | *Citrus* Cultivars (Cultivar Code) | Transgenic Events Codes (Cultivar and Gene) | Number of Transgenic Events |
|---|---|---|---|---|---|
| 4 (187 events + 157 Swingle | SoD2 + 7 + SP | GenScript (13) | Hamlin (04) | 413 | 15 |
| | | | Rhode Red (05) | 513 | 14 |
| | | | Rio Red (02) | 213 | 18 |
| | | | Frost Eureka Lemon (10) | 1013 | 30 |
| | | | Frost Lisbon Lemon (11) | 1113 | 33 |
| | | | Swingle Rootstock (12) | 1213 | 157 |
| | | | Flying Dragon Rootstock (09) | 913 | 46 |
| | | | C22 (08) | 813 | 15 |
| | | | Carrizo Citrange (07) | 713 | 16 |
| 4 | SoD2 + 7 | GenScript (07 + 08) | Hamlin (04) | 0413 | 15 |
| | | | Rohde Red (05) | 0513 | 1 |
| | | | Rio Red (02) | 0213 | 7 |
| | | | Carrizo Citrange (CC) | CC2 + 7 | 6 |
| 5 | SoD2 + 7-no SP | DNA 2.0 (16) | Hamlin (04) | 416 | Multiple GUS positive plants |
| | | | Frost Eureka Lemon (10) | 1013 | Multiple GUS positive plants |
| | | | Frost Lisbon Lemon (11) | 1113 | Multiple GUS positive plants |
| | | | Rhode Red (05) | 516 | Multiple GUS positive plants |

A. Transformation of Orange

Figure 3:
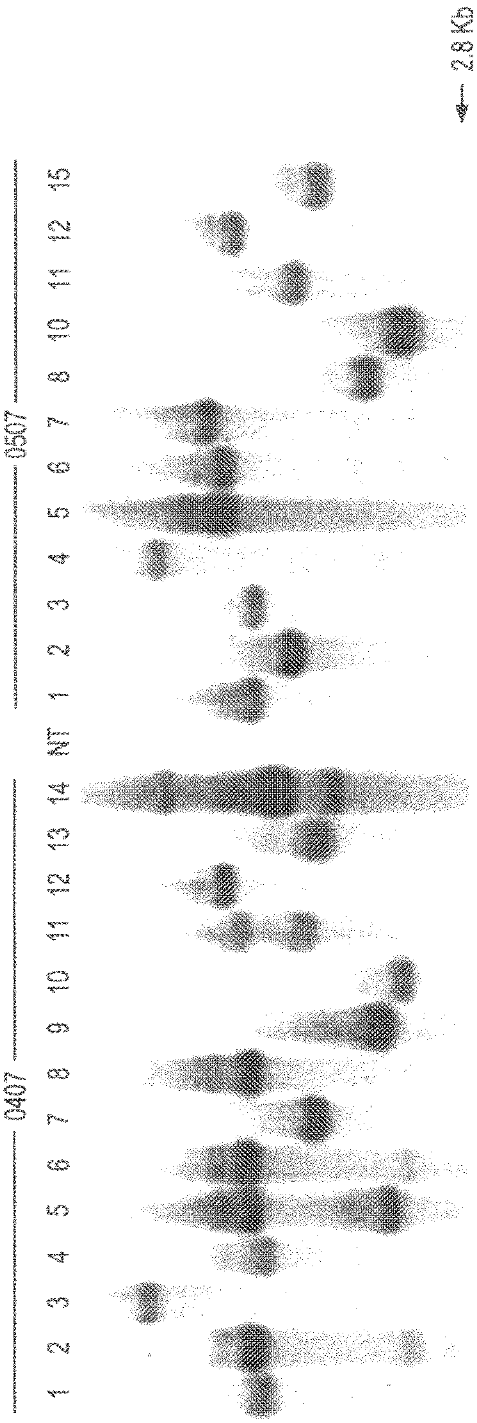
FIG. 3 is a representation of a Southern blot showing insertion number among transgenic events in Hamlin and Rhode Red transformed with a SoD2 (07) nucleic acid comprising a GenScript-optimized sequence for expression in *Citrus*, according to a specific example embodiment of the disclosure.
Figure 4:
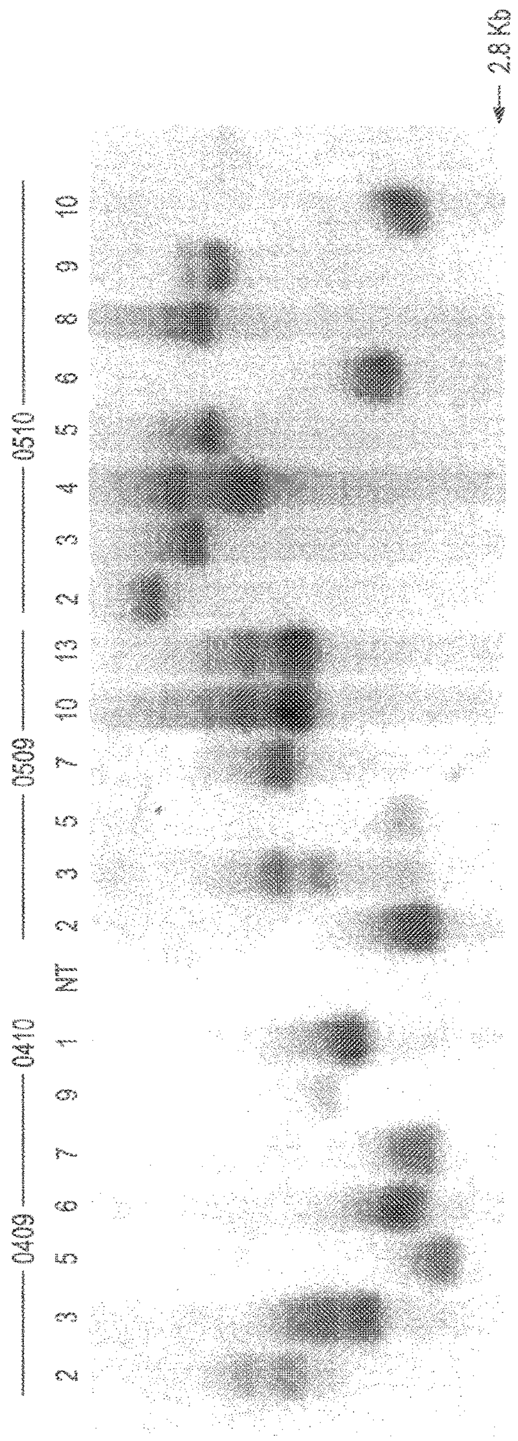
FIG. 4 is a representation of a Southern blot showing insertion number among transgenic events in Hamlin and Rhode Red transformed with SoD2 (09) or SoD7 (10) nucleic acids, each comprising a CODA-optimized sequence for expression in *Citrus*, according to specific example embodiments of the disclosure.

Orange plants were transformed with a single construct comprising GenScript-optimized SoD2 with signal peptide ("07"), GenScript-optimized SoD7 with signal peptide ("08"), CODA-optimized SoD2 with signal peptide ("09"), or CODA-optimized SoD2 with signal peptide ("10"). FIG. 3 is a representation of a Southern blot showing insertion number among transgenic events in Hamlin transformed with GenScript-optimized SoD2 (0407) and Rhode Red transformed with GenScript-optimized SoD2 (0507). FIG. 4 is a representation of a Southern blot showing insertion number among transgenic events in Hamlin transformed with CODA-optimized SoD2 (0409) or CODA-optimized SoD7 (0410) and Rhode Red transformed with CODA-optimized SoD2 (0509) or CODA-optimized SoD7 (0510). Additional transformation events are shown for GenScript-optimized SoD7 ("08") and CODA-optimized SoD2 ("09") in Hamlin in FIG. 9.

Figure 5:
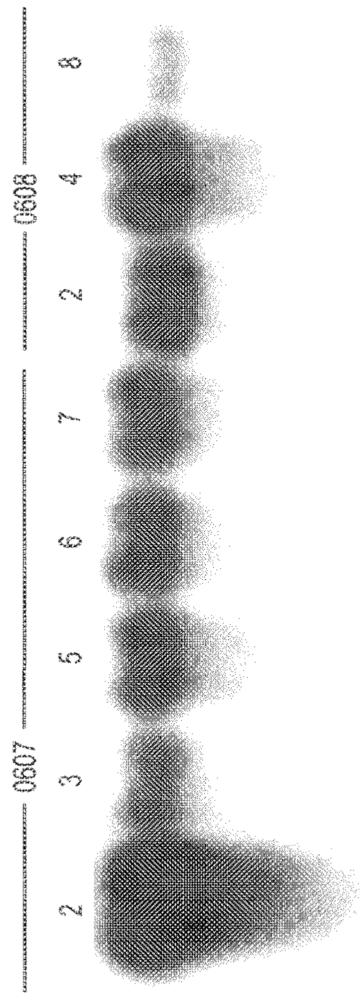
FIG. 5 is a representation of a northern blot showing RNA transcripts among transgenic events in Marrs, transformed with SoD2 (07) or SoD7 (08) nucleic acids, each comprising a GenScript-optimized sequence for expression in *Citrus*, according to a specific example embodiment of the disclosure.
Figure 6:
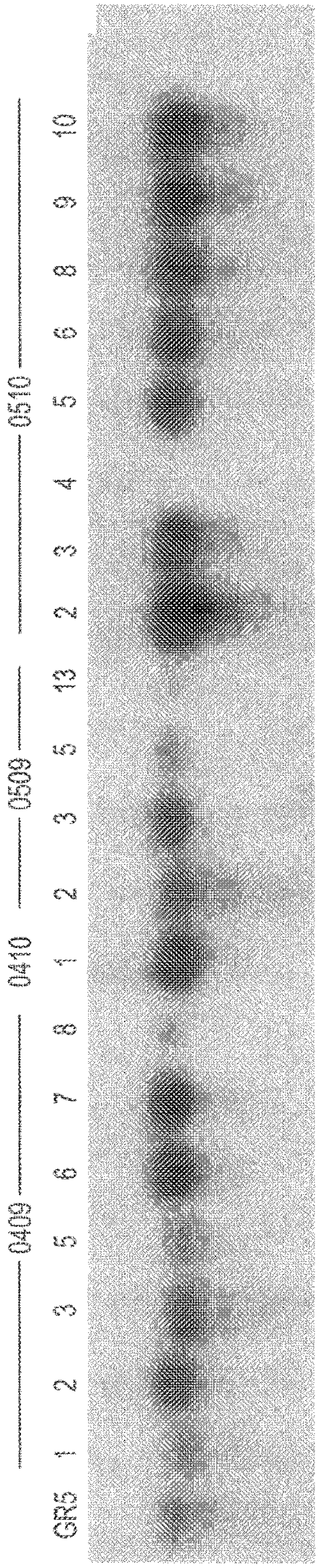
FIG. 6 is a representation of a northern blot showing RNA transcripts among transgenic events in Hamlin and Rhode Red, transformed with SoD2 (09) or SoD7 (10) nucleic acids, each comprising a CODA-optimized sequence for expression in *Citrus*, according to a specific example embodiment of the disclosure.
Figure 7:
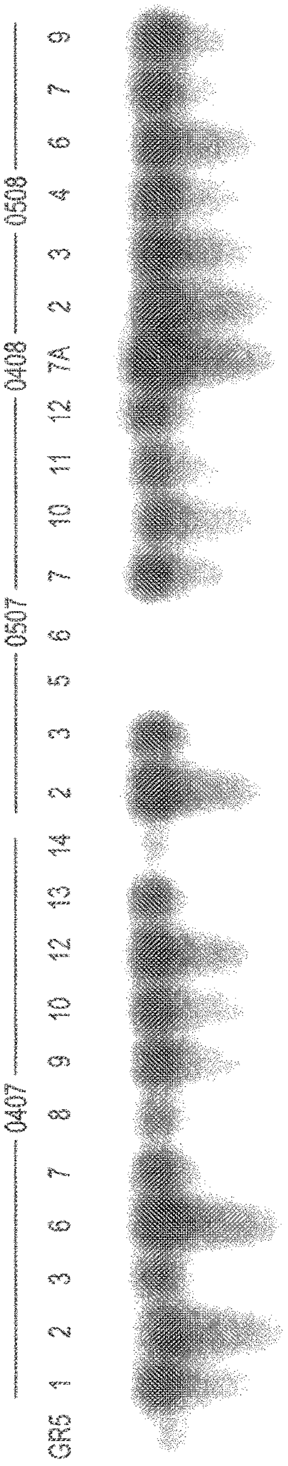
FIG. 7 is a representation of a northern blot showing RNA transcripts among transgenic events in Hamlin and Rhode Red, transformed with SoD2 (07) or SoD7 (08) nucleic acids, each comprising a GenScript-optimized sequence for expression in *Citrus*, according to a specific example embodiment of the disclosure.

Transgenic plants of the orange cultivars Hamlin, Rhode Red, and Marrs (n=82) produce high levels of transcripts of these antimicrobial genes (Table 2 and FIGS. 5-7). FIG. 5 is a representation of a northern blot showing RNA transcripts among transgenic events in Marrs, transformed with genes SoD2 (0607) or SoD7 (0608) GenScript-optimized for codon use in *Citrus*. FIG. 6 is a representation of a northern blot showing RNA transcripts among transgenic events in Hamlin transformed with CODA-optimized SoD2 (0409) or CODA-optimized SoD7 (0410) and Rhode Red transformed with CODA-optimized SoD2 (0509) or CODA-optimized SoD7 (0510). FIG. 7 is a representation of a northern blot showing RNA transcripts among transgenic events in Hamlin transformed with GenScript-optimized SoD2 (0407) or GenScript-optimized SoD7 (0408) and Rhode Red transformed with GenScript-optimized SoD2 (0507) or GenScript-optimized SoD7 (0508). For identification, Table 2 contains the transgenic event codes for cultivar and gene combination.

Figure 8:
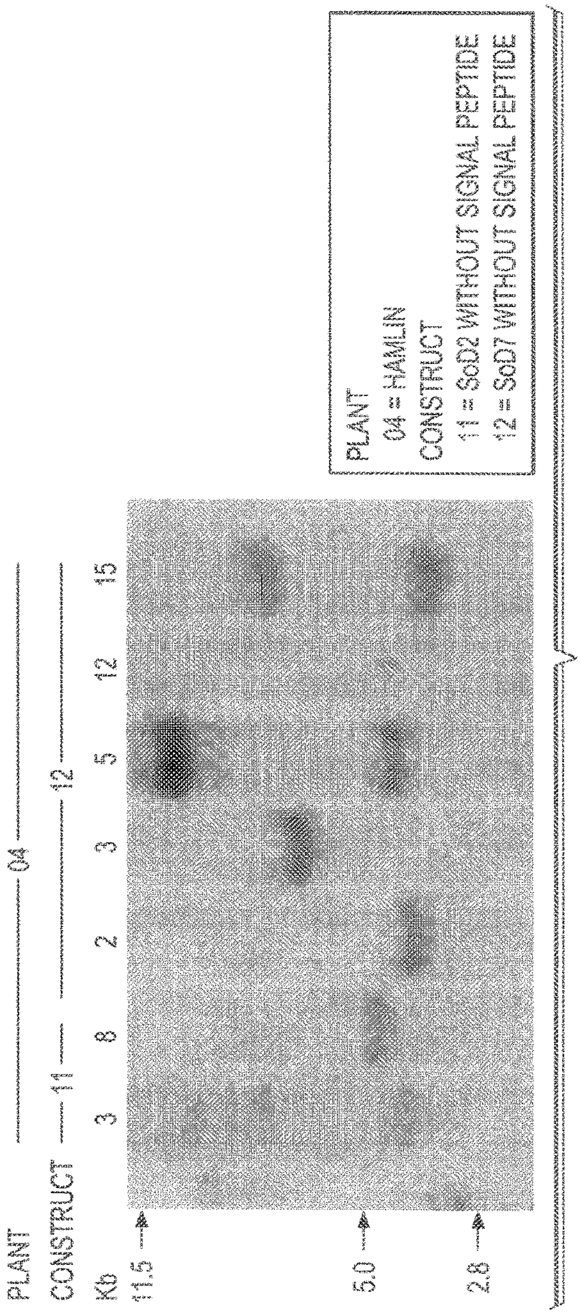
FIG. 8 is a representation of a Southern blot confirming insertion of SoD2 or SoD7 in Hamlin plants, transformed with SoD2 (11) or SoD7 (12) nucleic acids, each comprising a DNA 2.0-optimized sequence for expression in *Citrus*, according to a specific example embodiment of the disclosure.

Orange plants (Hamlin) were also transformed with a single construct comprising DNA 2.0-optimized SoD2 without signal peptide ("11") or DNA 2.0-optimized SoD7 without signal peptide ("12"). FIG. 8 is a representation of a Southern blot confirming insertion of SoD2 or SoD7 in these orange plants. Additional transformation events are shown for SoD7 (12) in Hamlin in FIG. 9.

B. Transformation of Grapefruit

Figure 9:
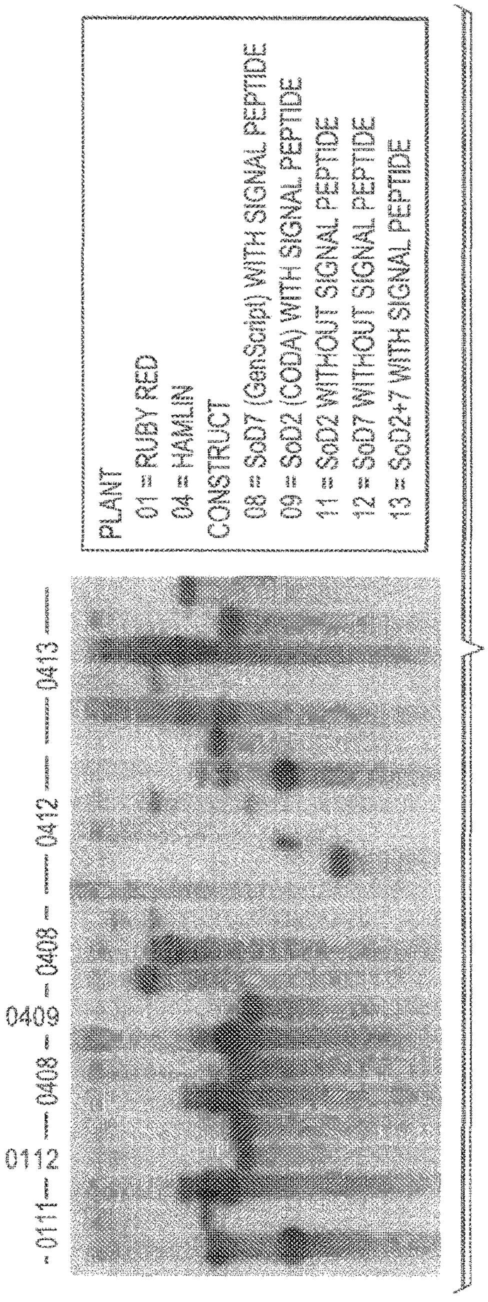
FIG. 9 is a representation of a Southern blot confirming insertion of defensins in Ruby Red (01) or Hamlin (04) transformed with SoD2 (09, 11), SoD7 (08, 12), or both SoD2 and SoD7 (13) nucleic acids, each comprising a sequence optimized for expression in *Citrus* using a sequence optimization algorithm (GenScript for 08 and 13; Coda for 09, and DNA 2.0 for 11 and 12), according to a specific example embodiment of the disclosure.
Figure 10:
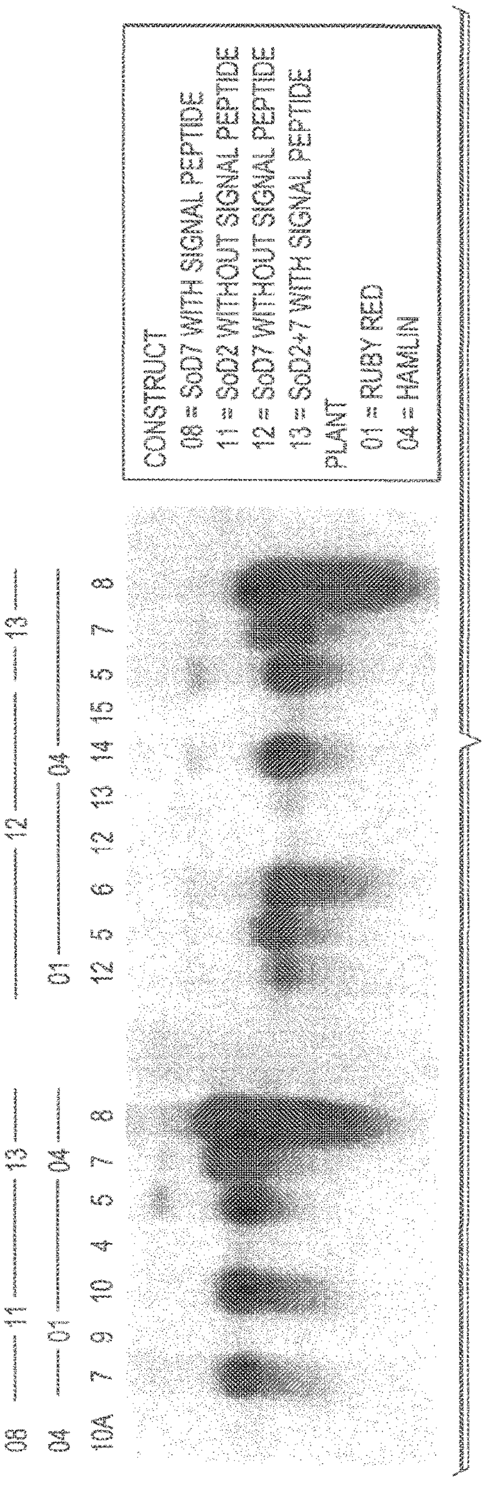
FIG. 10 is a representation of a northern blot showing RNA transcripts among transgenic events in Ruby Red (01) or Hamlin (04), transformed with SoD2 (11), SoD7 (08, 12), or both SoD2 and SoD7 (13) nucleic acids, each comprising a GenScript-optimized sequence (08 and 13) or DNA 2.0- optimized sequence (11 and 12) for expression in *Citrus*, according to a specific example embodiment of the disclosure.

Ruby Red ("01") plants were transformed with a single construct comprising DNA 2.0-optimized SoD2 without signal peptide ("11") or DNA 2.0-optimized SoD7 without signal peptide ("12"). FIG. 9 is a representation of a Southern blot (membrane was exposed to probes for both SoD2 and SoD7) confirming insertion of SoD2 or SoD7 in these grapefruit plants. FIG. 10 is a representation of a northern blot (membrane was exposed to probes for both SoD2 and SoD7) showing RNA transcripts among transgenic events in Ruby Red transformed with SoD2 (0111) or SoD7 (0112). For identification, Table 2 contains the transgenic event codes for cultivar and gene combination.

C. Transformation of Carrizo Citrange and C22

Carrizo Citrange and C22 rootstocks have been transformed with a construct comprising uidA and either SoD2 or SoD7 or SoD2+SoD7. FIG. 11 is a representation of a Southern blot confirming insertion of SoD2 (lanes marked "07") and SoD7 (lanes marked "08") in these Carrizo Citrange plants. FIG. 12 is a representation of a northern blot showing RNA transcripts isolated from these Carrizo Citrange plants (marked "CC") transformed with SoD2 (GenScript-optimized sequence with signal peptide) and SoD7 (GenScript-optimized sequence with signal peptide). For identification, Table 2 contains the transgenic event codes for cultivar and gene combination. A number of C22 transformation events have been confirmed in each by positive GUS staining.

Swingle and Flying Dragon (citrus rootstock) plants were transformed with various constructs including a single construct comprising GenScript-optimized SoD2 and SoD7 with signal peptide. Successful transformation of C22, Flying Dragon, and Swingle plants has been at least confirmed by positive GUS staining.

D. Transformation of Lemon

Frost Lisbon and Frost Eureka (lemon) plants were transformed with various constructs including a single construct comprising GenScript-optimized SoD2 and SoD7 with signal peptide. Successful transformation of C22, Flying Dragon, and Swingle plants has been at least confirmed by positive GUS staining.

E. Status of Transformation Events

The following cultivars of citrus and citrus rootstock have been transformed (seedling epicotyls) with synthetic sequences of SoD2 and SoD7 genes encoding antimocrobial from spinach (*Spinacia oleracea*), with the transformation even being stably maintained for between two and five years.

Orange:
- 'Hamlin' Sweet Orange
- 'Marrs' Sweet Orange
- 'Rhode Red' Valencia

Grapefruit:
- 'Rio Red' Grapefruit
- 'Ruby Red' Grapefruit

Lemon:
- 'Frost Eureka' Lemon
- 'Frost Lisbon' Lemon
- 'Limoneria 8A' Lemon

Lime:
- Key Lime

Rootstock:
- 'Carrizo'
- 'C22'
- 'Flying Dragon'
- 'Swingle'
- 'Benton Citrange'

Example 8: Canker Disease Resistance Assay

Canker disease resistance was assessed using a detached leaf assay generally as described by Francis M I et al., 2010, *Eur J Plant Pathol* 127:571-578. Briefly, detached immature leaves (~75% expanded) were triple rinsed in sterile water to remove debris, sanitized by brief immersion in 70% ethanol followed by 0.5% sodium hypochloride, and again triple rinsed in sterile water. Sanitized leaves (3-4 per replicate×3 replicates) were infiltrated on their abaxial surface with an aqueous suspension of an Xcc strain isolated in Dade County Florida. Inoculated leaves were pressed on the surface of soft water agar plates, parafilm sealed, and incubated in an environmentally-controlled growth chamber.

FIG. 13A shows the result of inoculating a non-transgenic 'Rio Red' leaf with the citrus canker pathogen, as described above, and FIG. 13B shows the result of inoculating a transgenic leaf from a plant of Rio Red' expressing SoD2 with the citrus canker pathogen, as described above. A large reduction in the size and number of lesion on the transgenic can be seen.

Example 9: *Citrus* Greening (HLB) Disease Resistance Assay by Grafting

FIG. 14 shows the result of graft inoculating non-transgenic 'Rio Red' (two trees on the left) or transgenic 'Rio Red' expressing SoD2 one tree on the right) with the citrus greening pathogen. A non-transgenic rootstock (Cleopatra mandarin) infected with HLB is used. Onto this rootstock several buds of transgenic 'Rio Red' are grafted and this is replicated. The same protocol is followed for non-transgenic buds of 'Rio Red'. After 8 weeks, vigorous growth can be seen from the transgenic graft, where there is no growth on the controls.

Example 10: *Citrus* Greening (HLB) Disease Resistance Assay by Psyllid Inoculation Resistance to bacterial infection and growth was assessed by two metrics. First, resistance was evaluated by the percentage of infection, namely the number of exposed plants that were infected. Second, a PCR-based method was used to amplify bacterial sequences. In this method, the relative degree of infection influences the number of PCR cycles required to produce detectable signal. For example a heavily infested plant might only require a few cycles while a plant with a low bacterial titer may require more cycles. In general, a plant that requires 30 or more cycles to observe detectable signal is regarded to be uninfected. Since some infections of citrus progress slowly, samples were collected for testing at 5 to 11 months after the time of first exposure and thereafter over a period of 6-9 months. The frequency of sample collection may vary from about every 45 days to about every 120 days. Ten to 15 replicates of each transgenic event plus non-transgenic controls are placed haphazardly in an insect proof green house that contains thousands' of psyllids carrying the citrus greening pathogen. The first PCR testing is done about five months after continuous exposure to psyllids. DNA extraction and PCR to detect the pathogen is essentially as described by Irey M S et al., 2006, *Proc. Fla. State Hort. Soc.* 119:89-93.

Example 11: Propagation and Resistance of Generation 1

Red Grapefruit (2 varieties) and Sweet Orange (3 varieties) were transformed with *Agrobacterium* comprising an expression vector having an artificial defensin gene construct that included a 2-amino acid insertion in the signal peptide and a single amino acid deletion in the coding sequence (SEQ ID NOS: 26 and 27). A total of 6 transformation events were further tested based on having high levels of SoD2 RNA expressed. Plants were cultivated as described herein and bacterial resistance was assessed as described. A first set of samples were collected after 11 months in the field (D0). Subsequent samples were collected the indicated number of days (42-471) after the first sampling (e.g., D42=11 months+42 days). Results are shown in Table 3.

TABLE 3

| Generation 1 Infection Data | | | | | | | | |
|---|---|---|---|---|---|---|---|---|
| Plant Line | N | 0 | 42 | 90 | 127 | 271 | 384 | 471 |
| GR 311 Hamlin | 1 | 0% | 0% | 0% | 0% | 100% | 100% | 100% |
| Non Transgenic Hamlin | 1 | 0% | 0% | 100% | 100% | 100% | 100% | 100% |

TABLE 3-continued

| Generation 1 Infection Data | | | | | | | | |
|---|---|---|---|---|---|---|---|---|
| Plant Line | N | 0 | 42 | 90 | 127 | 271 | 384 | 471 |
| GR 420 Grapefruit | 1 | 0% | 0% | 0% | 0% | 0% | 100% | 100% |
| GR 824 Grapefruit | 2 | 0% | 0% | 50% | 50% | 100% | 100% | 100% |
| GR 867 Grapefruit | 1 | 0% | 0% | 0% | 0% | 100% | 100% | 100% |
| GR 882 Grapefruit | 2 | 0% | 0% | 0% | 50% | 50% | 50% | 50% |
| GR 890 Grapefruit | 1 | 0% | 0% | 0% | 0% | 0% | 100% | 100% |
| Non Transgenic Grapefruit | 7 | 0% | 0% | 0% | 14% | 0% | 57% | 57% |
| Non Transgenic Grapefruit Border | 6 | 0% | 0% | 0% | 0% | 50% | 50% | 50% |
| Total | 22 | 0% | 0% | 9% | 18% | 41% | 68% | 68% |

Example 12: Propagation and Resistance of Generation 2

Sweet Orange (2 varieties) were transformed with *Agrobacterium* comprising one of the following defensin gene constructs:

(a) GenScript-optimized SoD2 with tobacco PR-1b signal peptide (SEQ ID NO: 9), (b) CODA-optimized SoD2 with tobacco PR-1b signal peptide (SEQ ID NO: 11), (c) GenScript-optimized SoD7 with tobacco PR-1b signal peptide (SEQ ID NO: 10), or (d) CODA-optimized SoD7 with tobacco PR-1b signal peptide (SEQ ID NO: 12).

A total of 71 transformation events were observed. Plants were cultivated as described herein and bacterial resistance was assessed as described. A first set of samples were collected after 5 months in the psyllid house (Day 0). Subsequent samples were collected the indicated number of days after the first sampling (e.g., Day 73=5 months+73 days). Results are shown in FIG. 15, FIG. 16, Table 4, and Table 5.

TABLE 4

| Generation 2 Infection Data | | | | | | | | | | | | |
|---|---|---|---|---|---|---|---|---|---|---|---|---|
| | | | | | 1st Sampling | | 2nd Sampling | | 3rd Sampling | | Partial 4th Sampling | |
| Code | Scion[1] | Genotype[2] | Rootstock[3] | Gene[4] | Day 0 | Mean Ct | Day 73 | Mean Ct | Day 170 | Mean Ct | Day 317 | Mean Ct |
| 0407-01 | H | SO | Cm | SoD2 (G) | 13% | 23.02 | 33% | 26.09 | 33% | 23.28 | | |
| 0407-02 | H | SO | Cm | SoD2 (G) | 0% | | 27% | 28.78 | 47% | 26.55 | | |
| 0407-03 | H | SO | Cm | SoD2 (G) | 0% | | 7% | 24.84 | 33% | 29.32 | | |
| 0407-04 | H | SO | Cm | SoD2 (G) | 20% | 25.56 | 27% | 27.18 | 40% | 25.28 | | |
| 0407-06 | H | SO | Cm | SoD2 (G) | 7% | 31.07 | 7% | 26.16 | 13% | 22.52 | 67% | 28.81 |
| 0407-07 | H | SO | Cm | SoD2 (G) | 20% | 27.37 | 13% | 25.96 | 27% | 25.85 | 80% | 27.26 |
| 0407-09 | H | SO | Cm | SoD2 (G) | 13% | 26.05 | 27% | 26.83 | 33% | 22.90 | | |
| 0407-10 | H | SO | Cm | SoD2 (G) | 7% | 23.57 | 27% | 26.04 | 47% | 25.32 | | |
| 0407-11 | H | SO | Cm | SoD2 (G) | 7% | 26.75 | 33% | 26.21 | 67% | 24.87 | | |
| 0407-12 | H | SO | Cm | SoD2 (G) | 7% | 31.66 | 13% | 24.51 | 33% | 23.39 | | |
| 0407-13 | H | SO | Cm | SoD2 (G) | 13% | 23.52 | 27% | 27.89 | 40% | 23.54 | | |
| 0408-01 | H | SO | Cm | SoD7 (G) | 13% | 24.88 | 27% | 25.55 | 53% | 26.15 | | |
| 0408-07A | H | SO | Cm | SoD7 (G) | 7% | 23.40 | 20% | 28.48 | 27% | 22.64 | 80% | 27.08 |
| Hamlin NT Control | H | SO | Cm | Control | 0% | | 20% | 28.83 | 40% | 24.59 | 87% | 25.92 |
| 0409-02 | H | SO | Cm | SoD2 (C) | 7% | 27.34 | 0% | | 20% | 24.04 | 80% | 26.23 |
| 0409-03 | H | SO | Cm | SoD2 (C) | 7% | 22.28 | 7% | 28.79 | 27% | 22.12 | 93% | 25.52 |
| 0409-06 | H | SO | Cm | SoD2 (C) | 0% | | 20% | 26.52 | 40% | 24.01 | | |
| 0409-07 | H | SO | Cm | SoD2 (C) | 0% | | 20% | 26.31 | 40% | 23.17 | | |
| 0410-01 | H | SO | Cm | SoD7 (C) | 0% | | 40% | 22.96 | 73% | 24.78 | | |
| 0507-01 | RR | SO | Cm | SoD2 (G) | 0% | | 47% | 26.35 | 60% | 23.60 | | |
| 0507-02 | RR | SO | Cm | SoD2 (G) | 13% | 28.26 | 40% | 22.18 | 47% | 25.14 | | |
| 0507-03 | RR | SO | Cm | SoD2 (G) | 13% | 24.61 | 47% | 26.64 | 60% | 23.59 | | |
| 0507-04 | RR | SO | Cm | SoD2 (G) | 13% | 26.21 | 27% | 25.25 | 40% | 24.63 | | |
| 0507-07 | RR | SO | Cm | SoD2 (G) | 0% | | 13% | 27.42 | 27% | 22.61 | 67% | 29.19 |
| O507-08 | RR | SO | Cm | SoD2 (G) | 7% | 25.97 | 40% | 26.37 | 40% | 24.03 | | |
| 0507-10 | RR | SO | Cm | SoD2 (G) | 7% | 26.04 | 27% | 25.71 | 40% | 25.29 | | |
| 0507-11 | RR | SO | Cm | SoD2 (G) | 0% | | 40% | 26.51 | 53% | 22.26 | | |
| 0507-12 | RR | SO | Cm | SoD2 (G) | 0% | | 20% | 17.61 | 13% | 22.56 | 77% | 27.17 |
| 0507-15 | RR | SO | Cm | SoD2 (G) | 13% | 24.49 | 53% | 25.65 | 73% | 23.10 | | |
| 0508-02 | RR | SO | Cm | SoD7 (G) | 13% | 29.40 | 47% | 26.25 | 73% | 23.90 | | |
| 0508-03 | RR | SO | Cm | SoD7 (G) | 7% | 31.44 | 33% | 24.53 | 60% | 25.37 | | |
| 0508-04 | RR | SO | Cm | SoD7 (G) | 13% | 25.65 | 20% | 28.00 | 60% | 25.74 | | |
| 0508-06 | RR | SO | Cm | SoD7 (G) | 0% | | 7% | 27.72 | 27% | 24.33 | 79% | 25.56 |
| 0508-07 | RR | SO | Cm | SoD7 (G) | 27% | 26.86 | 67% | 25.30 | 100% | 24.76 | 100% | 21.87 |
| 0508-08 | RR | SO | Cm | SoD7 (G) | 7% | 24.35 | 27% | 24.55 | 53% | 23.07 | | |
| 0508-09 | RR | SO | Cm | SoD7 (G) | 20% | 25.55 | 33% | 24.69 | 60% | 24.40 | | |
| 0508-10 | RR | SO | Cm | SoD7 (G) | 7% | 25.96 | 33% | 25.94 | 47% | 23.30 | | |
| Rhode Red NT Control | RR | SO | Cm | Control | 13% | 27.03 | 27% | 25.64 | 67% | 25.46 | 100% | 22.32 |
| 0509-02 | RR | SO | Cm | SoD2 (C) | 13% | 24.36 | 53% | 23.07 | 60% | 23.77 | | |
| 0509-03 | RR | SO | Cm | SoD2 (C) | 13% | 25.28 | 27% | 26.60 | 53% | 26.02 | | |
| 0509-07 | RR | SO | Cm | SoD2 (C) | 7% | 30.19 | 20% | 24.85 | 47% | 25.71 | | |
| 0509-10 | RR | SO | Cm | SoD2 (C) | 20% | 27.29 | 20% | 24.93 | 67% | 26.26 | | |

TABLE 4-continued

Generation 2 Infection Data

| Code | Scion[1] | Genotype[2] | Rootstock[3] | Gene[4] | 1st Sampling Day 0 | 1st Sampling Mean Ct | 2nd Sampling Day 73 | 2nd Sampling Mean Ct | 3rd Sampling Day 170 | 3rd Sampling Mean Ct | Partial 4th Sampling Day 317 | Partial 4th Sampling Mean Ct |
|---|---|---|---|---|---|---|---|---|---|---|---|---|
| 0510-02 | RR | SO | Cm | SoD7 (C) | 7% | 30.66 | 27% | 23.36 | 47% | 24.42 | | |
| 0510-03 | RR | SO | Cm | SoD7 (C) | 7% | 22.01 | 20% | 24.70 | 53% | 25.39 | | |
| 0510-05 | RR | SO | Cm | SoD7 (C) | 7% | 31.54 | 7% | 31.03 | 7% | 31.22 | 17% | 35.78 |
| 0510-06 | RR | SO | Cm | SoD7 (C) | 0% | | 33% | 26.56 | 80% | 24.48 | 93% | 23.67 |
| 0510-08 | RR | SO | Cm | SoD7 (C) | 7% | 23.07 | 47% | 25.29 | 60% | 22.32 | | |
| 0510-09 | RR | SO | Cm | SoD7 (C) | 0% | | 33% | 24.63 | 47% | 24.02 | | |
| 0510-10 | RR | SO | Cm | SoD7 (C) | 0% | | 20% | 27.68 | 60% | 25.16 | | |
| Extra NT Controls | | | | | | | | | | | | |
| Hamlin | H | SO | Cm | Control | 0% | | 40% | 27.29 | 47% | 23.25 | | |
| Hamlin | H | SO | Cm | Control | 7% | 24.49 | 13% | 24.87 | 33% | 25.58 | | |
| Hamlin | H | SO | Cm | Control | 0% | | 33% | 24.44 | 33% | 25.82 | | |
| Rhode Red | RR | SO | Cm | Control | 7% | 24.61 | 33% | 26.27 | 27% | 22.98 | | |
| Rhode Red | RR | SO | Cm | Control | 0% | | 40% | 27.07 | 33% | 24.49 | | |
| Rhode Red | RR | SO | Cm | Control | 7% | 24.36 | 33% | 29.01 | 47% | 26.50 | | |

[1]H = Hamlin; RR = Rhode Red
[2]SO = Sweet Orange
[3]Cm = Cleopatra mandarin
[4](G) = GenScript-optimized sequence; (C) = CODA-optimized sequence

Example 13: Propagation and Resistance of Generation 3

One Sweet Orange variety and one grapefruit variety were transformed with *Agrobacterium* comprising one of the following defensin gene constructs:

(a) GenScript-optimized SoD2 with no signal peptide (SEQ ID NO: 3), or (b) GenScript-optimized SoD7 with no signal peptide (SEQ ID NO: 4).

A total of 36 transformation events were observed. Plants were cultivated as described herein and bacterial resistance was assessed as described. A first set of samples were collected after 5 months in the psyllid house (Day 0). Subsequent samples were collected the indicated number of days after the first sampling (e.g., Day 103=5 months+103 days). Results are shown in FIG. 16 and Table 5.

TABLE 5

Generations 2 and 3 Infection Data

| Code | Scion[1] | Genotype[2] | Rootstock[3] | Gene[4] | 1st Sampling Day 0 | 2nd Sampling Day 103 | 2nd Sampling Avg Ct | 2nd Sampling Ct of Positive | 3rd Sampling Day 215 | 3rd Sampling Avg Ct | 3rd Sampling Ct of Positive |
|---|---|---|---|---|---|---|---|---|---|---|---|
| 41103 | H | SO | Cm | SoD2 (−P) | 10% | 10% | 37.98 | 24.78 | 10% | 36.83 | 19.62 |
| 41108 | H | SO | Cm | SoD2 (−P) | 0% | 0% | 40.00 | | 0% | 38.93 | |
| 41107 | H | SO | Cm | SoD2 (−P) | 10% | 14% | 37.24 | 23.44 | 14% | 35.28 | 21.02 |
| 41110 | H | SO | Cm | SoD2 (−P) | 0% | 10% | 38.18 | 26.35 | 20% | 35.24 | 23.33 |
| 40918 | H | SO | Cm | SoD2 (C) | 0% | 0% | 39.74 | | 10% | 36.97 | 21.53 |
| 40915 | H | SO | Cm | SoD2 (C) | 0% | 11% | 38.07 | 25.22 | 22% | 34.31 | 24.44 |
| 41004 | H | SO | Cm | SoD7 (C) | 0% | 10% | 38.37 | 23.72 | 20% | 35.24 | 25.54 |
| 40814 | H | SO | Cm | SoD7 (G) | 0% | 20% | 36.62 | 26.39 | 10% | 36.85 | 24.35 |
| 40817 | H | SO | Cm | SoD7 (G) | 10% | 10% | 37.97 | 22.93 | 30% | 34.17 | 23.40 |
| 11206 | RR | Gf | Cm | SoD7 (−P) | 0% | 30% | 35.18 | 23.93 | 40% | 32.27 | 24.69 |
| 11204 | RR | Gf | Cm | SoD7 (−P) | 0% | 10% | 37.63 | 24.56 | 30% | 33.49 | 22.16 |
| 40813 | H | SO | Cm | SoD7 (G) | 10% | 11% | 37.73 | 22.63 | 44% | 31.96 | 22.62 |
| 11201 | RR | Gf | Cm | SoD7 (−P) | 0% | 30% | 35.87 | 26.76 | 30% | 33.71 | 23.06 |
| 41109 | H | SO | Cm | SoD2 (−P) | 0% | 10% | 38.46 | 24.64 | 10% | 37.25 | 22.14 |
| 11208 | RR | Gf | Cm | SoD7 (−P) | 0% | 0% | 39.82 | | 0% | 38.42 | |
| 11108 | RR | Gf | Cm | SoD2 (−P) | 0% | 0% | 38.60 | | 13% | 36.15 | 21.66 |
| 11103 | RR | Gf | Cm | SoD2 (−P) | 0% | 20% | 36.98 | 26.00 | 20% | 33.73 | 19.99 |
| 60811 | M | SO | Cm | SoD7 (G) | 0% | 0% | 39.66 | | 0% | 39.03 | |
| Marrs WT | M | SO | Cm | Control | 0% | 10% | 38.81 | 28.14 | 20% | 35.57 | 24.93 |
| 40820 | H | SO | Cm | SoD7 (G) | 10% | 20% | 36.99 | 25.96 | 30% | 34.94 | 23.65 |
| 41101 | H | SO | Cm | SoD2 (−P) | 0% | 10% | 37.65 | 23.09 | 20% | 34.53 | 21.92 |
| Ruby Red WT | RR | Gf | Cm | Control | 0% | 0% | 39.39 | | 30% | 34.88 | 26.93 |
| 11105 | RR | Gf | Cm | SoD2 (−P) | 0% | 10% | 38.64 | 26.38 | 20% | 36.32 | 24.70 |
| 40810 A | H | SO | Cm | SoD7 (G) | 0% | 25% | 35.46 | 24.94 | 50% | 30.83 | 23.08 |
| 11203 | RR | Gf | Cm | SoD7 (−P) | 0% | 20% | 37.84 | 29.19 | 20% | 35.55 | 21.51 |
| 40914 | H | SO | Cm | SoD2 (C) | 0% | 0% | 39.66 | | 30% | 35.22 | 26.78 |
| 40812 | H | SO | Cm | SoD7 (G) | 0% | 10% | 37.99 | 27.44 | 20% | 35.67 | 21.75 |
| 41102 | H | SO | Cm | SoD2 (−P) | 10% | 40% | 35.03 | 27.58 | 60% | 29.83 | 23.83 |

TABLE 5-continued

Generations 2 and 3 Infection Data

| Code | Scion[1] | Genotype[2] | Rootstock[3] | Gene[4] | 1st Sampling Day 0 | 2nd Sampling Day 103 | Avg Ct | Ct of Positive | 3rd Sampling Day 215 | Avg Ct | Ct of Positive |
|---|---|---|---|---|---|---|---|---|---|---|---|
| Hamlin WT | H | SO | Cm | Control | 0% | 40% | 33.76 | 24.41 | 50% | 29.52 | 22.14 |
| 60813 | M | SO | Cm | SoD7 (G) | 0% | 0% | 40.00 | | 13% | 37.06 | 24.02 |
| 60804 | M | SO | Cm | SoD7 (G) | 10% | 0% | 39.80 | | 0% | 37.74 | |
| 60703 | M | SO | Cm | SoD2 (G) | 0% | 33% | 36.35 | 30.88 | 33% | 36.07 | 25.07 |
| 60862 | M | SO | Cm | SoD7 (G) | 0% | 0% | 39.18 | | 10% | 37.87 | 31.23 |
| 60702 | M | SO | Cm | SoD2 (G) | 0% | 10% | 38.30 | 27.16 | 20% | 35.46 | 24.11 |
| 41211 | H | SO | Cm | SoD7 (−P) | 10% | 20% | 36.47 | 24.33 | 30% | 34.02 | 21.20 |
| 41203 | H | SO | Cm | SoD7 (−P) | 0% | 0% | 39.93 | | 0% | 38.17 | |
| 60812 | M | SO | Cm | SoD7 (G) | 0% | 0% | 40.00 | | 10% | 36.79 | 23.40 |
| 60810 | M | SO | Cm | SoD7 (G) | 10% | 20% | 37.25 | 26.25 | 70% | 27.87 | 23.44 |
| 60767 | M | SO | Cm | SoD2 (G) | 0% | 10% | 38.51 | 25.13 | 40% | 33.77 | 25.40 |
| 60701 | M | SO | Cm | SoD2 (G) | 0% | 20% | 37.45 | 28.07 | 50% | 30.37 | 23.85 |
| 41210 | H | SO | Cm | SoD7 (−P) | 0% | 0% | 39.60 | | 20% | 34.62 | 22.91 |
| 41202 | H | SO | Cm | SoD7 (−P) | 10% | 17% | 35.89 | 23.81 | 50% | 30.85 | 22.69 |
| 60706 | M | SO | Cm | SoD2 (G) | 0% | 10% | 37.64 | 25.23 | 50% | 30.82 | 23.24 |
| 41209 | H | SO | Cm | SoD7 (−P) | 0% | 40% | 33.36 | 24.97 | 70% | 27.11 | 22.03 |
| 41113 | H | SO | Cm | SoD2 (−P) | 20% | 60% | 31.02 | 25.03 | 80% | 25.36 | 21.70 |
| 41215 | H | SO | Cm | SoD7 (−P) | 20% | 40% | 33.73 | 24.32 | 70% | 25.95 | 21.94 |
| 60808 | M | SO | Cm | SoD7 (G) | 0% | 0% | 39.35 | | 22% | 36.32 | 22.11 |
| 41208 | H | SO | Cm | SoD7 (−P) | 0% | 0% | 39.62 | | 11% | 37.30 | 22.04 |
| 41112 | H | SO | Cm | SoD2 (−P) | 20% | 20% | 35.94 | 25.32 | 40% | 31.22 | 22.22 |
| 41214 | H | SO | Cm | SoD7 (−P) | 0% | 20% | 36.57 | 24.47 | 50% | 29.72 | 21.99 |
| 60705 | M | SO | Cm | SoD2 (G) | 0% | 10% | 37.96 | 23.82 | 10% | 36.57 | 21.02 |
| 41204 | H | SO | Cm | SoD7 (−P) | 0% | 0% | 40.00 | | 10% | 36.50 | 22.28 |
| 41111 | H | SO | Cm | SoD2 (−P) | 10% | 13% | 37.98 | 23.82 | 25% | 35.18 | 24.46 |
| Hamlin WT | H | SO | Cm | Control | 0% | 25% | 35.56 | 26.41 | 55% | 29.82 | 22.51 |
| Marrs WT | M | SO | Cm | Control | 0% | 0% | 39.16 | | 33% | 33.11 | 22.73 |

[1]H = Hamlin; RR = Ruby Red; M = Marrs
[2]SO = Sweet Orange; Gf = Grapefruit
[3]Cm = Cleopatra mandarin
[4](G) = GenScript-optimized sequence; (C) = CODA-optimized sequence; (−P) = DNA 2.0-optimized sequence with no signal peptide

Example 14: Propagation and Resistance of Generation 4

A first line of Sweet Orange (2 varieties), one grapefruit, and two rootstocks were prepared to co-express (i) GenScript SoD2 with tobacco PR-1b signal peptide (SEQ ID NO: 9) and (ii) GenScript SoD7 with tobacco PR-1b signal peptide (SEQ ID NO: 10). More specifically, plants were transformed with a double defensin construct comprising, in a 5' to 3' direction SoD2, uidA, and SoD7 (13). A total of 29 transformation events were observed with another 28 GUS-positive candidates in tissue culture or just out of tissue culture. Plants confirmed to co-express SoD2 and SoD7 will be cultivated and evaluated in infection assays to determine the degree to which coexpression prevents, ameliorates, and/or treats infection.

FIG. 9 is a representation of a Southern blot (membrane was exposed to probes for both SoD2 and SoD7) showing insertion number among transgenic events in Hamlin transformed with a double defensin construct comprising SoD2 and SoD7 (0413). FIG. 10 also shows insertion number among transgenic events in Hamlin transformed with a double defensin construct comprising SoD2 and SoD7 (0413).

Rio Red plants (02) were transformed with a double defensin construct (13). FIG. 17 is a representation of a Southern blot confirming insertion of both SoD2 and SoD7 in these Rio Red plants. DNA was cut with a single restriction enzyme that cut within SoD2, uidA, and SoD7 and blotted with both SoD2 and SoD7 probes simultaneously. FIG. 18 is a representation of a northern blot showing RNA transcripts isolated from Rio Red plants (marked "02") transformed with SoD2 (GenScript-optimized sequence with signal peptide) and SoD7 (GenScript-optimized sequence with signal peptide). RNA transcripts isolated from Hamlin plants (marked "04") are also shown.

Example 15: Propagation and Resistance of Generation 5

Evaluation of coexpression of SoD2 and SoD7 is underway. A line of Sweet Orange (1 variety) was prepared to co-express (i) DNA 2.0 SoD2 with no signal peptide (SEQ ID NO: 30) and (ii) DNA 2.0 SoD7 with no signal peptide (SEQ ID NO: 31). Transformation and expression may be confirmed by Southern and northern blotting analysis. Plants may be cultivated as described herein and bacterial resistance evaluated as described. Plants confirmed to co-express SoD2 and SoD7 may be cultivated and evaluated in infection assays to determine the degree to which coexpression prevents, ameliorates, and/or treats infection.

Example 16: Expression of Defensin Constructs in Various Plants

Stable expression of defensin constructs comprising nucleic acid sequences codon-optimized for citrus has been confirmed in the following:

| Cultivar | Gene Code | # Events |
|---|---|---|
| Rio Red Grapefruit | 13 | 18 |
| Ruby Red Grapefruit | 11 and 12 | 12 |

-continued

| Cultivar | Gene Code | # Events |
|---|---|---|
| Hamlin Sweet Orange | 07, 08, 09, 10, 11, 12, 13, and 16 | over 86 |
| Marrs Sweet Orange | 07 and 08 | 13 |
| Rohde Red Valencia Orange | 07, 08, 09, 10, 13 | over 48 |
| Frost Eureka Lemon | 13 and 16 | over 30 |
| Frost Lisbon Lemon | 13 and 16 | over 33 |
| C22 and Carrizo Citrange Rootstocks | 07, 08, 13 | 42 |
| Flying dragon and Swingle Rootstocks | 13 | Multiple GUS+ |

For all constructs, individual transformation events have been found spanning a range of expression levels from no expression (e.g., since Southern results demonstrate the gene is present, often in multiple copies, it may be that the transgene has been silenced) to low expression to high expression.

Example 17: Antibodies to SoD2 and SoD7

Antibodies were raised to SoD2 and SoD7. Full length SoD7 peptide was synthesized by GenScript. Aliquots of synthetic SoD7 (200 ug each time) were injected into each of 2 different rabbits every three weeks for a total of 4 injections. Sera was collected 2 weeks after the third and 2 weeks after the fourth injections. IgG was purified using a Protein A column. SoD7 specific IgG was purified by passing the IgG preparation over a column of synthetic SoD7 conjugated to agarose beads and then eluting with a low pH buffer Eluate was screened for binding to a dilution series from 1 ng to 100 ng synthetic SoD7. FIG. 19 is a Western blot illustrating binding of the purified SoD7-specific IgG antibodies to about 20 ng of SoD7 peptide in either transgenic plants (lanes 3, 4, and 6-9), non-transgenic plants spiked with synthetic SoD7 peptide (lane 5), or pure synthetic SoD7 (lane 10).

Example 18: Spinach Defensin Sequences and Codon Optimization

Spinach (*Spinacea oleracea*, viroflay) defensin gene sequences were assembled using next-generation sequencing reads deposited in NCBI sequence read archive (SRA) by employing bioinformatics tools and methods (e.g., Dohm et al., 2013, *Nature,* 505, 546-549; Yao et al., 2005, *Plant Mol. Biol,* 57, 445-460). SEQ ID NOs: 81, 82, 83, 84, 85, and 86 are specific example embodiments of assembled scaffold regions that comprise nucleic acid sequences of spinach (*Spinacia oleracea*) defensin genes. Table 6 illustrates specific example embodiments of assembled scaffold regions, nucleic acid sequences, and peptide sequences of spinach defensins.

TABLE 6

Example embodiments of assembled scaffold regions, nucleic acid sequences, and peptide sequences from Spinach (*Spinacea oleracea*, viroflay) encoding defensin genes.

| Spinach Scaffold Region (SEQ ID NO) | Nucleic Acid Sequence of Defensin Gene (SEQ ID NO) | Genscript Optimized Synthetic Defensin Gene (SEQ ID NO) | VGD Optimized Synthetic Defensin Gene (SEQ ID NO) | Defensin Peptide Sequence (SEQ ID NO) |
|---|---|---|---|---|
| 81 | 39 | 46 | 52 | 32 |
| 82 | 40 | 47 | 53 | 33 |
| 83 | 41 | 48 | 54 | 34 |
| 84 | 42 | NA | 55 | 35 |
| 84 | 43 | 49 | 56 | 36 |
| 85 | 44 | 50 | 57 | 37 |
| 86 | 45 | 51 | 58 | 38 |

SEQ ID NOs: 39, 40, 41, 42, 43, 44, and 45 are specific example embodiments of nucleic acid sequences of spinach (*Spinacia oleracea*) defensin genes, Def1, Def2, Def3, Def4. Defy, Def6, and Def7, respectively.

Nucleic acid sequences encoding defensin genes (e.g. SEQ ID NOS: 39-45) were optimized using the GenScript codon-optimization algorithm. Briefly, the algorithm uses a complex sorting matrix, including transcription, translation and protein folding, to sift through over 10,000 candidate sequences to identify a predicted best sequence for expression in a given organism. SEQ ID NOs 46, 47, 48, 49, 50, and 51 are specific example embodiments of Genscript codon optimized sequences of SEQ ID NOs: 39, 40, 41, 43, 44, and 45, respectively.

Nucleic acid sequences encoding defensin genes (e.g. SEQ ID NOS: 39-45) were optimized in a two-step approach using the Visual Gene Developer (VGD) platform of Jung S and McDonald K, 2011, *BMC Bioinformatics* 12: 340-353. First, the sequences were optimized for minimum mRNA secondary structure and binding energy (Gibbs free energy [G]=−0.2 to 0 kcal/base). Next, the optimized mRNA sequences were subjected to favorable synonymous codon optimization using a pre-calculated Codon Adaptation Index (CAI) for *Citrus sinensis* (Csi). The Csi-CAI was calculated from a codon usage matrix generated using data from 116 Csi codon sequences (47126 codons) available in Kazusa codon database (www.kazusa.or.jp/codon). SEQ ID NOs 52, 53, 54, 55, 56, 57, and 58 are specific example embodiments of VGD codon optimized sequences of SEQ ID NOs: 39, 40, 41, 42, 43, 44, and 45, respectively.

Predicted mRNA secondary structures of SEQ ID NOs: 39, 40, 41, 42, 43, 44, and 45, may be constructed using the Visual Gene Developer platform of Jung S and McDonald K, 2011, *BMC Bioinformatics* 12: 340-353.

Example 19: SEQ ID NOS 32, 33, 34, 35, 36, 37, and 38 Peptide Sequence Alignment SEQ ID NOs: 32, 33, 34, 35, 36, 37, and 38 are specific example embodiments of defensin peptide sequences from spinach (*Spinacia oleracea*).

Multiple sequence alignment of SEQ ID NO: 32 (Genomic D1), SEQ ID NO: 33 (Genomic D2), SEQ ID NO: 34 (Genomic D3), SEQ ID NO: 35 (Genomic D4), SEQ ID NO: 36 (Genomic D5), SEQ ID NO: 37 (Genomic D6), and SEQ ID NO: 38 (Genomic D7) was performed using ClustalW. FIG. 20 illustrates the resulting alignment of the spinach defensin peptides. The consensus symbols are indicated below the alignments with identically conserved residues indicated by black shading and an asterisk. Amino acids with >50% identity are shaded gray and marked with a period.

FIG. 21A and FIG. 21B illustrate the results of phylogenetic analyses of SEQ ID NOs: 32, 33, 34, 35, 36, 37, and 38. Using the sequence alignment from FIG. 20, tree construction was performed following (A) the Neighbor Joining method as illustrated in FIG. 21A, and (B) the Maximum Likelihood method as illustrated in FIG. 21B.

In the neighbor joining analysis shown in FIG. 21A, optimal tree topology with a minimum sum of branch length value settings were selected. A Bootstrap test with 1000 replicates resulted in the percentage of replicate trees in which associated taxa clustered together. These values are indicated next to their respective branches in FIG. 21A. Branch length units indicate the number of amino acid substitutions per site, and represent evolutionary distances as computed using the Poisson correction method.

FIG. 21B illustrates a maximum likelihood tree wherein the tree topology with the highest log likelihood is shown. The heuristic search was performed using initial tree(s) generated using the Neighbor-Join and BioNJ algorithms to a matrix of pairwise distances under the JTT substitution model, followed by selection of a tree topology with superior log likelihood value.

Example 21: Peptide Sequence Analysis of Spinach Defensins

Multiple sequence alignment of SEQ ID NO: 32 (Genomic D1), SEQ ID NO: 33 (Genomic D2), SEQ ID NO: 34 (Genomic D3), SEQ ID NO: 35 (Genomic D4), SEQ ID NO: 36 (Genomic D5), SEQ ID NO: 37 (Genomic D6), SEQ ID NO: 38 (Genomic D7), and reported spinach defensin subfamily IV sequences (Segura D1-Segura D7) as described by Segura, A. et al., 1998, *FEBS Letters* 435: 159-162 was performed using ClustalW. FIG. 22 illustrates the resulting alignment. The consensus symbols are indicated below the alignments with identically conserved residues indicated by black shading and an asterisk. Amino acids with >50% identity are shaded gray and marked with a period.

Phylogenetic analyses were performed using the multiple sequence alignment illustrated in FIG. 22. Tree construction was performed using (A) the Neighbor Joining method as illustrated in FIG. 23A, and (B) the Maximum Likelihood method as illustrated in FIG. 23B.

In the neighbor joining analysis shown in FIG. 23A, optimal tree topology with a minimum sum of branch length value settings were selected. A Bootstrap test with 1000 replicates resulted in the percentage of replicate trees in which associated taxa clustered together. These values are indicated next to their respective branches in FIG. 23A. Branch length units indicate the number of amino acid substitutions per site, and represent evolutionary distances as computed using the Poisson correction method.

FIG. 23B illustrates a maximum likelihood tree wherein the tree topology with the highest log likelihood is shown. The heuristic search was performed using initial tree(s) generated using the Neighbor-Join and BioNJ algorithms to a matrix of pairwise distances under the JTT substitution model, followed by selection of a tree topology with superior log likelihood value.

Example 22: Peptide Sequence Analysis of Defensins

Multiple sequence alignment was performed using ClustalW to compare the following peptide sequences: SEQ ID NO: 32 (Genomic D1); SEQ ID NO: 33 (Genomic D2); SEQ ID NO: 34 (Genomic D3); SEQ ID NO: 35 (Genomic D4); SEQ ID NO: 36 (Genomic D5); SEQ ID NO: 37 (Genomic D6); SEQ ID NO: 38 (Genomic D7); reported spinach defensin subfamily IV sequences (Segura D1-Segura D7) as described by Segura, A. et al., 1998, *FEBS Letters* 435: 159-162; representative group I defensin sequences (Rs-AFP2, At-AFP1, Hs-AFP1) as illustrated in Segura et al.; representative group II defensin sequences (Ah-Ampl), Dm-AMP1) as illustrated in Segura et al.; and representative group III defensing sequences (St-PTH1, SIalpha2) as illustrated in Segura et. al. FIG. 24 illustrates the resulting alignment. The consensus symbols are indicated below the alignments with identically conserved residues indicated by black shading and an asterisk. Amino acids with >50% identity are shaded gray and marked with a period.

Phylogenetic analyses were performed using the multiple sequence alignment illustrated in FIG. 24. Tree construction was performed using (A) the Neighbor Joining method as illustrated in FIG. 25A, and (B) the Maximum Likelihood method as illustrated in FIG. 25B.

In the neighbor joining analysis shown in FIG. 25A, optimal tree topology with a minimum sum of branch length value settings were selected. A Bootstrap test with 1000 replicates resulted in the percentage of replicate trees in which associated taxa clustered together. These values are indicated next to their respective branches in FIG. 25A. Branch length units indicate the number of amino acid substitutions per site, and represent evolutionary distances as computed using the Poisson correction method.

FIG. 25B illustrates a maximum likelihood tree wherein the tree topology with the highest log likelihood is shown. The heuristic search was performed using initial tree(s) generated using the Neighbor-Join and BioNJ algorithms to a matrix of pairwise distances under the JTT substitution model, followed by selection of a tree topology with superior log likelihood value.

Example 23: Constructs

Table 7 illustrates specific example embodiments of chimeric nucleic acid sequences encoding a signal peptide and a defensin gene codon-optimized for citrus. Signal peptides and structural gene coding sequences shown are flanked on either side by specific restriction enzyme sites. These sequences were used to construct expression cassettes, vectors, and transformed *Agrobacterium* for preparation of transgenic plants.

TABLE 7

| Example embodiments of chimeric nucleotide sequences of defensin genes. The nucleotide sequences were optimized for codon usage in *Citrus*. | | |
|---|---|---|
| Defensin Gene | Source of the Optimized Synthetic Gene (SEQ ID NO) | A chimeric nucleotide sequence. The 5' nucleotides include the cloning site and a preferred context for the start codon. The 3' nucleotides include the cloning site. |
| Def2 | GenScript (47) | SEQ ID NO: 59 |
| | VGD (53) | SEQ ID NO: 60 |

FIG. 26A and FIG. 26B illustrate specific example embodiments of expression cassettes encoding a defensin gene codon-optimized for citrus. Upstream of the defensin gene coding sequences is a promoter sequence, a translational enhancer, and a XbaI restriction enzyme site. While downstream of the defensin gene coding sequence is a KpnI restriction enzyme site, a translational enhancer, and a terminator sequence. The entire construct is flanked by the left and right borders of the Ti plasmid. FIG. 27 illustrates specific example embodiments of expression cassettes encoding a multiple defensin genes, with each defensin gene codon-optimized for citrus. FIG. 28 illustrates the potential combinations for co-expression of spinach defensins.

Example 24: Constructs

Examples of successful generation of transgenic plants achieved using the compositions and methods of the disclosure are shown in Tables 8 and 9.

TABLE 8

| *Citrus* | | |
|---|---|---|
| Genomic Spinach Defensin Expression Construct | Number of Transgenic Events | Variety-Citrus |
| Defensin 1 | 1 | Mexican Lime |
| Defensin 3 | 1 | Mexican Lime |
| Defensin 5 | 4 | Mexican Lime |
| Defensin 6 | 4 | Mexican Lime |
| Defensin 3 | 2 | Sour Orange (root stock) |
| Defensin 6 | 2 | Sour Orange (root stock) |
| Defensin 1 | 8 | Frost Lisbon Lemon |
| Defensin 2 | 11 | Frost Lisbon Lemon |

TABLE 9

| Potato | | |
|---|---|---|
| Genomic Spinach Defensin Expression Construct | Number of Transgenic Events | Variety-Potato |
| Defensin 1 | 4 | Atlantic |
| Defensin 2 | 6 | Atlantic |
| Defensin 3 | 2 | Atlantic |
| Defensin 5 | 8 | Atlantic |
| Defensin 6 | 8 | Atlantic |
| Defensin 7 | 2 | Atlantic |

What is claimed is:

1. A citrus or potato plant comprising at least one heterologous *Spinach oleracea* defensin peptide comprising a first heterologous *Spinach oleracea* defensin peptide, wherein the amino acid sequence of the first heterologous *Spinach oleracea* defensin peptide is at least 95% identical to SEQ ID NO: 32, at least 95% identical to SEQ ID NO: 33, at least 95% identical to SEQ ID NO: 34, at least 95% identical to SEQ ID NO: 35, at least 95% identical to SEQ ID NO: 36, at least 95% identical to SEQ ID NO: 37, or at least 95% identical to SEQ ID NO: 38, and wherein the *Spinach oleracea* defensin peptide has anti-microbial activity against *Xanthomonas axonopodis* and *Candidatus Liberibacter asiaticus* in the citrus or potato plant.

2. The citrus or potato plant according to claim 1, wherein the amino acid sequence of the first heterologous *Spinach oleracea* defensin peptide is at least 98% identical to the amino acid sequence of SEQ ID NO: 32, at least 98% identical to the amino acid sequence of SEQ ID NO: 33, at least 98% identical to the amino acid sequence of SEQ ID NO: 34, at least 98% identical to the amino acid sequence of SEQ ID NO: 35, at least 98% identical to the amino acid sequence of SEQ ID NO: 36, at least 98% identical to the amino acid sequence of SEQ ID NO: 37, or at least 98% identical to the amino acid sequence of SEQ ID NO: 38, and wherein the *Spinach oleracea* defensin peptide has anti-microbial activity against *Xanthomonas axonopodis* and *Candidatus Liberibacter asiaticus* in the citrus or potato plant.

3. The citrus or potato plant according to claim 1, wherein the amino acid sequence of the first heterologous *Spinach oleracea* defensin peptide is 100% identical to the amino acid sequence of SEQ ID NO: 32, 100% identical to the amino acid sequence of SEQ ID NO: 33, 100% identical to the amino acid sequence of SEQ ID NO: 34, 100% identical to the amino acid sequence of SEQ ID NO: 35, 100% identical to the amino acid sequence of SEQ ID NO: 36, 100% identical to the amino acid sequence of SEQ ID NO: 37, or 100% identical to the amino acid sequence of SEQ ID NO: 38, and wherein the *Spinach oleracea* defensin peptide has anti-microbial activity against *Xanthomonas axonopodis* and *Candidatus Liberibacter asiaticus* in the citrus or potato plant.

4. The citrus or potato plant according to claim 1 further comprising a second heterologous *Spinach oleracea* defensin peptide, wherein the amino acid sequence of the second heterologous *Spinach oleracea* defensin peptide is at least 95% identical to SEQ ID NO: 32, at least 95% identical to SEQ ID NO: 33, at least 95% identical to SEQ ID NO: 34, at least 95% identical to SEQ ID NO: 35, at least 95% identical to SEQ ID NO: 36, at least 95% identical to SEQ ID NO: 37, or at least 95% identical to SEQ ID NO: 38, and wherein the *Spinach oleracea* defensin peptide has anti-microbial activity against *Xanthomonas axonopodis* and *Candidatus Liberibacter asiaticus* in the citrus or potato plant.

5. The citrus or potato plant according to claim 4, wherein the amino acid sequence of the second heterologous *Spinach*

*oleracea* defensin peptide is at least 98% identical to the amino acid sequence of SEQ ID NO: 32, at least 98% identical to the amino acid sequence of SEQ ID NO: 33, at least 98% identical to the amino acid sequence of SEQ ID NO: 34, at least 98% identical to the amino acid sequence of SEQ ID NO: 35, at least 98% identical to the amino acid sequence of SEQ ID NO: 36, at least 98% identical to the amino acid sequence of SEQ ID NO: 37, or at least 98% identical to the amino acid sequence of SEQ ID NO: 38, and wherein the *Spinach oleracea* defensin peptide has anti-microbial activity against *Xanthomonas axonopodis* and *Candidatus Liberibacter asiaticus* in the citrus or potato plant.

6. The citrus or potato plant according to claim 4, wherein the amino acid sequence of the second heterologous *Spinach oleracea* defensin peptide is 100% identical to the amino acid sequence of SEQ ID NO: 32, 100% identical to the amino acid sequence of SEQ ID NO: 33, 100% identical to the amino acid sequence of SEQ ID NO: 34, 100% identical to the amino acid sequence of SEQ ID NO: 35, 100% identical to the amino acid sequence of SEQ ID NO: 36, 100% identical to the amino acid sequence of SEQ ID NO: 37, or 100% identical to the amino acid sequence of SEQ ID NO: 38, and wherein the *Spinach oleracea* defensin peptide has anti-microbial activity against *Xanthomonas axonopodis* and *Candidatus Liberibacter asiaticus* in the citrus or potato plant.

7. The citrus or potato plant according to claim 4, wherein the amino acid sequence of the first heterologous *Spinach oleracea* defensin peptide and the amino acid sequence of the second heterologous *Spinach oleracea* defensin peptide are different.

8. A citrus or potato plant comprising at least one heterologous *Spinach oleracea* defensin nucleic acid comprising a first heterologous *Spinach oleracea* defensin nucleic acid, wherein the nucleic acid sequence of the first heterologous *Spinach oleracea* defensin nucleic acid is at least 98% identical to SEQ ID NO: 46, at least 98% identical to SEQ ID NO: 47, at least 98% identical to SEQ ID NO: 48, at least 98% identical to SEQ ID NO: 49, at least 98% identical to SEQ ID NO: 50, at least 98% identical to SEQ ID NO: 51, at least 98% identical to SEQ ID NO: 52, at least 98% identical to SEQ ID NO: 53, at least 98% identical to SEQ ID NO: 54, at least 98% identical to SEQ ID NO: 55, at least 98% identical to SEQ ID NO: 56, at least 98% identical to SEQ ID NO: 57, or at least 98% identical to SEQ ID NO: 58, and wherein the *Spinach oleracea* defensin peptide has anti-microbial activity against *Xanthomonas axonopodis* and *Candidatus Liberibacter asiaticus* in the citrus or potato plant.

9. The citrus or potato plant according to claim 8, wherein the nucleic acid sequence of the first heterologous *Spinach oleracea* defensin nucleic acid is at least 99% identical to SEQ ID NO: 46, at least 99% identical to SEQ ID NO: 47, at least 99% identical to SEQ ID NO: 48, at least 99% identical to SEQ ID NO: 49, at least 99% identical to SEQ ID NO: 50, at least 99% identical to SEQ ID NO: 51, at least 99% identical to SEQ ID NO: 52, at least 99% identical to SEQ ID NO: 53, at least 99% identical to SEQ ID NO: 54, at least 99% identical to SEQ ID NO: 55, at least 99% identical to SEQ ID NO: 56, at least 99% identical to SEQ ID NO: 57, or at least 99% identical to SEQ ID NO: 58, and wherein *the Spinach oleracea* defensin peptide has anti-microbial activity against *Xanthomonas axonopodis* and *Candidatus Liberibacter asiaticus* in the citrus or potato plant.

10. The citrus or potato plant according to claim 8, wherein the nucleic acid sequence of the first heterologous *Spinach oleracea* defensin nucleic acid is 100% identical to the nucleic acid sequence of SEQ ID NO: 46, 100% identical to the nucleic acid sequence of SEQ ID NO: 47, 100% identical to the nucleic acid sequence of SEQ ID NO: 48, 100% identical to the nucleic acid sequence of SEQ ID NO: 49, 100% identical to the nucleic acid sequence of SEQ ID NO: 50, 100% identical to the nucleic acid sequence of SEQ ID NO: 51, 100% identical to the nucleic acid sequence of SEQ ID NO: 52, 100% identical to the nucleic acid sequence of SEQ ID NO: 53, 100% identical to the nucleic acid sequence of SEQ ID NO: 54, 100% identical to the nucleic acid sequence of SEQ ID NO: 55, 100% identical to the nucleic acid sequence of SEQ ID NO: 56, 100% identical to the nucleic acid sequence of SEQ ID NO: 57, or 100% identical to the nucleic acid sequence of SEQ ID NO: 58, and wherein the *Spinach oleracea* defensin peptide has anti-microbial activity against *Xanthomonas axonopodis* and *Candidatus Liberibacter asiaticus* in the citrus or potato plant.

11. The citrus or potato plant according to claim 8, further comprising a second heterologous *Spinach oleracea* defensin nucleic acid, wherein the nucleic acid sequence of the second heterologous *Spinach oleracea* defensin nucleic acid is at least 98% identical to SEQ ID NO: 46, at least 98% identical to SEQ ID NO: 47, at least 98% identical to SEQ ID NO: 48, at least 98% identical to SEQ ID NO: 49, at least 98% identical to SEQ ID NO: 50, at least 98% identical to SEQ ID NO: 51, or at least 98% identical to SEQ ID NO: 52, at least 98% identical to SEQ ID NO: 53, at least 98% identical to SEQ ID NO: 54, at least 98% identical to SEQ ID NO: 55, at least 98% identical to SEQ ID NO: 56, at least 98% identical to SEQ ID NO: 57, or at least 98% identical to SEQ ID NO: 58, and wherein the *Spinach oleracea* defensin peptide has anti-microbial activity against *Xanthomonas axonopodis* and *Candidatus Liberibacter asiaticus* in the citrus or potato plant.

12. The citrus or potato plant according to claim 8 further comprising a second heterologous *Spinach oleracea* defensin nucleic acid, wherein the nucleic acid sequence of the second heterologous *Spinach oleracea* defensin nucleic acid is at least 99% identical to SEQ ID NO: 46, at least 99% identical to SEQ ID NO: 47, at least 99% identical to SEQ ID NO: 48, at least 99% identical to SEQ ID NO: 49, at least 99% identical to SEQ ID NO: 50, at least 99% identical to SEQ ID NO: 51, or at least 99% identical to SEQ ID NO: 52, at least 99% identical to SEQ ID NO: 53, at least 99% identical to SEQ ID NO: 54, at least 99% identical to SEQ ID NO: 55, at least 99% identical to SEQ ID NO: 56, at least 99% identical to SEQ ID NO: 57, or at least 99% identical to SEQ ID NO: 58, and wherein the *Spinach oleracea* defensin peptide has anti-microbial activity against *Xanthomonas axonopodis* and *Candidatus Liberibacter asiaticus* in the citrus or potato plant.

13. The citrus or potato plant according to claim 8 further comprising a second heterologous *Spinach oleracea* defensin nucleic acid, wherein the nucleic acid sequence of the second heterologous *Spinach oleracea* defensin nucleic acid is 100% identical to SEQ ID NO: 46, 100% identical to SEQ ID NO: 47, 100% identical to SEQ ID NO: 48, 100% identical to SEQ ID NO: 49, 100% identical to SEQ ID NO: 50, 100% identical to SEQ ID NO: 51, 100% identical to SEQ ID NO: 52, 100% identical to SEQ ID NO: 53, 100% identical to SEQ ID NO: 54, 100% identical to SEQ ID NO: 55, 100% identical to SEQ ID NO: 56, 100% identical to SEQ ID NO: 57, or 100% identical to SEQ ID NO: 58, and wherein the *Spinach oleracea* defensin peptide has anti-microbial activity against *Xanthomonas axonopodis* and *Candidatus Liberibacter asiaticus* in the citrus or potato plant.

14. The citrus or potato plant according to claim 11, wherein the nucleic acid sequence of the first heterologous *Spinach oleracea* defensin nucleic acid and the nucleic acid sequence of the second heterologous *Spinach oleracea* defensin nucleic acid are different.

15. A composition comprising at least one heterologous *Spinach oleracea* defensin peptide comprising a first heterologous *Spinach oleracea* defensin peptide, wherein the amino acid sequence of the first heterologous *Spinach oleracea* defensin peptide is at least 95% identical to SEQ ID NO: 32, at least 95% identical to SEQ ID NO: 33, at least 95% identical to SEQ ID NO: 34, at least 95% identical to SEQ ID NO: 35, at least 95% identical to SEQ ID NO: 36, at least 95% identical to SEQ ID NO: 37, or at least 95% identical to SEQ ID NO: 38, and wherein the *Spinach oleracea* defensin peptide has anti-microbial activity against *Xanthomonas axonopodis* and *Candidatus Liberibacter asiaticus* in a citrus or potato plant.

16. The composition according to claim 15, wherein the amino acid sequence of the first heterologous *Spinach oleracea* defensin peptide is at least 98% identical to the amino acid sequence of SEQ ID NO: 32, at least 98% identical to the amino acid sequence of SEQ ID NO: 33, at least 98% identical to the amino acid sequence of SEQ ID NO: 34, at least 98% identical to the amino acid sequence of SEQ ID NO: 35, at least 98% identical to the amino acid sequence of SEQ ID NO: 36, at least 98% identical to the amino acid sequence of SEQ ID NO: 37, or at least 98% identical to the amino acid sequence of SEQ ID NO: 38, and wherein the *Spinach oleracea* defensin peptide has anti-microbial activity against *Xanthomonas axonopodis* and *Candidatus Liberibacter asiaticus* in a citrus or potato plant.

17. The composition according to claim 15, wherein the amino acid sequence of the first heterologous *Spinach oleracea* defensin peptide is 100% identical to the amino acid sequence of SEQ ID NO: 32, 100% identical to the amino acid sequence of SEQ ID NO: 33, 100% identical to the amino acid sequence of SEQ ID NO: 34, 100% identical to the amino acid sequence of SEQ ID NO: 35, 100% identical to the amino acid sequence of SEQ ID NO: 36, 100% identical to the amino acid sequence of SEQ ID NO: 37, or 100% identical to the amino acid sequence of SEQ ID NO: 38, and wherein the *Spinach oleracea* defensin peptide has anti-microbial activity against *Xanthomonas axonopodis* and *Candidatus Liberibacter asiaticus* in a citrus or potato plant.

18. The composition according to claim 15 further comprising a second heterologous *Spinach oleracea* defensin peptide, wherein the amino acid sequence of the second heterologous *Spinach oleracea* defensin peptide is at least 95% identical to SEQ ID NO: 32, at least 95% identical to SEQ ID NO: 33, at least 95% identical to SEQ ID NO: 34, at least 95% identical to SEQ ID NO: 35, at least 95% identical to SEQ ID NO: 36, at least 95% identical to SEQ ID NO: 37, or at least 95% identical to SEQ ID NO: 38, and wherein the *Spinach oleracea* defensin peptide has anti-microbial activity against *Xanthomonas axonopodis* and *Candidatus Liberibacter asiaticus* in a citrus or potato plant.

19. The composition according to claim 18, wherein the amino acid sequence of the second heterologous *Spinach oleracea* defensin peptide is at least 98% identical to the amino acid sequence of SEQ ID NO: 32, at least 98% identical to the amino acid sequence of SEQ ID NO: 33, at least 98% identical to the amino acid sequence of SEQ ID NO: 34, at least 98% identical to the amino acid sequence of SEQ ID NO: 35, at least 98% identical to the amino acid sequence of SEQ ID NO: 36, at least 98% identical to the amino acid sequence of SEQ ID NO: 37, or at least 98% identical to the amino acid sequence of SEQ ID NO: 38, and wherein the *Spinach oleracea* defensin peptide has anti-microbial activity against *Xanthomonas axonopodis* and *Candidatus Liberibacter asiaticus* in a citrus or potato plant.

20. The composition according to claim 18, wherein the amino acid sequence of the second heterologous *Spinach oleracea* defensin peptide is 100% identical to the amino acid sequence of SEQ ID NO: 32, 100% identical to the amino acid sequence of SEQ ID NO: 33, 100% identical to the amino acid sequence of SEQ ID NO: 34, 100% identical to the amino acid sequence of SEQ ID NO: 35, 100% identical to the amino acid sequence of SEQ ID NO: 36, 100% identical to the amino acid sequence of SEQ ID NO: 37, or 100% identical to the amino acid sequence of SEQ ID NO: 38, and wherein the *Spinach oleracea* defensin peptide has anti-microbial activity against *Xanthomonas axonopodis* and *Candidatus Liberibacter asiaticus* in a citrus or potato plant.

21. The composition according to claim 18, wherein the amino acid sequence of the first heterologous *Spinach oleracea* defensin peptide and the amino acid sequence of the second heterologous *Spinach oleracea* defensin peptide are different.

* * * * *

SEQUENCE LISTING

```
<160> NUMBER OF SEQ ID NOS: 119

<210> SEQ ID NO 1
<211> LENGTH: 52
<212> TYPE: PRT
<213> ORGANISM: Spinacia oleracea
<220> FEATURE:
<221> NAME/KEY: MISC_FEATURE
<222> LOCATION: (1)..(52)
<223> OTHER INFORMATION: mat_peptide; SoD2 peptide

<400> SEQUENCE: 1

Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Gly Tyr Pro Ala Gly Asp Cys Lys Gly Ile Arg Arg Arg Cys Met Cys
        35                  40                  45

Ser Lys Pro Cys
    50


<210> SEQ ID NO 2
<211> LENGTH: 38
<212> TYPE: PRT
<213> ORGANISM: Spinacia oleracea
<220> FEATURE:
<221> NAME/KEY: MISC_FEATURE
<222> LOCATION: (1)..(38)
<223> OTHER INFORMATION: mat_peptide; SoD7 peptide

<400> SEQUENCE: 2

Gly Ile Phe Ser Ser Arg Lys Cys Lys Thr Pro Ser Lys Thr Phe Lys
```

-continued

```
1               5                   10                  15

Gly Tyr Cys Thr Arg Asp Ser Asn Cys Asp Thr Ser Cys Arg Tyr Glu
            20                  25                  30

Gly Tyr Pro Ala Gly Asp
        35
```

<210> SEQ ID NO 3
<211> LENGTH: 162
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: SoD2 codon-optimized with GenScript

<400> SEQUENCE: 3

```
ggtattttct catctaggaa gtgcaaaact ccttcaaaga cttttaaggg aatttgcact     60

agggattcta attgcgatac ttcttgcaga tacgagggat atccagctgg cgattgcaaa    120

ggaattagga ggagatgtat gtgttcaaag ccatgttaat aa                       162
```

<210> SEQ ID NO 4
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: SoD7 codon-optimized with GenScript

<400> SEQUENCE: 4

```
ggaattttct cttcaaggaa gtgcaagact ccatctaaga ctttcaaggg atattgtact     60

agggattcta actgcgatac atcatgcaga tacgagggct atcctgctgg cgattaataa    120
```

<210> SEQ ID NO 5
<211> LENGTH: 162
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: SoD2 codon-optimized with CODA

<400> SEQUENCE: 5

```
ggtatctttt ctagtagaaa gtgtaagact ccttctaaga cttttaaagg tatttgcact     60

agagattcta attgtgacac ttcttgtaga tatgaaggtt atcctgctgg tgattgtaag    120

ggtattagaa gaagatgtat gtgttctaag ccttgttaat ag                       162
```

<210> SEQ ID NO 6
<211> LENGTH: 120
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: SoD7 codon-optimized with CODA

<400> SEQUENCE: 6

```
ggtatttttt catctcgtaa gtgtaagact ccttctaaga cttttaaggg ttattgcact     60

agagattcta attgtgatac atcttgtaga tatgaaggtt atcctgctgg tgattaatag    120
```

<210> SEQ ID NO 7
<211> LENGTH: 82
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chimeric peptide comprising a signal peptide and SoD2
<220> FEATURE:
<221> NAME/KEY: SIGNAL
<222> LOCATION: (1)..(30)
<223> OTHER INFORMATION: PR-1b signal peptide
<220> FEATURE:
<221> NAME/KEY: mat_peptide
<222> LOCATION: (31)..(82)
<223> OTHER INFORMATION: SoD2 peptide

<400> SEQUENCE: 7

```
Met Gly Phe Phe Leu Phe Ser Gln Met Pro Ser Phe Phe Leu Val Ser
-30                 -25                 -20                 -15

Thr Leu Leu Leu Phe Leu Ile Ile Ser His Ser Ser His Ala Gly Ile
                -10                 -5              -1   1

Phe Ser Ser Arg Lys Cys Lys Thr Pro Ser Lys Thr Phe Lys Gly Ile
        5                   10                  15

Cys Thr Arg Asp Ser Asn Cys Asp Thr Ser Cys Arg Tyr Glu Gly Tyr
    20                  25                  30

Pro Ala Gly Asp Cys Lys Gly Ile Arg Arg Arg Cys Met Cys Ser Lys
35                  40                  45                  50

Pro Cys
```

<210> SEQ ID NO 8
<211> LENGTH: 68
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chimeric peptide comprising a signal peptide and SoD7
<220> FEATURE:
<221> NAME/KEY: SIGNAL
<222> LOCATION: (1)..(30)
<223> OTHER INFORMATION: PR-1b signal peptide
<220> FEATURE:
<221> NAME/KEY: mat_peptide
<222> LOCATION: (31)..(68)
<223> OTHER INFORMATION: SoD7 peptide

<400> SEQUENCE: 8

```
Met Gly Phe Phe Leu Phe Ser Gln Met Pro Ser Phe Phe Leu Val Ser
-30                 -25                 -20                 -15

Thr Leu Leu Leu Phe Leu Ile Ile Ser His Ser Ser His Ala Gly Ile
                -10                 -5              -1   1

Phe Ser Ser Arg Lys Cys Lys Thr Pro Ser Lys Thr Phe Lys Gly Tyr
        5                   10                  15

Cys Thr Arg Asp Ser Asn Cys Asp Thr Ser Cys Arg Tyr Glu Gly Tyr
    20                  25                  30

Pro Ala Gly Asp
35
```

<210> SEQ ID NO 9
<211> LENGTH: 268

-continued

<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding a signal peptide
      and SoD2 codon-optimized with GenScript
<220> FEATURE:
<221> NAME/KEY: misc_feature
<222> LOCATION: (1)..(6)
<223> OTHER INFORMATION: XbaI restriction site
<220> FEATURE:
<221> NAME/KEY: misc_feature
<222> LOCATION: (11)..(100)
<223> OTHER INFORMATION: sig_peptide; PR-1b signal peptide
<220> FEATURE:
<221> NAME/KEY: CDS
<222> LOCATION: (101)..(256)
<223> OTHER INFORMATION: GenScript-optimized SoD2 (07)
<220> FEATURE:
<221> NAME/KEY: misc_feature
<222> LOCATION: (263)..(268)
<223> OTHER INFORMATION: XbaI restriction site

<400> SEQUENCE: 9

```
tctagaaaca atgggcttct tccttttctc tcaaatgcct tcatttttcc ttgtttctac      60

tcttcttctt tttcttatta tttctcattc ttctcatgct ggt att ttc tca tct       115
                                            Gly Ile Phe Ser Ser
                                            1               5

agg aag tgc aaa act cct tca aag act ttt aag gga att tgc act agg       163
Arg Lys Cys Lys Thr Pro Ser Lys Thr Phe Lys Gly Ile Cys Thr Arg
                10                  15                  20

gat tct aat tgc gat act tct tgc aga tac gag gga tat cca gct ggc       211
Asp Ser Asn Cys Asp Thr Ser Cys Arg Tyr Glu Gly Tyr Pro Ala Gly
            25                  30                  35

gat tgc aaa gga att agg agg aga tgt atg tgt tca aag cca tgt           256
Asp Cys Lys Gly Ile Arg Arg Arg Cys Met Cys Ser Lys Pro Cys
        40                  45                  50

taataatcta ga                                                         268
```

<210> SEQ ID NO 10
<211> LENGTH: 226
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding a signal peptide
      and SoD7 codon-optimized with GenScript
<220> FEATURE:
<221> NAME/KEY: misc_feature
<222> LOCATION: (1)..(6)
<223> OTHER INFORMATION: XbaI restriction site
<220> FEATURE:
<221> NAME/KEY: misc_feature
<222> LOCATION: (11)..(100)
<223> OTHER INFORMATION: sig_peptide; PR-1b signal peptide
<220> FEATURE:
<221> NAME/KEY: CDS
<222> LOCATION: (101)..(214)
<223> OTHER INFORMATION: GenScript-optimized SoD7 (08)
<220> FEATURE:
<221> NAME/KEY: misc_feature
<222> LOCATION: (221)..(226)
<223> OTHER INFORMATION: XbaI restriction site

<400> SEQUENCE: 10

```
tctagaaaca atgggtttct tcttgttttc tcaaatgcct tcattctttc ttgtttcaac      60
```

-continued

```
tttgcttctt tttcttatta tttctcattc atctcatgct gga att ttc tct tca      115
                                            Gly Ile Phe Ser Ser
                                            1               5

agg aag tgc aag act cca tct aag act ttc aag gga tat tgt act agg      163
Arg Lys Cys Lys Thr Pro Ser Lys Thr Phe Lys Gly Tyr Cys Thr Arg
                10                  15                  20

gat tct aac tgc gat aca tca tgc aga tac gag ggc tat cct gct ggc      211
Asp Ser Asn Cys Asp Thr Ser Cys Arg Tyr Glu Gly Tyr Pro Ala Gly
            25                  30                  35

gat taataatcta ga                                                    226
Asp
```

<210> SEQ ID NO 11
<211> LENGTH: 268
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chimeric nucleic acid encoding a signal peptide and SoD2 codon-optimized with CODA
<220> FEATURE:
<221> NAME/KEY: misc_feature
<222> LOCATION: (1)..(6)
<223> OTHER INFORMATION: XbaI restriction site
<220> FEATURE:
<221> NAME/KEY: misc_feature
<222> LOCATION: (11)..(100)
<223> OTHER INFORMATION: sig_peptide; PR-1b signal peptide
<220> FEATURE:
<221> NAME/KEY: CDS
<222> LOCATION: (101)..(256)
<223> OTHER INFORMATION: CODA-optimized SoD2 (09)
<220> FEATURE:
<221> NAME/KEY: misc_feature
<222> LOCATION: (263)..(268)
<223> OTHER INFORMATION: Sac I, SstI restriction site

<400> SEQUENCE: 11

```
tctagaaaca atgggtttct ttttgttttc tcaaatgcct tcatttttcc ttgtgtctac     60

tcttcttctt tttcttatta tttctcattc ttctcatgct ggt atc ttt tct agt      115
                                            Gly Ile Phe Ser Ser
                                            1               5

aga aag tgt aag act cct tct aag act ttt aaa ggt att tgc act aga      163
Arg Lys Cys Lys Thr Pro Ser Lys Thr Phe Lys Gly Ile Cys Thr Arg
                10                  15                  20

gat tct aat tgt gac act tct tgt aga tat gaa ggt tat cct gct ggt      211
Asp Ser Asn Cys Asp Thr Ser Cys Arg Tyr Glu Gly Tyr Pro Ala Gly
            25                  30                  35

gat tgt aag ggt att aga aga aga tgt atg tgt tct aag cct tgt          256
Asp Cys Lys Gly Ile Arg Arg Arg Cys Met Cys Ser Lys Pro Cys
        40                  45                  50

taataggagc tc                                                        268
```

<210> SEQ ID NO 12
<211> LENGTH: 226
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chimeric nucleic acid encoding a signal peptide and SoD7 codon-optimized with CODA
<220> FEATURE:
<221> NAME/KEY: misc_feature
<222> LOCATION: (1)..(6)

```
<223> OTHER INFORMATION: XbaI restriction site
<220> FEATURE:
<221> NAME/KEY: misc_feature
<222> LOCATION: (11)..(100)
<223> OTHER INFORMATION: sig_peptide; PR-1b signal peptide
<220> FEATURE:
<221> NAME/KEY: CDS
<222> LOCATION: (101)..(214)
<223> OTHER INFORMATION: CODA-optimized SoD7 (10)
<220> FEATURE:
<221> NAME/KEY: misc_feature
<222> LOCATION: (221)..(226)
<223> OTHER INFORMATION: SacI, SstI restriction site

<400> SEQUENCE: 12

tctagaaaca atgggattct ttttgttttc tcaaatgcct tctttctttc ttgtgtctac      60

tcttcttctt tttcttatta tttctcattc ttctcatgct ggt att ttt tca tct       115
                                             Gly Ile Phe Ser Ser
                                             1               5

cgt aag tgt aag act cct tct aag act ttt aag ggt tat tgc act aga       163
Arg Lys Cys Lys Thr Pro Ser Lys Thr Phe Lys Gly Tyr Cys Thr Arg
                10                  15                  20

gat tct aat tgt gat aca tct tgt aga tat gaa ggt tat cct gct ggt       211
Asp Ser Asn Cys Asp Thr Ser Cys Arg Tyr Glu Gly Tyr Pro Ala Gly
            25                  30                  35

gat taataggagc tc                                                     226
Asp


<210> SEQ ID NO 13
<211> LENGTH: 1462
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SoD2 expression cassette comprising a chimeric
      nucleic acid encoding a signal peptide and SoD2
<220> FEATURE:
<221> NAME/KEY: misc_feature
<222> LOCATION: (1)..(780)
<223> OTHER INFORMATION: promoter; 35SP
<220> FEATURE:
<221> NAME/KEY: misc_feature
<222> LOCATION: (781)..(923)
<223> OTHER INFORMATION: 5'UTR; TEV 5' UTR
<220> FEATURE:
<221> NAME/KEY: misc_feature
<222> LOCATION: (924)..(929)
<223> OTHER INFORMATION: XbaI restriction site
<220> FEATURE:
<221> NAME/KEY: misc_feature
<222> LOCATION: (934)..(1023)
<223> OTHER INFORMATION: sig_peptide; PR-1b signal peptide
<220> FEATURE:
<221> NAME/KEY: CDS
<222> LOCATION: (1024)..(1179)
<223> OTHER INFORMATION: encodes SoD2 peptide
<220> FEATURE:
<221> NAME/KEY: misc_feature
<222> LOCATION: (1186)..(1191)
<223> OTHER INFORMATION: SacI, SstI restriction site
<220> FEATURE:
<221> NAME/KEY: misc_feature
<222> LOCATION: (1192)..(1257)
<223> OTHER INFORMATION: polylinker
<220> FEATURE:
<221> NAME/KEY: misc_feature
<222> LOCATION: (1257)..(1462)
<223> OTHER INFORMATION: terminator; 35ST

<400> SEQUENCE: 13
```

-continued

```
atggtggagc acgacactct cgtctactcc aagaatatca aagatacagt ctcagaagac     60

caaagggcta ttgagacttt tcaacaaagg gtaatatcgg gaaacctcct cggattccat    120

tgcccagcta tctgtcactt catcaaaagg acagtagaaa aggaaggtgg cacctacaaa    180

tgccatcatt gcgataaagg aaaggctatc gttcaagatg cctctgccga cagtggtccc    240

aaagatggac ccccacccac gaggagcatc gtggaaaaag aagacgttcc aaccacgtct    300

tcaaagcaag tggattgatg tgataacatg gtggagcacg acactctcgt ctactccaag    360

aatatcaaag atacagtctc agaagaccaa agggctattg agacttttca acaaagggta    420

atatcgggaa acctcctcgg attccattgc ccagctatct gtcacttcat caaaaggaca    480

gtagaaaagg aaggtggcac ctacaaatgc catcattgcg ataaaggaaa ggctatcgtt    540

caagatgcct ctgccgacag tggtcccaaa gatggacccc cacccacgag gagcatcgtg    600

gaaaaagaag acgttccaac cacgtcttca aagcaagtgg attgatgtga tatctccact    660

gacgtaaggg atgacgcaca atcccactat ccttcgcaag accttcctct atataaggaa    720

gttcatttca tttggagagg acacgctgaa atcaccagtc tctctctaca aatctatctc    780

aaataacaaa tctcaacaca acatatacaa aacaaacgaa tctcaagcaa tcaagcattc    840

tacttctatt gcagcaattt aaatcatttc ttttaaagca aaagcaattt tctgaaaatt    900

ttcaccattt acgaacgata gcatctagaa acaatgggct tcttcctttt ctctcaaatg    960

ccttcatttt tccttgtttc tactcttctt ctttttctta ttatttctca ttcttctcat   1020

gct ggt att ttc tca tct agg aag tgc aaa act cct tca aag act ttt     1068
    Gly Ile Phe Ser Ser Arg Lys Cys Lys Thr Pro Ser Lys Thr Phe
    1               5                   10                  15

aag gga att tgc act agg gat tct aat tgc gat act tct tgc aga tac     1116
Lys Gly Ile Cys Thr Arg Asp Ser Asn Cys Asp Thr Ser Cys Arg Tyr
                20                  25                  30

gag gga tat cca gct ggc gat tgc aaa gga att agg agg aga tgt atg     1164
Glu Gly Tyr Pro Ala Gly Asp Cys Lys Gly Ile Arg Arg Arg Cys Met
            35                  40                  45

tgt tca aag cca tgt taataatcta gaacgcgtga attcgaggcc tcggatccct     1219
Cys Ser Lys Pro Cys
        50

cgaggagctc ggtacccggg gtccgcaaaa atcaccagtc tctctctaca aatctatctc   1279

tctctatttt tctccagaat aatgtgtgag tagttcccag ataagggaat tagggttctt   1339

atagggtttc gctcatgtgt tgagcatata agaaaccctt agtatgtatt tgtatttgta   1399

aaatacttct atcaataaaa tttctaattc ctaaaaccaa aatccagtga cctgcaggca   1459

tgc                                                                  1462
```

<210> SEQ ID NO 14
<211> LENGTH: 1420
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: SoD7 expression cassette comprising a chimeric
nucleic acid encoding a signal peptide and SoD7
<220> FEATURE:
<221> NAME/KEY: misc_feature
<222> LOCATION: (1)..(780)
<223> OTHER INFORMATION: promoter; 35SP
<220> FEATURE:
<221> NAME/KEY: misc_feature
<222> LOCATION: (781)..(923)
<223> OTHER INFORMATION: 5'UTR; TEV 5' UTR -continued

```
<220> FEATURE:
<221> NAME/KEY: misc_feature
<222> LOCATION: (924)..(929)
<223> OTHER INFORMATION: XbaI restriction site
<220> FEATURE:
<221> NAME/KEY: misc_feature
<222> LOCATION: (934)..(1023)
<223> OTHER INFORMATION: sig_peptide; PR-1b signal peptide
<220> FEATURE:
<221> NAME/KEY: CDS
<222> LOCATION: (1024)..(1137)
<223> OTHER INFORMATION: Encodes SoD7 peptide
<220> FEATURE:
<221> NAME/KEY: misc_feature
<222> LOCATION: (1144)..(1149)
<223> OTHER INFORMATION: SacI, SstI restriction site
<220> FEATURE:
<221> NAME/KEY: misc_feature
<222> LOCATION: (1150)..(1215)
<223> OTHER INFORMATION: polylinker
<220> FEATURE:
<221> NAME/KEY: misc_feature
<222> LOCATION: (1216)..(1420)
<223> OTHER INFORMATION: terminator; 35ST

<400> SEQUENCE: 14

atggtggagc acgacactct cgtctactcc aagaatatca aagatacagt ctcagaagac      60

caaagggcta ttgagacttt tcaacaaagg gtaatatcgg gaaacctcct cggattccat     120

tgcccagcta tctgtcactt catcaaaagg acagtagaaa aggaaggtgg cacctacaaa     180

tgccatcatt gcgataaagg aaaggctatc gttcaagatg cctctgccga cagtggtccc     240

aaagatggac ccccacccac gaggagcatc gtggaaaaag aagacgttcc aaccacgtct     300

tcaaagcaag tggattgatg tgataacatg gtggagcacg acactctcgt ctactccaag     360

aatatcaaag atacagtctc agaagaccaa agggctattg agacttttca acaaagggta     420

atatcgggaa acctcctcgg attccattgc ccagctatct gtcacttcat caaaaggaca     480

gtagaaaagg aaggtggcac ctacaaatgc catcattgcg ataaaggaaa ggctatcgtt     540

caagatgcct ctgccgacag tggtcccaaa gatggacccc cacccacgag gagcatcgtg     600

gaaaaagaag acgttccaac cacgtcttca aagcaagtgg attgatgtga tatctccact     660

gacgtaaggg atgacgcaca atcccactat ccttcgcaag accttcctct atataaggaa     720

gttcatttca tttggagagg acacgctgaa atcaccagtc tctctctaca aatctatctc     780

aaataacaaa tctcaacaca acatatacaa aacaaacgaa tctcaagcaa tcaagcattc     840

tacttctatt gcagcaattt aaatcatttc ttttaaagca aaagcaattt tctgaaaatt     900

ttcaccattt acgaacgata gcatctagaa acaatgggtt tcttcttgtt ttctcaaatg     960

ccttcattct ttcttgtttc aactttgctt ctttttctta ttatttctca ttcatctcat    1020

gct gga att ttc tct tca agg aag tgc aag act cca tct aag act ttc     1068
    Gly Ile Phe Ser Ser Arg Lys Cys Lys Thr Pro Ser Lys Thr Phe
    1               5                   10                  15

aag gga tat tgt act agg gat tct aac tgc gat aca tca tgc aga tac     1116
Lys Gly Tyr Cys Thr Arg Asp Ser Asn Cys Asp Thr Ser Cys Arg Tyr
                20                  25                  30

gag ggc tat cct gct ggc gat taataatcta gaacgcgtga attcgaggcc        1167
Glu Gly Tyr Pro Ala Gly Asp
            35

tcggatccct cgaggagctc ggtacccggg gtccgcaaaa atcaccagtc tctctctaca    1227

aatctatctc tctctatttt tctccagaat aatgtgtgag tagttcccag ataagggaat    1287

tagggttctt atagggtttc gctcatgtgt tgagcatata agaaaccctt agtatgtatt    1347
```

```
tgtatttgta aaatacttct atcaataaaa tttctaattc ctaaaaccaa aatccagtga   1407

cctgcaggca tgc                                                      1420


<210> SEQ ID NO 15
<211> LENGTH: 1424
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding a signal peptide
      and SoD2
<220> FEATURE:
<221> NAME/KEY: misc_feature
<222> LOCATION: (1)..(780)
<223> OTHER INFORMATION: promoter; 35SP
<220> FEATURE:
<221> NAME/KEY: misc_feature
<222> LOCATION: (781)..(923)
<223> OTHER INFORMATION: 5'UTR; TEV 5' UTR
<220> FEATURE:
<221> NAME/KEY: misc_feature
<222> LOCATION: (924)..(929)
<223> OTHER INFORMATION: XbaI restriction site
<220> FEATURE:
<221> NAME/KEY: misc_feature
<222> LOCATION: (934)..(1023)
<223> OTHER INFORMATION: sig_peptide; PR-1b signal peptide
<220> FEATURE:
<221> NAME/KEY: CDS
<222> LOCATION: (1024)..(1179)
<223> OTHER INFORMATION: Encodes SoD2 peptide
<220> FEATURE:
<221> NAME/KEY: misc_feature
<222> LOCATION: (1186)..(1191)
<223> OTHER INFORMATION: SacI, SstI restriction site
<220> FEATURE:
<221> NAME/KEY: misc_feature
<222> LOCATION: (1192)..(1219)
<223> OTHER INFORMATION: polylinker
<220> FEATURE:
<221> NAME/KEY: misc_feature
<222> LOCATION: (1220)..(1424)
<223> OTHER INFORMATION: terminator; 35ST

<400> SEQUENCE: 15

atggtggagc acgacactct cgtctactcc aagaatatca aagatacagt ctcagaagac     60

caaagggcta ttgagacttt tcaacaaagg gtaatatcgg gaaacctcct cggattccat    120

tgcccagcta tctgtcactt catcaaaagg acagtagaaa aggaaggtgg cacctacaaa    180

tgccatcatt gcgataaagg aaaggctatc gttcaagatg cctctgccga cagtggtccc    240

aaagatggac ccccacccac gaggagcatc gtggaaaaag aagacgttcc aaccacgtct    300

tcaaagcaag tggattgatg tgataacatg gtggagcacg acactctcgt ctactccaag    360

aatatcaaag atacagtctc agaagaccaa agggctattg agacttttca acaaagggta    420

atatcgggaa acctcctcgg attccattgc ccagctatct gtcacttcat caaaaggaca    480

gtagaaaagg aaggtggcac ctacaaatgc catcattgcg ataaaggaaa ggctatcgtt    540

caagatgcct ctgccgacag tggtcccaaa gatggacccc cacccacgag gagcatcgtg    600

gaaaaagaag acgttccaac cacgtcttca aagcaagtgg attgatgtga tatctccact    660

gacgtaaggg atgacgcaca atcccactat ccttcgcaag acccttcctct atataaggaa    720

gttcatttca tttggagagg acacgctgaa atcaccagtc tctctctaca aatctatctc    780

aaataacaaa tctcaacaca acatatacaa aacaaacgaa tctcaagcaa tcaagcattc    840

tacttctatt gcagcaattt aaatcatttc ttttaaagca aaagcaattt tctgaaaatt    900
```

-continued

```
ttcaccattt acgaacgata gcatctagaa acaatgggtt tctttttgtt ttctcaaatg    960

ccttcatttt tccttgtgtc tactcttctt ctttttctta ttatttctca ttcttctcat   1020

gct ggt atc ttt tct agt aga aag tgt aag act cct tct aag act ttt     1068
    Gly Ile Phe Ser Ser Arg Lys Cys Lys Thr Pro Ser Lys Thr Phe
    1               5                   10                  15

aaa ggt att tgc act aga gat tct aat tgt gac act tct tgt aga tat     1116
Lys Gly Ile Cys Thr Arg Asp Ser Asn Cys Asp Thr Ser Cys Arg Tyr
                20                  25                  30

gaa ggt tat cct gct ggt gat tgt aag ggt att aga aga aga tgt atg     1164
Glu Gly Tyr Pro Ala Gly Asp Cys Lys Gly Ile Arg Arg Arg Cys Met
            35                  40                  45

tgt tct aag cct tgt taataggagc tcggtacccg ggtccgcaa aaatcaccag     1219
Cys Ser Lys Pro Cys
        50

tctctctcta caaatctatc tctctctatt tttctccaga ataatgtgtg agtagttccc   1279

agataaggga attagggttc ttatagggtt tcgctcatgt gttgagcata taagaaaccc   1339

ttagtatgta tttgtatttg taaaatactt ctatcaataa aatttctaat tcctaaaacc   1399

aaaatccagt gacctgcagg catgc                                         1424
```

```
<210> SEQ ID NO 16
<211> LENGTH: 1388
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding a signal peptide
      and SoD7
<220> FEATURE:
<221> NAME/KEY: misc_feature
<222> LOCATION: (1)..(780)
<223> OTHER INFORMATION: promoter; 35SP
<220> FEATURE:
<221> NAME/KEY: misc_feature
<222> LOCATION: (781)..(923)
<223> OTHER INFORMATION: 5'UTR; TEV 5' UTR
<220> FEATURE:
<221> NAME/KEY: misc_feature
<222> LOCATION: (781)..(923)
<223> OTHER INFORMATION: XbaI restriction site
<220> FEATURE:
<221> NAME/KEY: misc_feature
<222> LOCATION: (934)..(1023)
<223> OTHER INFORMATION: sig_peptide; PR-1b signal peptide
<220> FEATURE:
<221> NAME/KEY: CDS
<222> LOCATION: (1024)..(1137)
<223> OTHER INFORMATION: Encodes SoD7 peptide
<220> FEATURE:
<221> NAME/KEY: misc_feature
<222> LOCATION: (1144)..(1149)
<223> OTHER INFORMATION: SacI, SstI restriction site
<220> FEATURE:
<221> NAME/KEY: misc_feature
<222> LOCATION: (1150)..(1177)
<223> OTHER INFORMATION: polylinker
<220> FEATURE:
<221> NAME/KEY: misc_feature
<222> LOCATION: (1178)..(1382)
<223> OTHER INFORMATION: terminator; 35ST

<400> SEQUENCE: 16

atggtggagc acgacactct cgtctactcc aagaatatca aagatacagt ctcagaagac     60

caaagggcta ttgagacttt tcaacaaagg gtaatatcgg gaaacctcct cggattccat    120
```

-continued

```
tgcccagcta tctgtcactt catcaaaagg acagtagaaa aggaaggtgg cacctacaaa    180

tgccatcatt gcgataaagg aaaggctatc gttcaagatg cctctgccga cagtggtccc    240

aaagatggac ccccacccac gaggagcatc gtggaaaaag aagacgttcc aaccacgtct    300

tcaaagcaag tggattgatg tgataacatg gtggagcacg acactctcgt ctactccaag    360

aatatcaaag atacagtctc agaagaccaa agggctattg agacttttca acaaagggta    420

atatcgggaa acctcctcgg attccattgc ccagctatct gtcacttcat caaaaggaca    480

gtagaaaagg aaggtggcac ctacaaatgc catcattgcg ataaaggaaa ggctatcgtt    540

caagatgcct ctgccgacag tggtcccaaa gatggacccc cacccacgag gagcatcgtg    600

gaaaaagaag acgttccaac cacgtcttca aagcaagtgg attgatgtga tatctccact    660

gacgtaaggg atgacgcaca atcccactat ccttcgcaag accttcctct atataaggaa    720

gttcatttca tttggagagg acacgctgaa atcaccagtc tctctctaca aatctatctc    780

aaataacaaa tctcaacaca acatatacaa aacaaacgaa tctcaagcaa tcaagcattc    840

tacttctatt gcagcaattt aaatcatttc ttttaaagca aaagcaattt tctgaaaatt    900

ttcaccattt acgaacgata gcatctagaa acaatgggat tctttttgtt ttctcaaatg    960

ccttctttct ttcttgtgtc tactcttctt ctttttctta ttatttctca ttcttctcat   1020

gct ggt att ttt tca tct cgt aag tgt aag act cct tct aag act ttt     1068
    Gly Ile Phe Ser Ser Arg Lys Cys Lys Thr Pro Ser Lys Thr Phe
    1               5                   10                  15

aag ggt tat tgc act aga gat tct aat tgt gat aca tct tgt aga tat     1116
Lys Gly Tyr Cys Thr Arg Asp Ser Asn Cys Asp Thr Ser Cys Arg Tyr
                20                  25                  30

gaa ggt tat cct gct ggt gat taataggagc tcggtacccg ggtccgcaa        1167
Glu Gly Tyr Pro Ala Gly Asp
            35

aaatcaccag tctctctcta caaatctatc tctctctatt tttctccaga ataatgtgtg   1227

agtagttccc agataaggga attagggttc ttatagggtt tcgctcatgt gttgagcata   1287

taagaaaccc ttagtatgta tttgtatttg taaaatactt ctatcaataa aatttctaat   1347

tcctaaaacc aaaatccagt gacctgcagg catgcgagag a                       1388


<210> SEQ ID NO 17
<211> LENGTH: 780
<212> TYPE: DNA
<213> ORGANISM: Cauliflower mosaic virus
<220> FEATURE:
<221> NAME/KEY: misc_feature
<222> LOCATION: (1)..(780)
<223> OTHER INFORMATION: promoter; CaMV 35S promoter

<400> SEQUENCE: 17

atggtggagc acgacactct cgtctactcc aagaatatca aagatacagt ctcagaagac     60

caaagggcta ttgagacttt tcaacaaagg gtaatatcgg gaaacctcct cggattccat    120

tgcccagcta tctgtcactt catcaaaagg acagtagaaa aggaaggtgg cacctacaaa    180

tgccatcatt gcgataaagg aaaggctatc gttcaagatg cctctgccga cagtggtccc    240

aaagatggac ccccacccac gaggagcatc gtggaaaaag aagacgttcc aaccacgtct    300

tcaaagcaag tggattgatg tgataacatg gtggagcacg acactctcgt ctactccaag    360

aatatcaaag atacagtctc agaagaccaa agggctattg agacttttca acaaagggta    420

atatcgggaa acctcctcgg attccattgc ccagctatct gtcacttcat caaaaggaca    480

gtagaaaagg aaggtggcac ctacaaatgc catcattgcg ataaaggaaa ggctatcgtt    540
```

caagatgcct ctgccgacag tggtcccaaa gatggacccc cacccacgag gagcatcgtg 600
gaaaaagaag acgttccaac cacgtcttca aagcaagtgg attgatgtga tatctccact 660
gacgtaaggg atgacgcaca atcccactat ccttcgcaag accttcctct atataaggaa 720
gttcatttca tttggagagg acacgctgaa atcaccagtc tctctctaca aatctatctc 780

<210> SEQ ID NO 18
<211> LENGTH: 143
<212> TYPE: DNA
<213> ORGANISM: Tobacco etch virus
<220> FEATURE:
<221> NAME/KEY: misc_feature
<222> LOCATION: (1)..(143)
<223> OTHER INFORMATION: enhancer; TEV 5'UTR translational enhancer

<400> SEQUENCE: 18
aaataacaaa tctcaacaca acatatacaa aacaaacgaa tctcaagcaa tcaagcattc 60
tacttctatt gcagcaattt aaatcatttc ttttaaagca aaagcaattt tctgaaaatt 120
ttcaccattt acgaacgata gca 143

<210> SEQ ID NO 19
<211> LENGTH: 205
<212> TYPE: DNA
<213> ORGANISM: Cauliflower mosaic virus
<220> FEATURE:
<221> NAME/KEY: misc_feature
<222> LOCATION: (1)..(205)
<223> OTHER INFORMATION: terminator; CaMV 35S terminator

<400> SEQUENCE: 19
tctctctcta caaatctatc tctctctatt tttctccaga ataatgtgtg agtagttccc 60
agataaggga attagggttc ttatagggtt tcgctcatgt gttgagcata taagaaaccc 120
ttagtatgta tttgtatttg taaaatactt ctatcaataa aatttctaat tcctaaaacc 180
aaaatccagt gacctgcagg catgc 205

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Zn5 Primer

<400> SEQUENCE: 20
ccaatgcatt gatcttcaaa tgggaatgaa t 31

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Zn6 Primer

<400> SEQUENCE: 21
aactgcagtt ctaagaccag tcaaacta 28

<210> SEQ ID NO 22

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Fcp Primer

<400> SEQUENCE: 22

ggcctctaga gttatggacg acgagacata gtaattgaag                          40


<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Rcp Primer

<400> SEQUENCE: 23

gcgcgagctc gatgaaactc caccatcccg atag                                34


<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: GUSF Primer

<400> SEQUENCE: 24

gtagaaaccc caacccgtga                                                20


<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: GUSR Primer

<400> SEQUENCE: 25

gcggattcac cacttgcaaa g                                              21


<210> SEQ ID NO 26
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Variant of SoD2 comprising two additional
      N-terminal amino acids and a Gly33 deletion relative to spinach
      SoD2
<220> FEATURE:
<221> NAME/KEY: SIGNAL
<222> LOCATION: (1)..(32)
<223> OTHER INFORMATION: Modified PR-1b signal peptide
<220> FEATURE:
<221> NAME/KEY: mat_peptide
<222> LOCATION: (33)..(83)
<223> OTHER INFORMATION: Putative mature SoD2 peptide with a Gly33
      deletion relative to spinach SoD2
```

<400> SEQUENCE: 26

```
Met Gly Phe Phe Leu Phe Ser Gln Met Pro Ser Phe Phe Leu Val Ser
        -30                 -25                 -20

Thr Leu Leu Leu Phe Leu Ile Ile Ser His Ser Ser His Ala Leu Glu
    -15                 -10                 -5              -1

Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Tyr Pro Ala Gly Asp Cys Lys Gly Ile Arg Arg Arg Cys Met Cys Ser
        35                  40                  45

Lys Pro Cys
    50
```

<210> SEQ ID NO 27
<211> LENGTH: 265
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Variant of SoD2 comprising two additional N-terminal amino acids and a Gly33 deletion relative to spinach SoD2
<220> FEATURE:
<221> NAME/KEY: misc_feature
<222> LOCATION: (8)..(103)
<223> OTHER INFORMATION: sig_peptide; PR-1b signal peptide fragment
<220> FEATURE:
<221> NAME/KEY: CDS
<222> LOCATION: (104)..(256)
<223> OTHER INFORMATION: Putative mature SoD2 peptide with a Gly33 deletion relative to spinach SoD2

<400> SEQUENCE: 27

```
ttaattaatg ggattctttc tcttttcaca aatgccctca ttctttcttg tgtcgacact      60

tctcttattc ctaataatat ctcactcttc tcatgcgctc gag gga ata ttc agc       115
                                                 Gly Ile Phe Ser
                                                 1

tcc cgc aag tgt aag acg cct tca aag act ttc aaa ggg ata tgt acg       163
Ser Arg Lys Cys Lys Thr Pro Ser Lys Thr Phe Lys Gly Ile Cys Thr
5                   10                  15                  20

aga gac tca aac tgt gac acc tca tgt cgt tac gaa tat ccg gca gga       211
Arg Asp Ser Asn Cys Asp Thr Ser Cys Arg Tyr Glu Tyr Pro Ala Gly
                25                  30                  35

gac tgt aaa gga ata cgt cgc aga tgt atg tgt agc aag cct tgt           256
Asp Cys Lys Gly Ile Arg Arg Arg Cys Met Cys Ser Lys Pro Cys
            40                  45                  50

tagaggcct                                                             265
```

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Core defensin based, in part, on Sod2 and Sod7
<220> FEATURE:
<221> NAME/KEY: MOD_RES
<222> LOCATION: (18)..(18)
<223> OTHER INFORMATION: Any amino acid

```
<400> SEQUENCE: 28

Gly Ile Phe Ser Ser Arg Lys Cys Lys Thr Pro Ser Lys Thr Phe Lys
1               5                   10                  15

Gly Xaa Cys Thr Arg Asp Ser Asn Cys Asp Thr Ser Cys Arg Tyr Glu
            20                  25                  30

Gly Tyr Pro Ala Gly Asp
        35


<210> SEQ ID NO 29
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Core defensin based, in part, on Sod2 and Sod7
<220> FEATURE:
<221> NAME/KEY: modified_base
<222> LOCATION: (52)..(54)
<223> OTHER INFORMATION: a, c, t or g
<220> FEATURE:
<221> NAME/KEY: misc_feature
<222> LOCATION: (52)..(52)
<223> OTHER INFORMATION: t, any other base, or absent (e.g., if 53 and
      54 are also absent)
<220> FEATURE:
<221> NAME/KEY: misc_feature
<222> LOCATION: (53)..(53)
<223> OTHER INFORMATION: a, any other base, or absent (e.g., if 52 and
      54 are also absent)
<220> FEATURE:
<221> NAME/KEY: misc_feature
<222> LOCATION: (54)..(54)
<223> OTHER INFORMATION: t, any other base, or absent (e.g., if 52 and
      53 are also absent)

<400> SEQUENCE: 29

ggaattttct cttcaaggaa gtgcaagact ccatctaaga ctttcaaggg annntgtact     60

agggattcta actgcgatac atcatgcaga tacgagggct atcctgctgg cgattaataa    120


<210> SEQ ID NO 30
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SoD2 codon-optimized with DNA 2.0

<400> SEQUENCE: 30

tctagaatgg gaatcttcag ttcgagaaag tgtaaaaccc cctcaaaaac attcaaaggt     60

atttgcacga gagattctaa ttgcgatact agctgccgtt atgagggtta ccctgctggc    120

gactgtaagg ggataaggag gagatgtatg tgctccaagc catgttaagg tacc          174


<210> SEQ ID NO 31
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: SoD7 codon-optimized with DNA 2.0

<400> SEQUENCE: 31
```

```
tctagaatgg gtatcttctc aagcagaaag tgcaaaacac cttctaaaac ctttaaggga      60

tattgtacta gggactccaa ttgtgatacg agttgccgtt acgagggcta tccagctggg     120

gattaaggta cc                                                         132


<210> SEQ ID NO 32
<211> LENGTH: 60
<212> TYPE: PRT
<213> ORGANISM: Spinacia oleracea
<220> FEATURE:
<221> NAME/KEY: MISC_FEATURE
<222> LOCATION: (1)..(60)
<223> OTHER INFORMATION: mat_peptide; Def1 peptide

<400> SEQUENCE: 32

Met Gly Pro Arg Lys Ala Glu Ala Gly Ile Phe Ser Ser Arg Lys Cys
1               5                   10                  15

Lys Thr Pro Ser Lys Thr Phe Lys Gly Ile Cys Thr Arg Asp Ser Asn
            20                  25                  30

Cys Asp Thr Ser Cys Arg Tyr Glu Gly Tyr Pro Ala Gly Asp Cys Lys
        35                  40                  45

Gly Ile Arg Arg Arg Cys Leu Cys Cys Thr His Thr
    50                  55                  60


<210> SEQ ID NO 33
<211> LENGTH: 83
<212> TYPE: PRT
<213> ORGANISM: Spinacia oleracea
<220> FEATURE:
<221> NAME/KEY: MISC_FEATURE
<222> LOCATION: (1)..(83)
<223> OTHER INFORMATION: mat_peptide; Def2 peptide

<400> SEQUENCE: 33

Met Lys Met Ser Met Arg Ser Ile Ala Val Val Phe Leu Val Cys Leu
1               5                   10                  15

Leu Val Leu Ser Thr Glu Glu Met Gly Pro Arg Lys Ala Asp Ala Gly
            20                  25                  30

Phe Phe Ser Ser Lys Lys Cys Lys Thr Pro Ser Lys Thr Phe Arg Gly
        35                  40                  45

Pro Cys Val Arg Asn Ala Asn Cys Asp Thr Ser Cys Arg Tyr Glu Gly
    50                  55                  60

Tyr Pro Ala Gly Asp Cys Lys Gly Ile Arg Arg Arg Cys Ile Cys Cys
65                  70                  75                  80

Thr His Ala


<210> SEQ ID NO 34
<211> LENGTH: 74
<212> TYPE: PRT
<213> ORGANISM: Spinacia oleracea
<220> FEATURE:
<221> NAME/KEY: MISC_FEATURE
<222> LOCATION: (1)..(74)
<223> OTHER INFORMATION: mat_peptide; Def3 peptide

<400> SEQUENCE: 34

Met Lys His Phe Gly Ala Ile Phe Leu Val Leu Leu Leu Val Leu Ala
1               5                   10                  15

Thr Glu His Gly Ala Arg Val Ala Glu Ala Arg Thr Cys Glu Thr Pro
            20                  25                  30

Ser Gln Lys Phe Lys Gly Ile Cys Ile Ser Asp Ser Asn Cys Glu Ser
```

```
        35                  40                  45

Ile Cys Asn Thr Glu Gly Phe Pro Asn Gly Glu Cys Ser Gly Leu Arg
    50                  55                  60

Arg Arg Cys Ile Cys Asn Thr Pro Cys Thr
65                  70


<210> SEQ ID NO 35
<211> LENGTH: 56
<212> TYPE: PRT
<213> ORGANISM: Spinacia oleracea
<220> FEATURE:
<221> NAME/KEY: MISC_FEATURE
<222> LOCATION: (1)..(56)
<223> OTHER INFORMATION: mat_peptide; Def4 peptide

<400> SEQUENCE: 35

Val Ser Thr Lys Val Ala Glu Ala Arg Ile Cys Ala Ser Pro Ser Pro
1               5                   10                  15

Thr Phe Lys Gly Ile Cys Phe Ser Ser Arg Asn Cys Glu Thr Asn Cys
            20                  25                  30

Asn Ser Val Lys Phe Ser Gly Gly Ser Cys Gln Gly Phe Arg Arg Arg
        35                  40                  45

Cys Met Cys Thr Lys Pro Cys Ala
    50                  55


<210> SEQ ID NO 36
<211> LENGTH: 74
<212> TYPE: PRT
<213> ORGANISM: Spinacia oleracea
<220> FEATURE:
<221> NAME/KEY: MISC_FEATURE
<222> LOCATION: (1)..(74)
<223> OTHER INFORMATION: mat_peptide; Def5 peptide

<400> SEQUENCE: 36

Met Arg Pro Phe Ala Ala Leu Phe Leu Val Leu Phe Leu Val Leu Ala
1               5                   10                  15

Thr Glu Ile Gly Pro Arg Val Val Glu Ala Arg Met Cys Ser Ser Pro
            20                  25                  30

Ser His Arg Phe Lys Gly Ile Cys Thr Ser Ser Arg Asn Cys Glu Asn
        35                  40                  45

Thr Cys Asn Ser Glu Arg Phe Ser Gly Gly Glu Cys Lys Gly Phe Arg
    50                  55                  60

Arg Arg Cys Met Cys Thr Gly Pro Cys Val
65                  70


<210> SEQ ID NO 37
<211> LENGTH: 90
<212> TYPE: PRT
<213> ORGANISM: Spinacia oleracea
<220> FEATURE:
<221> NAME/KEY: MISC_FEATURE
<222> LOCATION: (1)..(90)
<223> OTHER INFORMATION: mat_peptide; Def6 peptide

<400> SEQUENCE: 37

Met Glu Arg Ser Ser Arg Val Phe Ser Val Val Leu Leu Met Leu Val
1               5                   10                  15

Leu Val Leu Ser Thr Asp Met Tyr Thr Asp Pro Val Ala Val Leu Ser
            20                  25                  30

Tyr Glu Ile Gly Thr Lys Val Ala Glu Ala Arg Ile Cys Glu Ser Ala
        35                  40                  45
```

Ser Tyr Arg Phe Lys Gly Ile Cys Val Ser Arg Ser Asn Cys Ala Asn
50 55 60

Val Cys Lys Asn Glu Gly Phe Pro Gly Gly Arg Cys Arg Gly Phe Arg
65 70 75 80

Arg Arg Cys Leu Cys Tyr Lys His Cys Gly
85 90

<210> SEQ ID NO 38
<211> LENGTH: 74
<212> TYPE: PRT
<213> ORGANISM: Spinacia oleracea
<220> FEATURE:
<221> NAME/KEY: MISC_FEATURE
<222> LOCATION: (1)..(74)
<223> OTHER INFORMATION: mat_peptide; Def6 peptide

<400> SEQUENCE: 38

Met Lys Pro Phe Val Ala Phe Val Leu Ala Phe Met Leu Val Leu Ala
1 5 10 15

Ile Glu Met Gly Pro Arg Val Ala Glu Ala Arg Met Cys Thr Asn Pro
20 25 30

Ser Arg Thr Phe Arg Gly Pro Cys Val Ser Asp Arg Asn Cys Glu Ser
35 40 45

Ser Cys Met Gly Glu Gly Phe Pro Gly Gly Ser Cys His Gly Phe Arg
50 55 60

Arg Lys Cys Val Cys Ser Lys Pro Cys Ala
65 70

<210> SEQ ID NO 39
<211> LENGTH: 183
<212> TYPE: DNA
<213> ORGANISM: Spinacia oleracea
<220> FEATURE:
<221> NAME/KEY: misc_feature
<222> LOCATION: (1)..(143)
<223> OTHER INFORMATION: Def1 nucleotide

<400> SEQUENCE: 39
atgggtccaa gaaaggcaga agctggaatt tttagctcga ggaaatgcaa aactccaagt 60
aaaacgttca agggaatatg tactagggac tccaattgtg acacttcttg taggtatgag 120
ggatatccag ctggagattg caagggtatt cgtagaagat gcttatgttg tacacatact 180
taa 183

<210> SEQ ID NO 40
<211> LENGTH: 252
<212> TYPE: DNA
<213> ORGANISM: Spinacia oleracea
<220> FEATURE:
<221> NAME/KEY: misc_feature
<222> LOCATION: (1)..(252)
<223> OTHER INFORMATION: Def2 nucleotide

<400> SEQUENCE: 40
atgaagatgt caatgaggtc gattgctgtg gttttccttg tgtgcctact tgtcttgtca 60
acagaagaaa tgggtccaag aaaggcagac gctggatttt tcagctcgaa gaaatgcaaa 120
acaccaagta aaacattcag gggaccttgt gtaaggaacg ccaactgtga cacttcttgt 180
aggtatgagg gatatccagc tggagattgc aagggtattc gtagaagatg tatttgttgt 240
acacatgctt aa 252

<210> SEQ ID NO 41
<211> LENGTH: 225
<212> TYPE: DNA
<213> ORGANISM: Spinacia oleracea
<220> FEATURE:
<221> NAME/KEY: misc_feature
<222> LOCATION: (1)..(225)
<223> OTHER INFORMATION: Def3 nucleotide

<400> SEQUENCE: 41
atgaagcact ttggggctat atttcttgtg ttgttgcttg ttctggccac agaacatgga 60
gcaagagtag cagaagcaag aacatgtgaa actccaagtc aaaagttcaa aggaatatgt 120
attagtgact ccaattgtga atcaatttgc aataccgaag gatttcctaa tggagaatgt 180
agtggccttc gcagaagatg catttgcaac acaccatgca cttaa 225

<210> SEQ ID NO 42
<211> LENGTH: 171
<212> TYPE: DNA
<213> ORGANISM: Spinacia oleracea
<220> FEATURE:
<221> NAME/KEY: misc_feature
<222> LOCATION: (1)..(171)
<223> OTHER INFORMATION: Def4 nucleotide

<400> SEQUENCE: 42
gtaagtacaa aagtagcaga agcaaggata tgtgctagtc caagtcccac gttcaaagga 60
atatgtttta gcagcaggaa ttgtgaaact aattgcaatt ctgtgaaatt ttctggagga 120
agttgtcaag gttttcgtag aagatgtatg tgcaccaagc cttgcgctta a 171

<210> SEQ ID NO 43
<211> LENGTH: 225
<212> TYPE: DNA
<213> ORGANISM: Spinacia oleracea
<220> FEATURE:
<221> NAME/KEY: misc_feature
<222> LOCATION: (1)..(225)
<223> OTHER INFORMATION: Def5 nucleotide

<400> SEQUENCE: 43
atgaggcctt ttgctgctct tttccttgtg ctcttccttg ttttggccac agagataggg 60
ccaagagtag tagaagcaag aatgtgttca tcaccaagtc ataggttcaa gggaatttgt 120
actagcagca ggaattgtga gaacacttgc aacagcgaac gattttcagg tggtgaatgt 180
aaaggctttc gcagaagatg tatgtgcacg ggaccctgcg tttaa 225

<210> SEQ ID NO 44
<211> LENGTH: 273
<212> TYPE: DNA
<213> ORGANISM: Spinacia oleracea
<220> FEATURE:
<221> NAME/KEY: misc_feature
<222> LOCATION: (1)..(273)
<223> OTHER INFORMATION: Def6 nucleotide

<400> SEQUENCE: 44
atggagcgtt cttcacgtgt gttttcagtt gttcttctca tgcttgttct tgtgttgtcc 60
acagatatgt acacagaccc agtggcggtt cttagttatg agattgggac aaaggtggcg 120
gaagcaagga tatgcgaatc tgcaagttac aggttcaagg gaatatgtgt gagcaggagc 180
aactgtgcta atgtttgcaa aaatgagggt ttccccggtg gccgttgccg cggtttccgt 240
cgtcgttgcc tctgttacaa acattgcggt taa 273

<210> SEQ ID NO 45
<211> LENGTH: 225
<212> TYPE: DNA
<213> ORGANISM: Spinacia oleracea
<220> FEATURE:
<221> NAME/KEY: misc_feature
<222> LOCATION: (1)..(225)
<223> OTHER INFORMATION: Def7 nucleotide

<400> SEQUENCE: 45
atgaagccct ttgtagcttt tgttcttgct ttcatgcttg tcttggccat agagatgggt 60
ccaagagtag cagaagcaag aatgtgcaca aatccgagta gaacattcag gggaccatgc 120
gttagtgacc ggaactgcga atcgtcgtgc atgggagagg gatttcccgg tggaagttgt 180
catggctttc gtagaaaatg cgtctgcagc aagccttgtg cttag 225

<210> SEQ ID NO 46
<211> LENGTH: 186
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Def1 codon-optimized with Genscript

<400> SEQUENCE: 46
atggggccaa gaaaagccga agccgggata ttcagctcaa gaaagtgcaa gacaccctcc 60
aagacattca aaggcatctg taccagggat tctaattgcg acacctcatg tagatatgag 120
ggttaccctg ctggagattg caagggtatt aggagaaggt gtctttgctg tactcataca 180
taatga 186

<210> SEQ ID NO 47
<211> LENGTH: 198
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Def2 codon-optimized with Genscript

<400> SEQUENCE: 47
atgacagagg agatgggtcc aaggaaagcc gacgctgggt tcttcagttc taaaaagtgc 60
aaaacaccaa gcaaaacatt cagaggccct tgcgttagaa atgctaactg cgatacttct 120
tgtagatatg agggttaccc agcaggagac tgcaagggta ttaggagaag gtgtatctgc 180
tgtacacatg cttaatga 198

<210> SEQ ID NO 48
<211> LENGTH: 228
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Def3 codon-optimized with Genscript

<400> SEQUENCE: 48
atgaaacact tcggggctat ctttttggtg ctcctgctcg tgctcgctac tgaacatggt 60
gccagagttg ctgaggctag aacctgtgaa accccctctc aaaagtttaa aggtatctgc 120
atctctgatt caaactgcga gagcatatgt aacacagaag gtttccctaa tggtgaatgc 180
agtggcctta ggagaaggtg catctgtaac actccatgta cataatga 228

<210> SEQ ID NO 49
<211> LENGTH: 228
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Def5 codon-optimized with Genscript

<400> SEQUENCE: 49
atgagaccct tcgccgcttt gtttttggtt ttgttcttgg tgctcgctac agagattgga 60
cccagagtgg tggaggccag gatgtgttct tcacctagcc ataggtttaa gggtatttgc 120
actagcagta ggaattgcga gaacacatgt aattccgaaa gattttctgg tggagagtgc 180
aaaggcttca ggagaaggtg catgtgtacc gggccatgtg tttaatga 228

<210> SEQ ID NO 50
<211> LENGTH: 276
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Def6 codon-optimized with Genscript

<400> SEQUENCE: 50
atggagagat cgtcaagagt ttttagcgtt gtgctgctta tgctggtgct ggttctgtct 60
actgatatgt ataccgaccc tgtggctgtt ctttcttatg agattggtac taaggtggct 120
gaggcaagaa tctgcgaatc tgcctcatac aggtttaagg gcatttgtgt tagcagaagt 180
aattgcgcaa acgtgtgcaa gaatgagggc tttcctggtg gaagatgcag ggggttcagg 240
agaaggtgct tgtgttataa gcattgtggt taatga 276

<210> SEQ ID NO 51
<211> LENGTH: 228
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Def7 codon-optimized with Genscript

<400> SEQUENCE: 51
atgaaacctt ttgtggcttt tgtgctggct tttatgctcg ttctggctat tgaaatgggt 60
ccaagagtgg ctgaggcaag gatgtgtact aatccttcta ggacttttag gggtccatgc 120
gttagtgata ggaactgcga gtcttcatgt atgggcgaag ggtttcccgg tggatcttgc 180
catggcttca ggagaaagtg cgtgtgttct aaaccttgtg cttaatga 228

<210> SEQ ID NO 52
<211> LENGTH: 186
<212> TYPE: DNA
<213> ORGANISM: Artificial Sequence
<220> FEATURE:
<223> OTHER INFORMATION: Description of Artificial Sequence: Synthetic polynucleotide
<220> FEATURE:

-continued

<223> OTHER INFORMATION: Def1 codon-optimized with VGD

<400> SEQUENCE: 52
atgggtccta ggaaggcaga ggctggaata tttagctcga ggaagtgcaa aaccccaagt 60
aaaacgttta agggaatttg tactagagac tccaattgtg acacttcgtg taggtatgag 120
ggatacccag ctggagattg caagggtatc aggagaaggt gcttatgctg tacacataca 180
taatag 186

<210> SEQ ID NO 53
<211> LENGTH: 198
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Def2 codon-optimized with VGD

<400> SEQUENCE: 53
atgacagaag agatgggccc gagaaaagca gacgctggat ttttctcatc caagaaatgc 60
aagacaccct caaaaacatt caggggacct tgtgtaagga acgctaactg tgacacttct 120
tgtaggtatg agggctatcc agctggagat tgcaagggta taaggagaag atgtatttgt 180
tgtacccatg cttaatag 198

<210> SEQ ID NO 54
<211> LENGTH: 228
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Def3 codon-optimized with VGD

<400> SEQUENCE: 54
atgaagcact ttggggctat attccttgtg cttttattag tcctcgcaac ggaacatgga 60
gcaagagtag cagaagcaag aacttgtgaa acgccaagtc aaaagttcaa aggcatctgt 120
atttccgact ccaattgtga aagcatttgc aataccgaag gatttccgaa tggagaatgt 180
tctggccttc gcagaagatg catttgcaac accccttgta cttaatag 228

<210> SEQ ID NO 55
<211> LENGTH: 177
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Def4 codon-optimized with VGD

<400> SEQUENCE: 55
atggtaagta caaaagttgc agaagcaagg atttgtgctt caccatctcc aacgtttaag 60
ggaatatgtt ttagtagccg taattgtgaa acgaattgca attccgtaaa attttctgga 120
ggaagttgtc agggttttag gagaagatgt atgtgcacaa agccctgcgc ttgatag 177

<210> SEQ ID NO 56
<211> LENGTH: 228
<212> TYPE: DNA
<213> ORGANISM: Artificial Sequence
<220> FEATURE:

<223> OTHER INFORMATION: Description of Artificial Sequence: Synthetic
polynucleotide
<220> FEATURE:
<223> OTHER INFORMATION: Def5 codon-optimized with VGD

<400> SEQUENCE: 56
atgagaccat ttgctgctct tttccttgtg cttttccttg tgttggctac agaaataggg 60
cccagggtgg tagaagcaag aatgtgctca agtccaagtc ataggttcaa gggcatttgc 120
acttcttcga gaaattgtga aaacacttgc aacagcgaac gattttcagg tggtgagtgt 180
aaaggctttc gcagaagatg tatgtgcacg ggaccctgtg tgtaatag 228

<210> SEQ ID NO 57
<211> LENGTH: 276
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Def6 codon-optimized with VGD

<400> SEQUENCE: 57
atggagaggt cttcacgtgt gttttcagtg gttctcctta tgttggttct tgtgttgagt 60
acagatatgt acacagaccc tgtagcagtt cttagttatg aaattgggac taaggtggca 120
gaagctcgca tttgtgaatc ggcaagttac aggttcaagg gaatatgtgt gtcaaggtca 180
aactgcgcta acgtttgcaa aaatgagggt ttcccaggtg gtcgttgccg ggatttaga 240 aggcggtgcc tttgctacaa acattgcggg tagtaa 276

<210> SEQ ID NO 58
<211> LENGTH: 228
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Def7 codon-optimized with VGD

<400> SEQUENCE: 58
atgaagcctt ttgtagcttt tgttctggct ttcatgcttg ttctcgccat agagatgggt 60
ccccgggtcg ctgaggcacg gatgtgcaca aatccgagca gaacattcag gggtccctgc 120
gttagcgaca ggaactgcga atcctcatgc atgggagagg gatttccggg tggtagttgc 180
catggattta gaagaaaatg cgtttgcagc aagccttgtg cttagtaa 228

<210> SEQ ID NO 59
<211> LENGTH: 271
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Chimeric nucleic acid encoding a signal peptide
and Def2 codon-optimized with Genscript
<220> FEATURE:
<221> NAME/KEY: misc_feature
<222> LOCATION: (1)..(6)
<223> OTHER INFORMATION: Restriction site for XbaI
<220> FEATURE:
<221> NAME/KEY: misc_feature
<222> LOCATION: (14)..(70)
<223> OTHER INFORMATION: sig_peptide; Def2 signal peptide
<220> FEATURE:

```
<221> NAME/KEY: CDS
<222> LOCATION: (71)..(259)
<223> OTHER INFORMATION: Genscript-optimized Def2 peptide
<220> FEATURE:
<221> NAME/KEY: misc_feature
<222> LOCATION: (266)..(271)
<223> OTHER INFORMATION: Restriction site for KpnI

<400> SEQUENCE: 59

tctagaaaca atgaagatgt caatgaggtc gatcgctgtg gttttcttgg tgtgcctatt     60

ggtgttgtca aca gag gag atg ggt cca agg aaa gcc gac gct ggg ttc       109
           Thr Glu Glu Met Gly Pro Arg Lys Ala Asp Ala Gly Phe
           1               5                   10

ttc agt tct aaa aag tgc aaa aca cca agc aaa aca ttc aga ggc cct      157
Phe Ser Ser Lys Lys Cys Lys Thr Pro Ser Lys Thr Phe Arg Gly Pro
    15                  20                  25

tgc gtt aga aat gct aac tgc gat act tct tgt aga tat gag ggt tac      205
Cys Val Arg Asn Ala Asn Cys Asp Thr Ser Cys Arg Tyr Glu Gly Tyr
30                  35                  40                  45

cca gca gga gac tgc aag ggt att agg aga agg tgt atc tgc tgt aca      253
Pro Ala Gly Asp Cys Lys Gly Ile Arg Arg Arg Cys Ile Cys Cys Thr
                50                  55                  60

cat gct taatgaggta cc                                                271
His Ala


<210> SEQ ID NO 60
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding a signal peptide
      and Def2 codon-optimized with VGD
<220> FEATURE:
<221> NAME/KEY: misc_feature
<222> LOCATION: (1)..(6)
<223> OTHER INFORMATION: Restriction site for XbaI
<220> FEATURE:
<221> NAME/KEY: misc_feature
<222> LOCATION: (10)..(66)
<223> OTHER INFORMATION: sig_peptide; Def2 signal peptide
<220> FEATURE:
<221> NAME/KEY: CDS
<222> LOCATION: (67)..(255)
<223> OTHER INFORMATION: VGD-optimized Def2 peptide
<220> FEATURE:
<221> NAME/KEY: misc_feature
<222> LOCATION: (262)..(267)
<223> OTHER INFORMATION: Restriction site for KpnI

<400> SEQUENCE: 60

tctagaatga agatgtcaat gaggtcgatc gctgtggttt tcttggtgtg cctattggtg     60

ttgtca aca gaa gag atg ggc ccg aga aaa gca gac gct gga ttt ttc       108
       Thr Glu Glu Met Gly Pro Arg Lys Ala Asp Ala Gly Phe Phe
       1               5                   10

tca tcc aag aaa tgc aag aca ccc tca aaa aca ttc agg gga cct tgt      156
Ser Ser Lys Lys Cys Lys Thr Pro Ser Lys Thr Phe Arg Gly Pro Cys
15                  20                  25                  30

gta agg aac gct aac tgt gac act tct tgt agg tat gag ggc tat cca      204
Val Arg Asn Ala Asn Cys Asp Thr Ser Cys Arg Tyr Glu Gly Tyr Pro
                35                  40                  45

gct gga gat tgc aag ggt ata agg aga aga tgt att tgt tgt acc cat      252
Ala Gly Asp Cys Lys Gly Ile Arg Arg Arg Cys Ile Cys Cys Thr His
            50                  55                  60
```

-continued

```
gct taatagggta cc                                                267
Ala


<210> SEQ ID NO 61
<211> LENGTH: 1493
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding Def1
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)..(1084)
<223> OTHER INFORMATION: mat_peptide; Def1 peptide
<220> FEATURE:
<221> NAME/KEY: misc_feature
<222> LOCATION: (1085)..(1090)
<223> OTHER INFORMATION: Restriction site for KpnI
<220> FEATURE:
<221> NAME/KEY: misc_feature
<222> LOCATION: (1091)..(1277)
<223> OTHER INFORMATION: 3'UTR; TEV 3' UTR
<220> FEATURE:
<221> NAME/KEY: misc_feature
<222> LOCATION: (1278)..(1283)
<223> OTHER INFORMATION: Restriction site for SmaI
<220> FEATURE:
<221> NAME/KEY: misc_feature
<222> LOCATION: (1302)..(1493)
<223> OTHER INFORMATION: terminator; 35ST

<400> SEQUENCE: 61

cctgcaggtc aacatggtgg agcacgacac acttgtctac tccaaaaata tcaaagatac     60

agtctcagaa gaccaaaggg caattgagac ttttcaacaa agggtaatat ccggaaacct    120

cctcggattc cattgcccag ctatctgtca ctttattgtg aagatagtgg aaaaggaagg    180

tggctcctac aaatgccatc attgcgataa aggaaaggcc atcgttgaag atgcctctgc    240

cgacagtggt cccaaagatg gacccccacc cacgaggagc atcgtggaaa aagaagacgt    300

tccaaccacg tcttcaaagc aagtggattg atgtgataac atggtggagc acgacacact    360

tgtctactcc aaaaatatca aagatacagt ctcagaagac caaagggcaa ttgagacttt    420

tcaacaaagg gtaatatccg gaaacctcct cggattccat tgcccagcta tctgtcactt    480

tattgtgaag atagtggaaa aggaaggtgg ctcctacaaa tgccatcatt gcgataaagg    540

aaaggccatc gttgaagatg cctctgccga cagtggtccc aaagatggac ccccacccac    600

gaggagcatc gtggaaaaag aagacgttcc aaccacgtct tcaaagcaag tggattgatg    660

tgatatctcc actgacgtaa gggatgacgc acaatcccac tatccttcgc aagacccttc    720

ctctatataa ggaagttcat ttcatttgga gaggaccctc aacacaacat atacaaaaca    780

aacgaatctc aagcaatcaa gcattctact tctattgcag caatttaaat catttctttt    840

aaagcaaaag caattttctg aaaattttca ccatttacga acgatagctc tagaaacaat    900

ggggccaaga aaagccgaag ccgggatatt cagctcaaga aagtgcaaga caccctccaa    960
```

```
gacattcaaa ggcatctgta ccagggattc taattgcgac acctcatgta gatatgaggg   1020

ttaccctgct ggagattgca agggtattag gagaaggtgt ctttgctgta ctcatacata   1080

atgaggtacc tagtttctgc gtgtctttgc tttccgcttt tatgcttatt gtaatatata   1140

tgaatagcta tttacagtgg gacttggtct tgtgttgaat agtatcttat atgttttaat   1200

atgtcttatt agtctcatta cttaggcgaa cgacaaagtg aggttacctc ggtctaactc   1260

tcctatgtag tgcgagaccc ggggtccgca aaaatcacca gtctctctct acaaatctat   1320

ctctctctat ttttctccag aataatgtgt gagtagttcc cagataaggg aattagggtt   1380

cttatagggt ttcgctcatg tgttgagcat ataagaaacc cttagtatgt atttgtattt   1440

gtaaaatact tctatcaata aaatttctaa ttcctaaaac caaaatccag tga          1493
```

```
<210> SEQ ID NO 62
<211> LENGTH: 1505
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding Def2
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)...(1096)
<223> OTHER INFORMATION: mat_peptide; Def2 peptide
<220> FEATURE:
<221> NAME/KEY: misc_feature
<222> LOCATION: (1097)..(1102)
<223> OTHER INFORMATION: Restriction site for KpnI
<220> FEATURE:
<221> NAME/KEY: misc_feature
<222> LOCATION: (1103)..(1289)
<223> OTHER INFORMATION: 3'UTR; TEV 3' UTR
<220> FEATURE:
<221> NAME/KEY: misc_feature
<222> LOCATION: (1290)..(1295)
<223> OTHER INFORMATION: Restriction site for SmaI
<220> FEATURE:
<221> NAME/KEY: misc_feature
<222> LOCATION: (1314)..(1505)
<223> OTHER INFORMATION: terminator; 35ST

<400> SEQUENCE: 62
```

```
cctgcaggtc aacatggtgg agcacgacac acttgtctac tccaaaaata tcaaagatac     60

agtctcagaa gaccaaaggg caattgagac ttttcaacaa agggtaatat ccggaaacct    120

cctcggattc cattgcccag ctatctgtca ctttattgtg aagatagtgg aaaaggaagg    180

tggctcctac aaatgccatc attgcgataa aggaaaggcc atcgttgaag atgcctctgc    240

cgacagtggt cccaaagatg gacccccacc cacgaggagc atcgtggaaa aagaagacgt    300

tccaaccacg tcttcaaagc aagtggattg atgtgataac atggtggagc acgacacact    360

tgtctactcc aaaaatatca aagatacagt ctcagaagac caaagggcaa ttgagacttt    420

tcaacaaagg gtaatatccg gaaacctcct cggattccat tgcccagcta tctgtcactt    480
```

```
tattgtgaag atagtggaaa aggaaggtgg ctcctacaaa tgccatcatt gcgataaagg    540

aaaggccatc gttgaagatg cctctgccga cagtggtccc aaagatggac ccccacccac    600

gaggagcatc gtggaaaaag aagacgttcc aaccacgtct tcaaagcaag tggattgatg    660

tgatatctcc actgacgtaa gggatgacgc acaatcccac tatccttcgc aagacccttc    720

ctctatataa ggaagttcat ttcatttgga gaggaccctc aacacaacat atacaaaaca    780

aacgaatctc aagcaatcaa gcattctact tctattgcag caatttaaat catttctttt    840

aaagcaaaag caattttctg aaaattttca ccatttacga acgatagctc tagaaacaat    900

gacagaggag atgggtccaa ggaaagccga cgctgggttc ttcagttcta aaaagtgcaa    960

aacaccaagc aaaacattca gaggcccttg cgttagaaat gctaactgcg atacttcttg   1020

tagatatgag ggttacccag caggagactg caagggtatt aggagaaggt gtatctgctg   1080

tacacatgct taatgaggta cctagtttct gcgtgtcttt gctttccgct tttatgctta   1140

ttgtaatata tatgaatagc tatttacagt gggacttggt cttgtgttga atagtatctt   1200

atatgtttta atatgtctta ttagtctcat tacttaggcg aacgacaaag tgaggttacc   1260

tcggtctaac tctcctatgt agtgcgagac ccggggtccg caaaaatcac cagtctctct   1320

ctacaaatct atctctctct atttttctcc agaataatgt gtgagtagtt cccagataag   1380

ggaattaggg ttcttatagg gtttcgctca tgtgttgagc atataagaaa cccttagtat   1440

gtatttgtat ttgtaaaata cttctatcaa taaaatttct aattcctaaa accaaaatcc   1500

agtga                                                               1505
```

<210> SEQ ID NO 63
<211> LENGTH: 1535
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding Def3
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5'UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)...(1126)
<223> OTHER INFORMATION: mat_peptide; Def3 peptide
<220> FEATURE:
<221> NAME/KEY: misc_feature
<222> LOCATION: (1127)..(1132)
<223> OTHER INFORMATION: Restriction site for KpnI
<220> FEATURE:
<221> NAME/KEY: misc_feature
<222> LOCATION: (1133)..(1319)
<223> OTHER INFORMATION: 3'UTR; TEV 3' UTR
<220> FEATURE:
<221> NAME/KEY: misc_feature
<222> LOCATION: (1320)..(1325)
<223> OTHER INFORMATION: Restriction site for SmaI
<220> FEATURE:
<221> NAME/KEY: misc_feature
<222> LOCATION: (1344)..(1535)
<223> OTHER INFORMATION: terminator; 35ST

<400> SEQUENCE: 63
cctgcaggtc aacatggtgg agcacgacac acttgtctac tccaaaaata tcaaagatac 60
agtctcagaa gaccaaaggg caattgagac ttttcaacaa agggtaatat ccggaaacct 120
cctcggattc cattgcccag ctatctgtca ctttattgtg aagatagtgg aaaaggaagg 180
tggctcctac aaatgccatc attgcgataa aggaaaggcc atcgttgaag atgcctctgc 240
cgacagtggt cccaaagatg gacccccacc cacgaggagc atcgtggaaa aagaagacgt 300
tccaaccacg tcttcaaagc aagtggattg atgtgataac atggtggagc acgacacact 360
tgtctactcc aaaaatatca aagatacagt ctcagaagac caaagggcaa ttgagacttt 420
tcaacaaagg gtaatatccg gaaacctcct cggattccat tgcccagcta tctgtcactt 480
tattgtgaag atagtggaaa aggaaggtgg ctcctacaaa tgccatcatt gcgataaagg 540
aaaggccatc gttgaagatg cctctgccga cagtggtccc aaagatggac ccccacccac 600
gaggagcatc gtggaaaaag aagacgttcc aaccacgtct tcaaagcaag tggattgatg 660
tgatatctcc actgacgtaa gggatgacgc acaatcccac tatccttcgc aagacccttc 720
ctctatataa ggaagttcat ttcatttgga gaggaccctc aacacaacat atacaaaaca 780
aacgaatctc aagcaatcaa gcattctact tctattgcag caatttaaat catttctttt 840
aaagcaaaag caattttctg aaaattttca ccatttacga acgatagctc tagaaacaat 900
gaaacacttc ggggctatct ttttggtgct cctgctcgtg ctcgctactg aacatggtgc 960
cagagttgct gaggctagaa cctgtgaaac cccctctcaa aagtttaaag gtatctgcat 1020
ctctgattca aactgcgaga gcatatgtaa cacagaaggt ttccctaatg gtgaatgcag 1080
tggccttagg agaaggtgca tctgtaacac tccatgtaca taatgaggta cctagtttct 1140
gcgtgtcttt gctttccgct tttatgctta ttgtaatata tatgaatagc tatttacagt 1200
gggacttggt cttgtgttga atagtatctt atatgtttta atatgtctta ttagtctcat 1260
tacttaggcg aacgacaaag tgaggttacc tcggtctaac tctcctatgt agtgcgagac 1320
ccggggtccg caaaaatcac cagtctctct ctacaaatct atctctctct atttttctcc 1380
agaataatgt gtgagtagtt cccagataag ggaattaggg ttcttatagg gtttcgctca 1440
tgtgttgagc atataagaaa cccttagtat gtatttgtat ttgtaaaata cttctatcaa 1500
taaaatttct aattcctaaa accaaaatcc agtga 1535

<210> SEQ ID NO 64
<211> LENGTH: 1535
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Chimeric nucleic acid encoding Def5
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature -continued
<222> LOCATION: (899)...(1126)
<223> OTHER INFORMATION: mat_peptide; Def5 peptide
<220> FEATURE:
<221> NAME/KEY: misc_feature
<222> LOCATION: (1127)..(1132)
<223> OTHER INFORMATION: Restriction site for KpnI
<220> FEATURE:
<221> NAME/KEY: misc_feature
<222> LOCATION: (1133)..(1319)
<223> OTHER INFORMATION: 3'UTR; TEV 3' UTR
<220> FEATURE:
<221> NAME/KEY: misc_feature
<222> LOCATION: (1320)..(1325)
<223> OTHER INFORMATION: Restriction site for SmaI
<220> FEATURE:
<221> NAME/KEY: misc_feature
<222> LOCATION: (1344)..(1535)
<223> OTHER INFORMATION: terminator; 35ST

<400> SEQUENCE: 64
cctgcaggtc aacatggtgg agcacgacac acttgtctac tccaaaaata tcaaagatac 60
agtctcagaa gaccaaaggg caattgagac ttttcaacaa agggtaatat ccggaaacct 120
cctcggattc cattgcccag ctatctgtca ctttattgtg aagatagtgg aaaaggaagg 180
tggctcctac aaatgccatc attgcgataa aggaaaggcc atcgttgaag atgcctctgc 240
cgacagtggt cccaaagatg gacccccacc cacgaggagc atcgtggaaa aagaagacgt 300
tccaaccacg tcttcaaagc aagtggattg atgtgataac atggtggagc acgacacact 360
tgtctactcc aaaaatatca aagatacagt ctcagaagac caaagggcaa ttgagacttt 420
tcaacaaagg gtaatatccg gaaacctcct cggattccat tgcccagcta tctgtcactt 480
tattgtgaag atagtggaaa aggaaggtgg ctcctacaaa tgccatcatt gcgataaagg 540
aaaggccatc gttgaagatg cctctgccga cagtggtccc aaagatggac ccccacccac 600
gaggagcatc gtggaaaaag aagacgttcc aaccacgtct tcaaagcaag tggattgatg 660
tgatatctcc actgacgtaa gggatgacgc acaatcccac tatccttcgc aagacccttc 720
ctctatataa ggaagttcat ttcatttgga gaggaccctc aacacaacat atacaaaaca 780
aacgaatctc aagcaatcaa gcattctact tctattgcag caatttaaat catttctttt 840
aaagcaaaag caattttctg aaaattttca ccatttacga acgatagctc tagaaacaat 900
gagacccttc gccgctttgt ttttggtttt gttcttggtg ctcgctacag agattggacc 960
cagagtggtg gaggccagga tgtgttcttc acctagccat aggtttaagg gtatttgcac 1020
tagcagtagg aattgcgaga acacatgtaa ttccgaaaga ttttctggtg gagagtgcaa 1080
aggcttcagg agaaggtgca tgtgtaccgg gccatgtgtt taatgaggta cctagtttct 1140
gcgtgtcttt gctttccgct tttatgctta ttgtaatata tatgaatagc tatttacagt 1200
gggacttggt cttgtgttga atagtatctt atatgtttta atatgtctta ttagtctcat 1260
tacttaggcg aacgacaaag tgaggttacc tcggtctaac tctcctatgt agtgcgagac 1320
ccggggtccg caaaaatcac cagtctctct ctacaaatct atctctctct atttttctcc 1380
agaataatgt gtgagtagtt cccagataag ggaattaggg ttcttatagg gtttcgctca 1440
tgtgttgagc atataagaaa cccttagtat gtatttgtat ttgtaaaata cttctatcaa 1500
taaaatttct aattcctaaa accaaaatcc agtga 1535

<210> SEQ ID NO 65
<211> LENGTH: 1583
<212> TYPE: DNA
<213> ORGANISM: Artificial Sequence
<220> FEATURE:

```
<223> OTHER INFORMATION: Description of Artificial Sequence: Synthetic
      polynucleotide
<220> FEATURE:
<223> OTHER INFORMATION: Chimeric nucleic acid encoding Def6
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)...(1174)
<223> OTHER INFORMATION: mat_peptide; Def6 peptide
<220> FEATURE:
<221> NAME/KEY: misc_feature
<222> LOCATION: (1175)..(1180)
<223> OTHER INFORMATION: Restriction site for KpnI
<220> FEATURE:
<221> NAME/KEY: misc_feature
<222> LOCATION: (1181)..(1367)
<223> OTHER INFORMATION: 3'UTR; TEV 3' UTR
<220> FEATURE:
<221> NAME/KEY: misc_feature
<222> LOCATION: (1368)..(1373)
<223> OTHER INFORMATION: Restriction site for SmaI
<220> FEATURE:
<221> NAME/KEY: misc_feature
<222> LOCATION: (1392)..(1583)
<223> OTHER INFORMATION: terminator; 35ST

<400> SEQUENCE: 65

cctgcaggtc aacatggtgg agcacgacac acttgtctac tccaaaaata tcaaagatac     60

agtctcagaa gaccaaaggg caattgagac ttttcaacaa agggtaatat ccggaaacct    120

cctcggattc cattgcccag ctatctgtca ctttattgtg aagatagtgg aaaaggaagg    180

tggctcctac aaatgccatc attgcgataa aggaaaggcc atcgttgaag atgcctctgc    240

cgacagtggt cccaaagatg gacccccacc cacgaggagc atcgtggaaa aagaagacgt    300

tccaaccacg tcttcaaagc aagtggattg atgtgataac atggtggagc acgacacact    360

tgtctactcc aaaaatatca aagatacagt ctcagaagac caaagggcaa ttgagacttt    420

tcaacaaagg gtaatatccg gaaacctcct cggattccat tgcccagcta tctgtcactt    480

tattgtgaag atagtggaaa aggaaggtgg ctcctacaaa tgccatcatt gcgataaagg    540

aaaggccatc gttgaagatg cctctgccga cagtggtccc aaagatggac ccccacccac    600

gaggagcatc gtggaaaaag aagacgttcc aaccacgtct tcaaagcaag tggattgatg    660

tgatatctcc actgacgtaa gggatgacgc acaatcccac tatccttcgc aagacccttc    720

ctctatataa ggaagttcat ttcatttgga gaggaccctc aacacaacat atacaaaaca    780

aacgaatctc aagcaatcaa gcattctact tctattgcag caatttaaat catttctttt    840

aaagcaaaag caattttctg aaaattttca ccatttacga acgatagctc tagaaacaat    900

ggagagatcg tcaagagttt ttagcgttgt gctgcttatg ctggtgctgg ttctgtctac    960

tgatatgtat accgaccctg tggctgttct ttcttatgag attggtacta aggtggctga   1020

ggcaagaatc tgcgaatctg cctcatacag gtttaagggc atttgtgtta gcagaagtaa   1080

ttgcgcaaac gtgtgcaaga atgagggctt tcctggtgga agatgcaggg ggttcaggag   1140

aaggtgcttg tgttataagc attgtggtta atgaggtacc tagtttctgc gtgtctttgc   1200
```

```
tttccgcttt tatgcttatt gtaatatata tgaatagcta tttacagtgg gacttggtct   1260

tgtgttgaat agtatcttat atgttttaat atgtcttatt agtctcatta cttaggcgaa   1320

cgacaaagtg aggttacctc ggtctaactc tcctatgtag tgcgagaccc ggggtccgca   1380

aaaatcacca gtctctctct acaaatctat ctctctctat tttctccag aataatgtgt   1440

gagtagttcc cagataaggg aattagggtt cttatagggt ttcgctcatg tgttgagcat   1500

ataagaaacc cttagtatgt atttgtattt gtaaaatact tctatcaata aaatttctaa   1560

ttcctaaaac caaaatccag tga                                           1583


<210> SEQ ID NO 66
<211> LENGTH: 1535
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding Def7
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (899)..(1126)
<223> OTHER INFORMATION: mat_peptide; Def7 peptide
<220> FEATURE:
<221> NAME/KEY: misc_feature
<222> LOCATION: (1127)..(1132)
<223> OTHER INFORMATION: Restriction site for KpnI
<220> FEATURE:
<221> NAME/KEY: misc_feature
<222> LOCATION: (1133)..(1319)
<223> OTHER INFORMATION: 3'UTR; TEV 3' UTR
<220> FEATURE:
<221> NAME/KEY: misc_feature
<222> LOCATION: (1320)..(1325)
<223> OTHER INFORMATION: Restriction site for SmaI
<220> FEATURE:
<221> NAME/KEY: misc_feature
<222> LOCATION: (1344)..(1535)
<223> OTHER INFORMATION: terminator; 35ST

<400> SEQUENCE: 66

cctgcaggtc aacatggtgg agcacgacac acttgtctac tccaaaaata tcaaagatac     60

agtctcagaa gaccaaaggg caattgagac ttttcaacaa agggtaatat ccggaaacct    120

cctcggattc cattgcccag ctatctgtca ctttattgtg aagatagtgg aaaaggaagg    180

tggctcctac aaatgccatc attgcgataa aggaaaggcc atcgttgaag atgcctctgc    240

cgacagtggt cccaaagatg gacccccacc cacgaggagc atcgtggaaa aagaagacgt    300

tccaaccacg tcttcaaagc aagtggattg atgtgataac atggtggagc acgacacact    360

tgtctactcc aaaaatatca aagatacagt ctcagaagac caaagggcaa ttgagacttt    420

tcaacaaagg gtaatatccg gaaacctcct cggattccat tgcccagcta tctgtcactt    480

tattgtgaag atagtggaaa aggaaggtgg ctcctacaaa tgccatcatt gcgataaagg    540

aaaggccatc gttgaagatg cctctgccga cagtggtccc aaagatggac ccccacccac    600
```

gaggagcatc gtggaaaaag aagacgttcc aaccacgtct tcaaagcaag tggattgatg 660
tgatatctcc actgacgtaa gggatgacgc acaatcccac tatccttcgc aagacccttc 720
ctctatataa ggaagttcat ttcatttgga gaggaccctc aacacaacat atacaaaaca 780
aacgaatctc aagcaatcaa gcattctact tctattgcag caatttaaat catttctttt 840
aaagcaaaag caattttctg aaaattttca ccatttacga acgatagctc tagaaacaat 900
gaaacctttt gtggcttttg tgctggcttt tatgctcgtt ctggctattg aaatgggtcc 960
aagagtggct gaggcaagga tgtgtactaa tccttctagg actttaggg gtccatgcgt 1020 tagtgatagg aactgcgagt cttcatgtat gggcgaaggg tttcccggtg gatcttgcca 1080
tggcttcagg agaaagtgcg tgtgttctaa accttgtgct taatgaggta cctagtttct 1140
gcgtgtcttt gctttccgct tttatgctta ttgtaatata tatgaatagc tatttacagt 1200
gggacttggt cttgtgttga atagtatctt atatgtttta atatgtctta ttagtctcat 1260
tacttaggcg aacgacaaag tgaggttacc tcggtctaac tctcctatgt agtgcgagac 1320
ccggggtccg caaaaatcac cagtctctct ctacaaatct atctctctct atttttctcc 1380
agaataatgt gtgagtagtt cccagataag ggaattaggg ttcttatagg gtttcgctca 1440
tgtgttgagc atataagaaa cccttagtat gtatttgtat ttgtaaaata cttctatcaa 1500
taaaatttct aattcctaaa accaaaatcc agtga 1535

<210> SEQ ID NO 67
<211> LENGTH: 1489
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Chimeric nucleic acid encoding Def1
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1080)
<223> OTHER INFORMATION: mat_peptide; Def1 peptide
<220> FEATURE:
<221> NAME/KEY: misc_feature
<222> LOCATION: (1081)..(1086)
<223> OTHER INFORMATION: Restriction site for KpnI
<220> FEATURE:
<221> NAME/KEY: misc_feature
<222> LOCATION: (1087)..(1273)
<223> OTHER INFORMATION: 3'UTR; TEV 3' UTR
<220> FEATURE:
<221> NAME/KEY: misc_feature
<222> LOCATION: (1274)..(1279)
<223> OTHER INFORMATION: Restriction site for SmaI
<220> FEATURE:
<221> NAME/KEY: misc_feature
<222> LOCATION: (1298)..(1489)
<223> OTHER INFORMATION: terminator; 35ST

<400> SEQUENCE: 67
cctgcaggtc aacatggtgg agcacgacac acttgtctac tccaaaaata tcaaagatac 60

-continued

```
agtctcagaa gaccaaaggg caattgagac ttttcaacaa agggtaatat ccggaaacct    120

cctcggattc cattgcccag ctatctgtca ctttattgtg aagatagtgg aaaaggaagg    180

tggctcctac aaatgccatc attgcgataa aggaaaggcc atcgttgaag atgcctctgc    240

cgacagtggt cccaaagatg gacccccacc cacgaggagc atcgtggaaa aagaagacgt    300

tccaaccacg tcttcaaagc aagtggattg atgtgataac atggtggagc acgacacact    360

tgtctactcc aaaaatatca aagatacagt ctcagaagac caaagggcaa ttgagacttt    420

tcaacaaagg gtaatatccg gaaacctcct cggattccat tgcccagcta tctgtcactt    480

tattgtgaag atagtggaaa aggaaggtgg ctcctacaaa tgccatcatt gcgataaagg    540

aaaggccatc gttgaagatg cctctgccga cagtggtccc aaagatggac ccccacccac    600

gaggagcatc gtggaaaaag aagacgttcc aaccacgtct tcaaagcaag tggattgatg    660

tgatatctcc actgacgtaa gggatgacgc acaatcccac tatccttcgc aagacccttc    720

ctctatataa ggaagttcat ttcatttgga gaggaccctc aacacaacat atacaaaaca    780

aacgaatctc aagcaatcaa gcattctact tctattgcag caatttaaat catttctttt    840

aaagcaaaag caattttctg aaaattttca ccatttacga acgatagctc tagaatgggt    900

cctaggaagg cagaggctgg aatatttagc tcgaggaagt gcaaaacccc aagtaaaacg    960

tttaagggaa tttgtactag agactccaat tgtgacactt cgtgtaggta tgagggatac   1020

ccagctggag attgcaaggg tatcaggaga aggtgcttat gctgtacaca tacataatag   1080

ggtacctagt ttctgcgtgt ctttgctttc cgcttttatg cttattgtaa tatatatgaa   1140

tagctattta cagtgggact tggtcttgtg ttgaatagta tcttatatgt tttaatatgt   1200

cttattagtc tcattactta ggcgaacgac aaagtgaggt tacctcggtc taactctcct   1260

atgtagtgcg agacccgggg tccgcaaaaa tcaccagtct ctctctacaa atctatctct   1320

ctctattttt ctccagaata atgtgtgagt agttcccaga taagggaatt agggttctta   1380

tagggtttcg ctcatgtgtt gagcatataa gaaaccctta gtatgtattt gtatttgtaa   1440

aatacttcta tcaataaaat ttctaattcc taaaaccaaa atccagtga               1489
```

<210> SEQ ID NO 68
<211> LENGTH: 1501
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chimeric nucleic acid encoding Def2
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1092)
<223> OTHER INFORMATION: mat_peptide; Def2 peptide
<220> FEATURE:
<221> NAME/KEY: misc_feature
<222> LOCATION: (1093)..(1098)
<223> OTHER INFORMATION: Restriction site for KpnI
<220> FEATURE:

<221> NAME/KEY: misc_feature
<222> LOCATION: (1099)..(1285)
<223> OTHER INFORMATION: 3'UTR; TEV 3' UTR
<220> FEATURE:
<221> NAME/KEY: misc_feature
<222> LOCATION: (1286)..(1291)
<223> OTHER INFORMATION: Restriction site for SmaI
<220> FEATURE:
<221> NAME/KEY: misc_feature
<222> LOCATION: (1310)..(1501)
<223> OTHER INFORMATION: terminator; 35ST

<400> SEQUENCE: 68
cctgcaggtc aacatggtgg agcacgacac acttgtctac tccaaaaata tcaaagatac 60
agtctcagaa gaccaaaggg caattgagac ttttcaacaa agggtaatat ccggaaacct 120
cctcggattc cattgcccag ctatctgtca ctttattgtg aagatagtgg aaaaggaagg 180
tggctcctac aaatgccatc attgcgataa aggaaaggcc atcgttgaag atgcctctgc 240
cgacagtggt cccaaagatg gacccccacc cacgaggagc atcgtggaaa aagaagacgt 300
tccaaccacg tcttcaaagc aagtggattg atgtgataac atggtggagc acgacacact 360
tgtctactcc aaaaatatca aagatacagt ctcagaagac caaagggcaa ttgagacttt 420
tcaacaaagg gtaatatccg gaaacctcct cggattccat tgcccagcta tctgtcactt 480
tattgtgaag atagtggaaa aggaaggtgg ctcctacaaa tgccatcatt gcgataaagg 540
aaaggccatc gttgaagatg cctctgccga cagtggtccc aaagatggac ccccacccac 600
gaggagcatc gtggaaaaag aagacgttcc aaccacgtct tcaaagcaag tggattgatg 660
tgatatctcc actgacgtaa gggatgacgc acaatcccac tatccttcgc aagacccttc 720
ctctatataa ggaagttcat ttcatttgga gaggaccctc aacacaacat atacaaaaca 780
aacgaatctc aagcaatcaa gcattctact tctattgcag caatttaaat catttctttt 840
aaagcaaaag caattttctg aaaattttca ccatttacga acgatagctc tagaatgaca 900
gaagagatgg gcccgagaaa agcagacgct ggatttttct catccaagaa atgcaagaca 960
ccctcaaaaa cattcagggg accttgtgta aggaacgcta actgtgacac ttcttgtagg 1020
tatgagggct atccagctgg agattgcaag ggtataagga gaagatgtat ttgttgtacc 1080
catgcttaat agggtaccta gtttctgcgt gtctttgctt tccgctttta tgcttattgt 1140
aatatatatg aatagctatt tacagtggga cttggtcttg tgttgaatag tatcttatat 1200
gttttaatat gtcttattag tctcattact taggcgaacg acaaagtgag gttacctcgg 1260
tctaactctc ctatgtagtg cgagacccgg ggtccgcaaa aatcaccagt ctctctctac 1320
aaatctatct ctctctattt ttctccagaa taatgtgtga gtagttccca gataagggaa 1380
ttagggttct tatagggttt cgctcatgtg ttgagcatat aagaaaccct tagtatgtat 1440
ttgtatttgt aaaatacttc tatcaataaa atttctaatt cctaaaacca aaatccagtg 1500
a 1501

<210> SEQ ID NO 69
<211> LENGTH: 1531
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<223> OTHER INFORMATION: Chimeric nucleic acid encoding Def3
<220> FEATURE:
<221> NAME/KEY: misc_feature
<222> LOCATION: (1)..(754)

<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1122)
<223> OTHER INFORMATION: mat_peptide; Def3 peptide
<220> FEATURE:
<221> NAME/KEY: misc_feature
<222> LOCATION: (1123)..(1128)
<223> OTHER INFORMATION: Restriction site for KpnI
<220> FEATURE:
<221> NAME/KEY: misc_feature
<222> LOCATION: (1129)..(1315)
<223> OTHER INFORMATION: 3'UTR; TEV 3' UTR
<220> FEATURE:
<221> NAME/KEY: misc_feature
<222> LOCATION: (1316)..(1321)
<223> OTHER INFORMATION: Restriction site for SmaI
<220> FEATURE:
<221> NAME/KEY: misc_feature
<222> LOCATION: (1340)..(1531)
<223> OTHER INFORMATION: terminator; 35ST

<400> SEQUENCE: 69
cctgcaggtc aacatggtgg agcacgacac acttgtctac tccaaaaata tcaaagatac 60
agtctcagaa gaccaaaggg caattgagac ttttcaacaa agggtaatat ccggaaacct 120
cctcggattc cattgcccag ctatctgtca ctttattgtg aagatagtgg aaaaggaagg 180
tggctcctac aaatgccatc attgcgataa aggaaaggcc atcgttgaag atgcctctgc 240
cgacagtggt cccaaagatg gacccccacc cacgaggagc atcgtggaaa aagaagacgt 300
tccaaccacg tcttcaaagc aagtggattg atgtgataac atggtggagc acgacacact 360
tgtctactcc aaaaatatca aagatacagt ctcagaagac caaagggcaa ttgagacttt 420
tcaacaaagg gtaatatccg gaaacctcct cggattccat tgcccagcta tctgtcactt 480
tattgtgaag atagtggaaa aggaaggtgg ctcctacaaa tgccatcatt gcgataaagg 540
aaaggccatc gttgaagatg cctctgccga cagtggtccc aaagatggac ccccacccac 600
gaggagcatc gtggaaaaag aagacgttcc aaccacgtct tcaaagcaag tggattgatg 660
tgatatctcc actgacgtaa gggatgacgc acaatcccac tatccttcgc aagacccttc 720
ctctatataa ggaagttcat ttcatttgga gaggaccctc aacacaacat atacaaaaca 780
aacgaatctc aagcaatcaa gcattctact tctattgcag caatttaaat catttctttt 840
aaagcaaaag caattttctg aaaattttca ccatttacga acgatagctc tagaatgaag 900
cactttgggg ctatattcct tgtgctttta ttagtcctcg caacggaaca tggagcaaga 960
gtagcagaag caagaacttg tgaaacgcca agtcaaaagt tcaaaggcat ctgtatttcc 1020
gactccaatt gtgaaagcat ttgcaatacc gaaggatttc cgaatggaga atgttctggc 1080
cttcgcagaa gatgcatttg caacacccct tgtacttaat agggtaccta gtttctgcgt 1140
gtctttgctt tccgctttta tgcttattgt aatatatatg aatagctatt tacagtggga 1200
cttggtcttg tgttgaatag tatcttatat gttttaatat gtcttattag tctcattact 1260
taggcgaacg acaaagtgag gttacctcgg tctaactctc ctatgtagtg cgagacccgg 1320
ggtccgcaaa aatcaccagt ctctctctac aaatctatct ctctctattt ttctccagaa 1380
taatgtgtga gtagttccca gataagggaa ttagggttct tatagggttt cgctcatgtg 1440

-continued ttgagcatat aagaaaccct tagtatgtat ttgtatttgt aaaatacttc tatcaataaa 1500
atttctaatt cctaaaacca aaatccagtg a 1531

<210> SEQ ID NO 70
<211> LENGTH: 1480
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chimeric nucleic acid encoding Def4
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1071)
<223> OTHER INFORMATION: mat_peptide; Def4 peptide
<220> FEATURE:
<221> NAME/KEY: misc_feature
<222> LOCATION: (1072)..(1077)
<223> OTHER INFORMATION: Restriction site for KpnI
<220> FEATURE:
<221> NAME/KEY: misc_feature
<222> LOCATION: (1078)..(1264)
<223> OTHER INFORMATION: 3'UTR; TEV 3' UTR
<220> FEATURE:
<221> NAME/KEY: misc_feature
<222> LOCATION: (1265)..(1270)
<223> OTHER INFORMATION: Restriction site for SmaI
<220> FEATURE:
<221> NAME/KEY: misc_feature
<222> LOCATION: (1289)..(1480)
<223> OTHER INFORMATION: terminator; 35ST

<400> SEQUENCE: 70
cctgcaggtc aacatggtgg agcacgacac acttgtctac tccaaaaata tcaaagatac 60
agtctcagaa gaccaaaggg caattgagac ttttcaacaa agggtaatat ccggaaacct 120
cctcggattc cattgcccag ctatctgtca ctttattgtg aagatagtgg aaaaggaagg 180
tggctcctac aaatgccatc attgcgataa aggaaaggcc atcgttgaag atgcctctgc 240
cgacagtggt cccaaagatg gacccccacc cacgaggagc atcgtggaaa aagaagacgt 300
tccaaccacg tcttcaaagc aagtggattg atgtgataac atggtggagc acgacacact 360
tgtctactcc aaaaatatca aagatacagt ctcagaagac caaagggcaa ttgagacttt 420
tcaacaaagg gtaatatccg gaaacctcct cggattccat tgcccagcta tctgtcactt 480
tattgtgaag atagtggaaa aggaaggtgg ctcctacaaa tgccatcatt gcgataaagg 540
aaaggccatc gttgaagatg cctctgccga cagtggtccc aaagatggac ccccacccac 600
gaggagcatc gtggaaaaag aagacgttcc aaccacgtct tcaaagcaag tggattgatg 660
tgatatctcc actgacgtaa gggatgacgc acaatcccac tatccttcgc aagacccttc 720
ctctatataa ggaagttcat ttcatttgga gaggaccctc aacacaacat atacaaaaca 780
aacgaatctc aagcaatcaa gcattctact tctattgcag caatttaaat catttctttt 840
aaagcaaaag caattttctg aaaattttca ccatttacga acgatagctc tagaatggta 900

```
agtacaaaag ttgcagaagc aaggatttgt gcttcaccat ctccaacgtt taagggaata    960

tgttttagta gccgtaattg tgaaacgaat tgcaattccg taaaattttc tggaggaagt   1020

tgtcagggtt ttaggagaag atgtatgtgc acaaagccct gcgcttgata gggtacctag   1080

tttctgcgtg tctttgcttt ccgcttttat gcttattgta atatatatga atagctattt   1140

acagtgggac ttggtcttgt gttgaatagt atcttatatg ttttaatatg tcttattagt   1200

ctcattactt aggcgaacga caaagtgagg ttacctcggt ctaactctcc tatgtagtgc   1260

gagacccggg gtccgcaaaa atcaccagtc tctctctaca aatctatctc tctctatttt   1320

tctccagaat aatgtgtgag tagttcccag ataagggaat tagggttctt atagggtttc   1380

gctcatgtgt tgagcatata agaaaccctt agtatgtatt tgtatttgta aaatacttct   1440

atcaataaaa tttctaattc ctaaaaccaa aatccagtga                         1480
```

```
<210> SEQ ID NO 71
<211> LENGTH: 1531
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Chimeric nucleic acid encoding Def5
<220> FEATURE:
<221> NAME/KEY: misc_feature
<222> LOCATION: (1)...(754)
<223> OTHER INFORMATION: promoter; 35SP
<220> FEATURE:
<221> NAME/KEY: misc_feature
<222> LOCATION: (758)...(888)
<223> OTHER INFORMATION: 5'UTR; TEV 5' UTR
<220> FEATURE:
<221> NAME/KEY: misc_feature
<222> LOCATION: (889)...(894)
<223> OTHER INFORMATION: Restriction site for XbaI
<220> FEATURE:
<221> NAME/KEY: misc_feature
<222> LOCATION: (895)...(1122)
<223> OTHER INFORMATION: mat_peptide; Def5 peptide
<220> FEATURE:
<221> NAME/KEY: misc_feature
<222> LOCATION: (1123)...(1128)
<223> OTHER INFORMATION: Restriction site for KpnI
<220> FEATURE:
<221> NAME/KEY: misc_feature
<222> LOCATION: (1129)...(1315)
<223> OTHER INFORMATION: 3'UTR; TEV 3' UTR
<220> FEATURE:
<221> NAME/KEY: misc_feature
<222> LOCATION: (1316)...(1321)
<223> OTHER INFORMATION: Restriction site for SmaI
<220> FEATURE:
<221> NAME/KEY: misc_feature
<222> LOCATION: (1340)...(1531)
<223> OTHER INFORMATION: terminator; 35ST

<400> SEQUENCE: 71

cctgcaggtc aacatggtgg agcacgacac acttgtctac tccaaaaata tcaaagatac     60

agtctcagaa gaccaaaggg caattgagac ttttcaacaa agggtaatat ccggaaacct    120

cctcggattc cattgcccag ctatctgtca ctttattgtg aagatagtgg aaaaggaagg    180

tggctcctac aaatgccatc attgcgataa aggaaaggcc atcgttgaag atgcctctgc    240

cgacagtggt cccaaagatg gacccccacc cacgaggagc atcgtggaaa aagaagacgt    300

tccaaccacg tcttcaaagc aagtggattg atgtgataac atggtggagc acgacacact    360

tgtctactcc aaaaatatca aagatacagt ctcagaagac caaagggcaa ttgagacttt    420
```

```
tcaacaaagg gtaatatccg gaaacctcct cggattccat tgcccagcta tctgtcactt    480

tattgtgaag atagtggaaa aggaaggtgg ctcctacaaa tgccatcatt gcgataaagg    540

aaaggccatc gttgaagatg cctctgccga cagtggtccc aaagatggac ccccacccac    600

gaggagcatc gtggaaaaag aagacgttcc aaccacgtct tcaaagcaag tggattgatg    660

tgatatctcc actgacgtaa gggatgacgc acaatcccac tatccttcgc aagacccttc    720

ctctatataa ggaagttcat ttcatttgga gaggaccctc aacacaacat atacaaaaca    780

aacgaatctc aagcaatcaa gcattctact tctattgcag caatttaaat catttctttt    840

aaagcaaaag caattttctg aaaattttca ccatttacga acgatagctc tagaatgaga    900

ccatttgctg ctcttttcct tgtgcttttc cttgtgttgg ctacagaaat agggcccagg    960

gtggtagaag caagaatgtg ctcaagtcca agtcataggt tcaagggcat ttgcacttct   1020

tcgagaaatt gtgaaaacac ttgcaacagc gaacgatttt caggtggtga gtgtaaaggc   1080

tttcgcagaa gatgtatgtg cacgggaccc tgtgtgtaat agggtaccta gtttctgcgt   1140

gtctttgctt tccgctttta tgcttattgt aatatatatg aatagctatt tacagtggga   1200

cttggtcttg tgttgaatag tatcttatat gttttaatat gtcttattag tctcattact   1260

taggcgaacg acaaagtgag gttacctcgg tctaactctc ctatgtagtg cgagacccgg   1320

ggtccgcaaa aatcaccagt ctctctctac aaatctatct ctctctattt ttctccagaa   1380

taatgtgtga gtagttccca gataagggaa ttagggttct tatagggttt cgctcatgtg   1440

ttgagcatat aagaaaccct tagtatgtat ttgtatttgt aaaatacttc tatcaataaa   1500

atttctaatt cctaaaacca aaatccagtg a                                  1531
```

<210> SEQ ID NO 72
<211> LENGTH: 1579
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chimeric nucleic acid encoding Def6
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1170)
<223> OTHER INFORMATION: mat_peptide; Def6 peptide
<220> FEATURE:
<221> NAME/KEY: misc_feature
<222> LOCATION: (1171)..(1176)
<223> OTHER INFORMATION: Restriction site for KpnI
<220> FEATURE:
<221> NAME/KEY: misc_feature
<222> LOCATION: (1177)..(1363)
<223> OTHER INFORMATION: 3'UTR; TEV 3' UTR
<220> FEATURE:
<221> NAME/KEY: misc_feature
<222> LOCATION: (1364)..(1369)
<223> OTHER INFORMATION: Restriction site for SmaI
<220> FEATURE:
<221> NAME/KEY: misc_feature
<222> LOCATION: (1388)..(1579)
<223> OTHER INFORMATION: terminator; 5ST

<400> SEQUENCE: 72
cctgcaggtc aacatggtgg agcacgacac acttgtctac tccaaaaata tcaaagatac 60
agtctcagaa gaccaaaggg caattgagac ttttcaacaa agggtaatat ccggaaacct 120
cctcggattc cattgcccag ctatctgtca ctttattgtg aagatagtgg aaaaggaagg 180
tggctcctac aaatgccatc attgcgataa aggaaaggcc atcgttgaag atgcctctgc 240
cgacagtggt cccaaagatg gacccccacc cacgaggagc atcgtggaaa aagaagacgt 300
tccaaccacg tcttcaaagc aagtggattg atgtgataac atggtggagc acgacacact 360
tgtctactcc aaaaatatca aagatacagt ctcagaagac caaagggcaa ttgagacttt 420
tcaacaaagg gtaatatccg gaaacctcct cggattccat tgcccagcta tctgtcactt 480
tattgtgaag atagtggaaa aggaaggtgg ctcctacaaa tgccatcatt gcgataaagg 540
aaaggccatc gttgaagatg cctctgccga cagtggtccc aaagatggac ccccacccac 600
gaggagcatc gtggaaaaag aagacgttcc aaccacgtct tcaaagcaag tggattgatg 660
tgatatctcc actgacgtaa gggatgacgc acaatcccac tatccttcgc aagacccttc 720
ctctatataa ggaagttcat ttcatttgga gaggaccctc aacacaacat atacaaaaca 780
aacgaatctc aagcaatcaa gcattctact tctattgcag caatttaaat catttctttt 840
aaagcaaaag caattttctg aaaattttca ccatttacga acgatagctc tagaatggag 900
aggtcttcac gtgtgttttc agtggttctc cttatgttgg ttcttgtgtt gagtacagat 960
atgtacacag accctgtagc agttcttagt tatgaaattg ggactaaggt ggcagaagct 1020
cgcatttgtg aatcggcaag ttacaggttc aagggaatat gtgtgtcaag gtcaaactgc 1080
gctaacgttt gcaaaaatga gggtttccca ggtggtcgtt gccggggatt tagaaggcgg 1140
tgcctttgct acaaacattg cgggtagtaa ggtacctagt ttctgcgtgt ctttgctttc 1200
cgcttttatg cttattgtaa tatatatgaa tagctattta cagtgggact tggtcttgtg 1260
ttgaatagta tcttatatgt tttaatatgt cttattagtc tcattactta ggcgaacgac 1320
aaagtgaggt tacctcggtc taactctcct atgtagtgcg agacccgggg tccgcaaaaa 1380
tcaccagtct ctctctacaa atctatctct ctctattttt ctccagaata atgtgtgagt 1440
agttcccaga taagggaatt agggttctta tagggtttcg ctcatgtgtt gagcatataa 1500
gaaaccctta gtatgtattt gtatttgtaa aatacttcta tcaataaaat ttctaattcc 1560
taaaaccaaa atccagtga 1579

<210> SEQ ID NO 73
<211> LENGTH: 1531
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Chimeric nucleic acid encoding Def7
<220> FEATURE:
<221> NAME/KEY: misc_feature
<222> LOCATION: (1)..(754)
<223> OTHER INFORMATION: promoter; 35SP
<220> FEATURE:
<221> NAME/KEY: misc_feature
<222> LOCATION: (758)..(888)
<223> OTHER INFORMATION: 5'UTR; TEV 5' UTR
<220> FEATURE:
<221> NAME/KEY: misc_feature
<222> LOCATION: (889)..(894)
<223> OTHER INFORMATION: Restriction site for XbaI
<220> FEATURE:
<221> NAME/KEY: misc_feature
<222> LOCATION: (895)..(1122)
<223> OTHER INFORMATION: mat_peptide; Def7 peptide
<220> FEATURE:
<221> NAME/KEY: misc_feature
<222> LOCATION: (1123)..(1128)
<223> OTHER INFORMATION: Restriction site for KpnI
<220> FEATURE:
<221> NAME/KEY: misc_feature
<222> LOCATION: (1129)..(1315)
<223> OTHER INFORMATION: 3'UTR; TEV 3' UTR
<220> FEATURE:
<221> NAME/KEY: misc_feature
<222> LOCATION: (1316)..(1321)
<223> OTHER INFORMATION: Restriction site for SmaI
<220> FEATURE:
<221> NAME/KEY: misc_feature
<222> LOCATION: (1340)..(1531)
<223> OTHER INFORMATION: terminator; 35ST

<400> SEQUENCE: 73
cctgcaggtc aacatggtgg agcacgacac acttgtctac tccaaaaata tcaaagatac 60
agtctcagaa gaccaaaggg caattgagac ttttcaacaa agggtaatat ccggaaacct 120
cctcggattc cattgcccag ctatctgtca ctttattgtg aagatagtgg aaaaggaagg 180
tggctcctac aaatgccatc attgcgataa aggaaaggcc atcgttgaag atgcctctgc 240
cgacagtggt cccaaagatg gacccccacc cacgaggagc atcgtggaaa aagaagacgt 300
tccaaccacg tcttcaaagc aagtggattg atgtgataac atggtggagc acgacacact 360
tgtctactcc aaaaatatca aagatacagt ctcagaagac caaagggcaa ttgagacttt 420
tcaacaaagg gtaatatccg gaaacctcct cggattccat tgcccagcta tctgtcactt 480
tattgtgaag atagtggaaa aggaaggtgg ctcctacaaa tgccatcatt gcgataaagg 540
aaaggccatc gttgaagatg cctctgccga cagtggtccc aaagatggac ccccacccac 600
gaggagcatc gtggaaaaag aagacgttcc aaccacgtct tcaaagcaag tggattgatg 660
tgatatctcc actgacgtaa gggatgacgc acaatcccac tatccttcgc aagacccttc 720
ctctatataa ggaagttcat ttcatttgga gaggaccctc aacacaacat atacaaaaca 780
aacgaatctc aagcaatcaa gcattctact tctattgcag caatttaaat catttctttt 840
aaagcaaaag caattttctg aaaattttca ccatttacga acgatagctc tagaatgaag 900
ccttttgtag cttttgttct ggctttcatg cttgttctcg ccatagagat gggtccccgg 960
gtcgctgagg cacggatgtg cacaaatccg agcagaacat tcaggggtcc ctgcgttagc 1020
gacaggaact gcgaatcctc atgcatggga gagggatttc cgggtggtag ttgccatgga 1080
tttagaagaa aatgcgtttg cagcaagcct tgtgcttagt aaggtaccta gtttctgcgt 1140
gtctttgctt tccgctttta tgcttattgt aatatatatg aatagctatt tacagtggga 1200
cttggtcttg tgttgaatag tatcttatat gttttaatat gtcttattag tctcattact 1260
taggcgaacg acaaagtgag gttacctcgg tctaactctc ctatgtagtg cgagacccgg 1320
ggtccgcaaa aatcaccagt ctctctctac aaatctatct ctctctattt ttctccagaa 1380
taatgtgtga gtagttccca gataagggaa ttagggttct tatagggttt cgctcatgtg 1440
ttgagcatat aagaaaccct tagtatgtat ttgtatttgt aaaatacttc tatcaataaa 1500
atttctaatt cctaaaacca aaatccagtg a 1531

<210> SEQ ID NO 74

<211> LENGTH: 754
<212> TYPE: DNA
<213> ORGANISM: Cauliflower mosaic virus
<220> FEATURE:
<221> NAME/KEY: misc_feature
<222> LOCATION: (1)..(754)
<223> OTHER INFORMATION: promoter; CaMV 35S promoter

<400> SEQUENCE: 74

```
cctgcaggtc aacatggtgg agcacgacac acttgtctac tccaaaaata tcaaagatac     60

agtctcagaa gaccaaaggg caattgagac ttttcaacaa agggtaatat ccggaaacct    120

cctcggattc cattgcccag ctatctgtca ctttattgtg aagatagtgg aaaaggaagg    180

tggctcctac aaatgccatc attgcgataa aggaaaggcc atcgttgaag atgcctctgc    240

cgacagtggt cccaaagatg gacccccacc cacgaggagc atcgtggaaa aagaagacgt    300

tccaaccacg tcttcaaagc aagtggattg atgtgataac atggtggagc acgacacact    360

tgtctactcc aaaaatatca aagatacagt ctcagaagac caaagggcaa ttgagacttt    420

tcaacaaagg gtaatatccg gaaacctcct cggattccat tgcccagcta tctgtcactt    480

tattgtgaag atagtggaaa aggaaggtgg ctcctacaaa tgccatcatt gcgataaagg    540

aaaggccatc gttgaagatg cctctgccga cagtggtccc aaagatggac ccccacccac    600

gaggagcatc gtggaaaaag aagacgttcc aaccacgtct tcaaagcaag tggattgatg    660

tgatatctcc actgacgtaa gggatgacgc acaatcccac tatccttcgc aagacccttc    720

ctctatataa ggaagttcat ttcatttgga gagg                                754
```

<210> SEQ ID NO 75
<211> LENGTH: 131
<212> TYPE: DNA
<213> ORGANISM: Tobacco etch virus
<220> FEATURE:
<221> NAME/KEY: misc_feature
<222> LOCATION: (1)..(131)
<223> OTHER INFORMATION: enhancer; TEV 5'UTR translational enhancer

<400> SEQUENCE: 75

```
ctcaacacaa catatacaaa acaaacgaat ctcaagcaat caagcattct acttctattg     60

cagcaattta aatcatttct tttaaagcaa aagcaatttt ctgaaaattt tcaccattta    120

cgaacgatag c                                                         131
```

<210> SEQ ID NO 76
<211> LENGTH: 187
<212> TYPE: DNA
<213> ORGANISM: Tobacco etch virus
<220> FEATURE:
<221> NAME/KEY: misc_feature
<222> LOCATION: (1)..(187)
<223> OTHER INFORMATION: enhancer; TEV 3'UTR translational enhancer

<400> SEQUENCE: 76

```
tagtttctgc gtgtctttgc tttccgcttt tatgcttatt gtaatatata tgaatagcta     60

tttacagtgg gacttggtct tgtgttgaat agtatcttat atgttttaat atgtcttatt    120

agtctcatta cttaggcgaa cgacaaagtg aggttacctc ggtctaactc tcctatgtag    180

tgcgaga                                                              187
```

<210> SEQ ID NO 77
<211> LENGTH: 192
<212> TYPE: DNA
<213> ORGANISM: Cauliflower mosaic virus
<220> FEATURE:
<221> NAME/KEY: misc_feature
<222> LOCATION: (1)..(192)
<223> OTHER INFORMATION: terminator; CaMV 35S terminator

<400> SEQUENCE: 77
tctctctcta caaatctatc tctctctatt tttctccaga ataatgtgtg agtagttccc 60
agataaggga attagggttc ttatagggtt tcgctcatgt gttgagcata taagaaaccc 120
ttagtatgta tttgtatttg taaaatactt ctatcaataa aatttctaat tcctaaaacc 180
aaaatccagt ga 192

<210> SEQ ID NO 78
<211> LENGTH: 1682
<212> TYPE: DNA
<213> ORGANISM: Arabidopsis thaliana
<220> FEATURE:
<221> NAME/KEY: misc_feature
<222> LOCATION: (1)..(1682)
<223> OTHER INFORMATION: promoter; PHT4;6 promoter

<400> SEQUENCE: 78
caaagatgga aattctaaaa accactccct gcaatttctt atgtttcgtt tttagctcta 60
tatttttccg ttttgtattt agtatttagg gtttaaggtt tgctttttaa atgtttgatc 120
tatgagttat caaatggttg tttgatctta tgaatataag ttataagtag taaaaaaaaa 180
atttagctgt tttatctatg aatttaattc aatttatgtt tagtacgtaa tctataaatt 240
tgactcaatt tatgtgcctt acactagtct aaaaataaaa gaattaccca caaatcaaaa 300
aaaattaagc taattagatc aaaattatga ttaagtaagt gattagaaaa gataacatta 360
taatctcaac atcaaggtgc tgtggtgtag tggttatcac gtttgcctta cacgcaaaag 420
gtctccagtt cgatcctggg cagcaccata tttttttata cctattcccc tctttttttc 480
acccgttaat taataaaata agaaatggcc gttacgtgat ttatctcacg gacataaaaa 540
tatcagcatc gtcgtcgttg accctaaaaa gcgatctcca tcatcttctt ttgtttcttc 600
taaattcttt cacaaaccct aaaattctcc tccgtcactg tcgacgacca ctgcgtttca 660
cactactctc tctctcgctc tctccaccgt taaacttcaa tacccatttg tcatttcccc 720
caaatctctc cgatttctta aatctaattt ggatttactt tgcctgtaaa accattcgca 780
ttgttacgca tccgattttg cagttcgaaa ctcgagttca acttcaattt gaggtagatt 840
tcgagaaaaa gctgaagaat ttcggaacaa ctaaggtaaa gctttgtgat tttgacttcg 900
gttttcgatt tacattgtga agactgaaga agagatatag gcaacacatt ccactgtgta 960
attcggctgc ttgatgctta attttaagat ttcttcttgg gttctcgttt ctttggtact 1020
taagtttaat tgaaagaaag cttggatttt ttgcgtctgt aaaacgaaat tgagtctctg 1080
tgataacatt ggaatcgtaa ttcattagga attaggattg ttgatccttc aatttagaac 1140
caatatgatt acgttatggc ttttgggaca aattcatttg cttgatacga acttttactt 1200
cagatttatt cttatttttt aagatctgtt tatctttatc ttttgatgtc atatttagga 1260
tatgttctta tcttctgtgt tgaaggattt gacttaattt tactttctag atgccttctt 1320
gtatgattgg agaagcgtaa gattgtgtat ttttaggatg cctaattgaa aatggataaa 1380
gttgtgttac ttatacctct ctcatatata tctcaacaga ggaacgtatt gggtttgagt 1440
ctattttgtt aatgatcaga ggagaattca tcagtcatat agaatcgtcc ctgcaagttt 1500
tgtgttaaca tgtatcacaa taagcaaatt aaactgcttt gaatatgtca ttgcagattt 1560
taacggtgga attggggagt cttgaagctt atttttcctc ctggtctctt ttttcttatg 1620
tggtggtgct tgagagggtt tttgtatgat ataaatgctc tagatcagag aaaaggtcta 1680
ac 1682

<210> SEQ ID NO 79
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: promoter; PHT4;2 promoter

<400> SEQUENCE: 79
atatcttgag aaacacgagc aatttctcat aaatgcctaa tagtttagcc gtttaggcat 60
ctcatgatct cactgtaaac tattaggata gttacacata cacttaaata atagttacac 120
atacatctaa tattttgaaa atcctttata ttctatgaat tatccacacc aaatgacatc 180
atgtgtgact gtataaatac gactacaaat ctatgtaacc tataccaatt acaaatatgt 240
ttttctatgt ttaatagcta taccgtttgt gtgtgatata tatgattagt tacattaaga 300
tactttaaca caattctaga tttctagtgc aatgcagtta tcaaatactt ctgattttga 360
attgacaaag cgacttaaaa acgattgatt gtaaaacaac ttaccacatg gcaagcacac 420
tcctaaacgc atcgaacaaa tccataaact gcatcataca tacaacaaat ccaatggctt 480
tgtcattagg atcactaccg tagcaccagt tggggcatag tgaaatacaa atgccttttt 540
cttatgtcat tgtcttaaac agacatgacc atctctctaa tttacgacta ctttttcctt 600
tttgggcttt gaatgaatca cgctttcaaa taattgggct gcttctttct ttcccatttt 660
agaccaattt caaagacaaa aaataaaact agcaattgct aaccgaaact ccggtatccc 720
ggttaacccg ttgtaggtgg ggctgacgtg ggtgcaatca ctttgtcata tcaacacatc 780
acgtgtctcc acgtaggatg cagcagaaac tatttactac attgactaaa atacccttca 840
ccaccaaaca ccaccagcac acgaaacttt catacgtttc tttcatggcg gattcgctct 900
ctcgctgaaa ctctctctct ctctcgttac tccaaccact cctaattatt cacatcatta 960
ttggcatgaa aagttaatct ttcctatata acaattatta 1000

<210> SEQ ID NO 80
<211> LENGTH: 2418
<212> TYPE: DNA
<213> ORGANISM: Arabidopsis thaliana
<220> FEATURE:
<221> NAME/KEY: misc_feature
<222> LOCATION: (1)..(2418)
<223> OTHER INFORMATION: promoter; TPS-Cin promoter

<400> SEQUENCE: 80
tcatggcaca tcgaggagaa actgtttcct tgtggtaatc ctttataatc tctgttgcta 60
ggaggagatt tttcattaat agtctatctt tcacaaaggc agattgattt gaagagatga 120
acttgggaag aatgattttg agtctgtttg caagaatctt cgatatcacc ttatagagaa 180
cattacagca tgatatcggt ctatagtcct tcatcatcac agcttctttt ctcttgggta 240
tcaaggccaa aatagtggag tttactcctt tgggtaggaa gcctgtctta aaaaaagatt 300
ggatggctac cacaaaatcg tttcctacta tcgaccatgt ctcgttaaag aactcacaag 360
tatatccgtc agggcctggg gatttatttg aaggcattga gaagagaact ttccgcacct 420
cctctgcagt gacttctagt gtgagcttgt cttgtcattc tcatcacatc tataatccag 480

```
tagagtttcc agttcctccc gcgaccaatc cacgtagtct ggcggtttga gcgttaaaaa    540
gtctctgaag tatcgaactg cctctgcttt tatttgctgc tgatttgatg caatatgtcc    600
atcatcacac ttaatctctc taacattgtt acgaacctcc cgaatctttg cagcattgta    660
gaaagtttta ttattttggt ctcctatctt catccaatgc agttttgctt tttgcctaag    720
gtagctttcc tcaatacccg acagccttaa ccacttctca tatgcgtccg cttcagctac    780
cactgcctgt gaagatggcc ttgtcatagt ttctgcttgc ttttcacata aagttttata    840
ggcttctttt gctttttttg agatatcacc aagtaactgc ttccccatct ttctgaaatg    900
tggcttcaga ccttttaatt tttttgataa gcggtgcatg gctgaggtag aatgaaagag    960
aggctgagtt gtcttccaaa gctcttctgt ctcacttctg aaatccgaat acgaaattaa   1020
agcatttata aatttaaaag gcctcttgac tcgttgttcc tgctccataa tatagaatcg   1080
acatcttagg tgatctgaac aaccgcctga ttcaaagacg ctgtaggact gttcatacta   1140
ttgcatccat tgcttgctaa tcagtaccct atccagcttc ttacatatta ctccttcctt   1200
tctcttgtta caccatgtgt atctctggcc ttggtagctc atatctgtta attcacaatg   1260
tctgattaag tcttgaaaat ctctcatccc ttggagaacg aatggagatg attcatagag   1320
tgaatggtcc tctccttcta atatctcatt aaagtctcca catattaacc aagctttgtt   1380
atagaacaaa ggggaatcat gatgatattt aatatcactc cacaaatcct ttctttctgc   1440
tgcaaaattt gatgcataaa caaacgacac aaagaactct tcttgtcttc cttctaataa   1500
gacagagcaa gtgatgagtt gtgacgtctt atatattgga gatacacgca cgttatcttc   1560
tattatcttt caatagtaat ttgatataaa ttaagataat gtgcagtgaa cgagtggcga   1620
ttgttaagcc aagtgaacat tatatacttt attttatact ttctccaagc ttcgaatgga   1680
gaatttattt ccatacgact aactctacct aaaagggcca tgtttgtttg ccaacataac   1740
acgacgatca cgagatacac ataacattta gaatttggag aagatacatt ttgtttgact   1800
tcactttttg tgcgaatggc tgttctacct gaaggggcca ttagtataat ttttttgtac   1860
ataataacgt caccaaatat aacacgagaa tcacgaggta cacaaatcat ttaggcttgg   1920
acattatcta atcaaataag ctatgatatc aaatttacat acatatagtg gcctcgtggg   1980
tataattaca caaggagctt ttggagaaaa agaagtgtgt gatttaaatg acaattatac   2040
aaatgtgtac aattatcaga tccaaagttc atgttttaaa tcatcaaaaa aataataatt   2100
gatgagttaa atgatatttt tttcatttag atttagttag attagttgta cggttgtacc   2160
attatttaat aatttaaaag ttgaaatgat tataatgtat aaaagttgaa aatattgtaa   2220
cagatataga ttaagcattt ttgcggtcaa tatattataa aagctttttt agctattaat   2280
tgaaaaatat tttacaccct tagatctttt gatctcctaa ttatataaaa tattttcttc   2340
taccgtttgt ctatataacc atatgtgttg tctagtgcat gtattcagcc acgaataaga   2400
gaatagtcta ctaaatca                                                 2418
```

<210> SEQ ID NO 81
<211> LENGTH: 2486
<212> TYPE: DNA
<213> ORGANISM: Spinacia oleracea
<220> FEATURE:
<221> NAME/KEY: CDS
<222> LOCATION: (1304)..(1483)
<223> OTHER INFORMATION: Def1 nucleotide
<220> FEATURE:
<221> NAME/KEY: misc_feature
<222> LOCATION: (1487)..(1768)

```
<223> OTHER INFORMATION: 3'UTR

<400> SEQUENCE: 81

actagtacta cctgttacta gagctgtcaa aacggttatt cgagttgggt ccgggtctga     60

tcatctcgag tctcgggtca tgaactggtc gggtcgggtc gggtcatttt atcaccgggt    120

gcaggtcggg ttcaggtcgg gttcagtcag gttgaaaatt tgtcgggtta tttttacatt    180

tcggtttagg tcgggttcgg ttcgggttcg ggtcgggtct tttctagcc gggtacaatt    240

atgggttcgg ggcttaacga gtcgggtcaa gttcggatcg gataattacc gggtcggtta    300

taattcaggt cgggttaaga ccgggtacga tagctatcgg gattagtcaa gttttaacct    360

tataattaac ttttataaat ttggttaaat ttggtttagc gtttttcact tgttctagat    420

taggtaatta taaaaaaata tattaacttg atttaagtta ttatttagtt aggtcaatga    480

caaatcggat tgtcaacaag tcgcgaaaat tcaggtaacg gattgtcacg aattgagtca    540

ataacaggtt tcatggaatt ataattggtt tcgggtttac atcgggtcgg gtgttgaatc    600

aggttcgggt catttttcgg tcgggtaagc tgactcagtt ttgttatcgg ttatatttcg    660

gtcgggtatc aggttcgggt tcgggtcttg cattaacggg tcgaaatcgg tcgtcggttt    720

taacgggttg gctacggtcg gattacgggt ttcctatttt aacaaaattt cggatctcgg    780

gttgggtccg ggtccttaaa aatacaggtc ggttcaggtc ggtttctcgg gtcgggtcag    840

tttttgacag ctctacgtgt tacggagtat gttttaattt ttttaaaaat ggctacaaat    900

aattaaatat caataattaa catgcatttt caatttgatg atttgggtat cataatagaa    960

acacagtatt atggttgaga cttgagatcg attaatcatg ggttgatagt ttgaattagt   1020

taaattttcg taattatttc attaatgtta agatctgatc cacgaaacat catattgtag   1080

ctaatgtccc aaattgataa aaagcagaat agcctaactc ctctgatctt gtaaagtgga   1140

ctatctaact aaatggccga ctaattcacc atcacaaatt aatgttctct aatatttttt   1200

ccgaccgtaa ttaagtacgt agatttgaca caaattttgg tgaaacatat agtcttgttt   1260

aattttaaca aatttgttgt gaattgtgtc atttacagaa gaa atg ggt cca aga     1315
                                                Met Gly Pro Arg
                                                1

aag gca gaa gct gga att ttt agc tcg agg aaa tgc aaa act cca agt     1363
Lys Ala Glu Ala Gly Ile Phe Ser Ser Arg Lys Cys Lys Thr Pro Ser
5                   10                  15                  20

aaa acg ttc aag gga ata tgt act agg gac tcc aat tgt gac act tct     1411
Lys Thr Phe Lys Gly Ile Cys Thr Arg Asp Ser Asn Cys Asp Thr Ser
                25                  30                  35

tgt agg tat gag gga tat cca gct gga gat tgc aag ggt att cgt aga     1459
Cys Arg Tyr Glu Gly Tyr Pro Ala Gly Asp Cys Lys Gly Ile Arg Arg
            40                  45                  50

aga tgc tta tgt tgt aca cat act taaactccaa atatcaatat caacaaactc     1513
Arg Cys Leu Cys Cys Thr His Thr
        55                  60

aatgtcgtgt acacctttcg tcccagatta gtagtcacgt tagtttgaac tattaagtta   1573

gggagctagt acgtacacac atatatcaat ctatgttgct tcgtgttgta gccatgaacg   1633

tatcttgtta tcgtgttgtt gttgttgtcg tcgtcgtcag acgtccgtcg ttgatgaatt   1693

ggtgaattct agctagcttc tatgtaaaag tatcggcaat tatacgttgt ccaagttatg   1753

gtgttgtaaa ataaaagtgt ttggattatg aatgaagcct agctaacttt caggttgacc   1813

ttgagcctag tcttttgagt atcctactaa ttactccctc catccccgga atactcgcaa   1873

cgtttttctt ataaagtcgt cccgaatttc tcacactgtt tctgtaaatg ttcattttct   1933
```

```
ttttgatatt atacttactc atggacccat gggcacgaca cccacctata tccctactcc   1993

ttaaaaaaaa cattaaaagg tgtaaagatt tgttttatac tctatcacgc cccctcacat   2053

aaaagccctt tggacttgaa gtgtggatgc aacataggcc tcctcatact cagcgcgaaa   2113

tattctactt tgaaatgagg ggtggatgag atttgaaccc gtgacctttg cgtcacgctg   2173

gctctgatac catgtcaaat gaccaactca accaaaagct taagctggtg gttgaagccc   2233

caagagtagt tttatactat cactacaaga atttgtgtct ttaacgacaa cctaattacg   2293

acgggtcaaa aatcccgtcg caaaagcctt ttgcgacggg gctaacaacc aaacaatgac   2353

gggaataacc gtcgcaaatg tcttttacga cgggtttacg acaaatttac gacgggattt   2413

ctattaacga cgaccccctt ttatgacggg ttcgcgacag gaaaacccgt cgttaatcaa   2473

cgattattgg cct                                                      2486
```

<210> SEQ ID NO 82
<211> LENGTH: 3767
<212> TYPE: DNA
<213> ORGANISM: Spinacia oleracea
<220> FEATURE:
<221> NAME/KEY: misc_feature
<222> LOCATION: (1946)..(1999)
<223> OTHER INFORMATION: 5'UTR
<220> FEATURE:
<221> NAME/KEY: CDS
<222> LOCATION: (2001)..(2064)
<223> OTHER INFORMATION: Def2 nucleotide
<220> FEATURE:
<221> NAME/KEY: misc_feature
<222> LOCATION: (2061)..(2579)
<223> OTHER INFORMATION: Intron
<220> FEATURE:
<221> NAME/KEY: CDS
<222> LOCATION: (2580)..(2764)
<223> OTHER INFORMATION: Def2 nucleotide
<220> FEATURE:
<221> NAME/KEY: misc_feature
<222> LOCATION: (2767)..(3126)
<223> OTHER INFORMATION: 3'UTR

<400> SEQUENCE: 82

```
aaaatttacc tagctttcta gttttgaatt taactttcac gaaatttcat tttttttaac     60

tcaaataatg ttaaccgaat ttgattagag tcgagtttgg ttctcaagca atagcggaga    120

cagggggcgg gtgaggcgtc caccccccca aaggaaaaaa aaagattaat atatatggta    180

ttaaatgtca ataaacattg tcaaacttgt cttgccccaa tgattgaatg atcaatattt    240

gacacaataa ccctatgatc aaatacctac attgacacat tatatacatt tcttttcttg    300

gctttttttt agttgatata aatttctcgc cccaatctg aaatttctgg ctccaccacc     360

gttctcaagc caaatcaatt acgattattg atgggtcatg gattctacat ttatgaagca    420

aatatagcta gacttggaaa aacgaacccg gctatgaaaa tctgatccaa tttatccgac    480

ctgttaccta attttgataa gaaaagacaa ctcaaaatca acccaaagtc taaattgacc    540

tgactcgtaa cctaaatcga catggaattg atttggtctg aaatgacccg atacatgaat    600

cgttcaaaat tgaattcatt atatcgattt tcactcgaaa taaaagtaaa ccgtactgaa    660

ataactgtaa aatttgaatc aacctaactc taatccgaaa cgaagaacaa ctcaaattta    720

cccatagctt aaacaaaata acacaaagtt tcataactaa aacaatatta ttatacttgg    780

tatatttgcc catgtcttat gtacgtctca tcttctcgat catatatagt ctcaaagagt    840

gatagagtag tatagaagac tagaatcccc taaattaact tgtaaatatg tgaaaaatgt    900
```

-continued

```
aacccttgtc aataactacc ctaacatctt tatcataatc caataaactc gatcatatcg    960

tatatgctta accctatatt aattattttg taagaaatat tgtaacaatc aacaaattaa   1020

cctaattaat cccaaaattc gaataaatcc gatttatacc caaacccgat ccaaagtaag   1080

aatgacataa aattatctga atcatgtcca taaaaaccca cttagtaggt ctaaacacat   1140

acagtgatac accatatgtt tttcttggtg tactagtcgg ttcaccttta gggcacgctt   1200

ggattgggtg taatggagta taggggtaat aaaagtcaaa ccaccataat aaaaggacaa   1260

tgaaggtgaa ttgaggtggt tgcaaggagg gtggtgtggt ggtattgtga tgagaagttg   1320

tggtagtggt ggtgttgtga ggagaaggga ggaaggggga agtacttacc ccccaaatga   1380

gggtaataat caccctagtg ggatggtggg taactattcc ctccatgatg agggtatttg   1440

ttccccctcc cctttttttt tttcttgcca acactagctt gtttcctttg ccaccacttc   1500

atcccctcat catcaccatc aattacctta gtttgacttt tattacccct ttaataaatt   1560

accctcaatc caagcatgcc cttagggtta atccggattc ggagcgagtt ctgagtggat   1620

agatttttc cccctcccaa ttgtaggtga gggtgatcga acacagggtt ctccctacta   1680

aattcagccc caatcaccac tgaaccaaca gacaattagt gatacatcat atgttaatat   1740

gttatggcgc ggtatttcca gctagtgatc taaagaccac acaaggtatg tcggtaagaa   1800

atcatttcaa acacaagccc cgtcagaaag aagcctttta gcgtcaagac aaatgcaata   1860

gtgtcccata ttatttgggc atataccctt gtcaatagtg aacattttct cctataaata   1920

atctatagtt tgtgttagtt ttgcataaca tatttacaat cttatacatt tatattcatc   1980

aataaattta aaaagaaatt atg aag atg tca atg agg tcg att gct gtg gtt   2033
                      Met Lys Met Ser Met Arg Ser Ile Ala Val Val
                      1               5                   10

ttc ctt gtg tgc cta ctt gtc ttg tca aca g gttactaatg ctatccttac     2084
Phe Leu Val Cys Leu Leu Val Leu Ser Thr
            15                  20

ttccttaccg tctttcaaat ttttattttg gaaactttct tatataaccc catattttat   2144

tttattttga tgtatgatta agagcaataa atagataaag tttgctaatg ctctgtccat   2204

gaccatacta tactaatgtt gttcttttta aacgagacca tacgtacttc tagacattaa   2264

tttccttaaa ttggaatcgt ttatgctttg attttagaca tatatccctt taattttaca   2324

acctaacttt gatctaataa gtacgtaata tcgtacatgc atgttactat taagtattga   2384

ttacttttga gtaggtcttc tatgagaccg ccatatgcat aagactgttt atgtcagctt   2444

taaagtgcac attgttagtt ataagtagat tacaccgtat aatgttggct taatcatgtt   2504

ttgttagttt taattagcta aaactccggc aattaaatta acaaagttgt tcctaaatat   2564

gtgatttgtt tgcag aa  gaa atg ggt cca aga aag gca gac gct gga ttt    2614
                 Glu Glu Met Gly Pro Arg Lys Ala Asp Ala Gly Phe
                             25                  30

ttc agc tcg aag aaa tgc aaa aca cca agt aaa aca ttc agg gga cct     2662
Phe Ser Ser Lys Lys Cys Lys Thr Pro Ser Lys Thr Phe Arg Gly Pro
    35                  40                  45

tgt gta agg aac gcc aac tgt gac act tct tgt agg tat gag gga tat     2710
Cys Val Arg Asn Ala Asn Cys Asp Thr Ser Cys Arg Tyr Glu Gly Tyr
50                  55                  60                  65

cca gct gga gat tgc aag ggt att cgt aga aga tgt att tgt tgt aca     2758
Pro Ala Gly Asp Cys Lys Gly Ile Arg Arg Arg Cys Ile Cys Cys Thr
                70                  75                  80

cat gct taaacgaata accctcaatg tcgtgtactc tgcttgtcca gaattaatag      2814
His Ala
```

tcacgttagt ttgaactatt acgttactaa acctggacga agatagggag tacgtgcgtg 2874 tgagtgtgtg actatctatc cagaattaat agtcacgtta gtttgaacta ttacgttact 2934 aaacctggac gaagataggg agtacgtgag tgtgagtgtg tgactatcta tctagcttgc 2994 tcggtcttgt aaccgtttct tgttatcgtt ttgttgttgt tgttgttgtt gttgttggac 3054 ttgttgtgaa tttcgacctc tatgtaatgt attggcaatt gtacgttgtc caagttatgg 3114 ttgtaaaata aaagagtttg catgaacgga gcctttcagg acttgagcct accgtaccct 3174 ttaatgaata tcctacacat catatgttaa attaatattc ttactagtca atttgttata 3234 tttatacgga gtacgtatat atacattgac gattgtaaac ttgtgataat gtgaataatg 3294 tgatgttata ttgtaaacta tataatgtga gtatatagtt acgttgtcgg agaattaagt 3354 gcatcatatc acaattcaca agtttacata aaaggtttaa tcaaacacat gatatgaatt 3414 tagaacattc taaactcata ctacatatat caaacctaga atttgtgaaa caatcacccc 3474 ttcaaagagt tctcactgta atttgggtga ggcacgtact cacaaaaaaa tagagggaga 3534 aacgtacatg atacactaca agaaattgta ctattaacga cgggaaatcc cgtcgcgaaa 3594 ggccaataat cgttgattaa cgacgggatt tgttgtcgtg agcccgtcat aaaagggggc 3654 cgtcgttaat agaaatcccg tcgtaaatcc gtcaaaaacc cgtcgtaaaa gacatttgcg 3714 acggttattc ccgtcattgt ttggttgtta gccccgtcgc aaaaggcttt tac 3767

<210> SEQ ID NO 83
<211> LENGTH: 2854
<212> TYPE: DNA
<213> ORGANISM: Spinacia oleracea
<220> FEATURE:
<221> NAME/KEY: CDS
<222> LOCATION: (973)..(1024)
<223> OTHER INFORMATION: Def3 nucleotide
<220> FEATURE:
<221> NAME/KEY: misc_feature
<222> LOCATION: (1025)..(1681)
<223> OTHER INFORMATION: Intron
<220> FEATURE:
<221> NAME/KEY: CDS
<222> LOCATION: (1682)..(1851)
<223> OTHER INFORMATION: Def3 nucleotide
<220> FEATURE:
<221> NAME/KEY: misc_feature
<222> LOCATION: (1854)..(2848)
<223> OTHER INFORMATION: 3'UTR

<400> SEQUENCE: 83
aggaatagtt aaatcatgag gaaagtcaaa taaataatat caatattata aatttgtgta 60
aacatttatt ttacacgtaa gtcgtttaat attaataaat gtagattttt gtttaaactt 120
aattatgaag aatcatatca gatcagacca gaccagatca gaccagaaca gatcagatca 180
gaaaaaataa gttcagatca gatcagacca gatcagatca ggagaaataa ggtgaactaa 240
acagggcctt actccatttt tcacacacac atgaaagaaa ataccaaaaa gaaaccacac 300
aagaaagaga gtttgataca cacttcatat atgagcaagt gcaaaaggta tgccaaaaaa 360
atccatatta tttttacact atttacataa tttattttgt ttattttttta tgattgatac 420 ttcaggaaaa acatattcat ttgggatctg gttagatctg tcttaatgaa tattttgcaa 480
attttaaatt tttattattt ttaattatca ataattaaag ataataattg ttcaagttat 540
acgttaataa tcgtgaaaaa caaagtgttg caattaaaaa gaaatgaagg aagtatgatg 600
caagggtgat agttaggtag atcacagtat ttaccacgtt cttgataaaa aaaatatttg 660
gtgaaaattt attagagttt ttcaattttt tattttttgt gccgaacaat gaagtaggca 720

```
caactatttc ttagaagtaa attatttaga gttagaacaa ttataaggaa tagctacaat    780

tttaaattga tcatcacaaa tctttcatga caaatattcc ttcaaaaaag tcattaaaga    840

cggagatgat aatagtcgtc atcgtttagg tgacaaatta aaactacctt aaagtttttt    900

attactcgta gttcttcttc attctattga tcttctctct atattttaaa gtgcttaaac    960

atgaaacaaa ca atg aag cac ttt ggg gct ata ttt ctt gtg ttg ttg ctt   1011
              Met Lys His Phe Gly Ala Ile Phe Leu Val Leu Leu Leu
              1               5                   10

gtt ctg gcc aca g gtataacaaa aatttcttcc ctttgaatta tacccagtaa       1064
Val Leu Ala Thr
    15

atagatctca tttgtagcaa attttacttt gtctccttac actacaaaaa ttgtaccatt   1124

aacgacggga aatcccgtca ctaaaggcca ataatcattg attaatgacg agattttctg   1184

tcgcaaaccc gtcataaaag ggggcgtcgt taatagaaaa tcccgtcgta aacccatcgt   1244

aaaagacatt tgcgacggtt gttcccgtct ttgtttggtt gttagccccg tcgcaaaagc   1304

cttttacgac aagattttg aaccgtcgta attagattgt cgttaaaaat acaaattctt    1364

atagtattag aaaatacaga gtaaatgaaa aaaataccct tattactaat tcgctatata   1424

tcgctatcct ctttacatct ttatgaattc taataatact acttattgag tatatcaaaa   1484

taatatggag tactatgtac gaagtatatt attactacta cttattacgg agtacgtaca   1544

taaagtagta ataaaatgac agttacttgt aaaatgatga ttgttttgtt aaaacttttt   1604

aataattttt ggatatttat tattgacctt tgcttttaat tttgttggga tttaattata   1664

ccatgaaaaa tacaaag aa  cat gga gca aga gta gca gaa gca aga aca      1713
                  Glu His Gly Ala Arg Val Ala Glu Ala Arg Thr
                          20                  25

tgt gaa act cca agt caa aag ttc aaa gga ata tgt att agt gac tcc     1761
Cys Glu Thr Pro Ser Gln Lys Phe Lys Gly Ile Cys Ile Ser Asp Ser
    30                  35                  40

aat tgt gaa tca att tgc aat acc gaa gga ttt cct aat gga gaa tgt     1809
Asn Cys Glu Ser Ile Cys Asn Thr Glu Gly Phe Pro Asn Gly Glu Cys
45                  50                  55                  60

agt ggc ctt cgc aga aga tgc att tgc aac aca cca tgc act             1851
Ser Gly Leu Arg Arg Arg Cys Ile Cys Asn Thr Pro Cys Thr
                65                  70

taatgtttaa ttatgctcat aattaattat gtttaattac taattgatgt gctttggaat   1911

agaaatttca tattttatgt acgttatgaa ttgaaatcta tttgtttcag aatagctagt   1971

aaaatctgaa acatttttca atacactttg tgtgttatgt tttaaaaaaa actatcggat   2031

aagacgcgtt tcagtctaat cgggataata atctcatata catatatagc atgtaaaatt   2091

ttggcgacat taatttatct cagattttac caactcaaaa tctgagttat ggagctcttt   2151

ccaagtattc tctccgtttt gaaataatgg ttacctttga cttttaacac tattcacaaa   2211

tttcaatttg actatcattt gttacttatg aataaggaaa aatatagccg tgtgagatgt   2271

tgtttgattt atttcgatgt gtacttttgt aatattaact tttttataat tttaacgatt   2331

acaaaattag atgtattaat cttcaaccat ttacattgac aagcataaaa agatgaagtg   2391

taatcattca atcgaaatgg aggagaaatt ccgagttaat atcagtgatt gtaaaaaatt   2451

tccaatcaaa tggcattttc gtaaacatta tgcccgaaaa atgtatatgg tataatgtta   2511

agtgttgact gtacatttgt aggtattgac tgtatatttg tagttattga ctgcatatta   2571

ctcggtgttg attgtatacc acttgtcgtt gatgtatatt ttatgattgc tgatgaatta   2631
```

-continued

```
ctaaaataca atattgttta ttggtaagtg attgactgta tatttgtagt tgtagattgt   2691

ttattagtag aagcttattg tatattgtga gctgttgact gtatattata tagttgttga   2751

tgtgttatga aaatacaata atgaccgtac atgtggtcca catttgatga catgtcacta   2811

tactttaacc cacatttaat ggcattttcg taataaaatc atc                     2854
```

<210> SEQ ID NO 84
<211> LENGTH: 3903
<212> TYPE: DNA
<213> ORGANISM: Spinacia oleracea
<220> FEATURE:
<221> NAME/KEY: CDS
<222> LOCATION: (57)..(224)
<223> OTHER INFORMATION: Def4 nucleotide
<220> FEATURE:
<221> NAME/KEY: misc_feature
<222> LOCATION: (228)..(308)
<223> OTHER INFORMATION: 3'UTR
<220> FEATURE:
<221> NAME/KEY: misc_feature
<222> LOCATION: (2069)..(2145)
<223> OTHER INFORMATION: 5'UTR
<220> FEATURE:
<221> NAME/KEY: CDS
<222> LOCATION: (2146)..(2197)
<223> OTHER INFORMATION: Def5 nucleotide
<220> FEATURE:
<221> NAME/KEY: misc_feature
<222> LOCATION: (2198)..(2730)
<223> OTHER INFORMATION: Intron
<220> FEATURE:
<221> NAME/KEY: CDS
<222> LOCATION: (2731)..(2900)
<223> OTHER INFORMATION: Def5 nucleotide
<220> FEATURE:
<221> NAME/KEY: misc_feature
<222> LOCATION: (2904)..(3013)
<223> OTHER INFORMATION: 3'UTR

<400> SEQUENCE: 84

```
tatttgtttc caattttcat gaatctaaca catttttttg tatatgggga gcagag gta     59
                                                              Val
                                                              1

agt aca aaa gta gca gaa gca agg ata tgt gct agt cca agt ccc acg      107
Ser Thr Lys Val Ala Glu Ala Arg Ile Cys Ala Ser Pro Ser Pro Thr
            5                   10                  15

ttc aaa gga ata tgt ttt agc agc agg aat tgt gaa act aat tgc aat      155
Phe Lys Gly Ile Cys Phe Ser Ser Arg Asn Cys Glu Thr Asn Cys Asn
        20                  25                  30

tct gtg aaa ttt tct gga gga agt tgt caa ggt ttt cgt aga aga tgt      203
Ser Val Lys Phe Ser Gly Gly Ser Cys Gln Gly Phe Arg Arg Arg Cys
    35                  40                  45

atg tgc acc aag cct tgc gct taattaaccg atggtgtgcc acgtgcgcgt         254
Met Cys Thr Lys Pro Cys Ala
50                  55

tcctcgtcat caataatcag cttgacattg gttaaaattt gcattaaaaa taaaagcaat    314

ttgacgcacg tgttctcttt acatcatctt cattcatcca caatcgagtg gatgcagtat    374

actatgtata tctatatata atcttatata caaagtgtgt actaatactt gtattatagt    434

tgtggtaact ttgcaatatg caaattaagt agtagtacta tgctacacta ataaattaat    494

gaaagctaca attcattaac aaagttgaaa gtattattta cgtttatctt taatttcgtt    554

ttattaacaa ctacttcgtg caaattttag atatttgaaa agtacaagtt aatacgaaat    614

atgagaattg aatagtcttc atttttaggg gtataaaact caatgcgtgg attatggata    674

tatgtgcacg atactcatgt actgcgtagg aaatgaacac aagtgtacaa cctagactat    734
```

```
ggacatatac acacaaatgc acacaaatgt acagcgtgga ccatggacat cacgatgctc    794

actgtgtagc aaatgaatac aggtgtatag attggaatat ggacatatgt gtatgatact    854

cattgtgttg caaattaaat gaacacaggt gtataatccg gactatagac atagaaaatg    914

aacaaaggtg cataacaata ctcattgttt agcaaaagag cacaagtgat gtcctcagtt    974

atggacatat gtgcactata ctcactatga tattatgaca aaagtgcatc atatgaatta   1034

ctttgtatat tttttaaaa aaaatcatat aaaaaaaaat ctcgtttcta tctactataa   1094

tcgcatgttc ttttagttac atatgctacg tacatttgta taccttcatt gcgtaataat   1154

tattgtgcac aatatgtcca taatctaatt tgcggtaaaa aattatccac cttctaacct   1214

ttttaaggga aaattacctt cttattttga tcacatgtac attcaaattc tttaccaaag   1274

gtaaatgggc ccggtagcac caattaggga tgacccgggt gagaaaaaat gtcagggtac   1334

cctgaatcga aattggaacc tgttaggaac ctgaggtttc ggaatcggaa cctgttgtgc   1394

aggttctggt tccggataac gaaatcggga acctgttgca acaggttccg gtttcggttc   1454

tcaatttccg gaatgggtac cttgttgggt accttgtaca tatcaattct aatatgaatt   1514

gaagtaccca aaataaggga ccgggacaaa taaaaatgtt ttctatgtcc aaaatataaa   1574

acaatccaag ctaatctttg gaacatataa atatagaatt acaatttaag cctaatctat   1634

aaaacaatta aagcccaaag cataaagtac atattttgtc caataaatta tcaatatttt   1694

atttgaagtt ttaaatgaca gggtaccctg aattagaacc ttagaacagg ttccggttcc   1754

ggttctcatt ttcaggaacc tgttacaaca gtgtttcggt ttcgattccg gttcccattt   1814

ttagaaacct gttgcaacaa gttccgatat gattctgatt tctgaaattt taacagggta   1874

ccgtgttgtg ctcaacccta ccgccaatta attgacaatt tatgagaaag tattttttct   1934

tctttatctt ttttaattgg aaaagaaata gttttgatat gagccacata aaagggatgg   1994

gtgatcacaa ttataatatt ggaaccacaa atatctaatc ctatataagt aacctctagt   2054

gttgttatct tgctcactca ccaaatacaa cttctacaag ttaatttcac taaacatctt   2114

cttaattaag agcttaatta tgaagcaatc a atg agg cct ttt gct gct ctt      2166
                                   Met Arg Pro Phe Ala Ala Leu
                                               60

ttc ctt gtg ctc ttc ctt gtt ttg gcc aca g gtacatttta ttcctcttcc     2217
Phe Leu Val Leu Phe Leu Val Leu Ala Thr
    65                  70

tttctaaaac ttataactta taatgtcatt atttttcgat ccttgtacgt cgtatgaagt   2277

atcaaattaa agttcgaata ataagaaaac taatcacgtc ttctctataa attctaaatt   2337

agtttatata gtgtatgtca cataattaac cacttacttt cataaatttt taatgcttct   2397

tcgtttctta atatctgcat cattttgact tttcacacta ttcatttaga aatatgtttt   2457

aagatgatga tcgaggattt tcactggccg tactactact agagacattg gatctatcaa   2517

accccgtctc ttataaaaca aacatgttga tttccttgac catttacgat tttttgtttt   2577

tgttttatga tgtgttaaga tatgaaattt aaacatatac tgagtatctt atagtatatc   2637

gagcatatct tttgacatct taccgtaact tagcagtatg tgacgtagtt atctaactcg   2697

ttaatatttt ctccttgtta tgaataaaaa aag ag  ata ggg cca aga gta gta    2750
                                     Glu Ile Gly Pro Arg Val Val
                                         75                  80

gaa gca aga atg tgt tca tca cca agt cat agg ttc aag gga att tgt     2798
Glu Ala Arg Met Cys Ser Ser Pro Ser His Arg Phe Lys Gly Ile Cys
                85                  90                  95
```

-continued

```
act agc agc agg aat tgt gag aac act tgc aac agc gaa cga ttt tca      2846
Thr Ser Ser Arg Asn Cys Glu Asn Thr Cys Asn Ser Glu Arg Phe Ser
            100                 105                 110

ggt ggt gaa tgt aaa ggc ttt cgc aga aga tgt atg tgc acg gga ccc      2894
Gly Gly Glu Cys Lys Gly Phe Arg Arg Arg Cys Met Cys Thr Gly Pro
        115                 120                 125

tgc gtt taattaatta acataattaa tgttaattaa gtgtgtgcaa tttccatcct       2950
Cys Val
    130

taaccttgta gttgagaggt ggatatatca tatatgtatg gttattagtt gaacgataat   3010

aaaattgtag catctatatg tttgaatcac tcggttgtac cattgtacgg agtatgttac   3070

tttgttaatc accactaccc caatcgatta ctattaatga aatgatgcat gtacgtgttt   3130

tttgtttgaa gttcgattgg agttatataa agatttgtga tagaagtaat ttcgtaagaa   3190

cttgatttaa ctatcttatg tatttatgta gttatgttac gtctatgttt gaacgtaatg   3250

ttcttttta acttattacg ttatttcgta tttcatatac tttaatttta gcttgttcga    3310

tctagtcact gtaacattca cattttcaat gccagcactg atcaatgaaa ctttctcgca   3370

ttaactaatt aaacttgaac ccaacatcaa attcggacta cttgaaccca ccacttgccg   3430

cctccaccgt acccaatatg tattccacaa tcattccgac tacaaaaaaa accaacttgc   3490

tttgctactt ctgtttgaga gaaaagttaa gcatgcattt tatatcaaat caagttgtga   3550

tataaaccgg ttgcttaact tttcccttga aaataaaaag taacaaggaa aaatcaatct   3610

attactatat attaaaagag acaccaggaa tgacacgtgt caatttctgg tgcgattttt   3670

tccggtcaaa aattactttc ctaaaaaaag tgtatctgtt tgattttagt tttattctct   3730

accttttta tataaactat ttatgtatgg aaacaaaata tatttagttt ataaattatg    3790

gcaataatag atacgacgta ataataatta ttctaaattg gcaatatttt agtcaatcgc   3850

tatattagta atggaaaata tatcactcaa tattttggtc aaattaccat att          3903


<210> SEQ ID NO 85
<211> LENGTH: 4294
<212> TYPE: DNA
<213> ORGANISM: Spinacia oleracea
<220> FEATURE:
<221> NAME/KEY: misc_feature
<222> LOCATION: (1944)..(2000)
<223> OTHER INFORMATION: 5'UTR
<220> FEATURE:
<221> NAME/KEY: CDS
<222> LOCATION: (2001)..(2064)
<223> OTHER INFORMATION: Def6 nucleotide
<220> FEATURE:
<221> NAME/KEY: misc_feature
<222> LOCATION: (2064)..(2653)
<223> OTHER INFORMATION: Intron
<220> FEATURE:
<221> NAME/KEY: CDS
<222> LOCATION: (2654)..(2689)
<223> OTHER INFORMATION: Def6 nucleotide
<220> FEATURE:
<221> NAME/KEY: misc_feature
<222> LOCATION: (2690)..(3121)
<223> OTHER INFORMATION: Intron
<220> FEATURE:
<221> NAME/KEY: CDS
<222> LOCATION: (3122)..(3291)
<223> OTHER INFORMATION: Def6 nucleotide
<220> FEATURE:
<221> NAME/KEY: misc_feature
<222> LOCATION: (3294)..(4176)
<223> OTHER INFORMATION: 3'UTR

<400> SEQUENCE: 85
```

-continued

```
tgtgtggggc tgataagatg aacgcgttac aattcttata atttttgcat atggtgtttt     60

caataccttc catcatatgc aagaagagtt tctctttaaa tacgacccca tttttgcttc    120

aactaggagc tttcctatta tatattcagg acacctcttt tatagaacca caaagtattt    180

gacagtttta ttttgttccc tctgttcttt cactctatta tcctttgttt tagccaaaaa    240

gttattcttc aacaagtttg gactagagca ggaatacaca ttgcttcaac caaatattag    300

ttggcccttg ggatggcctg ttagagtcta tcctggtccc caggtatgtt acacacccgc    360

atttcattaa ctttctctta aacatgacca gtatttgtgt tagagtggaa gaatgcatcc    420

attgcttaga aaattattta atctgcaatt ctgcataaga gatgtacgta ctgtataaaa    480

gtactacgta aatggtattg atatgcttac atattattga ttagtgagtg acttgaacat    540

gttgtacatg gtgtgagtac ttttgaattt gtgagtacca tctgaaatca aaacaaatta    600

ctataaattg tatcacgatt atcattttgc tagaaaggag acatgttatg aaagactggc    660

ctctcggacc tttccatatt tatcttgcag agctgtagaa tatgctaatt gaaataatat    720

aggattccct agtacattaa atctactaag atcgaaatgt tctagtgttt ttatctaagt    780

gaaggtctaa tgtcatgcat ttattttgtg tttgtccgag gatgggtatg gatgacttca    840

agtctttcca ccaagcaatg ttgctgctga tcagcgtggt ggacgtgttg gaacttgcaa    900

ccggctgtat gaggtggtcc taagattcaa aggacgagta ttggcaatgt catgttgtta    960

agttataaga cagtgaaact cttatttgat atgatagaaa tgaaattgaa tcatattatt   1020

tcagttgtta aattagcatc agctttaaaa tggttgcttt tattttttat tacatgtact   1080

ttattaacta aaaagagcta tagaataaaa aaagcccgac gaaaaatata gaatccgctt   1140

acaaatacca tcgtttttta gtttaatgct actaatttta attcatactt cgtattaaat   1200

tggttggtga gtgcactaaa gtttttgtca ttacaagaga tttgacaaca cttatatatt   1260

aaatgctgct aaatgtggca acatcaacaa cgcttattaa aagcactatt atttttttaa   1320

cagcgctagt aattcacagc ccttataaag cgctatgttt aaatgaaaaa aacgttgtta   1380

aaagcttatt gtggtgtagt gtaaaaaagc aaatcagtca ctatctctct ctagttcttt   1440

tcacttatct aatttacgta ttatatcgta caaagatctc tcagacacac tctgtgatgg   1500

tctaccgatc atataggtga tcgactaaaa ggagacaacg gtcaaacacg tcaacggtta   1560

aactaatccc caaaatatta tctttgtagt ttttcatgca gaaacatatt acaccgtaaa   1620

aaacattatg aaacaaactt aaaaaaaaaa aaaaaaaaag taaacgtcca ttataattcg   1680

gaggtactaa tattctaata ttagaaagtg tatgtgaaca taagaacgtg taatatggca   1740

gccaacgcaa aagaaaacta cataatttga tctgagtcac tttagtgtgt tcatctatgc   1800

tttttctaga tcgatcttaa tttctttttc gtcagcagct ttttctagat ctatctttaa   1860

taaacataaa attaaaagaa attaaaaata aaaaggaaaa ataccaaagt ttcggctata   1920

taaagaagtg tgttgttggt agtgataatc gtgtgccaca aaatataatc ctcgtacttt   1980

gaaattaagg agtgaataaa atg gag cgt tct tca cgt gtg ttt tca gtt gtt   2033
                      Met Glu Arg Ser Ser Arg Val Phe Ser Val Val
                      1               5                   10

ctt ctc atg ctt gtt ctt gtg ttg tcc aca g gtttatgttc tttctcgtaa     2084
Leu Leu Met Leu Val Leu Val Leu Ser Thr
            15                  20

tttcatttta tttatttcca attaaatcat tctgctcaaa tatttaattt gtttgttgct   2144

tttaattaat taatctcacg ccctactaat cacaaataat gaatactttg catatatcac   2204
```

-continued

```
ttgctcttat ttgatttatg caaagtgata aaagtcaaaa tttgcgacaa attatttgtt   2264

ttgtaactat attttccaaa tagattaaaa atatataata ttattagatt gtaattttta   2324

ttttttaatt tacaagataa aatgagtaat atatatggtt tccttctttt ttatggacta   2384

ccttatttaa atatatattg tcgtagtaaa agtatatcga tgactgtaaa aataatttga   2444

tgagtcttga actaccttgt ttaaataaat attgtaatag tcgtcattta cgaactttat   2504

catcacccgt gctttatttt taaagaactt gacttcatga ttggccatga ccaattaagc   2564

taaaaaaact cataattaac ttatttaagg gggggcaaca aggttagatg aatttgatgt   2624

tttttttttt tcattctaac cattgatag at  atg tac aca gac cca gtg gcg     2676
                                Asp Met Tyr Thr Asp Pro Val Ala
                                            25

gtt ctt agt tat g gtataaatgg gctggtgaaa agttccataa tttatttcta       2729
Val Leu Ser Tyr
30

attccaaccc taatatttta aatataattg tataaattgc ataatgtttc tatagtccct   2789

cctaaaactg ttcaaaatcc gcaacttcat agacagtaat aagtttcttc gttaatatgc   2849

ataaagtact ccgatccacc atattaatat tgtttaatca tcctaaaata ttgaggttac   2909

aaatgacgta ctataacaag ttttcttagc taaaatacgt tgttattaaa tgttatgcta   2969

gaatatgtat ttaatcggtt aagtcccctt actgcaacct cccaataccc ccaatacgag   3029

atatctgcat gtgaacgtaa ctaacatatt gtttatgaat catgttaaat ctctgtattc   3089

tttattcatg ttcttaattg tctttcttac ag ag  att ggg aca aag gtg gcg     3141
                                    Glu Ile Gly Thr Lys Val Ala
                                        35                  40

gaa gca agg ata tgc gaa tct gca agt tac agg ttc aag gga ata tgt     3189
Glu Ala Arg Ile Cys Glu Ser Ala Ser Tyr Arg Phe Lys Gly Ile Cys
                45                  50                  55

gtg agc agg agc aac tgt gct aat gtt tgc aaa aat gag ggt ttc ccc     3237
Val Ser Arg Ser Asn Cys Ala Asn Val Cys Lys Asn Glu Gly Phe Pro
            60                  65                  70

ggt ggc cgt tgc cgc ggt ttc cgt cgt cgt tgc ctc tgt tac aaa cat     3285
Gly Gly Arg Cys Arg Gly Phe Arg Arg Arg Cys Leu Cys Tyr Lys His
        75                  80                  85

tgc ggt taattgttat gccacggcca ctttcctatg tgctagtgct tatgacattg      3341
Cys Gly
    90

atctgaagta ccttcttaat tgacgtgttc ttattgttgt tttaagttca aataatgtgt   3401

aatcctgttt cttttgcgtc gtaagttaaa ttgatctatg atctttaaat tgtattccgt   3461

atgttggtac cttcttaatg gtttgtagtt taattaaatt ttactttcac gcgtaactaa   3521

tttgaagatt tttgcacatt tacttgcttt tttgggtcta tataatatag ttcatctgtt   3581

ccataacaat gttctggtat attttttttt tacgtttgtc aatgcacatt ttatatcatt   3641

ttcatatcta atataatatt aaaaattata aaatttaata ttattaaagt aatcattaag   3701

acaaatcgaa tcaaacattg cgtgaatatg tttttttctta tatattggat tagaaagaat   3761

ttagaagttt tgcatcaact gtgaatagtg tcaaaaacct aaattgtaac atcattatga   3821

aacgaaggag tatcaaatta tgctactccg tctcaattta cttttccttt ttttatatcc   3881

tatgtacttt gcgccatttc cttttcgaaa attttctcct ctccactttt ttcttgagtt   3941

aattctcacc atccacctac tcattttctt ttctttagtt tttcattctc ctaaaactct   4001

accccgtgat tttagatcat ttaaagttca aaaataactc tacaaggtag agtttgagca   4061

atatcaacca ttgaatgaaa aatcaacagc tcatatatta tcttttcaaa atttccctat   4121
```

ttttctcat taatatccac ccttttattt tcccctccta ctcatttaaa ataaaggtga 4181 ttttatacct tagattcaac tccaaaccgg caaactccag actcttcaat aaaaatacta 4241 gagtagtttt ctactgactt ttatcaaact ttaaaataaa attgaaattg aat 4294

<210> SEQ ID NO 86
<211> LENGTH: 4527
<212> TYPE: DNA
<213> ORGANISM: Spinacia oleracea
<220> FEATURE:
<221> NAME/KEY: misc_feature
<222> LOCATION: (1914)..(2000)
<223> OTHER INFORMATION: 5'UTR
<220> FEATURE:
<221> NAME/KEY: CDS
<222> LOCATION: (2001)..(2052)
<223> OTHER INFORMATION: Def7 nucleotide
<220> FEATURE:
<221> NAME/KEY: misc_feature
<222> LOCATION: (2053)..(3353)
<223> OTHER INFORMATION: Intron
<220> FEATURE:
<221> NAME/KEY: CDS
<222> LOCATION: (3355)..(3524)
<223> OTHER INFORMATION: Def7 nucleotide
<220> FEATURE:
<221> NAME/KEY: misc_feature
<222> LOCATION: (3527)..(3661)
<223> OTHER INFORMATION: 3'UTR

<400> SEQUENCE: 86
attttcattt tatattttgg taaatacttt gaagtagggt gataacgact atgtttcacg 60 gttaatttc ctttatactt cgtttgggct ttgacaacct cttttttttt tttttttttt 120
tggtgcgaat gagccacaaa ggcggggatg agaatcgatc ccatgatcac ctggaaccgg 180
aatgaaagct ctaaccaact gagctaccca ttactctttt tgacaaccta tattaattat 240
caagtgtggg gatgtaaacg agtcgaatca aggagtatat ttaaagtttg cctactgtct 300
caaacaaaaa aagtttgtct actgttgggc tagctgatgc aagtttaagc ccaacttgat 360
tcaccatttt ttcatacttc gtatgagcct ttcttaaatc ctaatagcaa taccctatat 420
tactacggag tactacgcat tatgatctag agttaatcgc attttagata attgatcatg 480
gtgtacaagg agctataatg caccctaaaa atataagtat aacttaaaga acatacctaa 540
cgtaaaataa acatgagttt taataaaaag tgaattaaca tattgcatgt tcttttgttg 600
taattttctt ttacatgtgt atatacttcc tccgtttcga aaatatcgca ctatgattga 660
cttttacttc tctaaccttt actttgactc ttaatatcac aaaccgtgtg caagtaaaaa 720
ttataaaaag aataatatta agaaaatata tatatcgata caaatctaat ataaccccac 780
atgactaaaa ttttcttact tacgaattac aaaaaattgc caaaatcata gtgtaaatag 840
tgtaaaaaac aaatggtgcg acatttttgg aacggatgaa gtatgttatt ttaggtgctc 900
accatactca ttatgtacca ttgttcatac ttagcccaca aattagagta aattttattt 960
taaaccaaat ttgaatagaa gttccgtata aggtacataa tatacgctaa ctatgtttgt 1020
cgatgaaagg cacggggtta cctaatatgt atgaccatgt gatcagtgat ggatcttgaa 1080
caattttaag aaaaaggaca gtagaaaaat taaacaatgt agcatgtatg caatttatac 1140
aataaaacac aaaattttgg gggagctgca actaaacctg gcaaatctga cccaaacccg 1200
aaaaactgac ccgattgatc tgatctgtaa cccgaaattg atctgaagcg acgacccaaa 1260
attaacctga aaactaaaca gaaccgaccc gaaaccgaaa ctgacccaga aatgatttga 1320

```
cctgaaatga ccagatatcc gaatgacccg aaccaaagta cccaaaaaga tcttcacccg   1380

aaaccgaata ttatttaaat ttttttatta taattttcat tttattaatt tatactgttt   1440

tgaattatag gaaaaagatt ttgttaatat tatgatagtg accaccaaat ctaaaaagaa   1500

acaacctaat caaaactaaa aatccaaaaa atttgatcca attaacccaa aaactcgatc   1560

taaccaaaaa aatctgatat aatccgaaaa ctcgatccga tatgaacgat ctgatacgaa   1620

ttgatcctat atgacccgat ccaatattga tccgaaatca tgacgagaac cagacccggc   1680

ccgattaaaa aaaaccgaac tcacccaaaa gccgagaatt atgtttaaaa aggttgtacg   1740

aagtttaaat attaggaaaa agaacgtgtc acatttatag tcatggtgat tcatgagatc   1800

tgtaacatgt acgtgtagct tcatttaggc attggtattt gcaccaaagc accatttggc   1860

aattgccatg cacaccatct tcccttataa aagtagcttt gtgtctgttt tcatcaccaa   1920

atcaaaacaa aacaaaaaaa acacaccata tattttccta attattattg aatttttttt   1980

atcaaatagt tcaagttgca atg aag ccc ttt gta gct ttt gtt ctt gct ttc   2033
                      Met Lys Pro Phe Val Ala Phe Val Leu Ala Phe
                      1               5                   10

atg ctt gtc ttg gcc ata g gtacaacttc cttgaccttc ctttgaatta          2082
Met Leu Val Leu Ala Ile
            15

agggtgtctg tttcataata tatgcctcat tttaattgtc ttcgttttaa ttgtcttcgt   2142

tagacgaaat gcttaacata agtgctatta gtctagctag tactctgtac tataagcata   2202

actataagca taatgtactt cctccgagtt gatttttaca ctatttacat attaattata   2262

ctttaattat actttgataa ttgttggtga tttataccta aggtaaaaca tagtcgtgtg   2322

ggatcttgtt aatttaatat gtctcgttaa aatattaact tttttataat ttttgttaat   2382

gagaaataaa tatattaatg atcaaagttg ttcattatgc atgaaagtga caaacattac   2442

agagtaaaaa tgaacagtgg aagtatatct tagtcacttc tagcaaaagg tgatcaaaat   2502

ttgggtctgg ttgggtttta acacataaca cataaatcat aaatcatgcc caaaatcata   2562

aattttgtgc tggttttgcg ggccgaaatg gggtttttaa agcaggattc gggttttggt   2622

ctaaaaatgc atattttagg ctatttaaat ccacactttt ttgggccgga ttgggttagt   2682

ggccgggcta tagttgacca agtctaatct tcaacttatt ttaacgtggg ataaataatc   2742

tttaattcac atgtgggtta atcttttaac agatacgtag tactccctcc gtttcttatt   2802

gttgtatccg ttttcatttt aagcgtttca tattgttgta tccatttaga atctattcta   2862

tttttggaca tatattttat cctaaaatac ccttacattt ctatctaatt accaaaatac   2922

ctaaagattc tacccatatt cccacctaat tttccccacc cataatattt aatttttttc   2982

cctactccat atacccactc tctcacctcc tttatcaccc atcattatca ctcctctctc   3042

ttaccttatt tctttattat tttcctactc ctttatttat tataatctct tacacctaat   3102

catttctctt acactcaatc attacactta tacccataca aatcaatatt tcaattttct   3162

taaaaaccac agcagattcc aaatggatac atcaaaaaga aatggaggga gtacttcgta   3222

catgatattg aacgaggcct tagtgtctat gagatgtttt agttttccat atatgttttt   3282

gctaaatttg ataattttaa ttttgcatgt ctaatttgtt gatgatattt gttgttgtgt   3342

ttaaaattaa ag ag  atg ggt cca aga gta gca gaa gca aga atg tgc aca   3392
              Glu Met Gly Pro Arg Val Ala Glu Ala Arg Met Cys Thr
                  20                  25                  30

aat ccg agt aga aca ttc agg gga cca tgc gtt agt gac cgg aac tgc     3440
Asn Pro Ser Arg Thr Phe Arg Gly Pro Cys Val Ser Asp Arg Asn Cys
            35                  40                  45
```

```
gaa tcg tcg tgc atg gga gag gga ttt ccc ggt gga agt tgt cat ggc     3488
Glu Ser Ser Cys Met Gly Glu Gly Phe Pro Gly Gly Ser Cys His Gly
            50                  55                  60

ttt cgt aga aaa tgc gtc tgc agc aag cct tgt gct tagacggcct          3534
Phe Arg Arg Lys Cys Val Cys Ser Lys Pro Cys Ala
        65                  70

tccaatttca tcttctttta tgtattagtc ttgtaccctc gtaatggagg aggaaacaag   3594

ccagggttat aaacaaatga aatgtgcacg ctttatgtac tttgtttatt tatgaaaaat   3654

taataaaatg tattatctct gttctttgaa agtttttttt gacgttttcg aatttcttag   3714

taagaaaatc ttgatcataa attatctcta ttatactacc tccatttcac aatacttgta   3774

tcatttattt atttattttc aagtatccca acatgcttct ttgaacatta atatctctca   3834

ctgcgtataa gtaaaaatta taaaaaatta cggagtaata tttataatcc tcacattaat   3894

acgaatttaa caagatttta ctagactatg tttactttta cataatgtga aagaacaatt   3954

gtcaaagtta gttaatgaat agtgtccaag atgcatctat tgcggaacgg aggaagtata   4014

tactagtcag aagcatgtgc tatgcacgta ttggcttaac gtacatttat aaattttta    4074

aacttgcata ttgtaatgca ctaaacacta aggtctttat agaccattac aaatattaaa   4134

ctaaaagtcg aattaatata taatgcaagg gtcctgtgct cgatcttctt gtaagtttta   4194

ctattcgtac ggagcattaa ttaagttgtt ttctactatt tataacataa aagacattta   4254

atcaaataaa agtttatcat tcttattcgc aagttaagaa atgtatacac cttgctctat   4314

taaaaatcgc atggagttat tcacattttc aaaaaaaaat attatacatg tacactctct   4374

gttttttttt aaatgcatca cttaaaattt cacattgttt atattgactt agatatttta   4434

ctaatatata cagagtaata atcaaatgtt attatgtaaa atgttgtttc acaatgcata   4494

ttttcttaat atcaactttt tataatattt acc                                4527
```

<210> SEQ ID NO 87
<211> LENGTH: 53
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Consensus sequence of Def3, Def4, Def5, Def6, and Def7 peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (3)..(3)
<223> OTHER INFORMATION: Ala or Val
<220> FEATURE:
<221> NAME/KEY: MOD_RES
<222> LOCATION: (7)..(7)
<223> OTHER INFORMATION: Thr or Ile or Met
<220> FEATURE:
<221> NAME/KEY: MOD_RES
<222> LOCATION: (9)..(9)
<223> OTHER INFORMATION: Glu or Ser or Ala or Thr
<220> FEATURE:
<221> NAME/KEY: MOD_RES
<222> LOCATION: (10)..(10)
<223> OTHER INFORMATION: Thr or Ser or Asn
<220> FEATURE:
<221> NAME/KEY: MOD_RES
<222> LOCATION: (11)..(11)
<223> OTHER INFORMATION: Pro or Ala
<220> FEATURE:

<221> NAME/KEY: MOD_RES
<222> LOCATION: (13)..(13)
<223> OTHER INFORMATION: Gln or Pro or His or Tyr or Arg
<220> FEATURE:
<221> NAME/KEY: MOD_RES
<222> LOCATION: (14)..(14)
<223> OTHER INFORMATION: Lys or Thr or Arg
<220> FEATURE:
<221> NAME/KEY: MOD_RES
<222> LOCATION: (16)..(16)
<223> OTHER INFORMATION: Lys or Arg
<220> FEATURE:
<221> NAME/KEY: MOD_RES
<222> LOCATION: (18)..(18)
<223> OTHER INFORMATION: Ile or Pro
<220> FEATURE:
<221> NAME/KEY: MOD_RES
<222> LOCATION: (20)..(20)
<223> OTHER INFORMATION: Ile or Phe or Thr or Val
<220> FEATURE:
<221> NAME/KEY: MOD_RES
<222> LOCATION: (22)..(22)
<223> OTHER INFORMATION: Asp or Ser or Arg
<220> FEATURE:
<221> NAME/KEY: MOD_RES
<222> LOCATION: (23)..(23)
<223> OTHER INFORMATION: Ser or Arg
<220> FEATURE:
<221> NAME/KEY: MOD_RES
<222> LOCATION: (26)..(26)
<223> OTHER INFORMATION: Glu or Ala
<220> FEATURE:
<221> NAME/KEY: MOD_RES
<222> LOCATION: (27)..(27)
<223> OTHER INFORMATION: Ser or Thr or Asn
<220> FEATURE:
<221> NAME/KEY: MOD_RES
<222> LOCATION: (28)..(28)
<223> OTHER INFORMATION: Ile or Asn or Thr or Val or Ser
<220> FEATURE:
<221> NAME/KEY: MOD_RES
<222> LOCATION: (30)..(30)
<223> OTHER INFORMATION: Asn or Lys or Met
<220> FEATURE:
<221> NAME/KEY: MOD_RES
<222> LOCATION: (31)..(31)
<223> OTHER INFORMATION: Thr or Ser or Asn or Gly
<220> FEATURE:
<221> NAME/KEY: MOD_RES
<222> LOCATION: (32)..(32)
<223> OTHER INFORMATION: Glu or Val
<220> FEATURE:
<221> NAME/KEY: MOD_RES
<222> LOCATION: (33)..(33)
<223> OTHER INFORMATION: Gly or Lys or Arg
<220> FEATURE:
<221> NAME/KEY: MOD_RES
<222> LOCATION: (35)..(35)
<223> OTHER INFORMATION: Pro or Ser
<220> FEATURE:
<221> NAME/KEY: MOD_RES
<222> LOCATION: (36)..(36)
<223> OTHER INFORMATION: Asn or Gly
<220> FEATURE:
<221> NAME/KEY: MOD_RES
<222> LOCATION: (38)..(38)
<223> OTHER INFORMATION: Glu or Ser or Arg
<220> FEATURE:
<221> NAME/KEY: MOD_RES
<222> LOCATION: (40)..(40)
<223> OTHER INFORMATION: Ser or Gln or Lys or Arg or His
<220> FEATURE:
<221> NAME/KEY: MOD_RES
<222> LOCATION: (42)..(42)
<223> OTHER INFORMATION: Leu or Phe
<220> FEATURE:
<221> NAME/KEY: MOD_RES
<222> LOCATION: (45)..(45)
<223> OTHER INFORMATION: Arg or Lys

```
<220> FEATURE:
<221> NAME/KEY: MOD_RES
<222> LOCATION: (47)..(47)
<223> OTHER INFORMATION: Ile or Met or Leu or Val
<220> FEATURE:
<221> NAME/KEY: MOD_RES
<222> LOCATION: (49)..(49)
<223> OTHER INFORMATION: Asn or Thr or Tyr or Ser
<220> FEATURE:
<221> NAME/KEY: MOD_RES
<222> LOCATION: (50)..(50)
<223> OTHER INFORMATION: Thr or Lys or Gly
<220> FEATURE:
<221> NAME/KEY: MOD_RES
<222> LOCATION: (51)..(51)
<223> OTHER INFORMATION: Pro or His
<220> FEATURE:
<221> NAME/KEY: MOD_RES
<222> LOCATION: (53)..(53)
<223> OTHER INFORMATION: Thr or Ala or Val or Gly

<400> SEQUENCE: 87

Xaa Val Xaa Glu Ala Arg Xaa Cys Xaa Xaa Xaa Ser Xaa Xaa Phe Xaa
1               5                   10                  15

Gly Xaa Cys Xaa Ser Xaa Xaa Asn Cys Xaa Xaa Xaa Cys Xaa Xaa Xaa
            20                  25                  30

Xaa Phe Xaa Xaa Gly Xaa Cys Xaa Gly Xaa Arg Arg Xaa Cys Xaa Cys
        35                  40                  45

Xaa Xaa Xaa Cys Xaa
    50


<210> SEQ ID NO 88
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Consensus sequence of Def3, Def4, Def5, Def6,
      and Def7 peptide
<220> FEATURE:
<221> NAME/KEY: MOD_RES
<222> LOCATION: (1)..(1)
<223> OTHER INFORMATION: Arg or Lys
<220> FEATURE:
<221> NAME/KEY: MOD_RES
<222> LOCATION: (7)..(7)
<223> OTHER INFORMATION: Thr or Ile or Met
<220> FEATURE:
<221> NAME/KEY: MOD_RES
<222> LOCATION: (9)..(9)
<223> OTHER INFORMATION: Glu or Ser or Ala or Thr
<220> FEATURE:
<221> NAME/KEY: MOD_RES
<222> LOCATION: (10)..(10)
<223> OTHER INFORMATION: Thr or Ser or Asn
<220> FEATURE:
<221> NAME/KEY: MOD_RES
<222> LOCATION: (13)..(13)
<223> OTHER INFORMATION: Gln or Pro or His or Tyr or Arg
<220> FEATURE:
<221> NAME/KEY: MOD_RES
<222> LOCATION: (14)..(14)
<223> OTHER INFORMATION: Lys or Thr or Arg
<220> FEATURE:
<221> NAME/KEY: MOD_RES
<222> LOCATION: (20)..(20)
<223> OTHER INFORMATION: Ile or Phe or Thr or Val
<220> FEATURE:
<221> NAME/KEY: MOD_RES
<222> LOCATION: (22)..(22)
<223> OTHER INFORMATION: Asp or Ser or Arg
<220> FEATURE:
```

<221> NAME/KEY: MOD_RES
<222> LOCATION: (23)..(23)
<223> OTHER INFORMATION: Ser or Arg
<220> FEATURE:
<221> NAME/KEY: MOD_RES
<222> LOCATION: (27)..(27)
<223> OTHER INFORMATION: Ser or Thr or Asn
<220> FEATURE:
<221> NAME/KEY: MOD_RES
<222> LOCATION: (28)..(28)
<223> OTHER INFORMATION: Ile or Asn or Thr or Val or Ser
<220> FEATURE:
<221> NAME/KEY: MOD_RES
<222> LOCATION: (30)..(30)
<223> OTHER INFORMATION: Asn or Lys or Met
<220> FEATURE:
<221> NAME/KEY: MOD_RES
<222> LOCATION: (31)..(31)
<223> OTHER INFORMATION: Thr or Ser or Asn or Gly
<220> FEATURE:
<221> NAME/KEY: MOD_RES
<222> LOCATION: (33)..(33)
<223> OTHER INFORMATION: Gly or Lys or Arg
<220> FEATURE:
<221> NAME/KEY: MOD_RES
<222> LOCATION: (35)..(35)
<223> OTHER INFORMATION: Pro or Ser
<220> FEATURE:
<221> NAME/KEY: MOD_RES
<222> LOCATION: (38)..(38)
<223> OTHER INFORMATION: Glu or Ser or Arg
<220> FEATURE:
<221> NAME/KEY: MOD_RES
<222> LOCATION: (40)..(40)
<223> OTHER INFORMATION: Ser or Gln or Lys or Arg or His
<220> FEATURE:
<221> NAME/KEY: MOD_RES
<222> LOCATION: (45)..(45)
<223> OTHER INFORMATION: Arg or Lys
<220> FEATURE:
<221> NAME/KEY: MOD_RES
<222> LOCATION: (47)..(47)
<223> OTHER INFORMATION: Ile or Met or Leu or Val
<220> FEATURE:
<221> NAME/KEY: MOD_RES
<222> LOCATION: (49)..(49)
<223> OTHER INFORMATION: Asn or Thr or Tyr or Ser
<220> FEATURE:
<221> NAME/KEY: MOD_RES
<222> LOCATION: (50)..(50)
<223> OTHER INFORMATION: Thr or Lys or Gly
<220> FEATURE:
<221> NAME/KEY: MOD_RES
<222> LOCATION: (53)..(53)
<223> OTHER INFORMATION: Thr or Ala or Val or Gly

<400> SEQUENCE: 88

```
Xaa Val Ala Glu Ala Arg Xaa Cys Xaa Xaa Pro Ser Xaa Xaa Phe Lys
1               5                   10                  15

Gly Ile Cys Xaa Ser Xaa Xaa Asn Cys Glu Xaa Xaa Cys Xaa Xaa Glu
            20                  25                  30

Xaa Phe Xaa Gly Gly Xaa Cys Xaa Gly Phe Arg Arg Xaa Cys Xaa Cys
        35                  40                  45

Xaa Xaa Pro Cys Xaa
    50
```

<210> SEQ ID NO 89
<211> LENGTH: 22
<212> TYPE: PRT
<213> ORGANISM: Spinacia oleracea
<220> FEATURE:
<221> NAME/KEY: MOD_RES
<222> LOCATION: (1)..(1)
<223> OTHER INFORMATION: Arg, Lys, or Met
<220> FEATURE:
<221> NAME/KEY: MISC_FEATURE
<222> LOCATION: (1)..(22)
<223> OTHER INFORMATION: mat_peptide Segura SoD1 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 89

Xaa Thr Cys Glu Ser Pro Ser His Lys Phe Lys Gly Pro Cys Ala Thr
1 5 10 15

Asn Arg Asn Cys Glu Ser
20

<210> SEQ ID NO 90
<211> LENGTH: 52
<212> TYPE: PRT
<213> ORGANISM: Spinacia oleracea
<220> FEATURE:
<221> NAME/KEY: MISC_FEATURE
<222> LOCATION: (1)..(58)
<223> OTHER INFORMATION: mat_peptide; Segura SoD2 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 90

Gly Ile Phe Ser Ser Arg Lys Cys Lys Thr Pro Ser Lys Thr Phe Lys
1 5 10 15

Gly Ile Cys Thr Arg Asp Ser Asn Cys Asp Thr Ser Cys Arg Tyr Glu
20 25 30

Gly Tyr Pro Ala Gly Asp Cys Lys Gly Ile Arg Arg Arg Cys Met Cys
35 40 45

Ser Lys Pro Cys
50

<210> SEQ ID NO 91
<211> LENGTH: 25
<212> TYPE: PRT
<213> ORGANISM: Spinacia oleracea
<220> FEATURE:
<221> NAME/KEY: MISC_FEATURE
<222> LOCATION: (1)..(25)
<223> OTHER INFORMATION: mat_peptide; Segura SoD3 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 91

Gly Ile Phe Ser Ser Arg Lys Cys Lys Thr Val Ser Lys Thr Phe Arg
1 5 10 15

Gly Ile Cys Thr Arg Asn Ala Asn Cys
20 25

<210> SEQ ID NO 92
<211> LENGTH: 23

<212> TYPE: PRT
<213> ORGANISM: Spinacia oleracea
<220> FEATURE:
<221> NAME/KEY: MISC_FEATURE
<222> LOCATION: (1)..(23)
<223> OTHER INFORMATION: mat_peptide; Segura SoD4 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 92

Met Phe Phe Ser Ser Lys Lys Cys Lys Thr Val Ser Lys Thr Phe Arg
1 5 10 15

Gly Pro Cys Val Arg Asn Ala
20

<210> SEQ ID NO 93
<211> LENGTH: 24
<212> TYPE: PRT
<213> ORGANISM: Spinacia oleracea
<220> FEATURE:
<221> NAME/KEY: MOD_RES
<222> LOCATION: (12)..(12)
<223> OTHER INFORMATION: Ser or Ala
<220> FEATURE:
<221> NAME/KEY: MISC_FEATURE
<222> LOCATION: (1)..(24)
<223> OTHER INFORMATION: mat_peptide; Segura SoD5 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 93

Met Phe Phe Ser Ser Lys Lys Cys Lys Thr Val Xaa Lys Thr Phe Arg
1 5 10 15

Gly Pro Cys Val Arg Asn Ala Asn
20

<210> SEQ ID NO 94
<211> LENGTH: 24
<212> TYPE: PRT
<213> ORGANISM: Spinacia oleracea
<220> FEATURE:
<221> NAME/KEY: MISC_FEATURE
<222> LOCATION: (1)..(24)
<223> OTHER INFORMATION: mat_peptide; Segura SoD6 peptide
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (22)..(23)
<223> OTHER INFORMATION: Any amino acid
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 94

Gly Ile Phe Ser Asn Met Tyr Xaa Arg Thr Pro Ala Gly Tyr Phe Arg
1 5 10 15

Gly Pro Xaa Gly Tyr Xaa Xaa Asn
20

<210> SEQ ID NO 95
<211> LENGTH: 38
<212> TYPE: PRT
<213> ORGANISM: Spinacia oleracea
<220> FEATURE:
<221> NAME/KEY: MISC_FEATURE
<222> LOCATION: (1)..(38)
<223> OTHER INFORMATION: mat_peptide; Segura SoD7 peptide
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 95

Gly Ile Phe Ser Ser Arg Lys Cys Lys Thr Pro Ser Lys Thr Phe Lys
1 5 10 15

Gly Tyr Cys Thr Arg Asp Ser Asn Cys Asp Thr Ser Cys Arg Tyr Glu
20 25 30

Gly Tyr Pro Ala Gly Asp
35

<210> SEQ ID NO 96
<211> LENGTH: 51
<212> TYPE: PRT
<213> ORGANISM: Raphanus sativus
<220> FEATURE:
<221> NAME/KEY: MISC_FEATURE
<222> LOCATION: (1)..(53)
<223> OTHER INFORMATION: mat_peptide; Rs-AFP2
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 96

Gln Lys Leu Cys Gln Arg Pro Ser Gly Thr Trp Ser Gly Val Cys Gly
1 5 10 15

Asn Asn Asn Ala Cys Lys Asn Gln Cys Ile Arg Leu Glu Lys Ala Arg
20 25 30

His Gly Ser Cys Asn Tyr Val Phe Pro Ala His Lys Cys Ile Cys Tyr
35 40 45

Phe Pro Cys
50

<210> SEQ ID NO 97
<211> LENGTH: 51
<212> TYPE: PRT
<213> ORGANISM: Arabidopsis thaliana
<220> FEATURE:
<221> NAME/KEY: MISC_FEATURE
<222> LOCATION: (1)..(51)
<223> OTHER INFORMATION: mat_peptide; At-AFP1
<300> PUBLICATION INFORMATION:
<301> AUTHORS: Segura, A., Moreno, M., Molina, A., & Garcia-Olmedo, F.

<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 97

```
Gln Lys Leu Cys Glu Arg Pro Ser Gly Thr Trp Ser Gly Val Cys Gly
1               5                   10                  15

Asn Ser Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50
```

<210> SEQ ID NO 98
<211> LENGTH: 54
<212> TYPE: PRT
<213> ORGANISM: Heuchera sanguinea
<220> FEATURE:
<221> NAME/KEY: MISC_FEATURE
<222> LOCATION: (1)..(54)
<223> OTHER INFORMATION: mat_peptide; Hs-AFP1
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 98

```
Asp Gly Val Lys Leu Cys Asp Val Pro Ser Gly Thr Trp Ser Gly His
1               5                   10                  15

Cys Gly Ser Ser Ser Lys Cys Ser Gln Gln Cys Lys Asp Arg Glu His
            20                  25                  30

Phe Ala Tyr Gly Gly Ala Cys His Tyr Gln Phe Pro Ser Val Lys Cys
        35                  40                  45

Phe Cys Lys Arg Gln Cys
    50
```

<210> SEQ ID NO 99
<211> LENGTH: 50
<212> TYPE: PRT
<213> ORGANISM: Aesculus hippocastanum
<220> FEATURE:
<221> NAME/KEY: MISC_FEATURE
<222> LOCATION: (1)..(50)
<223> OTHER INFORMATION: mat_peptide; Ah-Amp1
<300> PUBLICATION INFORMATION:
<301> AUTHORS: Segura, A., Moreno, M., Molina, A., & Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 99

```
Leu Cys Asn Glu Arg Pro Ser Gln Thr Trp Ser Gly Asn Cys Gly Asn
1               5                   10                  15

Thr Ala His Cys Asp Lys Gln Cys Gln Asp Trp Glu Lys Ala Ser His
            20                  25                  30

Gly Ala Cys His Lys Arg Glu Asn His Trp Lys Cys Phe Cys Tyr Phe
        35                  40                  45
```

```
Asn Cys
    50


<210> SEQ ID NO 100
<211> LENGTH: 50
<212> TYPE: PRT
<213> ORGANISM: Dahlia merckii
<220> FEATURE:
<221> NAME/KEY: MISC_FEATURE
<222> LOCATION: (1)..(50)
<223> OTHER INFORMATION: mat_peptide; Dm-Amp1
<300> PUBLICATION INFORMATION:
<301> AUTHORS: Segura, A., Moreno, M., Molina, A., &  Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 100

Glu Leu Cys Glu Lys Ala Ser Lys Thr Trp Ser Gly Asn Cys Gly Asn
1               5                   10                  15

Thr Gly His Cys Asp Asn Gln Cys Lys Ser Trp Glu Gly Ala Ala His
            20                  25                  30

Gly Ala Cys His Val Arg Asn Gly Lys His Met Cys Phe Cys Tyr Phe
        35                  40                  45

Asn Cys
    50


<210> SEQ ID NO 101
<211> LENGTH: 47
<212> TYPE: PRT
<213> ORGANISM: Solanum tuberosum
<220> FEATURE:
<221> NAME/KEY: MISC_FEATURE
<222> LOCATION: (1)..(47)
<223> OTHER INFORMATION: mat_peptide; St-PTH1
<300> PUBLICATION INFORMATION:
<301> AUTHORS: Segura, A., Moreno, M., Molina, A., &  Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09

<400> SEQUENCE: 101

Arg His Cys Glu Ser Leu Ser His Arg Phe Lys Gly Pro Cys Thr Arg
1               5                   10                  15

Asp Ser Asn Cys Ala Ser Val Cys Glu Thr Glu Arg Phe Ser Gly Gly
            20                  25                  30

Asn Cys His Gly Phe Arg Arg Arg Cys Phe Cys Thr Lys Pro Cys
        35                  40                  45


<210> SEQ ID NO 102
<211> LENGTH: 47
<212> TYPE: PRT
<213> ORGANISM: Sorghum bicolor
<220> FEATURE:
<221> NAME/KEY: MISC_FEATURE
<222> LOCATION: (1)..(47)
<223> OTHER INFORMATION: mat_peptide; Sialpha2
<300> PUBLICATION INFORMATION:
<301> AUTHORS: Segura, A., Moreno, M., Molina, A., &  Garcia-Olmedo, F.
<302> TITLE: Novel defensin subfamily from spinach (Spinacea oleracea)
<303> JOURNAL: FEBS Letters
<304> VOLUME: 435
<306> PAGES: 159-162
<307> DATE: 1998-07-09
```

<400> SEQUENCE: 102

Arg Val Cys Met Lys Gly Ser Ala Gly Phe Lys Gly Leu Cys Met Arg
1 5 10 15

Asp Gln Asn Cys Ala Gln Val Cys Leu Gln Glu Gly Trp Gly Gly Gly
20 25 30

Asn Cys Asp Gly Val Met Arg Gln Cys Lys Cys Ile Arg Gln Cys
35 40 45

<210> SEQ ID NO 103
<211> LENGTH: 52
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chimeric nucleic acid encoding a signal peptide and SoD2 codon-optimized with GenScript

<400> SEQUENCE: 103

Gly Ile Phe Ser Ser Arg Lys Cys Lys Thr Pro Ser Lys Thr Phe Lys
1 5 10 15

Gly Ile Cys Thr Arg Asp Ser Asn Cys Asp Thr Ser Cys Arg Tyr Glu
20 25 30

Gly Tyr Pro Ala Gly Asp Cys Lys Gly Ile Arg Arg Arg Cys Met Cys
35 40 45

Ser Lys Pro Cys
50

<210> SEQ ID NO 104
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chimeric nucleic acid encoding a signal peptide and SoD7 codon-optimized with GenScript

<400> SEQUENCE: 104

Gly Ile Phe Ser Ser Arg Lys Cys Lys Thr Pro Ser Lys Thr Phe Lys
1 5 10 15

Gly Tyr Cys Thr Arg Asp Ser Asn Cys Asp Thr Ser Cys Arg Tyr Glu
20 25 30

Gly Tyr Pro Ala Gly Asp
35

<210> SEQ ID NO 105
<211> LENGTH: 52
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chimeric nucleic acid encoding a signal peptide and SoD2 codon-optimized with CODA

<400> SEQUENCE: 105

Gly Ile Phe Ser Ser Arg Lys Cys Lys Thr Pro Ser Lys Thr Phe Lys
1 5 10 15

Gly Ile Cys Thr Arg Asp Ser Asn Cys Asp Thr Ser Cys Arg Tyr Glu
20 25 30

```
Gly Tyr Pro Ala Gly Asp Cys Lys Gly Ile Arg Arg Arg Cys Met Cys
        35                  40                  45

Ser Lys Pro Cys
    50


<210> SEQ ID NO 106
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric nucleic acid encoding a signal peptide
      and SoD7 codon-optimized with CODA

<400> SEQUENCE: 106

Gly Ile Phe Ser Ser Arg Lys Cys Lys Thr Pro Ser Lys Thr Phe Lys
1               5                   10                  15

Gly Tyr Cys Thr Arg Asp Ser Asn Cys Asp Thr Ser Cys Arg Tyr Glu
            20                  25                  30

Gly Tyr Pro Ala Gly Asp
        35


<210> SEQ ID NO 107
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SoD2 expression cassette comprising a chimeric
      nucleic acid encoding a signal peptide and SoD2

<400> SEQUENCE: 107

Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Gly Tyr Pro Ala Gly Asp Cys Lys Gly Ile Arg Arg Arg Cys Met Cys
        35                  40                  45

Ser Lys Pro Cys
    50


<210> SEQ ID NO 108
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: SoD7 expression cassette comprising a chimeric
      nucleic acid encoding a signal peptide and SoD7

<400> SEQUENCE: 108

Gly Ile Phe Ser Ser Arg Lys Cys Lys Thr Pro Ser Lys Thr Phe Lys
1               5                   10                  15

Gly Tyr Cys Thr Arg Asp Ser Asn Cys Asp Thr Ser Cys Arg Tyr Glu
            20                  25                  30

Gly Tyr Pro Ala Gly Asp
        35
```

<210> SEQ ID NO 109
<211> LENGTH: 52
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chimeric nucleic acid encoding a signal peptide and SoD2

<400> SEQUENCE: 109

```
Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Gly Tyr Pro Ala Gly Asp Cys Lys Gly Ile Arg Arg Arg Cys Met Cys
        35                  40                  45

Ser Lys Pro Cys
    50
```

<210> SEQ ID NO 110
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Chimeric nucleic acid encoding a signal peptide and SoD7

<400> SEQUENCE: 110

```
Gly Ile Phe Ser Ser Arg Lys Cys Lys Thr Pro Ser Lys Thr Phe Lys
1               5                   10                  15

Gly Tyr Cys Thr Arg Asp Ser Asn Cys Asp Thr Ser Cys Arg Tyr Glu
            20                  25                  30

Gly Tyr Pro Ala Gly Asp
        35
```

<210> SEQ ID NO 111
<211> LENGTH: 51
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Variant of SoD2 comprising two additional N-terminal amino acids and a Gly33 deletion relative to spinach SoD2

<400> SEQUENCE: 111

```
Gly Ile Phe Ser Ser Arg Lys Cys Lys Thr Pro Ser Lys Thr Phe Lys
1               5                   10                  15

Gly Ile Cys Thr Arg Asp Ser Asn Cys Asp Thr Ser Cys Arg Tyr Glu
            20                  25                  30

Tyr Pro Ala Gly Asp Cys Lys Gly Ile Arg Arg Arg Cys Met Cys Ser
        35                  40                  45

Lys Pro Cys
    50
```

<210> SEQ ID NO 112
<211> LENGTH: 63

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric nucleic acid encoding a signal peptide
      and Def2 codon-optimized with Genscript

<400> SEQUENCE: 112

Thr Glu Glu Met Gly Pro Arg Lys Ala Asp Ala Gly Phe Phe Ser Ser
1               5                   10                  15

Lys Lys Cys Lys Thr Pro Ser Lys Thr Phe Arg Gly Pro Cys Val Arg
            20                  25                  30

Asn Ala Asn Cys Asp Thr Ser Cys Arg Tyr Glu Gly Tyr Pro Ala Gly
        35                  40                  45

Asp Cys Lys Gly Ile Arg Arg Arg Cys Ile Cys Cys Thr His Ala
    50                  55                  60


<210> SEQ ID NO 113
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Chimeric nucleic acid encoding a signal peptide
      and Def2 codon-optimized with VGD

<400> SEQUENCE: 113

Thr Glu Glu Met Gly Pro Arg Lys Ala Asp Ala Gly Phe Phe Ser Ser
1               5                   10                  15

Lys Lys Cys Lys Thr Pro Ser Lys Thr Phe Arg Gly Pro Cys Val Arg
            20                  25                  30

Asn Ala Asn Cys Asp Thr Ser Cys Arg Tyr Glu Gly Tyr Pro Ala Gly
        35                  40                  45

Asp Cys Lys Gly Ile Arg Arg Arg Cys Ile Cys Cys Thr His Ala
    50                  55                  60


<210> SEQ ID NO 114
<211> LENGTH: 60
<212> TYPE: PRT
<213> ORGANISM: Spinacia oleracea

<400> SEQUENCE: 114

Met Gly Pro Arg Lys Ala Glu Ala Gly Ile Phe Ser Ser Arg Lys Cys
1               5                   10                  15

Lys Thr Pro Ser Lys Thr Phe Lys Gly Ile Cys Thr Arg Asp Ser Asn
            20                  25                  30

Cys Asp Thr Ser Cys Arg Tyr Glu Gly Tyr Pro Ala Gly Asp Cys Lys
        35                  40                  45

Gly Ile Arg Arg Arg Cys Leu Cys Cys Thr His Thr
    50                  55                  60


<210> SEQ ID NO 115
<211> LENGTH: 83
<212> TYPE: PRT
<213> ORGANISM: Spinacia oleracea

<400> SEQUENCE: 115

Met Lys Met Ser Met Arg Ser Ile Ala Val Val Phe Leu Val Cys Leu
1               5                   10                  15
```

```
Leu Val Leu Ser Thr Glu Glu Met Gly Pro Arg Lys Ala Asp Ala Gly
            20                  25                  30

Phe Phe Ser Ser Lys Lys Cys Lys Thr Pro Ser Lys Thr Phe Arg Gly
        35                  40                  45

Pro Cys Val Arg Asn Ala Asn Cys Asp Thr Ser Cys Arg Tyr Glu Gly
    50                  55                  60

Tyr Pro Ala Gly Asp Cys Lys Gly Ile Arg Arg Arg Cys Ile Cys Cys
65                  70                  75                  80

Thr His Ala


<210> SEQ ID NO 116
<211> LENGTH: 74
<212> TYPE: PRT
<213> ORGANISM: Spinacia oleracea

<400> SEQUENCE: 116

Met Lys His Phe Gly Ala Ile Phe Leu Val Leu Leu Leu Val Leu Ala
1               5                   10                  15

Thr Glu His Gly Ala Arg Val Ala Glu Ala Arg Thr Cys Glu Thr Pro
            20                  25                  30

Ser Gln Lys Phe Lys Gly Ile Cys Ile Ser Asp Ser Asn Cys Glu Ser
        35                  40                  45

Ile Cys Asn Thr Glu Gly Phe Pro Asn Gly Glu Cys Ser Gly Leu Arg
    50                  55                  60

Arg Arg Cys Ile Cys Asn Thr Pro Cys Thr
65                  70


<210> SEQ ID NO 117
<211> LENGTH: 130
<212> TYPE: PRT
<213> ORGANISM: Spinacia oleracea

<400> SEQUENCE: 117

Val Ser Thr Lys Val Ala Glu Ala Arg Ile Cys Ala Ser Pro Ser Pro
1               5                   10                  15

Thr Phe Lys Gly Ile Cys Phe Ser Ser Arg Asn Cys Glu Thr Asn Cys
            20                  25                  30

Asn Ser Val Lys Phe Ser Gly Gly Ser Cys Gln Gly Phe Arg Arg Arg
        35                  40                  45

Cys Met Cys Thr Lys Pro Cys Ala Met Arg Pro Phe Ala Ala Leu Phe
    50                  55                  60

Leu Val Leu Phe Leu Val Leu Ala Thr Glu Ile Gly Pro Arg Val Val
65                  70                  75                  80

Glu Ala Arg Met Cys Ser Ser Pro Ser His Arg Phe Lys Gly Ile Cys
                85                  90                  95

Thr Ser Ser Arg Asn Cys Glu Asn Thr Cys Asn Ser Glu Arg Phe Ser
            100                 105                 110

Gly Gly Glu Cys Lys Gly Phe Arg Arg Arg Cys Met Cys Thr Gly Pro
        115                 120                 125

Cys Val
    130


<210> SEQ ID NO 118
<211> LENGTH: 90
<212> TYPE: PRT
<213> ORGANISM: Spinacia oleracea
```

-continued

```
<400> SEQUENCE: 118

Met Glu Arg Ser Ser Arg Val Phe Ser Val Val Leu Leu Met Leu Val
1               5                   10                  15

Leu Val Leu Ser Thr Asp Met Tyr Thr Asp Pro Val Ala Val Leu Ser
            20                  25                  30

Tyr Glu Ile Gly Thr Lys Val Ala Glu Ala Arg Ile Cys Glu Ser Ala
        35                  40                  45

Ser Tyr Arg Phe Lys Gly Ile Cys Val Ser Arg Ser Asn Cys Ala Asn
    50                  55                  60

Val Cys Lys Asn Glu Gly Phe Pro Gly Gly Arg Cys Arg Gly Phe Arg
65                  70                  75                  80

Arg Arg Cys Leu Cys Tyr Lys His Cys Gly
                85                  90


<210> SEQ ID NO 119
<211> LENGTH: 74
<212> TYPE: PRT
<213> ORGANISM: Spinacia oleracea

<400> SEQUENCE: 119

Met Lys Pro Phe Val Ala Phe Val Leu Ala Phe Met Leu Val Leu Ala
1               5                   10                  15

Ile Glu Met Gly Pro Arg Val Ala Glu Ala Arg Met Cys Thr Asn Pro
            20                  25                  30

Ser Arg Thr Phe Arg Gly Pro Cys Val Ser Asp Arg Asn Cys Glu Ser
        35                  40                  45

Ser Cys Met Gly Glu Gly Phe Pro Gly Gly Ser Cys His Gly Phe Arg
    50                  55                  60

Arg Lys Cys Val Cys Ser Lys Pro Cys Ala
65                  70
```